(12) United States Patent
Brown et al.

(10) Patent No.: US 9,112,157 B2
(45) Date of Patent: Aug. 18, 2015

(54) HOLE TRANSPORT MATERIALS INCLUDING OLED APPLICATIONS

(71) Applicant: Plextronics, Inc., Pittsburgh, PA (US)

(72) Inventors: Christopher T. Brown, Pittsburgh, PA (US); Jing Wang, Gibsonia, PA (US); Christophe Rene Gaston Grenier, Pittsburgh, PA (US); Christopher R. Knittel, Pittsburgh, PA (US); Victor Miranda, Bethel Park, PA (US); Amanda Gavin, Pittsburgh, PA (US)

(73) Assignee: SOLVAY USA, INC., Cranbury, NJ (US)

( * ) Notice: Subject to any disclaimer, the term of this patent is extended or adjusted under 35 U.S.C. 154(b) by 0 days.

(21) Appl. No.: 13/894,412

(22) Filed: May 14, 2013

(65) Prior Publication Data

US 2013/0324716 A1    Dec. 5, 2013

Related U.S. Application Data

(60) Provisional application No. 61/647,428, filed on May 15, 2012.

(51) Int. Cl.

| | | |
|---|---|---|
| *C07C 211/54* | (2006.01) | |
| *H01L 51/54* | (2006.01) | |
| *H01L 51/00* | (2006.01) | |
| *C07D 495/14* | (2006.01) | |
| *C07D 409/04* | (2006.01) | |
| *C07D 409/14* | (2006.01) | |
| *C07D 495/04* | (2006.01) | |
| *C07D 407/12* | (2006.01) | |
| *H01L 51/50* | (2006.01) | |

(52) U.S. Cl.
CPC ............ *H01L 51/006* (2013.01); *C07D 407/12* (2013.01); *C07D 409/04* (2013.01); *C07D 409/14* (2013.01); *C07D 495/04* (2013.01); *C07D 495/14* (2013.01); *H01L 51/0061* (2013.01); *H01L 51/0069* (2013.01); *H01L 51/0071* (2013.01); *H01L 51/0074* (2013.01); *H01L 51/0094* (2013.01); *H01L 51/5056* (2013.01)

(58) Field of Classification Search
USPC ........... 548/521; 549/448; 564/426; 428/690, 428/917
See application file for complete search history.

(56) References Cited

U.S. PATENT DOCUMENTS

| | | | |
|---|---|---|---|
| 5,034,296 A | 7/1991 | Ong et al. | |
| 5,055,366 A | 10/1991 | Yu et al. | |
| 5,149,609 A | 9/1992 | Yu et al. | |
| 5,589,320 A | 12/1996 | Ohnishi et al. | |
| 5,759,709 A | 6/1998 | Doi et al. | |
| 5,895,692 A | 4/1999 | Shirasaki et al. | |
| 7,125,633 B2 | 10/2006 | Mishra et al. | |
| 8,535,974 B2 * | 9/2013 | Brown et al. | ................... 438/99 |
| 2003/0008174 A1 | 1/2003 | Suzuki et al. | |
| 2004/0106004 A1 | 6/2004 | Li | |
| 2005/0184287 A1 | 8/2005 | Herron et al. | |
| 2006/0032528 A1 | 2/2006 | Wang | |
| 2006/0063037 A1 | 3/2006 | Kim et al. | |
| 2006/0078761 A1 | 4/2006 | Williams et al. | |
| 2008/0248313 A1 | 10/2008 | Seshadri et al. | |
| 2008/0286566 A1 | 11/2008 | Prakash | |
| 2009/0159877 A1 | 6/2009 | Meng | |
| 2009/0230361 A1 | 9/2009 | Seshadri et al. | |
| 2009/0256117 A1 | 10/2009 | Seshadri et al. | |
| 2010/0072462 A1 | 3/2010 | Brown et al. | |
| 2010/0108954 A1 | 5/2010 | Benson-Smith et al. | |
| 2010/0109000 A1 | 5/2010 | Mathai et al. | |
| 2010/0187500 A1 | 7/2010 | Prakash | |
| 2010/0187510 A1 | 7/2010 | Rostovtsev | |
| 2010/0207109 A1 | 8/2010 | Hsu et al. | |
| 2010/0213446 A1 | 8/2010 | Zhang et al. | |
| 2010/0244665 A1 | 9/2010 | Herron et al. | |
| 2010/0273007 A1 | 10/2010 | Sheina | |
| 2010/0292399 A1 | 11/2010 | Brown et al. | |
| 2011/0017988 A1 | 1/2011 | Yasukawa et al. | |
| 2011/0147725 A1 | 6/2011 | Seshadri | |
| 2012/0001127 A1 | 1/2012 | Brown et al. | |
| 2012/0003790 A1 | 1/2012 | Brown et al. | |
| 2013/0009137 A1 | 1/2013 | Brown et al. | |

FOREIGN PATENT DOCUMENTS

| | | |
|---|---|---|
| CN | 101 899 223 A | 12/2010 |
| JP | 2003-261473 A | 9/2003 |
| JP | 2006-135146 A | 5/2006 |
| WO | WO 2006/036755 | 4/2006 |

(Continued)

OTHER PUBLICATIONS

Yuan et al. J. Org. Chem. 2007, 72, 7915-7922.*
Yuan et al. J. Org. Chem. 2006, 71, 7858-7861.*
International Search Report and Written Opinion received in connection with International Application No. PCT/US2013/041033; mailed Nov. 25, 2013.
Ash, M, *Handbook of Solvents*, 2$^{nd}$ Ed. (Syapse Information Resources, 2003).
Baryshnikov et al, "Structures and Spectral Properties of Truxene Dye 5", Optics and Spectroscopy, Nauka/interperiodica, MO., vol. 112, No. 2, pp. 168-174 (2012).
Cheremisnoff, N.P., *Industrial Solvents Handbook*, 2$^{nd}$ Ed. (Marcel Dekker, New York, 2003).
Forrest, "The Path to Ubiquitous and Low-Cost Organic Electronic Appliances on Plastic," Nature, 428, Apr. 29, 2004, 911-918.

(Continued)

*Primary Examiner* — Nyeemah A Grazier
(74) *Attorney, Agent, or Firm* — The Marbury Law Group, PLLC

(57) ABSTRACT

The composition described here comprises at least one hole-transporting compound, wherein the hole-transporting compound comprises a core covalently bonded to at least two arylamine groups, wherein the arylamine group optionally comprises one or more intractability groups. The composition can provide good film formation and stability when coated onto hole injection layers. Solution processing of hole transporting layers of OLEDs can be achieved with the composition described here. Good mobility can be achieved.

20 Claims, 3 Drawing Sheets

(56) References Cited

FOREIGN PATENT DOCUMENTS

| WO | WO 2006/086480 | 8/2006 |
|---|---|---|
| WO | WO/2007/076146 | 7/2007 |
| WO | WO 2007/079103 | 7/2007 |
| WO | WO 2007/120143 | 10/2007 |
| WO | WO 2007/145979 | 12/2007 |
| WO | WO 2008/024378 | 2/2008 |
| WO | WO 2008/024379 | 2/2008 |
| WO | WO 2008/024380 | 2/2008 |
| WO | WO 2008/073149 | 6/2008 |
| WO | WO 2008/106210 | 9/2008 |
| WO | WO 2008/150872 | 12/2008 |
| WO | WO 2008/150943 | 12/2008 |
| WO | WO 2009/018009 | 2/2009 |
| WO | WO 2009/052085 | 4/2009 |
| WO | WO 2009/055532 | 4/2009 |
| WO | WO 2009/067419 | 5/2009 |
| WO | WO 2009/097377 | 8/2009 |
| WO | WO 2009/111339 | 9/2009 |
| WO | WO 2009/111675 | 9/2009 |
| WO | WO 2009/126918 | 10/2009 |
| WO | WO 2009/140570 | 11/2009 |
| WO | WO 2010/051259 | 5/2010 |
| WO | WO 2010/059240 | 5/2010 |
| WO | WO 2010/059646 | 5/2010 |
| WO | WO 2010/062558 | 6/2010 |
| WO | WO 2010/093592 | 8/2010 |
| WO | WO 2012/003482 | 1/2012 |

OTHER PUBLICATIONS

Friend et al., "Electroluminescence in Conjugated Polymers," *Nature*, 397, 121-128, Jan. 14, 1999.
Hansen, C.M., Durkee, J. and Kontogeorgis, G, *Hanson Solubility Parameters: A User's Handbook* (Taylor and Francis, 2007).
Shen et al., "How to Make Ohmic Contact to Organic Semiconductors," *ChemPhysChem*, 2004, 5, 16-25.
Shirota et al., "Charge Carrier Transporting Molecular Materials and their Applications in Devices," *Chem. Rev.*, 2007, 107, 953-1010.
Tang et al. "Organic electroluminescent diodes", Appl. Phys. Lett., vol. 51, pp. 913-915 (1987).
Wypych, G., *Handbook of Solvents (Chemical)* (Noyes Publications, 2000).
*Highly Efficient OLEDS with Phosphorescent Materials* (Ed. H. Yerrin), 2008, Wiley-VCH.
*Organic Light Emitting Devices: Synthesis, Properties, and Applications* (Eds. Mullen. Scherf), 2006.
*Organic Light Emitting Methods and Devices*, (Li and Meng), 2007, CRC.

* cited by examiner

HOLE TRANSPORT MATERIALS INCLUDING OLED APPLICATIONS

RELATED APPLICATIONS

This application claims priority to U.S. provisional application 61/647,428 filed May 15, 2012 and is hereby incorporated herein by reference.

BACKGROUND

A need exists to provide better organic electronic devices such as organic light emitting devices (OLEDs) including better materials used in the devices. In particular, better OLED devices and materials, including hole transporting materials, are needed. An OLED operation is based on injection, transport and recombination of two types of charge carriers: holes and electrons. It is important in an OLED device to control the injection and transport of these two types of carriers so as to enable the recombination to occur in the emissive layer where the luminescent species are located. The location where these species meet and recombine can dictate the efficiency and lifetime of the device.

In particular, a need exists for novel hole transporting materials with great properties such as solubility, thermal stability, and electronic energy levels such as HOMO and LUMO, so that the materials can be adapted for different applications and to function with different materials such as light emitting layers, photoactive layers, and electrodes. In particular, good solubility and intractability properties are important. The ability to formulate the system for a particular application and provide the required balance of properties are also important.

Additional background material can be found in, for example, (a) Charge carrier transporting molecular materials and their applications in devices, Shirota, et al., *Chem. Rev.*, 2007, 107, 953-1010, (b) Organic electroluminescent diodes, Tang, et al., *Appl. Phys. Lett.* 1987, 51, 913-915. Hole transport is important for a variety of electronics applications.

SUMMARY

Provided herein are compositions comprising one or more novel hole transporting compounds, said hole transporting compound comprises a hole transporting core covalently bonded to one or more arylamine (AA) groups, each AA group is optionally substituted with one or more intractability groups. In the structures shown below, additional AA groups can be included as appropriate.

In a first embodiment, the hole transporting compound is represented by

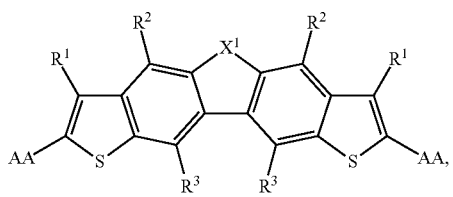

wherein $X^1$ is S, O, NR, $CR_2$, $SiR_2$ or $GeR_2$, wherein each R is an optionally substituted alkyl, aryl, heteroalkyl, heteroaryl, or intractability group, and wherein each of $R^1$, $R^2$ and $R^3$ is H, F, or an optionally substituted alkyl, aryl, heteroalkyl, heteroaryl, or intractability group.

In alternative, related first embodiment, the hole transporting compound is represented by:

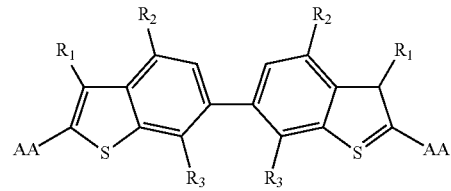

In a second embodiment, the hole transporting compound is represented by

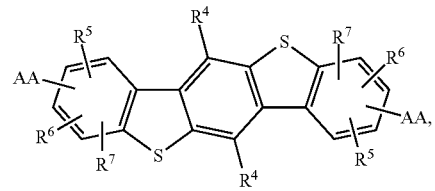

wherein each of $R^4$, $R^5$, $R^6$ and $R^7$ is H, F, or an optionally substituted alkyl, aryl, heteroalkyl, heteroaryl, or intractability group.

In a third embodiment, the hole transporting compound is represented by

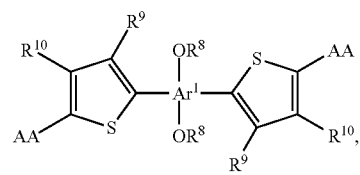

wherein $Ar^1$ comprises an optionally substituted aryl or heteroaryl group, wherein each of $R^8$, $R^9$ and $R^{10}$ is H, F, or an optionally substituted alkyl, aryl, heteroalkyl, heteroaryl, or intractability group. A related third embodiment is:

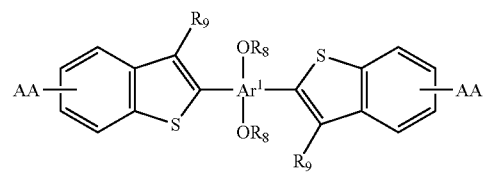

In a fourth embodiment, the hole transporting compound is represented by

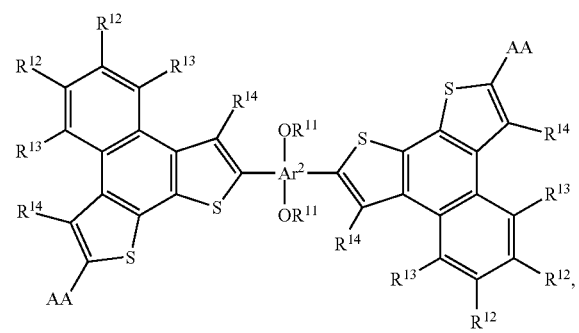

wherein Ar² comprises an optionally substituted aryl or heteroaryl group, wherein each of R¹¹, R¹², R¹³ and R¹⁴ is H, F, or an optionally substituted alkyl, aryl, heteroalkyl, heteroaryl, or intractability group.

In a fifth embodiment, the hole transporting compound is represented by AA-Ar³—Ar³-AA, wherein each Ar³ comprises an optionally substituted aryl or heteroaryl group comprising two five-membered rings and one six membered ring fused together, wherein each ring optionally has one or more members replaced with S, O, NR, CR₂, SiR₂ and GeR₂, and wherein each R is an optionally substituted alkyl, aryl, heteroalkyl, heteroaryl, or intractability group.

In a sixth embodiment, the hole transporting compound is represented by AA-Ar⁴-AA, wherein Ar⁴ comprises an optionally substituted aryl or heteroaryl group comprising six rings fused together, wherein each ring optionally has one or more members replaced with S, O, NR, CR₂, SiR₂ and GeR₂, and wherein each R is an optionally substituted alkyl, aryl, heteroalkyl, heteroaryl, or intractability group.

In a seventh embodiment, the hole transporting compound is represented by

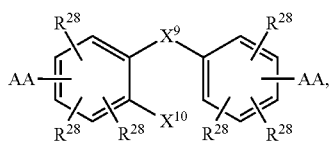

wherein each of X⁹ and X¹⁰ is S, O, NR, CR₂, SiR₂ or GeR₂, wherein each R is an optionally substituted alkyl, aryl, heteroalkyl, heteroaryl, or intractability group, and wherein each of R²⁸ is H, F, or an optionally substituted alkyl, aryl, heteroalkyl, heteroaryl, or intractability group.

In an eighth embodiment, the hole transporting compound is represented by

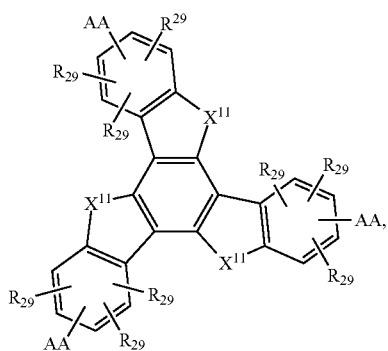

wherein each of X¹¹ is S, O, NR, CR₂, SiR₂ or GeR₂, wherein each R is an optionally substituted alkyl, aryl, heteroalkyl, heteroaryl, or intractability group, and wherein each of R²⁹ is H, F, or an optionally substituted alkyl, aryl, heteroalkyl, heteroaryl, or intractability group. In one embodiment, R²⁹ is H or an intractability group.

In a ninth embodiment, the hole transporting compound is represented by

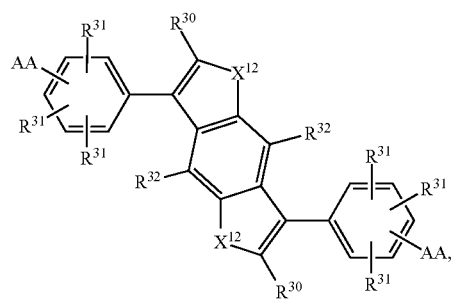

wherein each of X¹² is S, O, NR, CR₂, SiR₂ or GeR₂, wherein each R is an optionally substituted alkyl, aryl, heteroalkyl, heteroaryl, or intractability group, and wherein each of R³⁰, R³¹ and R³² is H, F, or an optionally substituted alkyl, aryl, heteroalkyl, heteroaryl, or intractability group.

In a tenth embodiment, the hole transporting compound is represented by

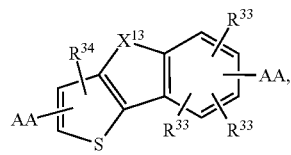

wherein X¹³ is S, O, NR, CR₂, SiR₂ or GeR₂, wherein each R is an optionally substituted alkyl, aryl, heteroalkyl, heteroaryl, or intractability group, and wherein each of R³³ and R³⁴ is H, F, or an optionally substituted alkyl, aryl, heteroalkyl, heteroaryl, or intractability group.

In an eleventh embodiment, the hole transporting compound is represented by

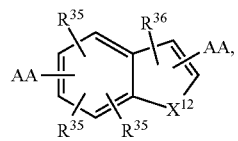

wherein X¹² is S, O, NR, CR₂, SiR₂ or GeR₂, wherein each R is an optionally substituted alkyl, aryl, heteroalkyl, heteroaryl, or intractability group, and wherein each of R³⁵ and R³⁶ is H, F, or an optionally substituted alkyl, aryl, heteroalkyl, heteroaryl, or intractability group.

In a twelfth embodiment, the hole transporting compound is represented by

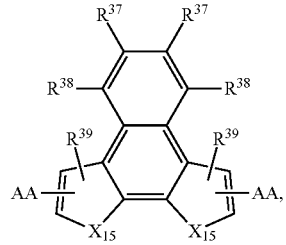

wherein each of X¹⁵ is S, O, NR, CR₂, SiR₂, GeR₂, or C=C, wherein each R is an optionally substituted alkyl, aryl, heteroalkyl, heteroaryl, or intractability group, and wherein each of $R^{37}$, $R^{38}$ and $R^{39}$ is H, F, or an optionally substituted alkyl, aryl, heteroalkyl, heteroaryl, or intractability group.

In a thirteenth embodiment, the hole transporting compound is represented by

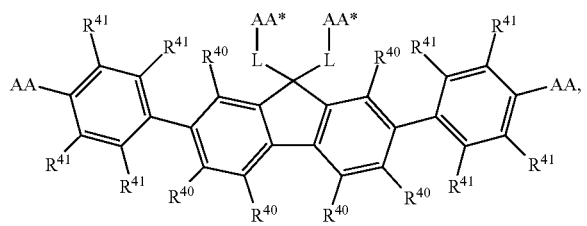

wherein each of $R^{40}$ and $R^{41}$ is H, F, or an optionally substituted alkyl, aryl, heteroalkyl, heteroaryl, or intractability group, wherein AA* is an arylamine group optionally substituted with one or more intractability groups, and wherein L is a linker group.

In a fourteenth embodiment, the hole transporting compound comprises two AA groups covalently bonded to a hole transporting core represented by

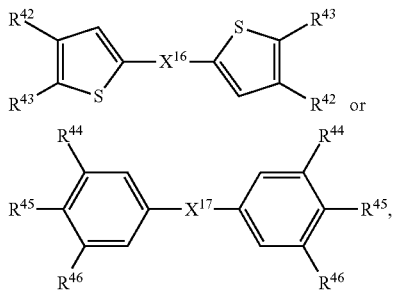

wherein each of $X^{16}$ and $X^{17}$ is S, O, NR, $CR_2$, $SiR_2$ or $GeR_2$, wherein each R is an optionally substituted alkyl, aryl, heteroalkyl, heteroaryl, or intractability group, wherein $R^{42}$ and $R^{43}$ are each independently H, F, or an optionally substituted alkyl, aryl, heteroalkyl, heteroaryl, or intractability group, or together forming a ring, and wherein $R^{44}$, $R^{45}$ and $R^{46}$ are each independently H, F, or an optionally substituted alkyl, aryl, heteroalkyl, heteroaryl, or intractability group, or together forming a ring.

In a fifteenth embodiment, the hole transporting compound is represented by

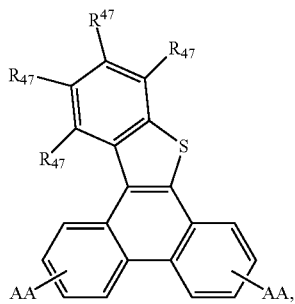

wherein each of $R^{47}$ is H, F, or an optionally substituted alkyl, aryl, heteroalkyl, heteroaryl, or intractability group.

In a sixteenth embodiment, the hole transporting compound is represented by

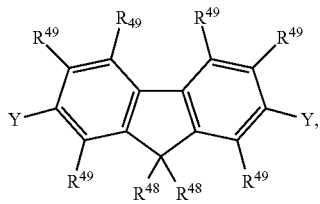

wherein Y is

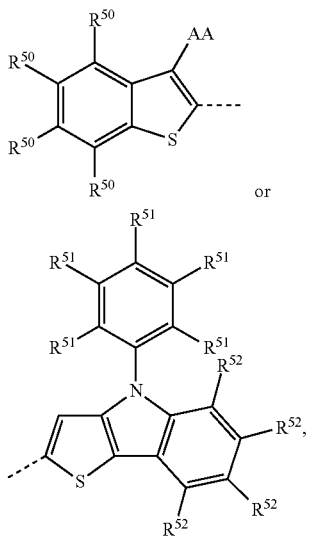

wherein each of $R^{49}$, $R^{50}$, $R^{51}$ and $R^{52}$ is H, F, or an optionally substituted alkyl, aryl, heteroalkyl, heteroaryl, or intractability group, and wherein $R^{48}$ is an optionally substituted alkyl, aryl, heteroalkyl, heteroaryl, or intractability group.

In an additional embodiment, a hole transporting compound is provided represented by:

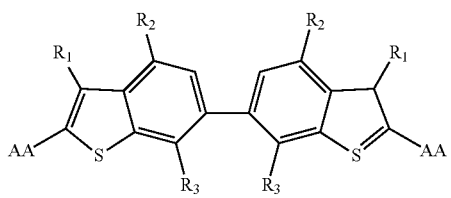

wherein each of $R^1$, $R^2$ and $R^3$ is independently H, F, or an optionally substituted alkyl, aryl, heteroalkyl, heteroaryl, or intractability group, and wherein AA is an arylamine moiety.

Also provided is a device comprising a hole transport layer, wherein the hole transport layer comprises any of the hole transporting compounds described above. In one embodiment, the device is OLED.

Moreover, also provided is a method comprising: (i) providing a substrate comprising a hole injection layer, (ii) coating the substrate with at least one ink composition comprising any of the hole transporting compounds described above to form a coated substrate, and (iii) heating the coated substrate.

Furthermore, also provided is a method for making a composition comprising any of the hole transporting compound described above, comprising reacting arylamine with a hole transporting core.

Also provided is a method comprising at least one catalytic amination reacting step of at least one aryl triflate compound with at least one arylamine compound in the presence of at least one metal and at least two phosphine compound ligands for the metal. The metal can be, for example, palladium. The aryl triflate compound can comprise at least two triflate groups. The arylamine compound can be, for example, at least one primary arylamine compound or at least one secondary arylamine compound. The at least two phosphine compound ligands can comprise, for example, (i) a trialkylphosphine such as t-Bu₃P, and (ii) Xphos, ("2-Dicyclohexylphosphino-2',4',6'-triisopropylbiphenyl").

At least one advantage for at least one embodiment described herein is that good mobility can be achieved which can, for example, lower the device operating voltage.

At least one advantage for at least one embodiment described herein is improved synthesis enabling production of new compounds with better purities under commercially realistic conditions.

DETAILED DESCRIPTION

Introduction

Figure 1:
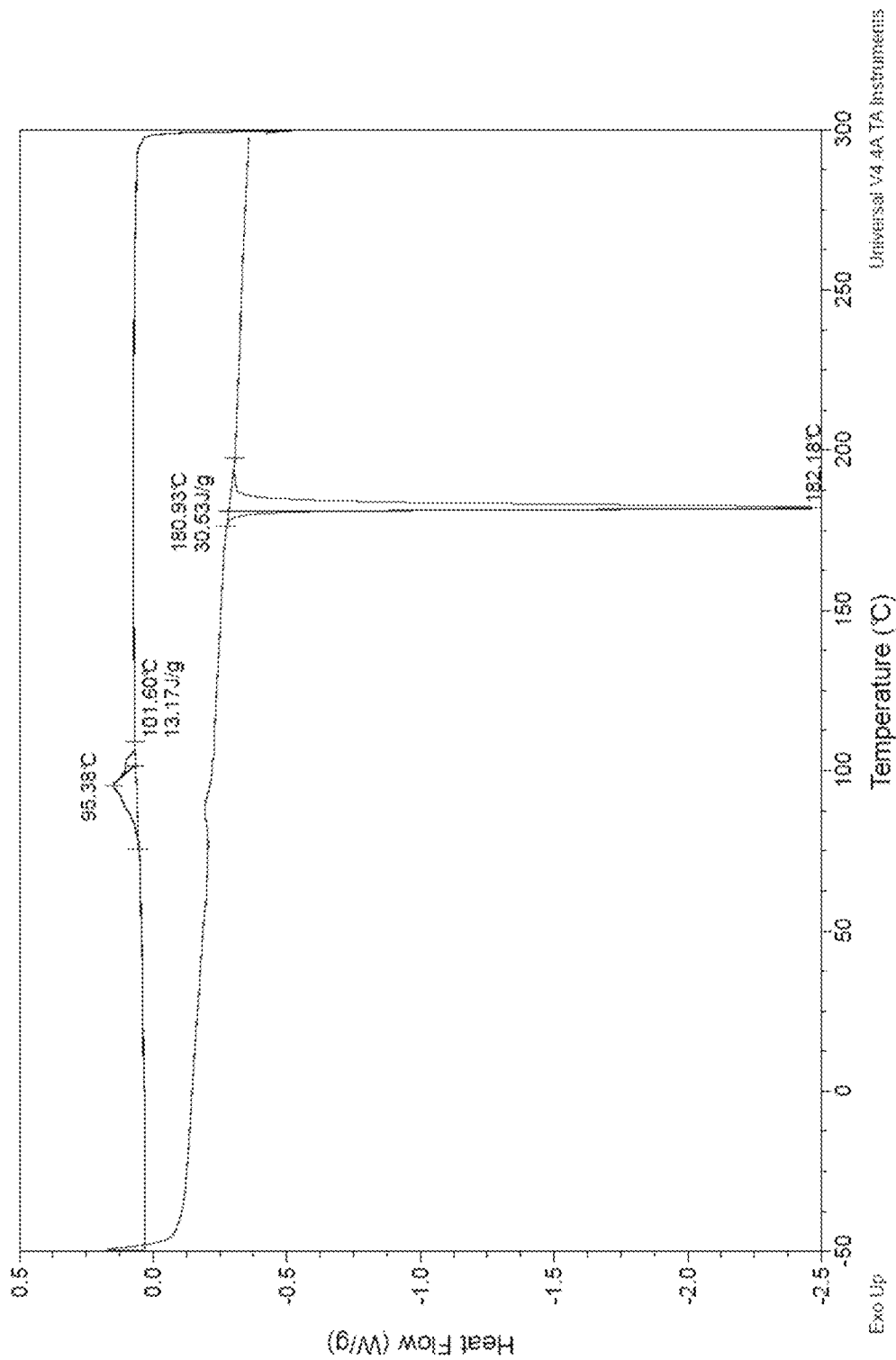
FIG. 1 shows DSC data of an exemplary embodiment of the hole transporting compounds described herein.

All references cited herein are incorporated by reference in their entirety. Priority U.S. provisional application 61/647,428 filed May 15, 2012 is hereby incorporated herein by reference in its entirety for all purposes including, for example, formulas, methods of making, working examples, and claims.

Organic electronics devices, including OLEDs, as well as materials to make organic electronic devices including hole injection layers and hole transport layers, are described in, for example, the following patent publications assigned to Plextronics, Inc.: WO 2006/036,755; WO 2006/086,480; WO 2008/073,149; WO 2009/126,918; WO 2009/111675; WO 2009/111339; WO 2010/051,259; WO 2010/059,240; WO 2010/059,646; WO 2010/062,558 and PCT/US2011/042861. OLED devices can comprise a variety of sub-categories including, for example, PLEDs, SMOLEDs, PHOLEDs, WOLEDs, and the like. OLED devices, materials, and methods are also described in, for example, (1) *Highly Efficient OLEDS with Phosphorescent Materials* (Ed. H. Yerrin), 2008, Wiley-VCH, (2) *Organic Light Emitting Devices: Synthesis, Properties, and Applications* (Eds. Mullen, Scherf), 2006, (3) *Organic Light Emitting Methods and Devices*, (Li and Meng), 2007, CRC.

Electroluminescent devices are described in, for example, Friend et al., "Electroluminescence in Conjugated Polymers," *Nature,* 397, 121-128, Jan. 14, 1999. Hole injection and transport are described in, for example, Shen et al., "How to Make Ohmic Contact to Organic Semiconductors," *Chem Phys Chem,* 2004, 5, 16-25. OLED devices are described in, for example, Forrest, "The Path to Ubiquitous and Low-Cost Organic Electronic Appliances on Plastic," *Nature,* 428, Apr. 29, 2004, 911-918.

Compounds and units within compounds which provide hole transport are known in the art. See, for example, U.S. Pat. Nos. 5,034,296; 5,055,366; 5,149,609; 5,589,320; 5,759,709; 5,895,692; and 7,125,633, as well as US Patent Publication Nos. 2005/0184287 and 2008/0286566. Hole transport materials, morphology, and devices (including arylamine compounds) are also described extensively in "Charge Carrier Transporting Molecular Materials and their Applications in Devices," Shirota et al., *Chem. Rev.,* 2007, 107, 953-1010.

Hole Transporting Compounds with a Variety of Core, Arylamine, and Intractability Groups Hole transport materials and compounds are known in the art. They typically comprise pi-electron systems. A leading example of a hole transport material is the arylamine set of compounds.

One embodiment provides, for example, a composition comprising: at least one compound comprising a hole transporting core; wherein the core is covalently bonded to a first arylamine group and also covalently bonded to a second arylamine group; and wherein the compound optionally comprises at least one intractability group; wherein the at least one intractability group is covalently bonded to the hole transporting core, the first arylamine group, the second arylamine group, or a combination thereof; and wherein the compound has a molecular weight of about 5,000 g/mole or less.

The hole transporting core can be a bivalent, trivalent, or higher valent group which links at least to a first and a second arylamine group. This compound arrangement can be also represented by AA1-C-AA2, wherein AA1 represents a first arylamine group, and AA2 represents a second arylamine group, and C represents the hole transporting core. The one or more intractability groups can be bonded to one or more of C, AA1 and AA2. In addition, the compound can comprise additional arylamine groups either in the hole transporting core or in the groups linked to the arylamine groups outside of the core.

A variety of aryl or heteroaryl groups can be used in the hole transporting core. Examples of aryl and heteroaryl groups, which can be optionally substituted, are known in the art and include benzene, naphthalene, anthracene, phenanthrene, perylene, tetracene, pyrene, benzpyrene, chrysene, triphenylene, acenaphtene, fluorene, and those derived therefrom. Examples of heteroaryls include furan, benzofuran, thiophene, benzothiophene, pyrrole, pyrazole, triazole, imidazole, oxadiazole, oxazole, thiazole, tetrazole, indole, cabazole, pyrroloimidazole, pyrrolopyrazole, pyrrolopyrole, thienopyrrole, thienothiophene, furopyrrole, furofuran, thienofuran, benzoisoxazole, benzoisothiazole, benzoimidazole, pyridine, pyrazine, pyridazine, pyrimidine, triazine, quinoline, isoquinoline, cinnnoline, quinoxaline, phenanthridine, benzoimidazole, perimidine, quinazoline, quinazolinone, azulene, and those derived therefrom. The aryl or heteroaryl groups can comprise fused ring systems.

Aryl and heteroaryl groups can be optionally substituted with a variety of substituents and/or solubilizing groups. Examples can be (independently) H, F, alkyl, aryl, alkoxy, aryloxy, fluoroalkyl, fluoroaryl, fluoroalkoxy, fluoroaryloxy, polyether, as well as intractability groups described herein. The substituent may optionally comprise at least one perfluoroalkyl group. Substituents on neighboring rings can fuse together to form a ring.

In one embodiment, for example, the hole transporting core comprises at least two aryl or heteroaryl rings. In another embodiment, the hole transporting core comprises at least three aryl or heteroaryl rings. In a further embodiment, the hole transporting core comprises at least four aryl or heteroaryl rings. In yet another embodiment, the hole transporting core comprises at least five aryl or heteroaryl rings. In yet a further embodiment, the hole transporting core comprises at least six aryl or heteroaryl rings. In one embodiment, the hole transport core comprises only carbocyclic rings. In one embodiment, the hole transport core comprises at least one spiro moiety. Spiro moieties in a hole transport compounds are described in, for example, US Pat. Pub. No. 2004/0106004 (Li).

The hole transporting core can comprise all carbon and hydrogen atoms. Alternatively, the hole transporting core can comprise heteroatoms such as O, S, N, P, Si, Ge, Se, Te, and the like. In one embodiment, the hole transport core comprises at least one, at least two, at least three, at least four, or at least six heteroatoms. In one embodiment, the hole transporting core comprises both O and S heteroatoms. In another embodiment, the hole transporting core comprises both N and S heteroatoms.

In one embodiment, the hole transport core comprises at least one heteroarylmoiety comprising at least one N. In one embodiment, the hole transport core comprises at least one heteroarylmoiety comprising at least one S. In one embodiment, the hole transport core comprises at least one heteroarylmoiety comprising at least one O.

In one embodiment, the hole transport core comprises at least one silole or germol ring. In one embodiment, the hole transport core comprises at least two silole or germol rings.

The hole transporting core can comprise fused rings. In one embodiment, the hole transport core comprises at least two, or at least three, or at least four, at least five, at least six or at least seven fused rings.

One or more substituent groups can be covalently bonded to the hole transporting core to increase solubility. A common example of such a solubilizing group is an optionally substituted alkyl or heteroalkyl moiety (an alkyl group, if used in a bivalent situation as spacer, can be also called alkylene; for example, propyl can be a propylene spacer). For example, C4 to C30, or C4 to C20, or C4 to C12 solublizing groups can be used. Heteroatoms include, for example, oxygen, nitrogen, and sulfur. One skilled in the art can examine the impact of the substituent group on solubility. In one embodiment, the hole transport core is functionalized with at least one solubilizing group. In one embodiment, the hole transport core is functionalized with at least two solubilizing groups. In one embodiment, the hole transport core is functionalized with at least one solubilizing group which has a least four carbon atoms. In one embodiment, the hole transport core is functionalized with at least one solublizing group which as an alkylene group comprising at least four carbon atoms. In one embodiment, the hole transport core is functionalized with at least one solubilizing group comprising at least one perfluoroalkyl group. Other solubilizing groups are shown in the structures herein.

The hole transporting compounds described herein include, but are not limited to, PLX-1 to PLX-16.

PLX-1 Hole Transporting Compounds

The first group of hole transporting compounds, PLX-1, is represented by formula (I):

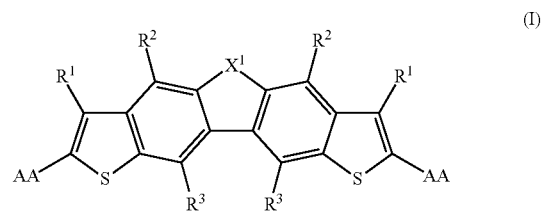

$X^1$ can comprise, for example, a heteroatom. In one embodiment, $X^1$ is S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking group. In a further embodiment, R comprises a crosslinking or polymerizable group, such as vinyl.

Each of $R^1$, $R^2$ and $R^3$ can be, for example, H, F, or an optionally substituted alkyl, aryl, heteroalkyl, heteroaryl, or intractability group. In one embodiment, each of $R^1$, $R^2$ and $R^3$ is hydrogen. In another embodiment, at least one of $R^1$, $R^2$ and $R^3$ comprises a moiety for improving solubility such as an optionally substituted linear or branched alkyl, alkoxy or polyether. In a further embodiment, at least one of $R^1$, $R^2$ and $R^3$ comprises an intractability group which can be a crosslinking or non-crosslinking group. In an additional embodiment, at least one of $R^1$, $R^2$ and $R^3$ comprises a crosslinking or polymerizable group, such as vinyl.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-1, $R^1$, $R^2$ and $R^3$ are each hydrogen, $X^1$ is $SiR_2$, and the hole transporting compound is represented by:

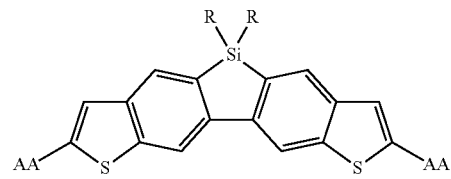

In another embodiment of PLX-1, $R^1$, $R^2$ and $R^3$ are each hydrogen, $X^1$ is NR, and the hole transporting compound is represented by:

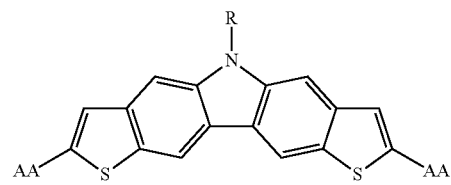

In a further embodiment of PLX-1, $R^1$, $R^2$ and $R^3$ are each hydrogen, $X^1$ is S, and the hole transporting compound is represented by:

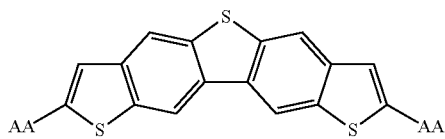

PLX-2 Hole Transporting Compounds

The second group of hole transporting compounds, PLX-2, is represented by formula (II):

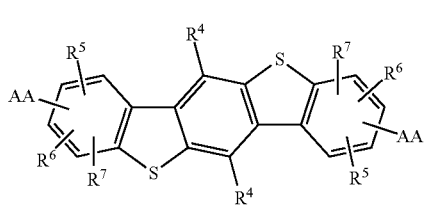

(II)

Each of $R^4$ can be, for example, H, F, or an optionally substituted alkyl, aryl, heteroalkyl, heteroaryl, or intractability group. In one embodiment, at least one of $R^4$ comprises a moiety for improving solubility such as an optionally substituted linear or branched alkyl, alkoxy or polyether. In another embodiment, at least one of $R^4$ comprises an intractability group, which can be a crosslinking or non-crosslinking group. In a further embodiment, at least one of $R^4$ comprises a crosslinking or polymerizable group, such as vinyl.

Each of $R^5$, $R^6$ and $R^7$ can be, for example, H, F, or an optionally substituted alkyl, aryl, heteroalkyl, heteroaryl, or intractability group. In one embodiment, each of $R^5$, $R^6$ and $R^7$ is hydrogen. In another embodiment, at least one of $R^5$, $R^6$ and $R^7$ comprises a moiety for improving solubility such as an optionally substituted linear or branched alkyl, alkoxy or polyether. In a further embodiment, at least one of $R^5$, $R^6$ and $R^7$ comprises an intractability group which can be a crosslinking or non-crosslinking group. In an additional embodiment, at least one of $R^5$, $R^6$ and $R^7$ comprises a crosslinking or polymerizable group, such as vinyl.

In one embodiment, each of $R^5$, $R^6$ and $R^7$ is hydrogen, and $R^4$ is not hydrogen.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-2, each of $R^5$, $R^6$ and $R^7$ is hydrogen, and the hole transporting compound is represented by:

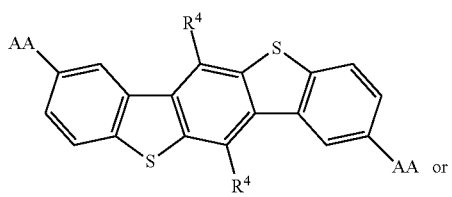

PLX-3 Hole Transporting Compounds

The third group of hole transporting compounds, PLX-3, is represented by formula (III):

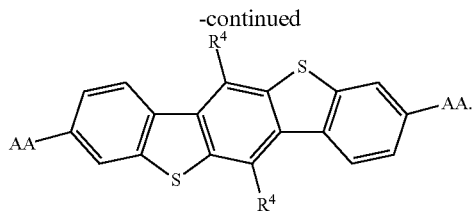

(III)

$Ar^1$ can be, for example, an optionally substituted aryl or heteroaryl group. In one embodiment, $Ar^1$ is an optionally substituted phenyl group. In another embodiment, $Ar^1$ is an optionally substituted biphenyl group. In a further embodiment, $Ar^1$ is an optionally substituted naphthyl group Each of $R^8$ can be, for example, hydrogen or an optionally substituted alkyl, aryl, heteroalkyl, heteroaryl, or intractability group. In one embodiment, at least one of $R^8$ comprises a moiety for improving solubility such as an optionally substituted linear or branched alkyl, alkoxy or polyether. In another embodiment, at least one of $R^8$ comprises an intractability group, which can be a crosslinking or non-crosslinking group. In a further embodiment, at least one of $R^8$ comprises a crosslinking or polymerizable group, such as vinyl.

Each of $R^9$ and $R^{10}$ can be, for example, H, F, or an optionally substituted alkyl, aryl, heteroalkyl, heteroaryl, or intractability group. In one embodiment, each of $R^9$ and $R^{10}$ is hydrogen. In another embodiment, at least one of $R^9$ and $R^{10}$ comprises a moiety for improving solubility such as an optionally substituted linear or branched alkyl, alkoxy or polyether. In a further embodiment, at least one of $R^9$ and $R^{10}$ comprises an intractability group which can be a crosslinking or non-crosslinking group. In an additional embodiment, at least one of $R^9$ and $R^{10}$ comprises a crosslinking or polymerizable group, such as vinyl.

In one embodiment, each of $R^9$ and $R^{10}$ is hydrogen, and $R^8$ is not hydrogen.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-3, each of $R^9$ and $R^{10}$ is hydrogen, and the hole transporting compound is represented by:

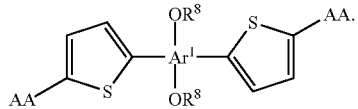

In another embodiment of PLX-3, each of $R^9$ and $R^{10}$ is hydrogen, $Ar^1$ is phenyl, and the hole transporting compound is represented by:

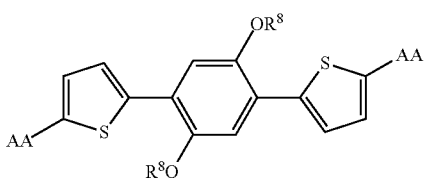

In a further embodiment of PLX-3, each of $R^9$ and $R^{10}$ is hydrogen, $Ar^1$ is naphthyl, and the hole transporting compound is represented by:

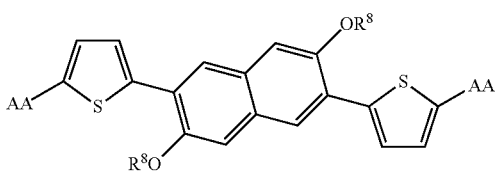

PLX-4 Hole Transporting Compounds

The fourth group of hole transporting compounds, PLX-4, is represented by formula (IV):

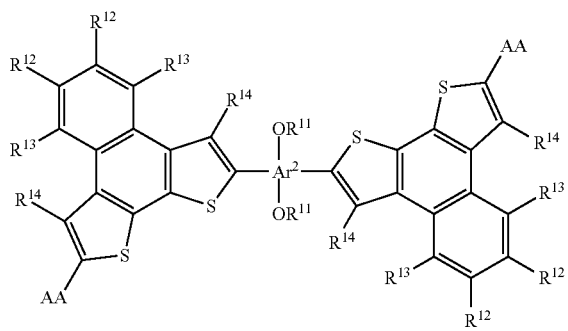

(IV)

$Ar^2$ can be, for example, an optionally substituted aryl or heteroaryl group. In one embodiment, $Ar^2$ is an optionally substituted phenyl group. In another embodiment, $Ar^2$ is an optionally substituted biphenyl group. In a further embodiment, $Ar^2$ is an optionally substituted naphthyl group Each of $R^{11}$ can be, for example, hydrogen or an optionally substituted alkyl, aryl, heteroalkyl, heteroaryl, or intractability group. In one embodiment, at least one of $R^{11}$ comprises a moiety for improving solubility such as an optionally substituted linear or branched alkyl, alkoxy or polyether. In another embodiment, at least one of $R^{11}$ comprises an intractability group, which can be a crosslinking or non-crosslinking group. In a further embodiment, at least one of $R^{11}$ comprises a crosslinking or polymerizable group, such as vinyl.

Each of $R^{12}$, $R^{13}$ and $R^{14}$ can be, for example, H, F, or an optionally substituted alkyl, aryl, heteroalkyl, heteroaryl, or intractability group. In one embodiment, each of $R^{13}$ and $R^{14}$ is hydrogen. In another embodiment, at least one of $R^{12}$, $R^{13}$ and $R^{14}$ comprises a moiety for improving solubility such as an optionally substituted linear or branched alkyl, alkoxy or polyether. In a further embodiment, at least one of $R^{12}$, $R^{13}$ and $R^{14}$ comprises an intractability group which can be a crosslinking or non-crosslinking group. In an additional embodiment, at least one of $R^{12}$, $R^{13}$ and $R^{14}$ comprises a crosslinking or polymerizable group, such as vinyl.

In one embodiment, each of $R^{13}$ and $R^{14}$ is hydrogen, and $R^{11}$ and $R^{12}$ are not hydrogen. In another embodiment, each of $R^{12}$, $R^{13}$ and $R^{14}$ is hydrogen, and $R^{11}$ is not hydrogen.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-4, each of $R^{13}$ and $R^{14}$ is hydrogen, and the hole transporting compound is represented by:

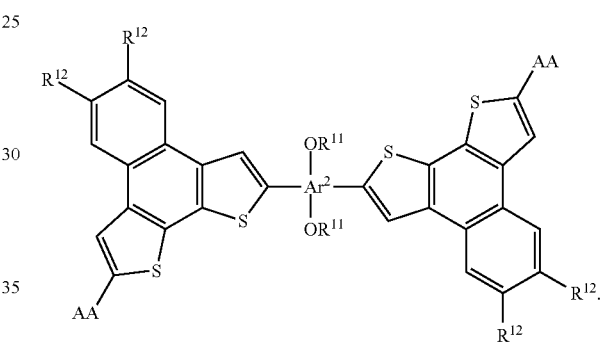

In another embodiment of PLX-4, each of $R^{13}$ and $R^{14}$ is hydrogen, $Ar^2$ is naphthyl and the hole transporting compound is represented by:

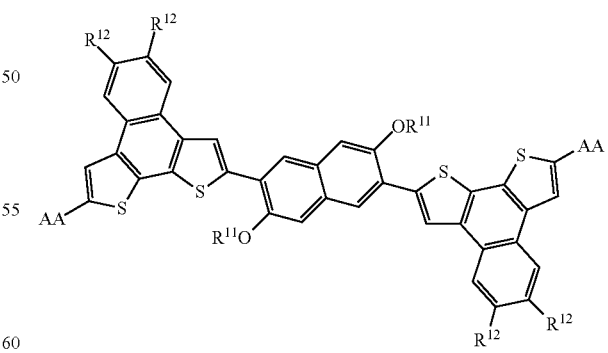

In another embodiment of PLX-4, each of $R^{13}$ and $R^{14}$ is hydrogen, $Ar^2$ is biphenyl, and the hole transporting compound is represented by:

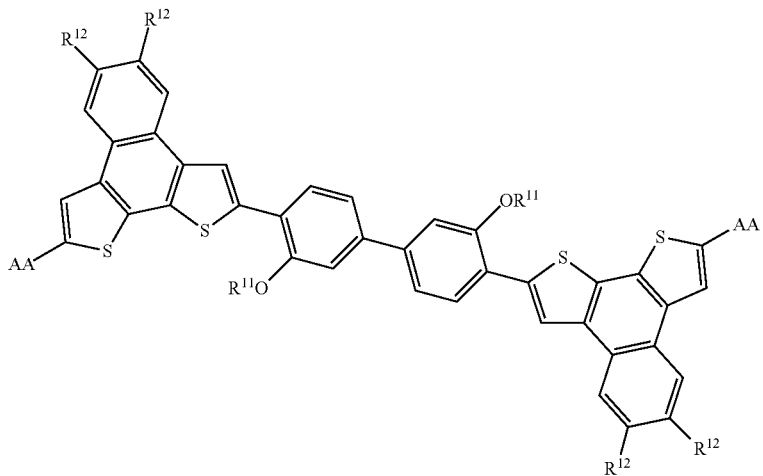

PLX-5 Hole Transporting Compounds

The fourth group of hole transporting compounds, PLX-5, is represented by formula (V):

$$AA\text{-}Ar^3\text{—}Ar^3\text{-}AA \qquad (V)$$

$Ar^3$ can be, for example, an optionally substituted aryl or heteroaryl group comprising three rings fused together, which comprises two five-membered rings and one six membered ring. Each ring can be, for example, optionally substituted with an alkyl, aryl, heteroalkyl, heteroaryl, or intractability group.

Further, each ring can comprise, for example, one or more ring members optionally replaced with S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group, which can be a crosslinking or non-crosslinking group. In a further embodiment, R comprises a crosslinking or polymerizable group, such as vinyl.

In one embodiment, each $Ar^3$ comprises at least one five-membered ring that comprises one S in the ring. In another embodiment, each $Ar^3$ comprises at least one five-membered ring that comprises one O in the ring. In a further embodiment, each $Ar^3$ at least one five-membered ring that comprises one S in the ring and at least one five-membered ring that comprises one O in the ring.

Each AA is an arylamine group optionally substituted with one or more intractability groups, such as vinyl. Alternatively, one AA is an arylamine group optionally substituted with one or more intractability groups, and the other AA is hydrogen.

In a first subgenus, PLX-5 is represented by formula (VI):

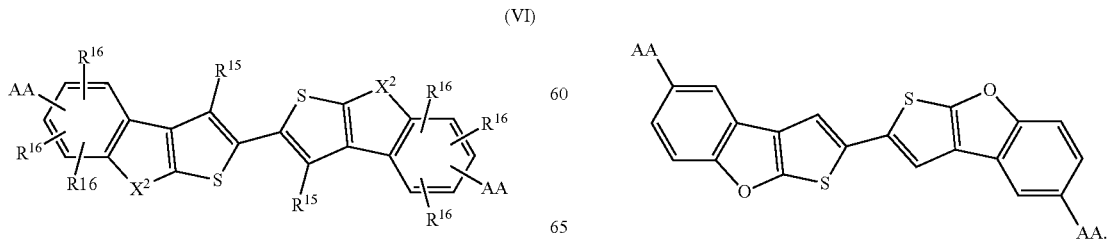

$X^2$ can be, for example, S, O, NR, $CR_2$, $SiR_2$ or $GeR_2$. R is described above. In one embodiment, $X^2$ is O.

Each of $R^{15}$ and $R^{16}$ can be, for example, H, F, or an optionally substituted alkyl, aryl, heteroalkyl, heteroaryl, or intractability group. In one embodiment, each of $R^{15}$ and $R^{16}$ is hydrogen. In another embodiment, at least one of $R^{15}$ and $R^{16}$ comprises a moiety for improving solubility such as an optionally substituted linear or branched alkyl, alkoxy or polyether. In a further embodiment, at least one of $R^{15}$ and $R^{16}$ comprises an intractability group which can be a crosslinking or non-crosslinking group. In an additional embodiment, at least one of $R^{15}$ and $R^{16}$ comprises a crosslinking or polymerizable group, such as vinyl.

In one embodiment, each of $R^{15}$ and $R^{16}$ is hydrogen, and the hole transporting compound is represented by:

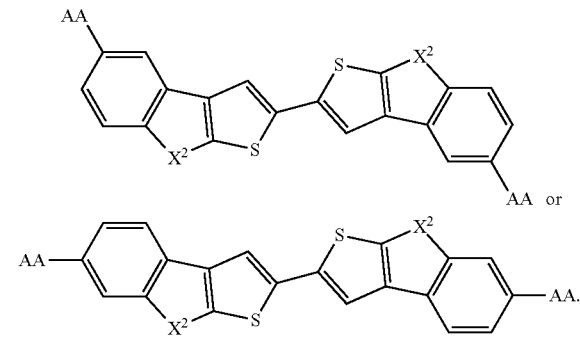

In another embodiment, each of $R^{15}$ and $R^{16}$ is hydrogen, $X^2$ is O, and the hole transporting compound is represented by:

In a second subgenus, PLX-5 is represented by formula (VII):

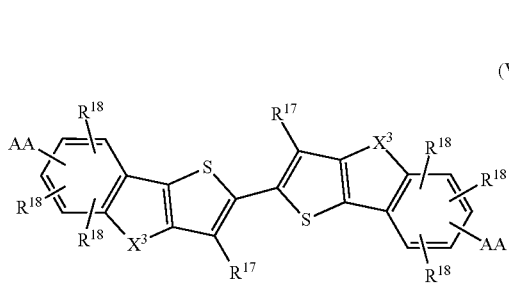

(VII)

$X^3$ can be, for example, S, O, NR, $CR_2$, $SiR_2$ or $GeR_2$. R is described above. In one embodiment, $X^3$ is O. In another embodiment, $X^3$ is $CR_2$.

Each of $R^{17}$ and $R^{18}$ can be, for example, H, F, or an optionally substituted alkyl, aryl, heteroalkyl, heteroaryl, or intractability group. In one embodiment, each of $R^{17}$ and $R^{18}$ is hydrogen. In another embodiment, at least one of $R^{17}$ and $R^{18}$ comprises a moiety for improving solubility such as an optionally substituted linear or branched alkyl, alkoxy or polyether. In a further embodiment, at least one of $R^{17}$ and $R^{18}$ comprises an intractability group which can be a crosslinking or non-crosslinking group. In an additional embodiment, at least one of $R^{17}$ and $R^{18}$ comprises a crosslinking or polymerizable group, such as vinyl.

In one embodiment, each of $R^{17}$ and $R^{18}$ is hydrogen, and the hole transporting compound is represented by:

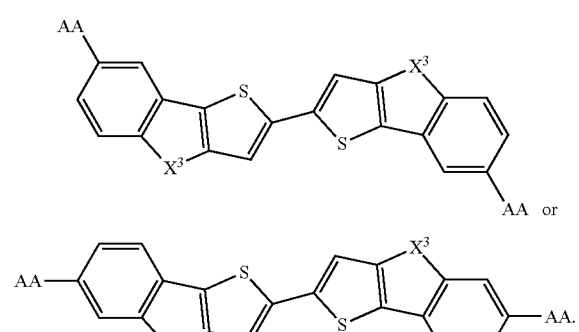

In another embodiment, each of $R^{17}$ and $R^{18}$ is hydrogen, $X^3$ is O, and the hole transporting compound is represented by:

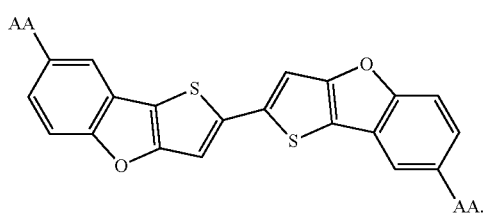

In a further embodiment, each of $R^{17}$ and $R^{18}$ is hydrogen, $X^3$ is $CR_2$, and the hole transporting compound is represented by:

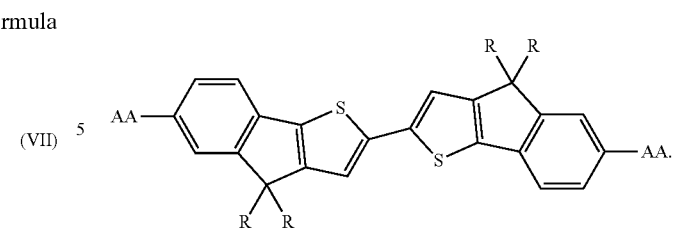

In a third subgenus, PLX-5 is represented by formula (VIII):

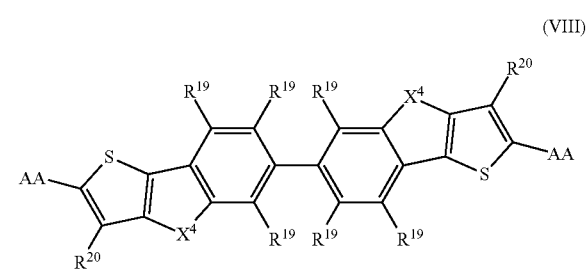

(VIII)

$X^4$ can be, for example, S, O, NR, $CR_2$, $SiR_2$ or $GeR_2$. R is described above. In one embodiment, $X^4$ is O. In another embodiment, $X^4$ is $CR_2$.

Each of $R^{19}$ and $R^{20}$ can be, for example, H, F, or an optionally substituted alkyl, aryl, heteroalkyl, heteroaryl, or intractability group. In one embodiment, each of $R^{19}$ and $R^{20}$ is hydrogen. In another embodiment, at least one of $R^{19}$ and $R^{20}$ comprises a moiety for improving solubility such as an optionally substituted linear or branched alkyl, alkoxy or polyether. In a further embodiment, at least one of $R^{19}$ and $R^{20}$ comprises an intractability group which can be a crosslinking or non-crosslinking group. In an additional embodiment, at least one of $R^{19}$ and $R^{20}$ comprises a crosslinking or polymerizable group, such as vinyl.

In one embodiment, each of $R^{19}$ and $R^{20}$ is hydrogen, and the hole transporting compound is represented by:

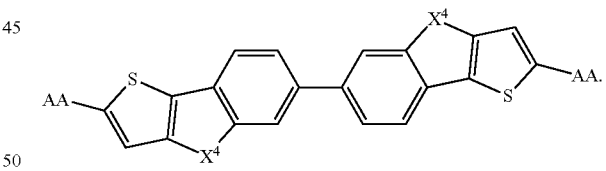

In another embodiment, each of $R^{19}$ and $R^{20}$ is hydrogen, $X^4$ is $CR_2$, and the hole transporting compound is represented by:

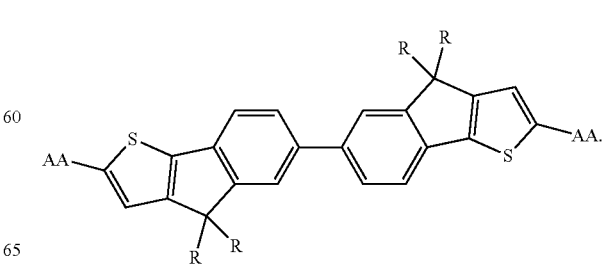

PLX-6 Hole Transporting Compounds

The fifth group of hole transporting compounds, PLX-5, is represented by formula (IX):

$$AA-Ar^4-AA \qquad (IX)$$

$Ar^4$ can be, for example, an optionally substituted aryl or heteroaryl group comprising six rings fused together. Each ring can be, for example, a five-membered ring or a six-membered ring. Each ring can be, for example, optionally substituted with an alkyl, aryl, heteroalkyl, heteroaryl, or intractability group. In one embodiment, $Ar^4$ comprises four six-membered rings and two five membered rings fused together. In another embodiment, $Ar^4$ comprises two six-membered rings and four five membered rings fused together. In a further embodiment, $Ar^4$ comprises six five-membered rings fused together, or six six-membered rings fused together.

In one embodiment, $Ar^4$ comprises six rings fused together in a linear fashion.

Further, each ring can comprise, for example, one or more ring members optionally replaced with S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group, which can be a crosslinking or non-crosslinking group. In a further embodiment, R comprises a crosslinking or polymerizable group, such as vinyl.

Each AA is an arylamine group optionally substituted with one or more intractability groups, such as vinyl. Alternatively, one AA is an arylamine group optionally substituted with one or more intractability groups, and the other AA is hydrogen.

In a first subgenus, PLX-6 is represented by formula (X):

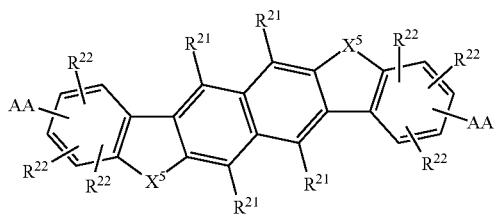

(X)

$X^5$ can be, for example, S, O, NR, $CR_7$, $SiR_2$ or $GeR_2$. R is described above. In one embodiment, $X^5$ is $SiR_2$ or $GeR_2$. In another embodiment, $X^5$ is O or NR.

Each of $R^{21}$ and $R^{22}$ can be, for example, H, F, or an optionally substituted alkyl, aryl, heteroalkyl, heteroaryl, or intractability group. In one embodiment, each of $R^{21}$ and $R^{22}$ is hydrogen. In another embodiment, at least one of $R^{21}$ and $R^{22}$ comprises a moiety for improving solubility such as an optionally substituted linear or branched alkyl, alkoxy or polyether. In a further embodiment, at least one of $R^{21}$ and $R^{22}$ comprises an intractability group which can be a crosslinking or non-crosslinking group. In an additional embodiment, at least one of $R^{21}$ and $R^{22}$ comprises a crosslinking or polymerizable group, such as vinyl.

In one embodiment, each of $R^{21}$ and $R^{22}$ is hydrogen, and the hole transporting compound is represented by:

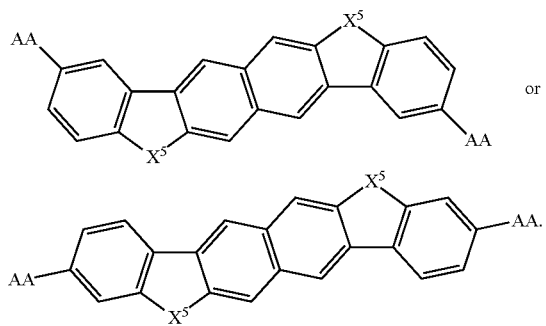

In another embodiment, each of $R^{21}$ and $R^{22}$ is hydrogen, $X^5$ is $SiR_2$, and the hole transporting compound is represented by:

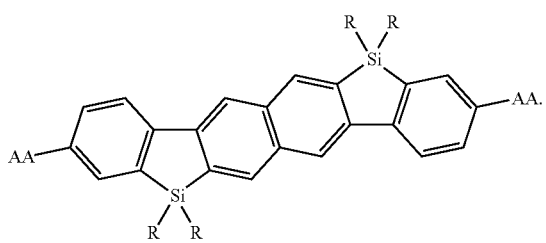

In a further embodiment, each of $R^{21}$ and $R^{22}$ is hydrogen, $X^5$ is $GeR_2$, and the hole transporting compound is represented by:

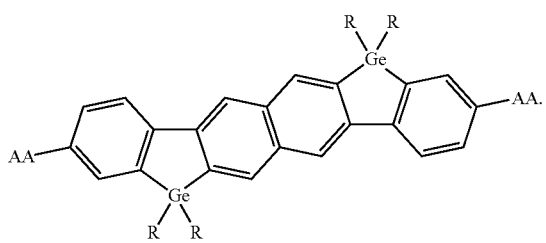

In a second subgenus, PLX-6 is represented by formula (XI):

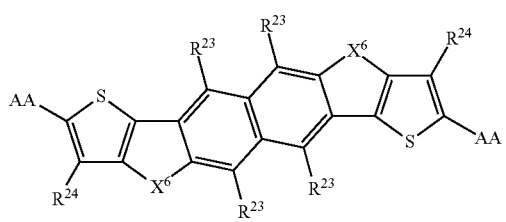

(XI)

$X^6$ can be, for example, S, O, NR, $CR_2$, $SiR_2$ or $GeR_2$. R is described above. In one embodiment, $X^6$ is $SiR_2$ or $GeR_2$. In another embodiment, $X^6$ is O or NR.

Each of $R^{23}$ and $R^{24}$ can be, for example, H, F, or an optionally substituted alkyl, aryl, heteroalkyl, heteroaryl, or intractability group. In one embodiment, each of $R^{23}$ and $R^{24}$ is hydrogen. In another embodiment, at least one of $R^{23}$ and $R^{24}$ comprises a moiety for improving solubility such as an optionally substituted linear or branched alkyl, alkoxy or polyether. In a further embodiment, at least one of $R^{23}$ and $R^{24}$ comprises an intractability group which can be a crosslinking or non-crosslinking group. In an additional embodiment, at least one of $R^{23}$ and $R^{24}$ comprises a crosslinking or polymerizable group, such as vinyl.

In one embodiment, each of $R^{23}$ and $R^{24}$ is hydrogen, and the hole transporting compound is represented by:

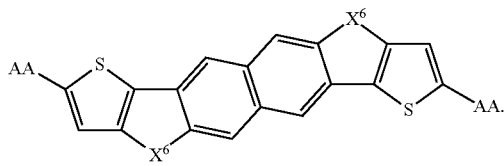

In another embodiment, each of $R^{23}$ and $R^{24}$ is hydrogen, $X^6$ is $SiR_2$, and the hole transporting compound is represented by:

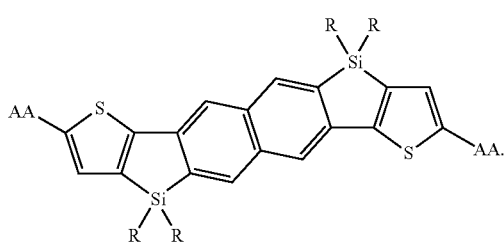

In a third subgenus, PLX-6 is represented by formula (XII):

(XII)

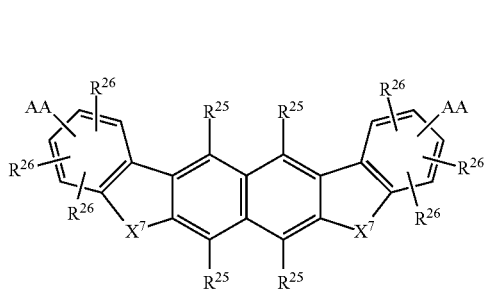

$X^7$ can be, for example, S, O, NR, $CR_2$, $SiR_2$ or $GeR_2$. R is described above. In one embodiment, $X^7$ is $SiR_2$ or $GeR_2$. In another embodiment, $X^7$ is O or NR.

Each of $R^{25}$ and $R^{26}$ can be, for example, H, F, or an optionally substituted alkyl, aryl, heteroalkyl, heteroaryl, or intractability group. In one embodiment, each of $R^{25}$ and $R^{26}$ is hydrogen. In another embodiment, at least one of $R^{25}$ and $R^{26}$ comprises a moiety for improving solubility such as an optionally substituted linear or branched alkyl, alkoxy or polyether. In a further embodiment, at least one of $R^{25}$ and $R^{26}$ comprises an intractability group which can be a crosslinking or non-crosslinking group. In an additional embodiment, at least one of $R^{25}$ and $R^{26}$ comprises a crosslinking or polymerizable group, such as vinyl.

In one embodiment, each of $R^{25}$ and $R^{26}$ is hydrogen, and the hole transporting compound is represented by:

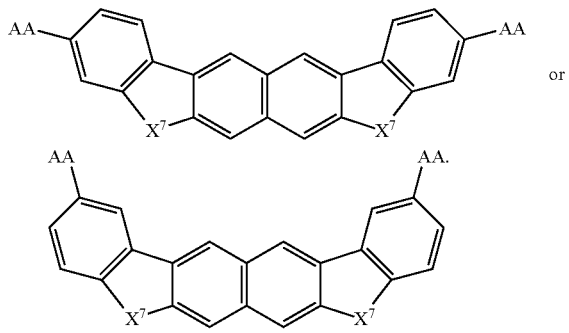

In another embodiment, each of $R^{25}$ and $R^{26}$ is hydrogen, $X^7$ is $SiR_2$, and the hole transporting compound is represented by:

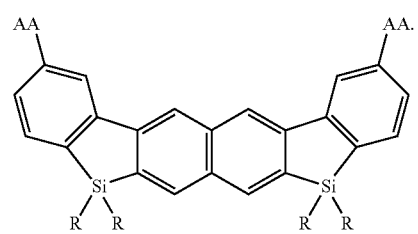

In a fourth subgenus, PLX-6 is represented by formula (XIII):

(XIII)

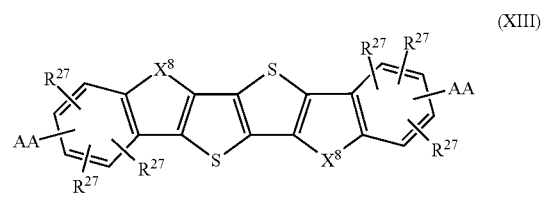

$X^8$ can be, for example, S, O, NR, $CR_2$, $SiR_2$ or $GeR_2$. R is described above. In one embodiment, $X^8$ is $SiR_2$ or $GeR_2$. In another embodiment, $X^8$ is O or NR.

Each of $R^{27}$ can be, for example, H, F, or an optionally substituted alkyl, aryl, heteroalkyl, heteroaryl, or intractability group. In one embodiment, each of $R^{27}$ is hydrogen. In another embodiment, at least one of $R^{27}$ comprises a moiety for improving solubility such as an optionally substituted linear or branched alkyl, alkoxy or polyether. In a further embodiment, at least one of $R^{27}$ comprises an intractability group which can be a crosslinking or non-crosslinking group. In an additional embodiment, at least one of $R^{27}$ comprises a crosslinking or polymerizable group, such as vinyl.

In one embodiment, each of $R^{27}$ is hydrogen, and the hole transporting compound is represented by:

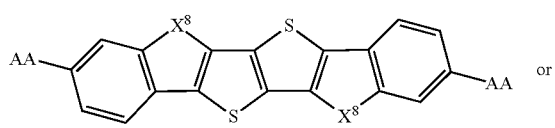

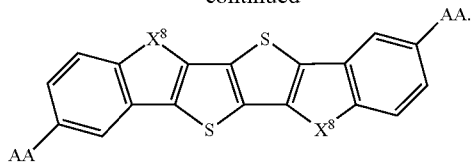

In another embodiment, each of $R^{27}$ is hydrogen, $X^8$ is $SiR_2$, and the hole transporting compound is represented by:

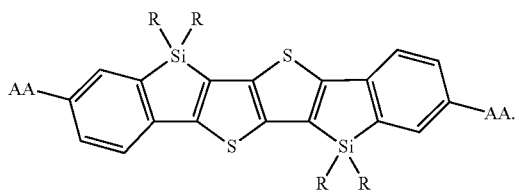

PLX-7 Hole Transporting Compounds

The seventh group of hole transporting compounds, PLX-7, is represented by formula (XIV):

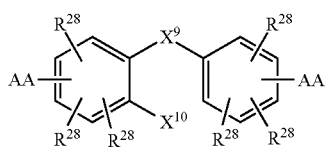

(XIV)

Each of $X^9$ and $X^{10}$ can comprise, for example, a heteroatom. In one embodiment, $X^9$ and $X^{10}$ is S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking group. In a further embodiment, R comprises a crosslinking or polymerizable group, such as vinyl.

In one embodiment, $X^9$ and $X^{10}$ are the same. In another embodiment, $X^9$ and $X^{10}$ are different. In one embodiment, $X^9$ is NR, wherein R is an intractability group. In one embodiment, $X^9$ is NR, and $X^{10}$ is $SiR_2$, $GeR_2$ or $CR_2$.

Each of $R^{28}$ can be, for example, H, F, or an optionally substituted alkyl, aryl, heteroalkyl, heteroaryl, or intractability group. In one embodiment, each of $R^{28}$ is hydrogen. In another embodiment, at least one of $R^{28}$ comprises a moiety for improving solubility such as an optionally substituted linear or branched alkyl, alkoxy or polyether. In a further embodiment, at least one of $R^{28}$ comprises an intractability group which can be a crosslinking or non-crosslinking group. In an additional embodiment, at least one of $R^{28}$ comprises a crosslinking or polymerizable group, such as vinyl.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-7, each of $R^{28}$ is hydrogen, $X^9$ is NR, R is an intractability group, and the hole transporting compound is represented by:

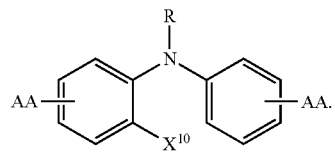

In another embodiment of PLX-7, each of $R^{28}$ is hydrogen, $X^9$ is NR, $X^{10}$ is $SiR_2$, and the hole transporting compound is represented by:

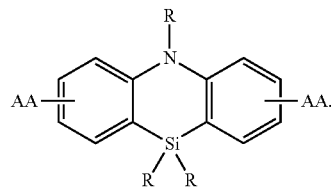

In another embodiment of PLX-7, each of $R^{28}$ is hydrogen, $X^9$ is NR, $X^{10}$ is $GeR_2$, and the hole transporting compound is represented by:

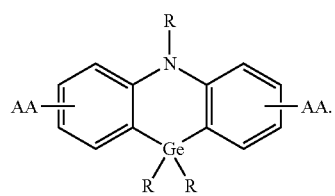

In another embodiment of PLX-7, each of $R^{28}$ is hydrogen, $X^9$ is NR, $X^{10}$ is $CR_2$, and the hole transporting compound is represented by:

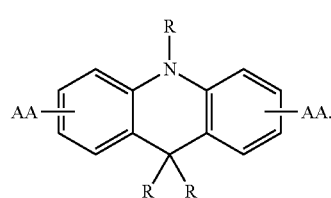

PLX-8 Hole Transporting Compounds

The eighth group of hole transporting compounds, PLX-8, is represented by formula (XV):

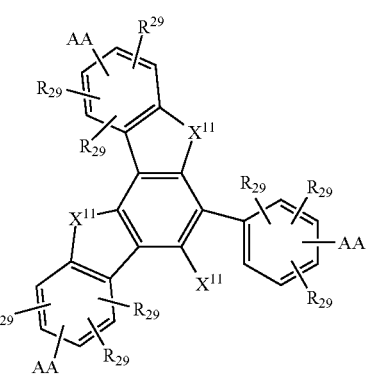

(XV)

Each of $X^{11}$ can comprise, for example, a heteroatom. In one embodiment, $X^{11}$ is S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking group. In a further embodiment, R comprises a crosslinking or polymerizable group, such as vinyl.

Each of $R^{29}$ can be, for example, H, F, or an optionally substituted alkyl, aryl, heteroalkyl, heteroaryl, or intractability group. In one embodiment, each of $R^{29}$ is hydrogen. In another embodiment, at least one of $R^{29}$ comprises a moiety for improving solubility such as an optionally substituted linear or branched alkyl, alkoxy or polyether. In a further embodiment, at least one of $R^{29}$ comprises an intractability group which can be a crosslinking or non-crosslinking group. In an additional embodiment, at least one of $R^{29}$ comprises a crosslinking or polymerizable group, such as vinyl.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-8, each of $R^{29}$ is hydrogen, and the hole transporting compound is represented by:

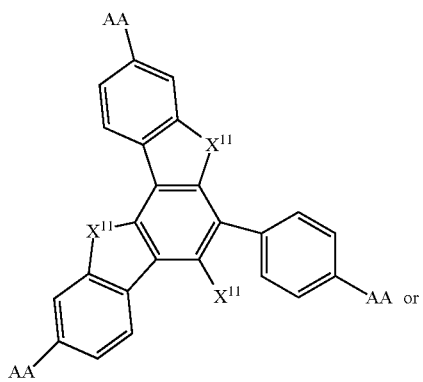

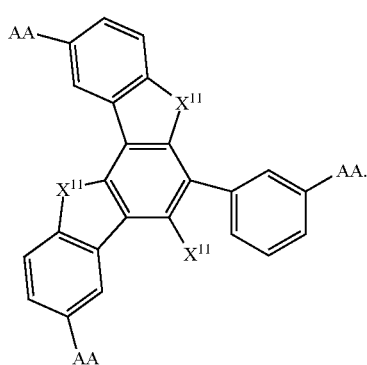

In another embodiment of PLX-8, each of $R^{29}$ is hydrogen, $X^{11}$ is S, and the hole transporting compound is represented by:

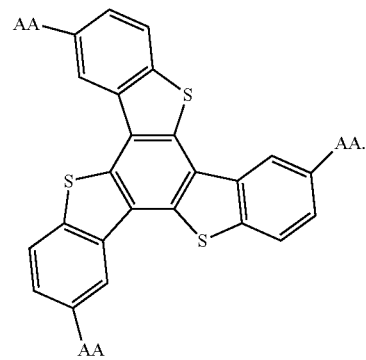

In a further embodiment of PLX-8, each of $R^{29}$ is hydrogen, $X^{11}$ is $CR_2$, and the hole transporting compound is represented by:

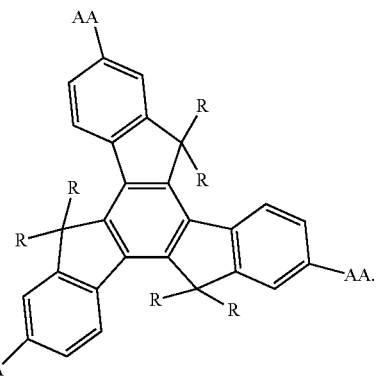

PLX-9 Hole Transporting Compounds

The ninth group of hole transporting compounds, PLX-9, is represented by formula (XVI):

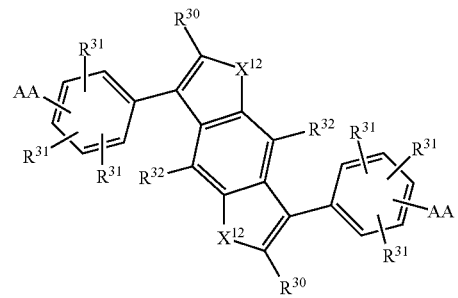

(XVI)

Each of $X^{12}$ can comprise, for example, a heteroatom. In one embodiment, $X^{12}$ is S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking group. In a further embodiment, R comprises a crosslinking or polymerizable group, such as vinyl.

Each of $R^{30}$ can be, for example, hydrogen or an optionally substituted alkyl, aryl, heteroalkyl, heteroaryl, or intractability group. In one embodiment, at least one of $R^{30}$ comprises an optionally substituted aryl or heteroaryl group. In another embodiment, at least one of $R^{30}$ comprises a moiety for improving solubility such as an optionally substituted linear or branched alkyl, alkoxy or polyether. In a further embodiment, at least one of $R^{30}$ comprises an intractability group which can be a crosslinking or non-crosslinking group. In an additional embodiment, at least one of $R^{30}$ comprises a crosslinking or polymerizable group, such as vinyl.

Each of $R^{31}$ and $R^{32}$ can be, for example, H, F, or an optionally substituted alkyl, aryl, heteroalkyl, heteroaryl, or intractability group. In one embodiment, each of $R^{31}$ and $R^{32}$ is hydrogen. In another embodiment, at least one of $R^{31}$ and $R^{32}$ comprises a moiety for improving solubility such as an optionally substituted linear or branched alkyl, alkoxy or polyether. In a further embodiment, at least one of $R^{31}$ and $R^{32}$ comprises an intractability group which can be a crosslinking or non-crosslinking group. In an additional embodiment, at least one of $R^{31}$ and $R^{32}$ comprises a crosslinking or polymerizable group, such as vinyl.

In one embodiment, each of $R^{31}$ and $R^{32}$ is hydrogen, and $R^{30}$ is not hydrogen. In another embodiment, each of $R^{31}$ and $R^{32}$ is hydrogen, and $R^{30}$ is an optionally substituted aryl or heteroaryl group.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-9, each of $R^{31}$ and $R^{32}$ is hydrogen, and the hole transporting compound is represented by:

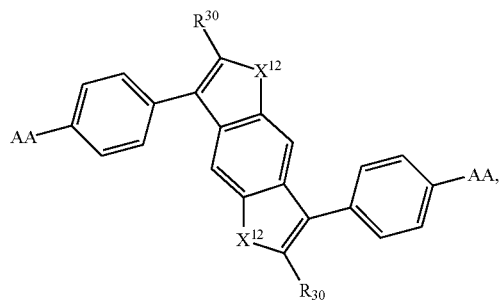

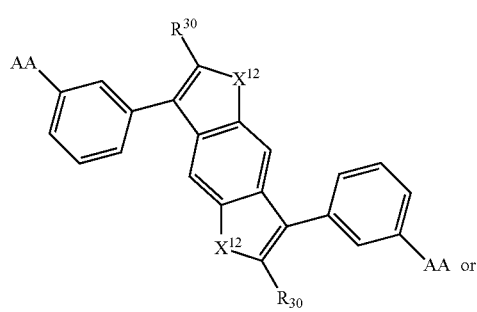

In another embodiment of PLX-9, each of $R^{31}$ and $R^{32}$ is hydrogen, $X^{12}$ is O, and the hole transporting compound is represented by:

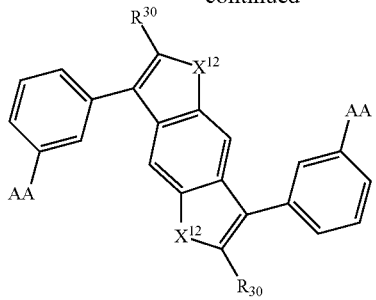

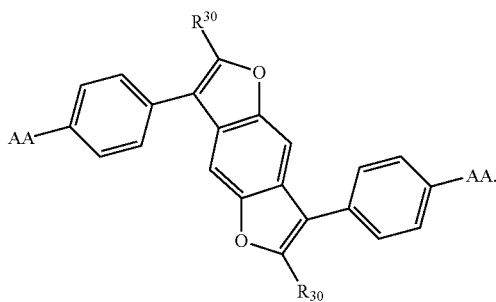

In a further embodiment of PLX-9, each of $R^{31}$ and $R^{32}$ is hydrogen, $R^{30}$ is phenyl, $X^{12}$ is O, and the hole transporting compound is represented by:

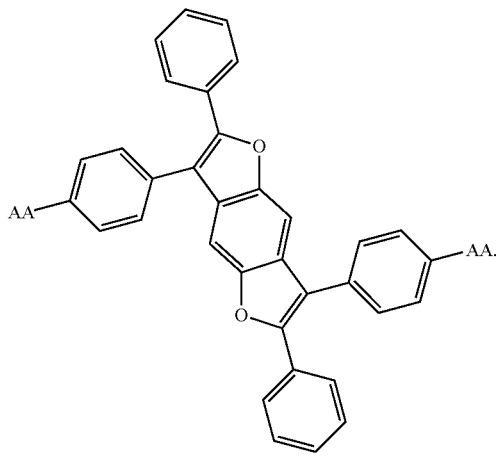

PLX-10 Hole Transporting Compounds

The tenth group of hole transporting compounds, PLX-10, is represented by formula (XVII):

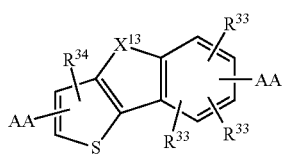

(XVII)

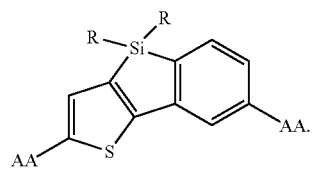

$X^{13}$ can comprise, for example, a heteroatom. In one embodiment, $X^{13}$ is S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking group. In a further embodiment, R comprises a crosslinking or polymerizable group, such as vinyl.

Each of $R^{33}$ and $R^{34}$ can be, for example, H, F, or an optionally substituted alkyl, aryl, heteroalkyl, heteroaryl, or intractability group. In one embodiment, each of $R^{33}$ and $R^{34}$ is hydrogen. In another embodiment, at least one of $R^{33}$ and $R^{34}$ comprises a moiety for improving solubility such as an optionally substituted linear or branched alkyl, alkoxy or polyether. In a further embodiment, at least one of $R^{33}$ and $R^{34}$ comprises an intractability group which can be a crosslinking or non-crosslinking group. In an additional embodiment, at least one of $R^{33}$ and $R^{34}$ comprises a crosslinking or polymerizable group, such as vinyl.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-10, each of $R^{33}$ and $R^{34}$ is hydrogen, and the hole transporting compound is represented by:

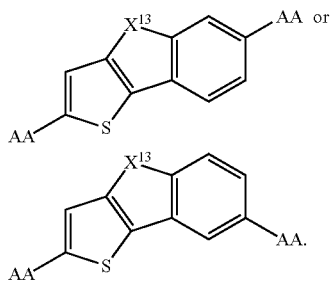

In another embodiment of PLX-10, each of $R^{33}$ and $R^{34}$ is hydrogen, $X^{13}$ is NR, and the hole transporting compound is represented by:

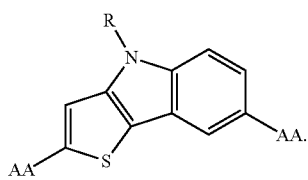

In a further embodiment of PLX-10, each of $R^{33}$ and $R^{34}$ is hydrogen, $X^{13}$ is $SiR_2$, and the hole transporting compound is represented by:

PLX-11 Hole Transporting Compounds

The eleventh group of hole transporting compounds, PLX-11, is represented by formula (XVIII):

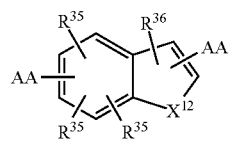

(XVIII)

$X^{12}$ can comprise, for example, a heteroatom. In one embodiment, $X^{14}_2$ is S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking group. In a further embodiment, R comprises a crosslinking or polymerizable group, such as vinyl.

Each of $R^{35}$ and $R^{36}$ can be, for example, H, F, or an optionally substituted alkyl, aryl, heteroalkyl, heteroaryl, or intractability group. In one embodiment, each of $R^{35}$ and $R^{36}$ is hydrogen. In another embodiment, at least one of $R^{35}$ and $R^{36}$ comprises a moiety for improving solubility such as an optionally substituted linear or branched alkyl, alkoxy or polyether. In a further embodiment, at least one of $R^{35}$ and $R^{36}$ comprises an intractability group which can be a crosslinking or non-crosslinking group. In an additional embodiment, at least one of $R^{35}$ and $R^{36}$ comprises a crosslinking or polymerizable group, such as vinyl.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-11, each of $R^{35}$ and $R^{36}$ is hydrogen, and the hole transporting compound is represented by:

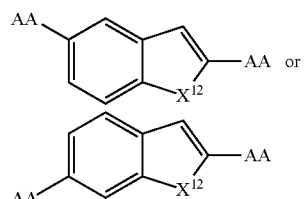

PLX-12 Hole Transporting Compounds

The twelfth group of hole transporting compounds, PLX-12, is represented by formula (XIX):

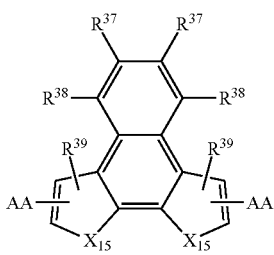

(XIX)

Each of $X^{15}$ can comprise, for example, a heteroatom. In one embodiment, $X^{15}$ is S, O, NR, $CR_2$, $SiR_2$, $GeR_2$, or C=C. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking group. In a further embodiment, R comprises a crosslinking or polymerizable group, such as vinyl.

Each of $R^{37}$ can be, for example, H, F, or an optionally substituted alkyl, aryl, heteroalkyl, heteroaryl, or intractability group. In one embodiment, at least one of $R^{37}$ comprises a moiety for improving solubility such as an optionally substituted linear or branched alkyl, alkoxy or polyether. In another embodiment, at least one of $R^{37}$ comprises an intractability group which can be a crosslinking or non-crosslinking group. In a further embodiment, at least one of $R^{37}$ comprises a crosslinking or polymerizable group, such as vinyl.

Each of $R^{38}$ and $R^{39}$ can be, for example, H, F, or an optionally substituted alkyl, aryl, heteroalkyl, heteroaryl, or intractability group. In one embodiment, each of $R^{38}$ and $R^{39}$ is hydrogen. In another embodiment, at least one of $R^{38}$ and $R^{39}$ comprises a moiety for improving solubility such as an optionally substituted linear or branched alkyl, alkoxy or polyether. In a further embodiment, at least one of $R^{38}$ and $R^{39}$ comprises an intractability group which can be a crosslinking or non-crosslinking group. In an additional embodiment, at least one of $R^{38}$ and $R^{39}$ comprises a crosslinking or polymerizable group, such as vinyl.

In one embodiment, each of $R^{38}$ and $R^{39}$ is hydrogen, and $R^{37}$ is not hydrogen.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-12, each of $R^{38}$ and $R^{39}$ is hydrogen, and the hole transporting compound is represented by:

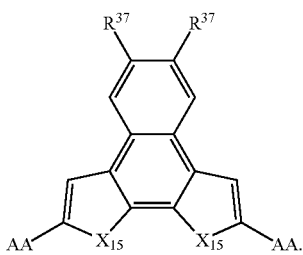

In another embodiment of PLX-12, each of $R^{38}$ and $R^{39}$ is hydrogen, $X^{15}$ is S, and the hole transporting compound is represented by:

In a further embodiment of PLX-12, each of $R^{38}$ and $R^{39}$ is hydrogen, $X^{15}$ is C=C, and the hole transporting compound is represented by:

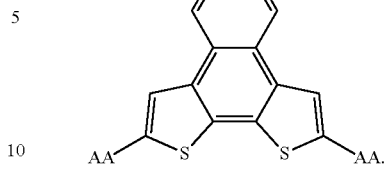

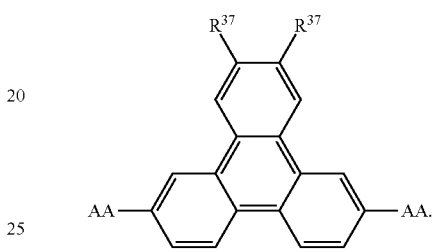

PLX-13 Hole Transporting Compounds

The thirteenth group of hole transporting compounds, PLX-13, is represented by formula (XX):

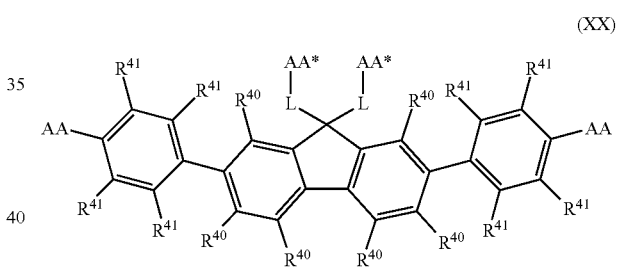

(XX)

Each AA and AA* can be, for example, an arylamine group optionally substituted with one or more intractability groups. The intractability group can be a crosslinking or non-crosslinking group. In one embodiment, the intractability group is a crosslinking or polymerizable group, such as vinyl.

In one embodiment, AA and AA* are the same. In another embodiment, AA and AA* are different.

Each L can be, for example, a linker group. In one embodiment, L is an alkylene or heteroalkylene group optionally substituted with one or more aromatic rings.

Each of $R^{40}$ and $R^{41}$ can be, for example, H, F, or an optionally substituted alkyl, aryl, heteroalkyl, heteroaryl, or intractability group. In one embodiment, each of $R^{40}$ and $R^{41}$ is hydrogen. In another embodiment, at least one of $R^{40}$ and $R^{41}$ comprises a moiety for improving solubility such as an optionally substituted linear or branched alkyl, alkoxy or polyether. In a further embodiment, at least one of $R^{40}$ and $R^{41}$ comprises an intractability group which can be a crosslinking or non-crosslinking group. In an additional embodiment, at least one of $R^{40}$ and $R^{41}$ comprises a crosslinking or polymerizable group, such as vinyl.

In one embodiment of PLX-13, each of $R^{40}$ and $R^{41}$ is hydrogen, and the hole transporting compound is represented by:

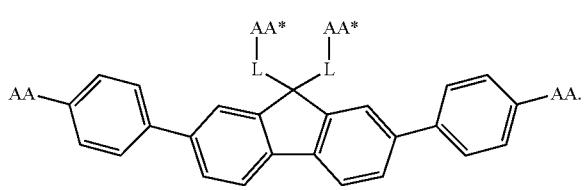

In another embodiment, PLX-13 is:

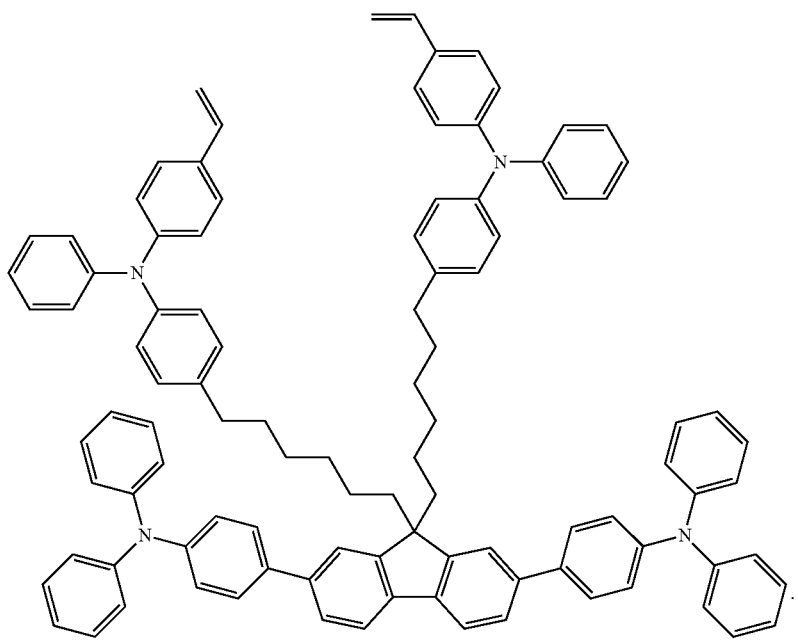 [SMILES: C=Cc1ccc(N(c2ccccc2)c2ccc(CCCCCCC3(CCCCCCc4ccc(N(c5ccccc5)c5ccc(C=C)cc5)cc4)c4cc(-c5ccc(N(c6ccccc6)c6ccccc6)cc5)ccc4-c4ccc(-c5ccc(N(c6ccccc6)c6ccccc6)cc5)cc43)cc2)cc1]

group. In a further embodiment, R comprises a crosslinking or polymerizable group, such as vinyl.

Each of $R^{42}$ and $R^{43}$ can be, for example, independently H, F, or an optionally substituted alkyl, aryl, heteroalkyl, heteroaryl, or intractability group, or together forming a ring. In one embodiment, each of $R^{42}$ and $R^{43}$ is hydrogen. In one embodiment, $R^{42}$ and $R^{43}$ together form a ring. An arylamine group optionally substituted with one or more intractability groups can bind to $R^{42}$ or $R^{43}$, or to a ring formed by $R^{42}$ and $R^{43}$.

In one embodiment, at least one of $R^{42}$ and $R^{43}$ comprises a moiety for improving solubility such as an optionally substituted linear or branched alkyl, alkoxy or polyether. In another embodiment, at least one of $R^{42}$ and $R^{43}$ comprises an intractability group which can be a crosslinking or non-crosslinking group. In a further embodiment, at least one of $R^{42}$ and $R^{43}$ comprises a crosslinking or polymerizable group, such as vinyl.

$X^{17}$ can comprise, for example, a heteroatom. In one embodiment, $X^{17}$ is S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking group. In a further embodiment, R comprises a crosslinking or polymerizable group, such as vinyl.

Each of $R^{44}$, $R^{45}$ and $R^{46}$ can be, for example, independently H, F, or an optionally substituted alkyl, aryl, heteroalkyl, heteroaryl, or intractability group, or together forming a ring. In one embodiment, each of $R^{44}$, $R^{45}$ and $R^{46}$ is hydrogen. In one embodiment, $R^{44}$, $R^{45}$ and $R^{46}$ together form a ring. An arylamine group optionally substituted with one or more intractability groups can bind to $R^{44}$, $R^{45}$ or $R^{46}$, or to a ring formed by $R^{44}$, $R^{45}$ and $R^{46}$.

In one embodiment, at least one of $R^{44}$, $R^{45}$ and $R^{46}$ comprises a moiety for improving solubility such as an optionally substituted linear or branched alkyl, alkoxy or polyether. In a PLX-14 Hole Transporting Compounds The fourteenth group of hole transporting compounds, PLX-14, comprises two arylamine groups connected a hole transporting core, wherein the hole transporting core is represented by formula (XXI) and (XXII):

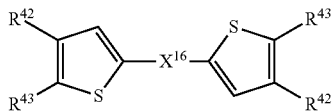
(XXI)

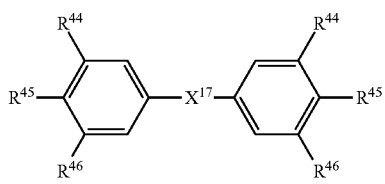
(XXII)

$X^{16}$ can comprise, for example, a heteroatom. In one embodiment, $X^{16}$ is S, O, NR, $CR_2$, $SiR_2$ or $GeR_2$. Each R can be, for example, an optionally substituted alkyl, aryl, heteroalkyl, heteroaryl, or intractability group. In one embodiment, R comprises a moiety for improving solubility such as an optionally substituted linear or branched alkyl, alkoxy or polyether. In another embodiment, R comprises an intractability group which can be a crosslinking or non-crosslinking another embodiment, at least one of $R^{44}$, $R^{45}$ and $R^{46}$ comprises an intractability group which can be a crosslinking or non-crosslinking group. In a further embodiment, at least one of $R^{44}$, $R^{45}$ and $R^{46}$ comprises a crosslinking or polymerizable group, such as vinyl.

In one embodiment of PLX-14, each of $R^{44}$, $R^{45}$ or $R^{46}$ is hydrogen, $X^{17}$ is $SiR_2$, and the hole transporting compound is represented by:

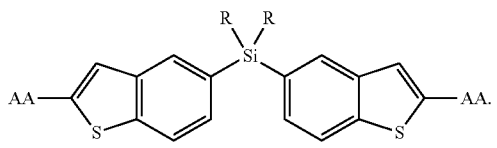

In another embodiment of PLX-14, each of $R^{44}$, $R^{45}$ or $R^{46}$ is hydrogen, $X^{17}$ is NR, and the hole transporting compound is represented by:

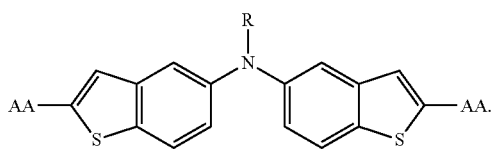

In a further embodiment of PLX-14, each of $R^{44}$, $R^{45}$ or $R^{46}$ is hydrogen, $X^{17}$ is NR, and the hole transporting compound is represented by:

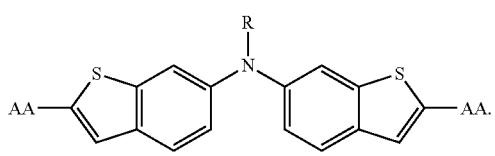

PLX-15 Hole Transporting Compounds

The fifteenth group of hole transporting compounds, PLX-15, is represented by formula (XXIII):

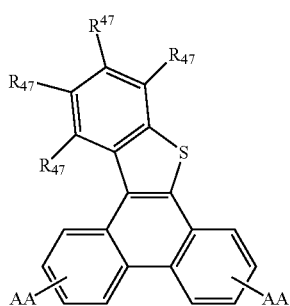

(XXIII)

Each of $R^{47}$ can be, for example, H, F, or an optionally substituted alkyl, aryl, heteroalkyl, heteroaryl, or intractability group. In one embodiment, at least one of $R^{47}$ comprises a moiety for improving solubility such as an optionally substituted linear or branched alkyl, alkoxy or polyether. In another embodiment, at least one of $R^{47}$ comprises an intractability group which can be a crosslinking or non-crosslinking group. In a further embodiment, at least one of $R^{47}$ comprises a crosslinking or polymerizable group, such as vinyl.

Each AA is an arylamine group optionally substituted with one or more intractability groups, such as vinyl. Alternatively, one AA is an arylamine group optionally substituted with one or more intractability groups, and the other AA is hydrogen.

In one embodiment of PLX-15, each of $R^{47}$ is hydrogen, and the hole transporting compound is represented by:

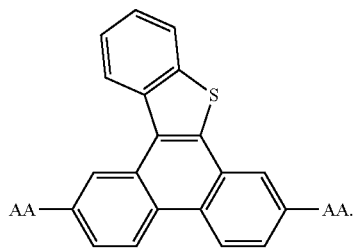

PLX-16 Hole Transporting Compounds

The sixteenth group of hole transporting compounds, PLX-16, is represented by formula (XXIV):

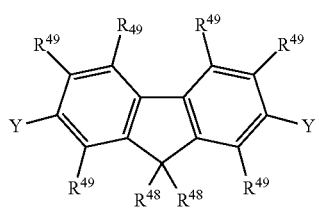

Each of $R^{48}$ can be, for example, an optionally substituted alkyl, aryl, heteroalkyl, heteroaryl, or intractability group. In one embodiment, at least one of $R^{48}$ comprises a moiety for improving solubility such as an optionally substituted linear or branched alkyl, alkoxy or polyether. In another embodiment, at least one of $R^{48}$ comprises an intractability group which can be a crosslinking or non-crosslinking group. In a further embodiment, at least one of $R^{48}$ comprises a crosslinking or polymerizable group, such as vinyl.

Each of $R^{49}$ can be, for example, H, F, or an optionally substituted alkyl, aryl, heteroalkyl, heteroaryl, or intractability group. In one embodiment, each of $R^{49}$ is hydrogen.

In one embodiment, each of $R^{49}$ is hydrogen, and at least one $R^{48}$ is not hydrogen.

Each Y is a hole transporting group.

In one example, Y is

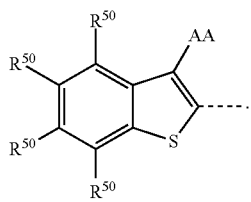

Each of $R^{50}$ can be, for example, H, F, or an optionally substituted alkyl, aryl, heteroalkyl, heteroaryl, or intractability group. In one embodiment, each of $R^{50}$ is hydrogen. AA is an arylamine group optionally substituted with one or more intractability groups.

In another example, Y is

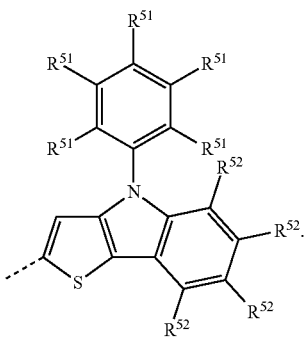

Each of $R^{51}$ and $R^{52}$ can be, for example, H, F, or an optionally substituted alkyl, aryl, heteroalkyl, heteroaryl, or intractability group. In one embodiment, each of $R^{51}$ and $R^{52}$ is hydrogen.

In one embodiment of PLX-16, $R^{48}$ comprises an intractability group, each of $R^{49}$ and $R^{50}$ is hydrogen, and the hole transporting compound is represented by:

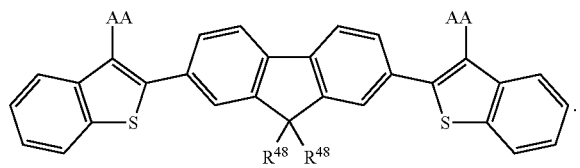

In another embodiment of PLX-16, $R^{48}$ comprises an intractability group, each of $R^{49}$, $R^{51}$ and $R^{52}$ is hydrogen, and the hole transporting compound is represented by:

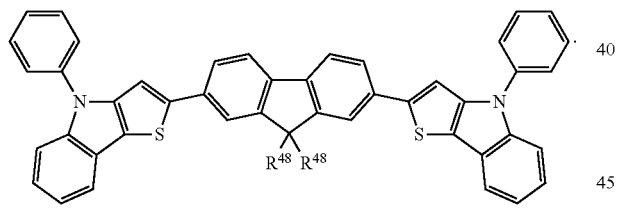

Arylamine Groups

Arylamine groups are generally known in the art. See, for example, US Pat. Pub. No. 2011/0017988 Yasukawa et. Al and other references cited herein. The arylamine group will have one valency on the nitrogen bonded to the hole transport core. The other two valencies on the nitrogen are bonded to aryl groups. This can be represented by N(R1)(R2)(R3), wherein R1-R3 are aryl groups which can be the same or different, independently of each other. The arylgroup can be a group free of heteroatoms or can be a heteroaryl group comprising at least one heteroatom.

In one embodiment, the first and second arylamine groups are the same arylamine group. In one embodiment, the first and second arylamine groups are different arylamine groups.

In one embodiment, each of the first and second arylamine groups are independently represented by —N(R1)(R2), wherein R1 and R2 are optionally substituted aryl or heteroaryl groups which may be the same or different.

In one embodiment, each of the first and second arylamine groups are independently represented by —N(R1)(R2), wherein at least one of R1 and R2 is an optionally substituted phenyl group (the remaining valency on the arylamine is linked to the hole transporting core).

In one embodiment, each of the first and second arylamine groups are independently represented by —N(R1)(R2), wherein at least one of R1 and R2 is an optionally substituted biphenyl group.

In one embodiment, each of the first and second arylamine groups are independently represented by —N(R1)(R2), wherein at least one of R1 and R2 is an optionally substituted carbazole group.

In one embodiment, each of the first and second arylamine groups are independently represented by —N(R1)(R2), wherein —N(R1)(R2) form an optionally substituted carbazole group.

In one embodiment, each of the first and second arylamine groups are independently represented by —N(R1)(R2), wherein at least one of R1 and R2 is an optionally substituted naphthyl group.

In one embodiment, each of the first and second arylamine groups are independently represented by —N(R1)(R2), wherein at least one of R1 and R2 is an optionally substituted thienobenzene group.

In one embodiment, each of the first and second arylamine groups are independently represented by —N(R1)(R2), wherein at least one of R1 and R2 is an optionally substituted fluorene group.

In one embodiment, each of the first and second arylamine groups are independently represented by —N(R1)(R2), wherein at least one of R1 and R2 is an optionally substituted group comprising at least two fused aromatic rings.

Some specific examples of arylamine groups described here are provided below:

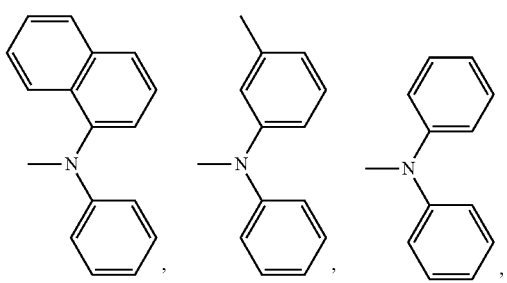

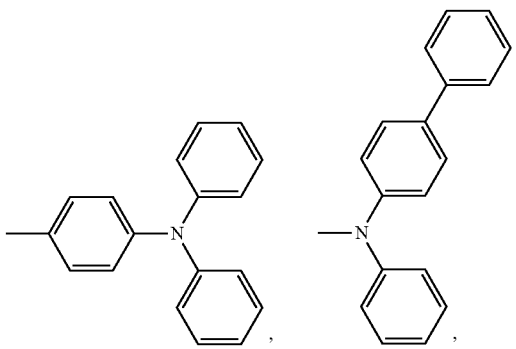

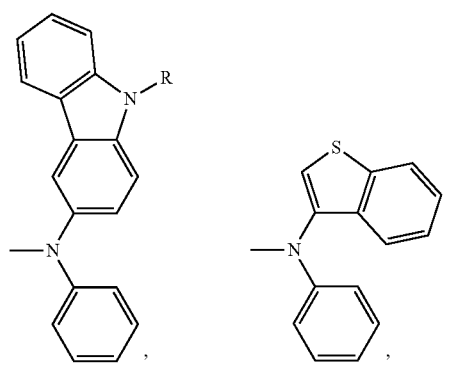
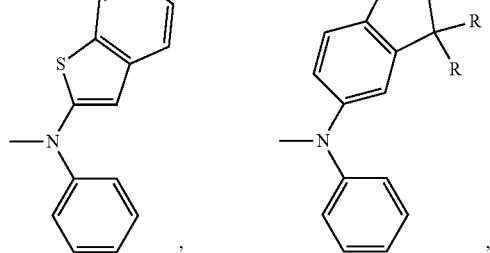
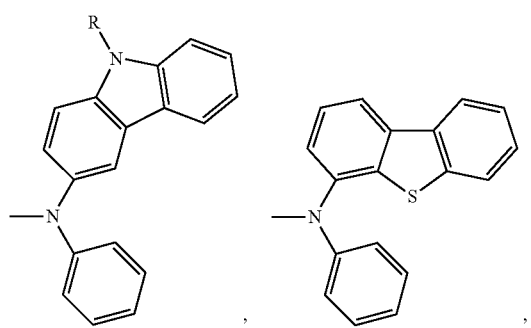
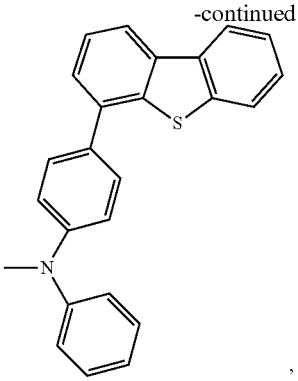
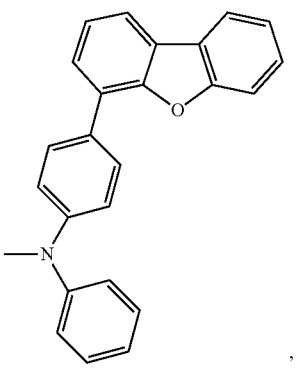
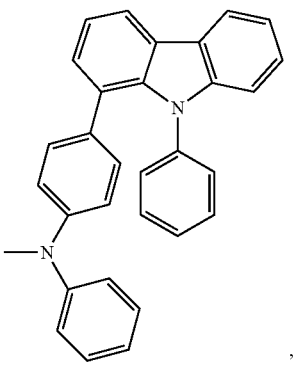
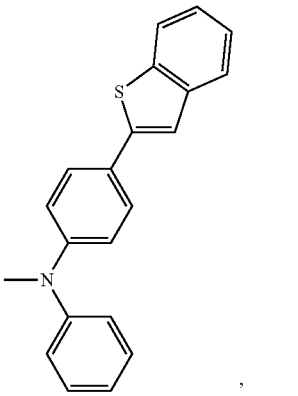
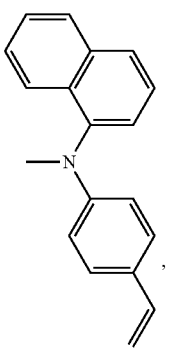

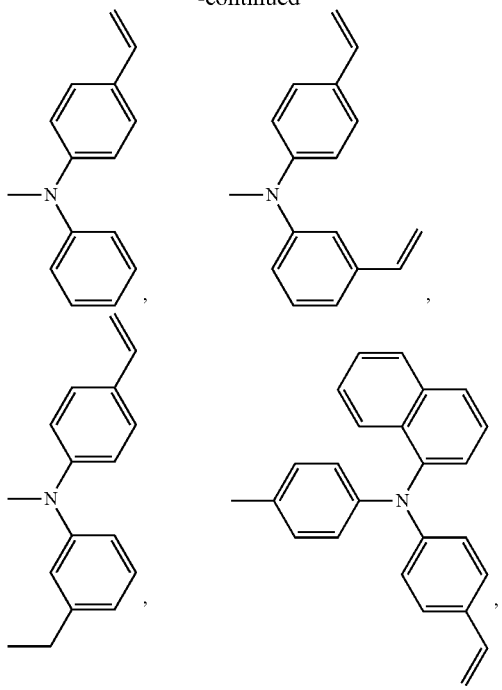
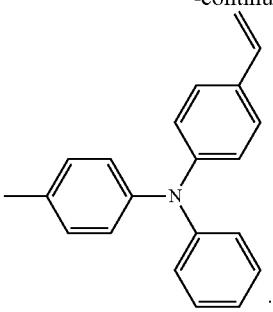
In one embodiment, arylamine groups optionally comprising one or more intractability groups can be covalently linked to the hole transporting core according to the following scheme:
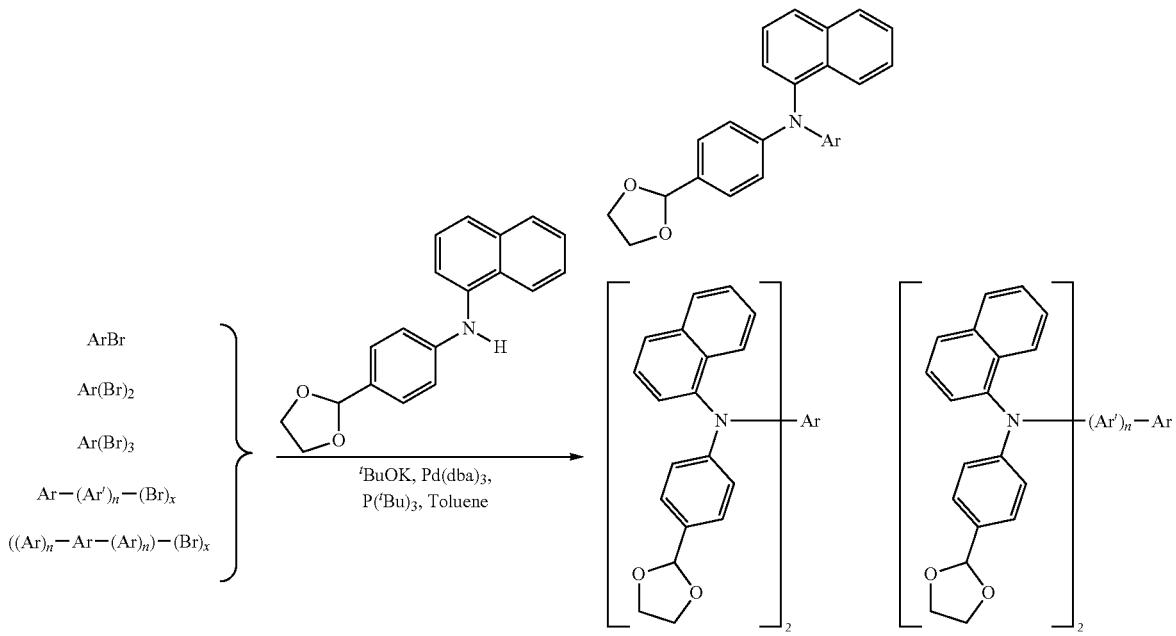

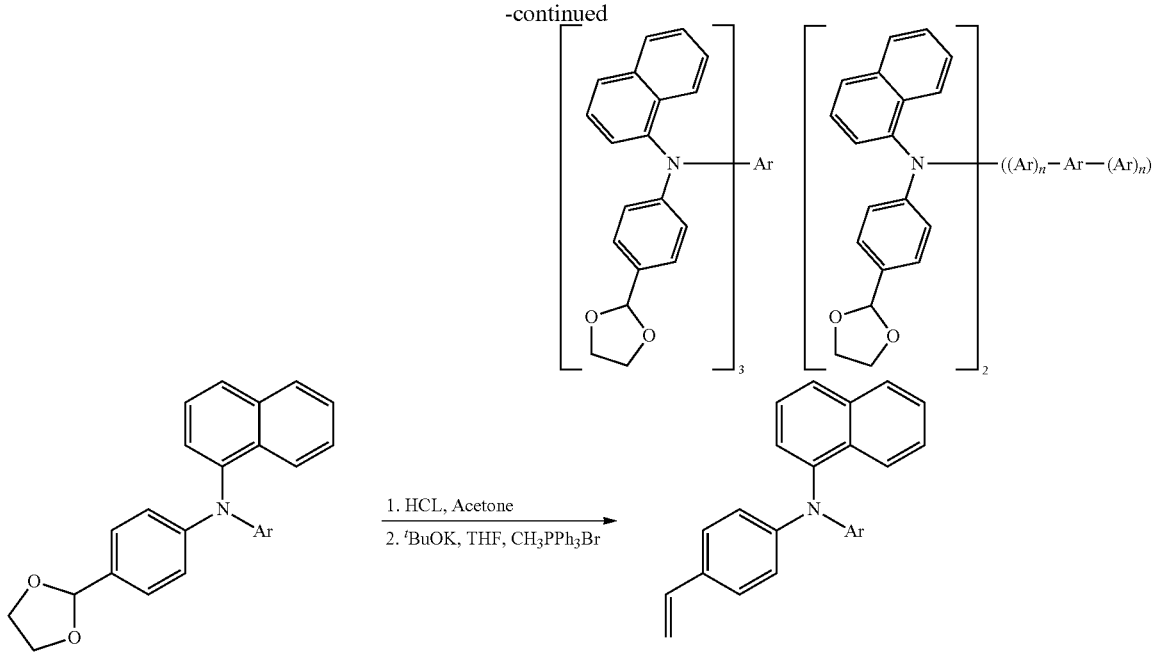

Intractability Groups

Intractability of hole transport materials is known in the art. See, for example, US Pat. Pub. Nos. 2009/0256117; 2010/0273007; and 2010/0292399. Intractability groups allow the materials to be sufficiently chemical and solvent resistant, allowing for solution processing.

In one embodiment, the intractability group comprises a polymerizable or crosslinking group. The crosslinking group allows for a covalent linkage between molecules and buildup of molecular weight to provide intractable, chemically resistant, and solvent resistant materials. In one embodiment, the intractability group comprises a non-crosslinking group. A non-crosslinking group can be a salt group, comprising cation and anion. Organic anions can be used including borates. Ammonium cations can be used.

In one embodiment, the intractability group can be linked to the rest of the molecule via a spacer. Examples of spacers include solubilizing groups, described herein, including alkylene groups. In one embodiment, the intractability group is a vinyl group, but is either linked to a non-aromatic group or is only linked to a single aromatic group as in a styrene conformation. In one embodiment, the intractability group is separated from a larger delocalized structure such as fused aromatic ring systems. This may, in some cases, improve stability. In one embodiment, the styrene group can be linked to the hole transporting core via a non-conjugated spacer such as an alkylene moiety.

In one embodiment, the intractability group comprises at least one ethylene moiety. In one embodiment, the intractability group comprises a vinyl group. In one embodiment, the vinyl group is linked to an oxygen atom (vinyleneoxy group) or in another embodiment to a carbon atom which is part of an aliphatic or aromatic group (e.g., propenyl; other examples include acryloyl, or methacryloyl). In one embodiment, the intractability group comprises a benzocyclobutane group. In one embodiment, the intractability group comprises an indene group (or indenyl).

In one embodiment for a non-crosslinking group, the intractability group comprises a quaternary ammonium group. In one embodiment, the intractability group comprises a quaternary ammonium group comprising a tetraarylborate anion. In one embodiment, the intractability group comprises a quaternary ammonium group comprising a pentafluorophenylborate anion. A spacer group can be used to provide linkage between the quaternary ammonium group and the arylamine group.

Some specific examples of intractability groups described here are provided below:

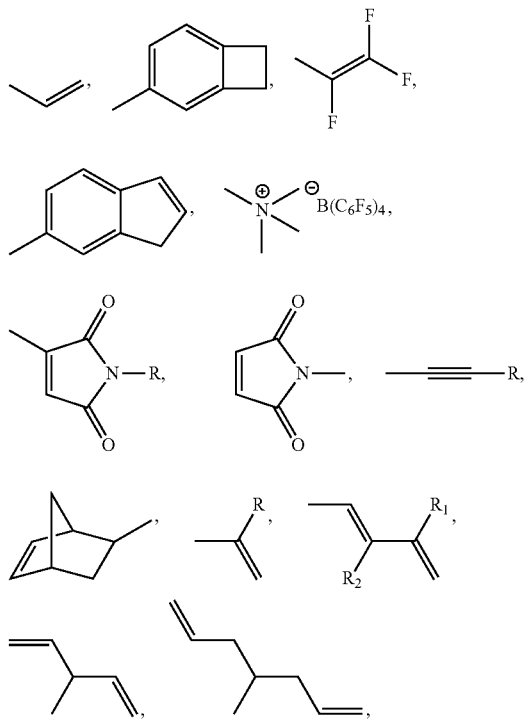

-continued

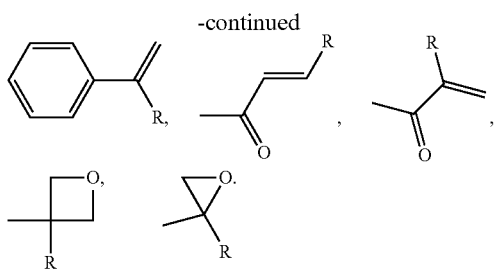

In one embodiment, for example, the compound comprises at least three intractability groups, and at least one intractability group is covalently bonded to the hole transport core, and at least one intractability group is covalently bonded to the first arylamine group, and at least one intractability group is covalently bonded to the second arylamine group.

In another embodiment, for example, the intractability group is, or the intractability groups are, covalently bonded to the hole transport core but not the first arylamine group or the second arylamine group.

In a further embodiment, for example, the intractability group is, or the intractability groups are, covalently bonded to the first arylamine group, the second arylamine group, or both, but is not bonded to the hole transport core.

In one embodiment, the compound comprises one intractability group. In another embodiment, the compound comprises two or more intractability groups. In a further embodiments, the compound comprises three, four, five, or six or more intractability groups. No particular upper limit exists, but the number of intractability groups can be 12 or less, or or less, or 8 or less, or 6 or less.

Synthesis of Hole Transporting Compounds

One skilled in the art can use organic chemistry to link together the core moiety, the arylamine moieties, and the intractability group or groups. Synthesis is described in, for example, March's *Advanced Organic Chemistry*, 6th Ed., Wiley, 2007, as well as in references cited herein. Synthesis of hole transporting compounds is described herein.

1. Synthesis of PLX-1

PLX-1 hole transporting compound can be synthesized according to, for example, the following steps: linking a heteroatom moiety to two fused-ring moieties; ring-closing to form a heteroring comprising said heteroatom, said heteroring is fused with said fused-ring moieties to form a hole transporting core comprising at least five rings fused together; functioning the hole transporting core with arylamine groups; and optionally forming one or more intractability groups on either the hole transporting core or the arylamine groups via deprotection.

In one embodiment, the fused-ring moiety is

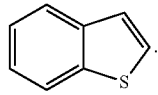

In one embodiment, the heteroatom moiety is S, O, NR, $CR_2$, $SiR_2$ or $GeR_2$, and wherein each R is an optionally substituted alkyl, aryl, heteroalkyl, heteroaryl, or vinyl group.

For example, PLX-1 hole transporting compound can be synthesized according to Scheme 1.

Scheme 1

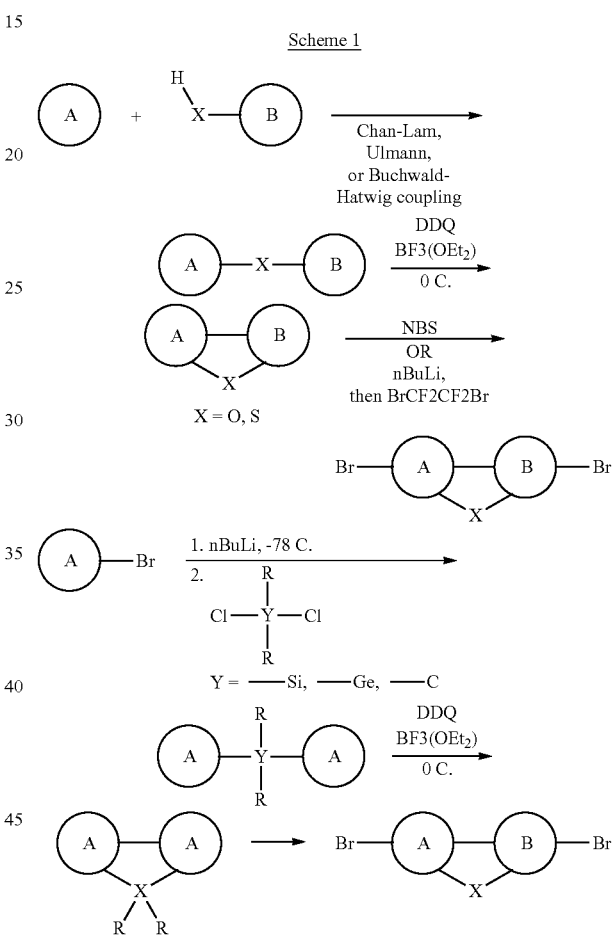

In one embodiment of PLX-1 according to formula (I), wherein $X^1$ is $SiR_2$ and each of $R^1$, $R^2$ and $R^3$ is hydrogen, the hole transporting compound can be synthesized, for example, as follows.

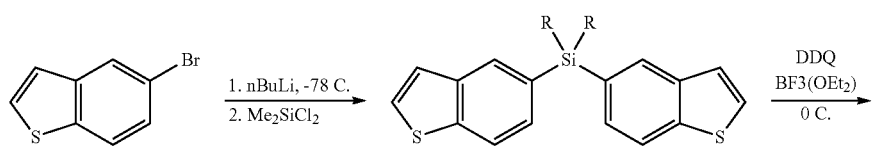

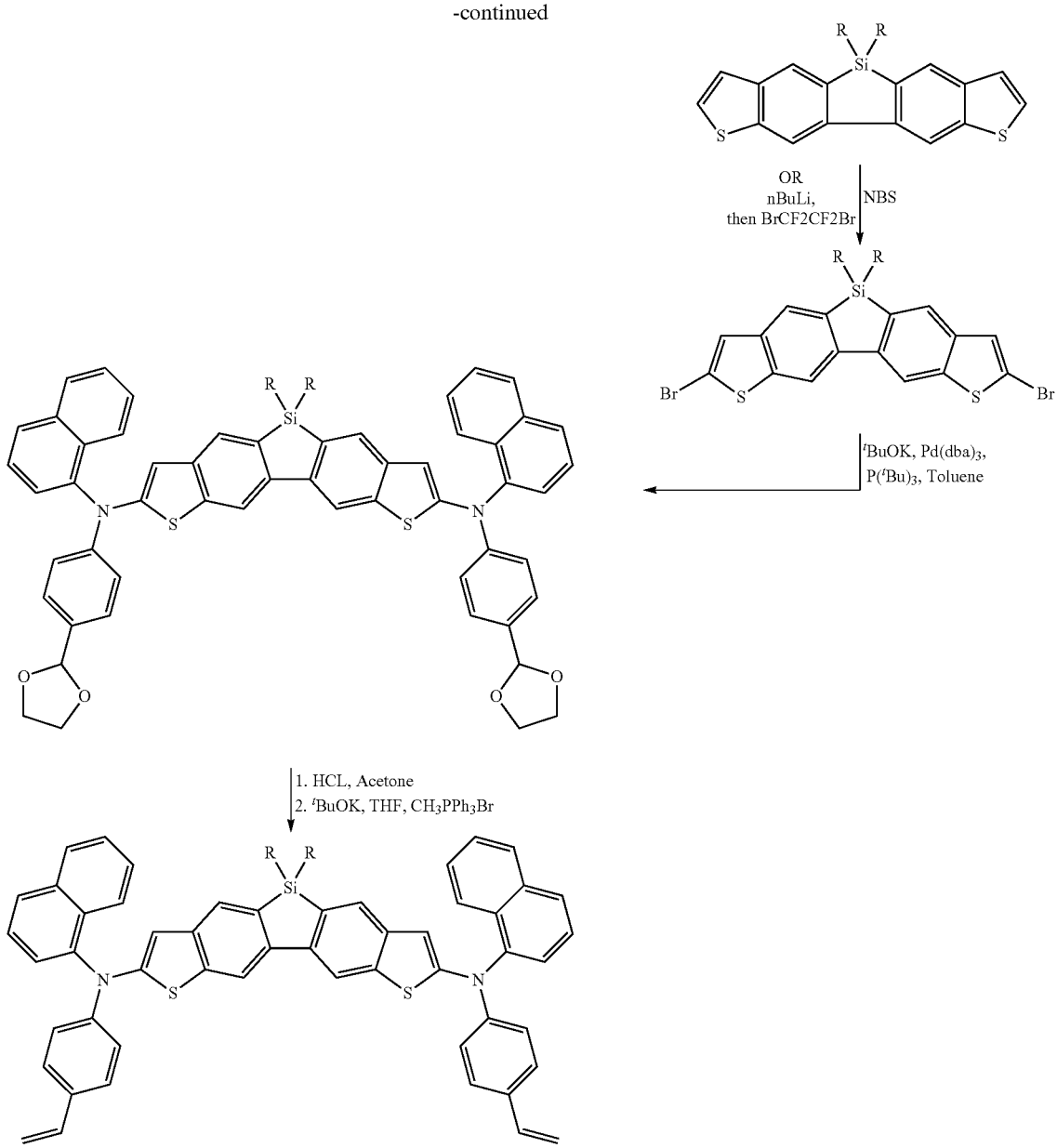
In another embodiment of PLX-1 according to formula (I), wherein $X^1$ is S and each of $R^1$, $R^2$ and $R^3$ is hydrogen, the hole transporting compound can be synthesized, for example, as follows.
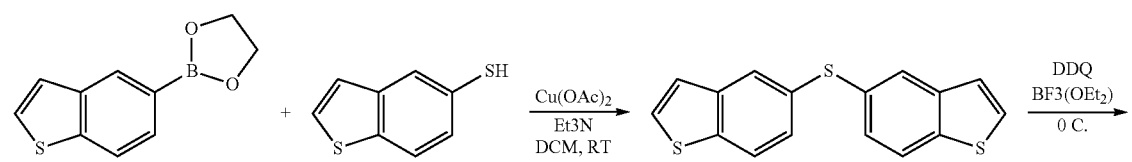

-continued
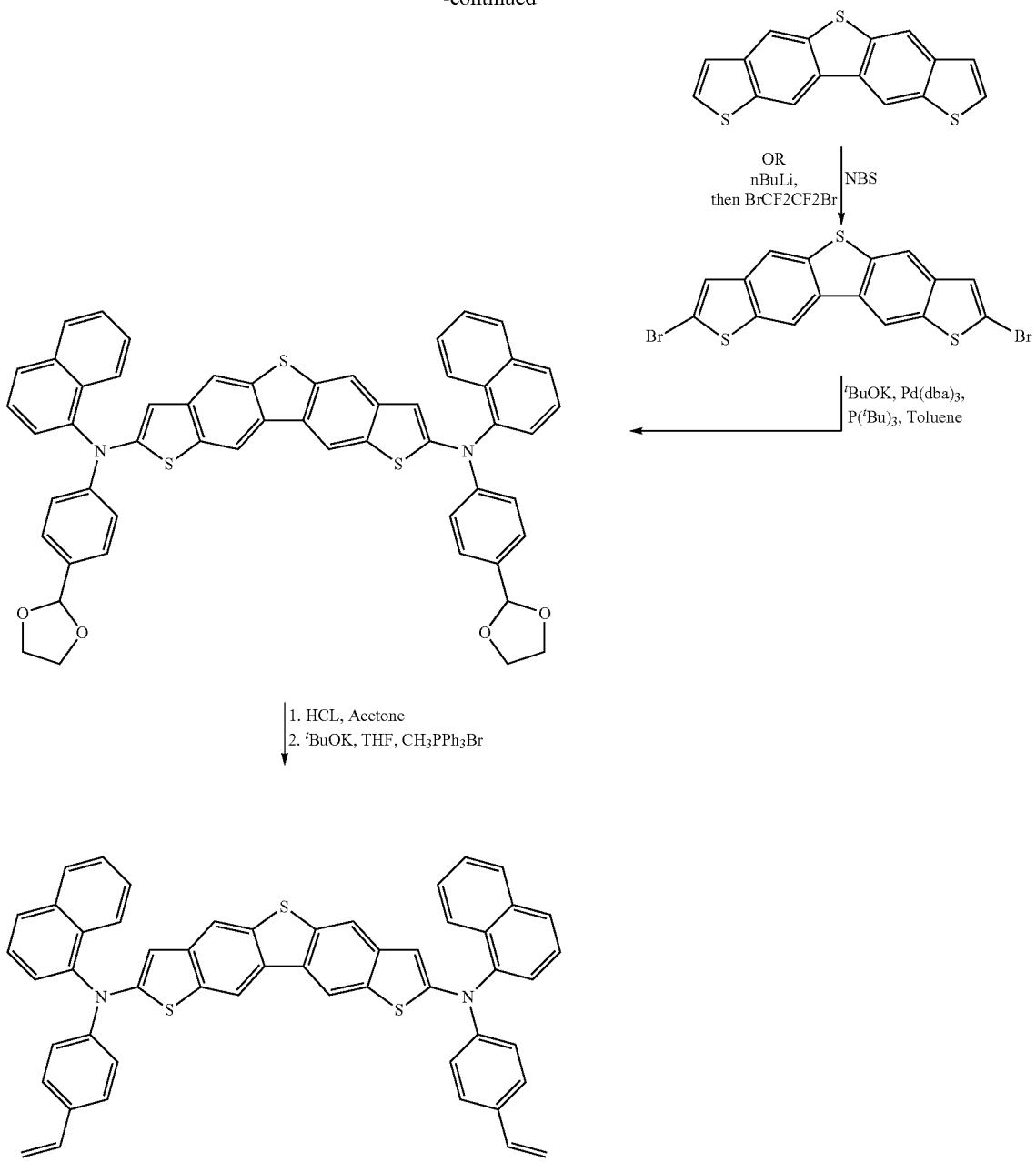
In a further embodiment of PLX-1 according to formula (I), wherein $X^1$ is NR and each of $R^1$, $R^2$ and $R^3$ is hydrogen, the hole transporting compound can be synthesized, for example, as follows.
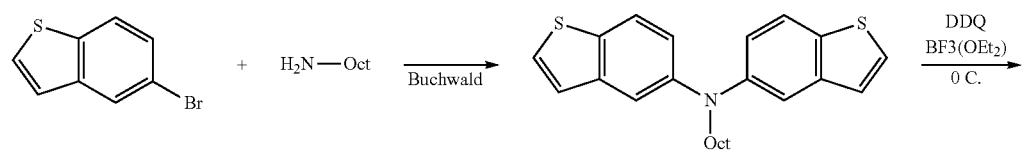

-continued

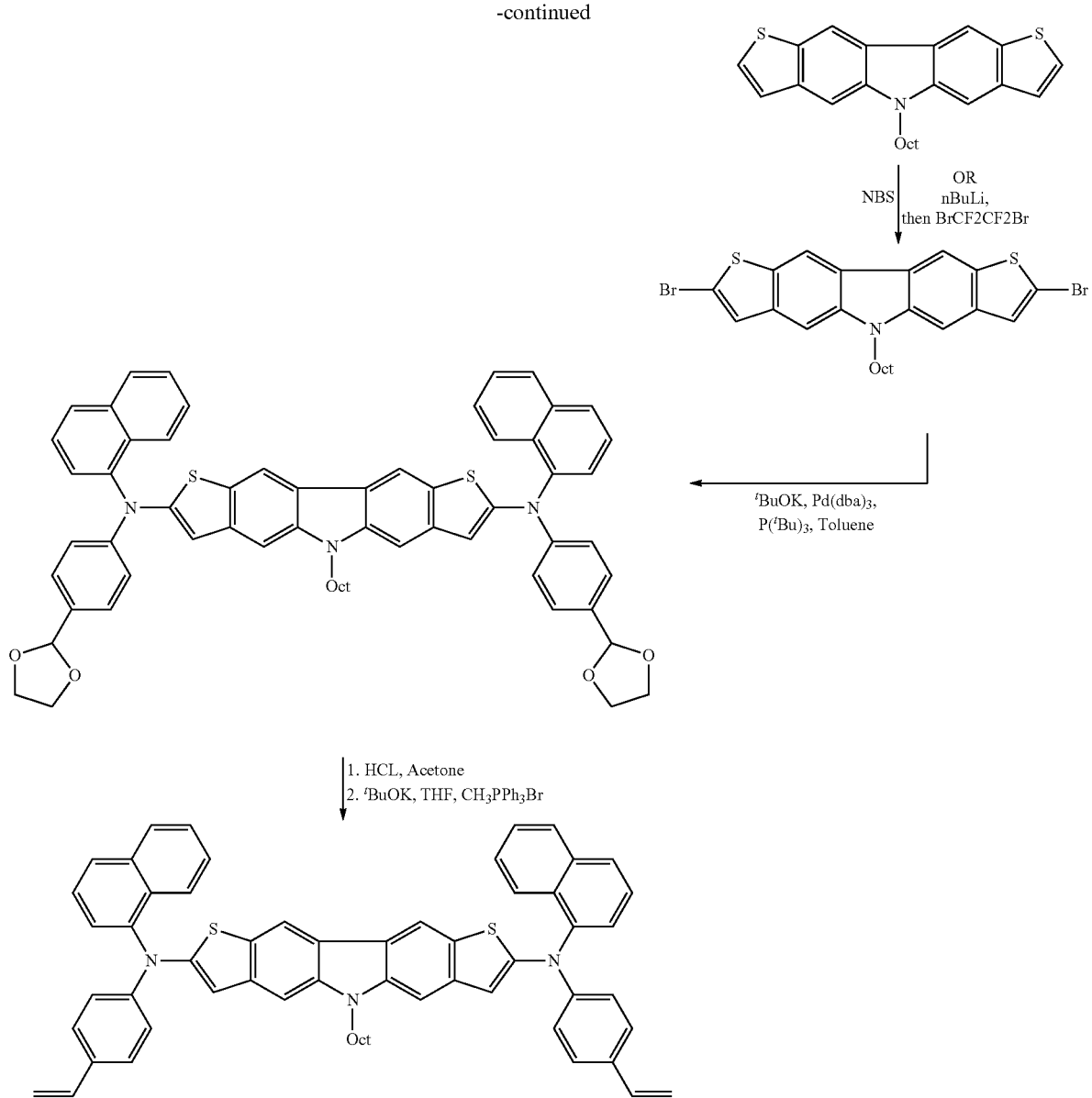

2. Synthesis of PLX-2

PLX-2 hole transporting compound can be synthesized according to, for example, the following steps: linking at least two heteroatom moieties to at least three aryl or heteroaryl moieties to form a structure comprising alternating heteroatoms and aryl or heteroaryl moieties; ring-closing to form at least two heterorings comprising said heteroatoms, said heterorings are fused with said aryl or heteroaryl moieties to form a hole transporting core comprising at least five rings fused together; functioning the hole transporting core with arylamine groups; and optionally forming one or more intractability groups on either the hole transporting core or the arylamine groups via deprotection.

In one embodiment, the aryl or heteroaryl moiety is phenyl.

In one embodiment, the heteroatom moiety is S, O, NR, $CR_2$, $SiR_2$ or $GeR_2$, and wherein each R is an optionally substituted alkyl, aryl, heteroalkyl, heteroaryl, or vinyl group.

For example, PLX-2 hole transporting compound can be synthesized according to Scheme 2.

Scheme 2

Alternate cores

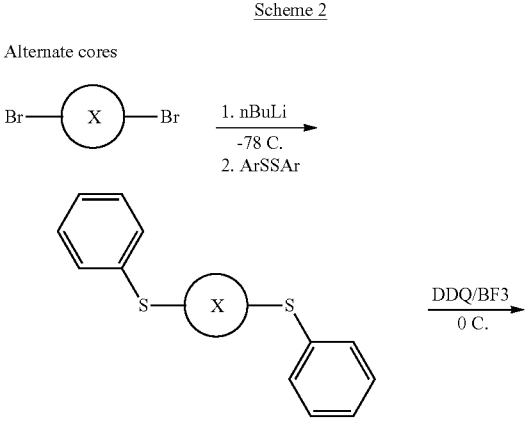

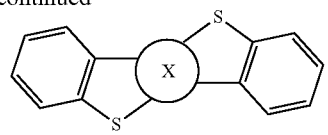
In one embodiment of PLX-2 according to formula (II), wherein each of $R^4$, $R^5$, $R^6$ and $R^7$ is hydrogen, the hole transporting compound can be synthesized, for example, as follows.
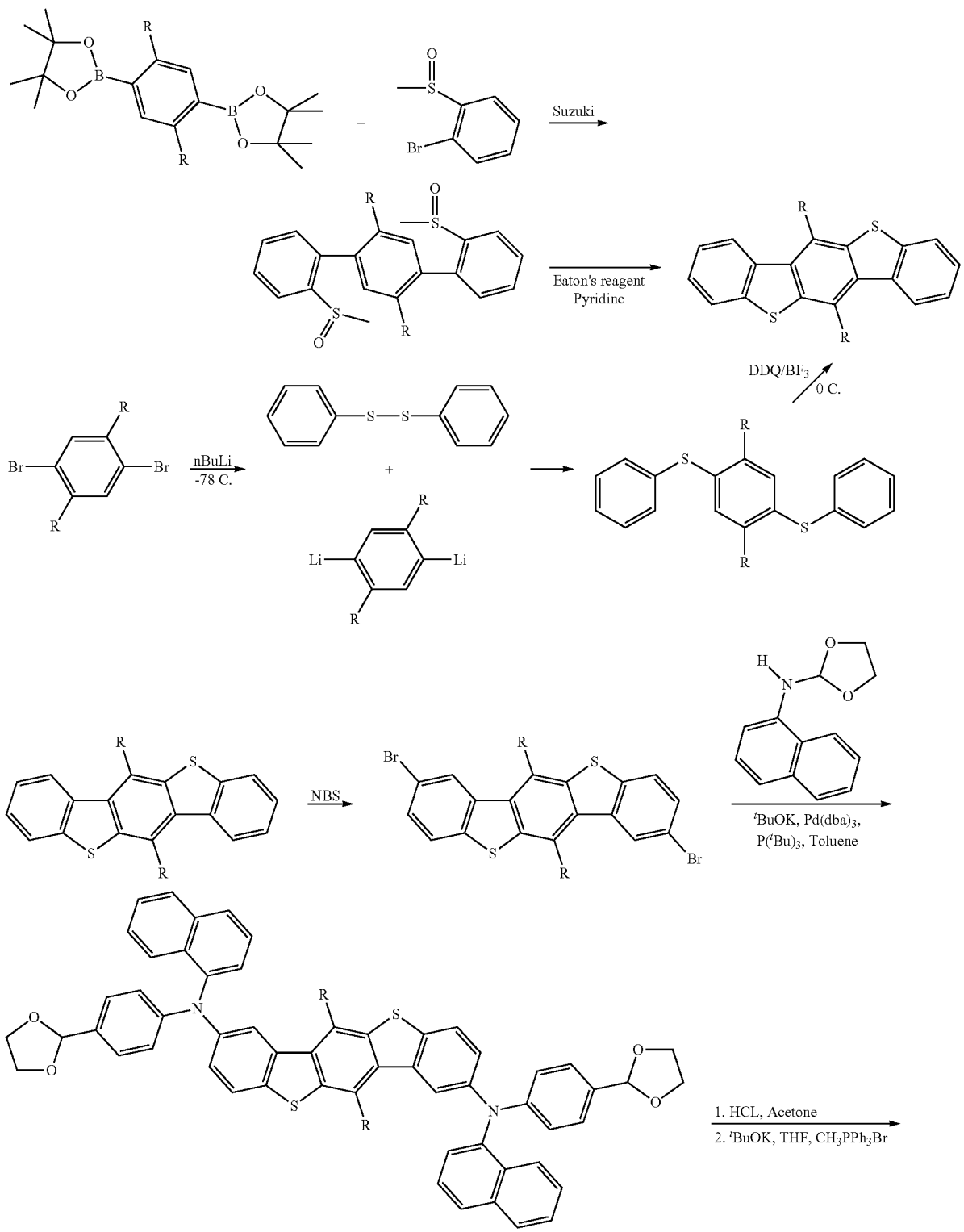

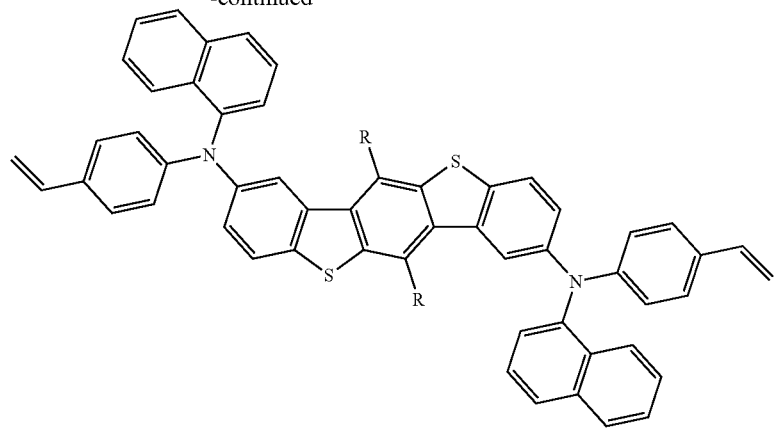

3. Synthesis of PLX-3

PLX-3 hole transporting compound can be synthesized according to, for example, the following steps: linking at least two heteroring moieties to an aryl or heteroaryl moiety form a hole transporting core, wherein said aryl or heteroaryl moiety comprises at least two substituents such as optionally substituted alkoxy or aryloxy; functioning the hole transporting core with arylamine groups; and optionally forming one or more intractability groups on either the hole transporting core or the arylamine groups via deprotection.

In one embodiment, the aryl or heteroaryl moiety is phenyl. In another embodiment, the aryl or heteroaryl moiety is naphthyl.

In one embodiment, the heteroring moiety is thiophene.

For example, PLX-3 hole transporting compound can be synthesized according to Scheme 3.

Scheme 3

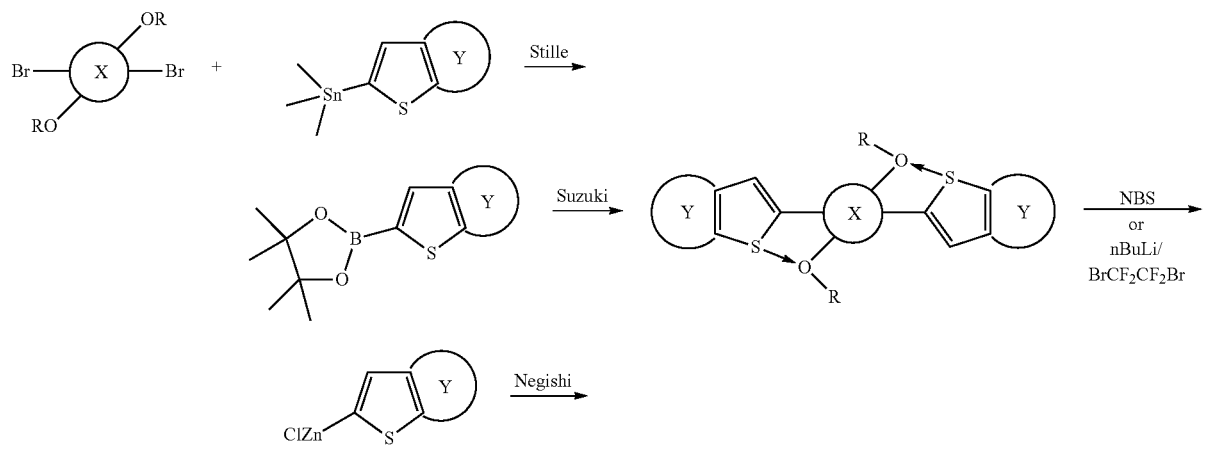

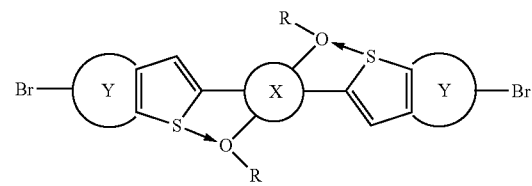

In one embodiment of PLX-3 according to formula (III), wherein Ar¹ is phenyl and each of $R^9$ and $R^{10}$ is hydrogen, the hole transporting compound can be synthesized, for example, as follows.
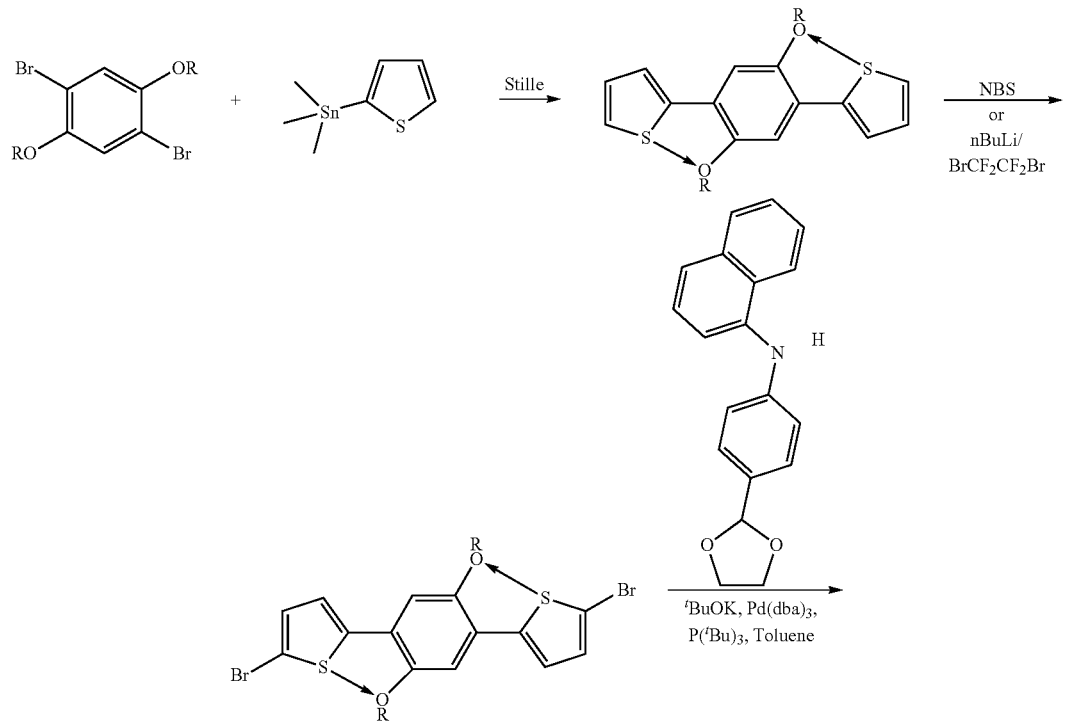
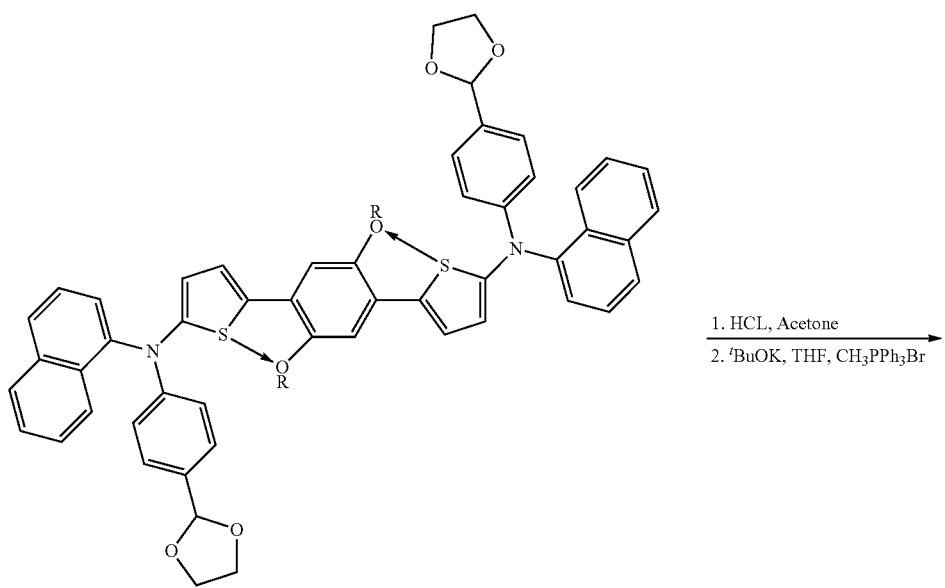

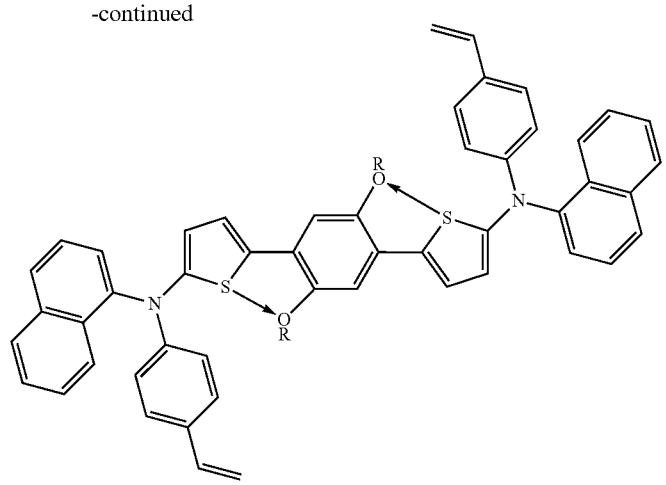
In another embodiment of PLX-3 according to formula (III), wherein $Ar^1$ is naphthyl and each of $R^9$ and $R^{10}$ is hydrogen, the hole transporting compound can be synthesized, for example, as follows.
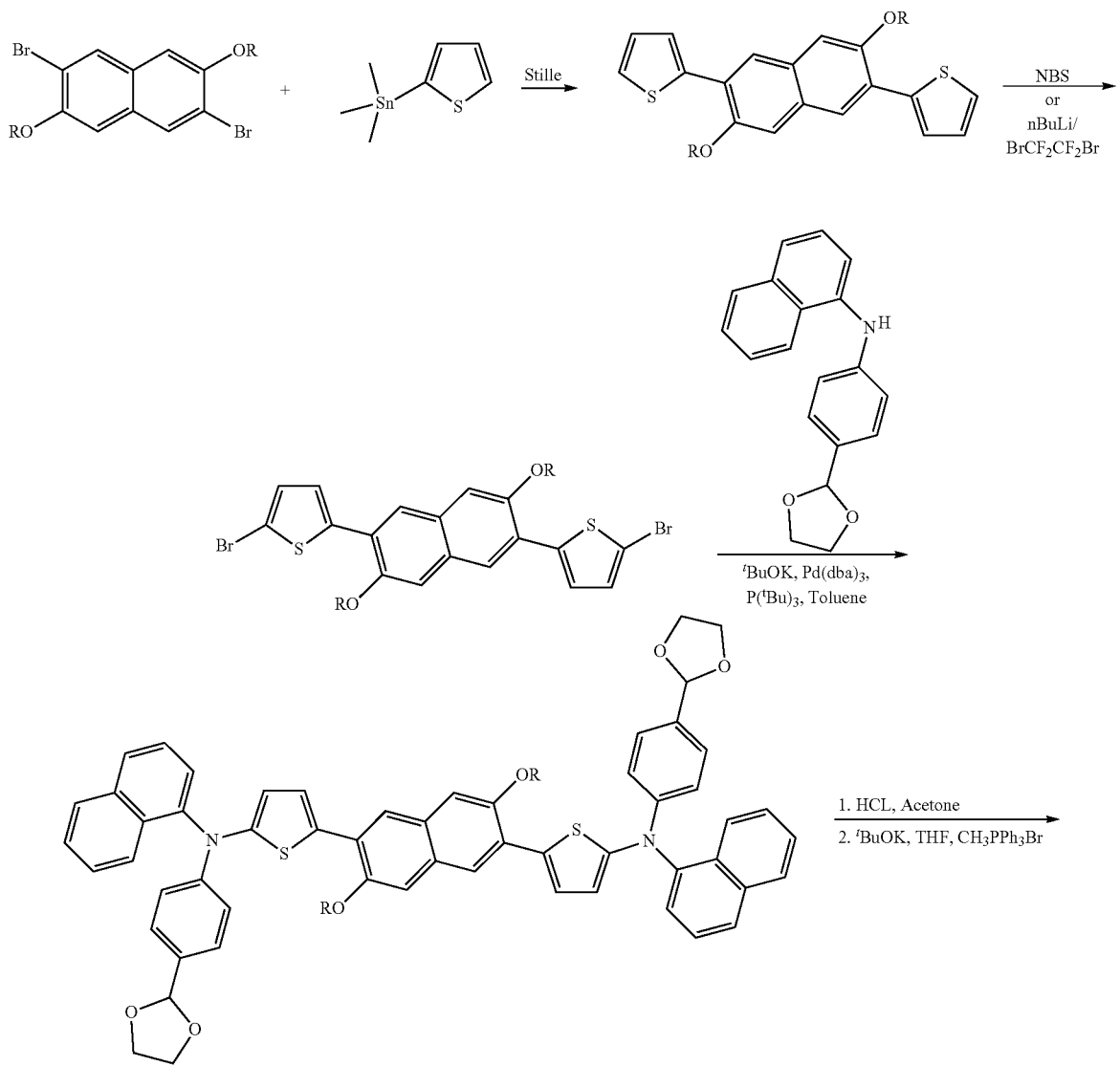

-continued

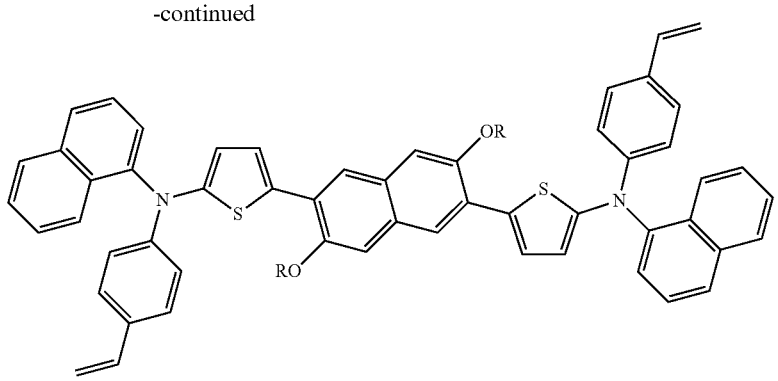

4. Synthesis of PLX-4

PLX-4 hole transporting compound can be synthesized according to, for example, the following steps: linking at least two fused-ring moieties to an aryl or heteroaryl moiety form a hole transporting core, wherein said aryl or heteroaryl moiety comprises at least two substituents such as optionally substituted alkoxy or aryloxy; functioning the hole transporting core with arylamine groups; and optionally forming one or more intractability groups on either the hole transporting core or the arylamine groups via deprotection.

In one embodiment, the aryl or heteroaryl moiety is biphenyl. In another embodiment, the aryl or heteroaryl moiety is naphthyl.

In one embodiment, the fused-ring moiety is

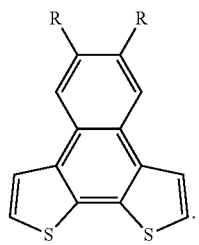

For example, PLX-4 hole transporting compound can be synthesized according to Scheme 3.

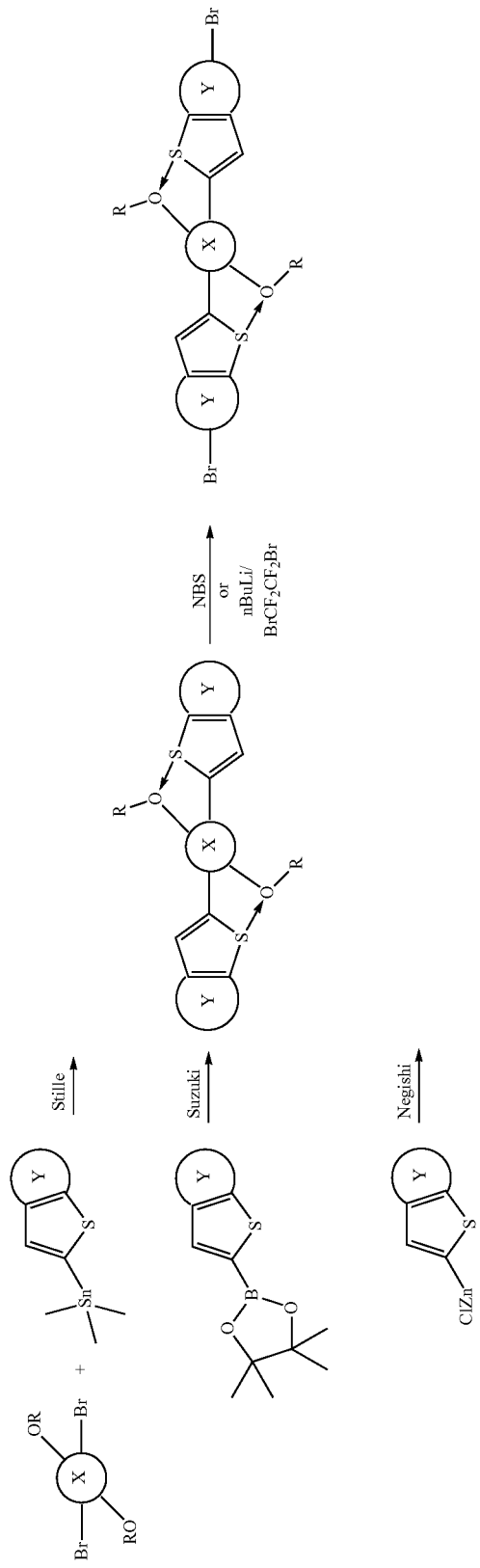

In one embodiment of PLX-4 according to formula (IV), wherein $Ar^2$ is naphthyl and each of $R^{12}$, $R^{13}$ and $R^{14}$ is hydrogen, the hole transporting compound can be synthesized, for example, as follows.
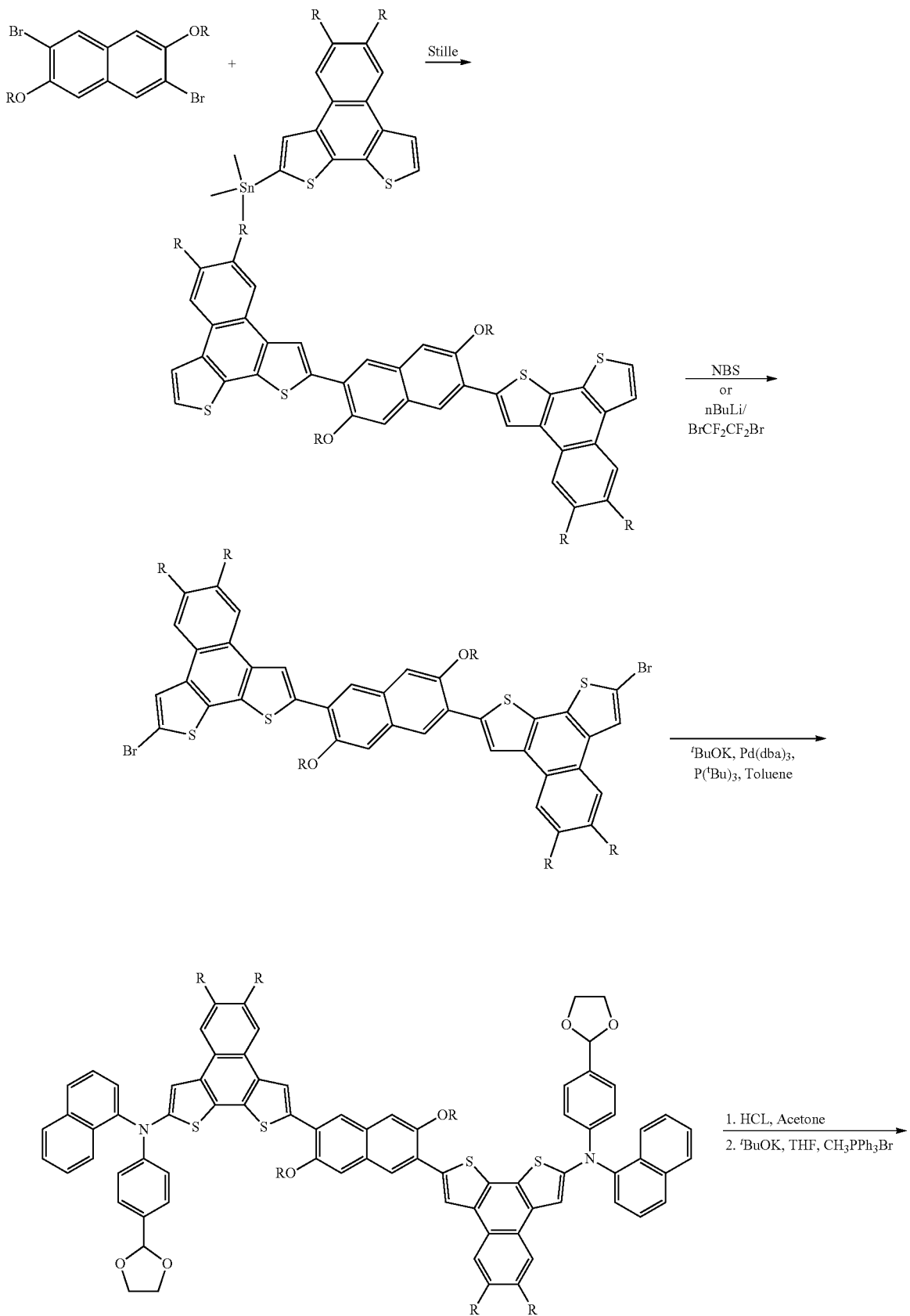

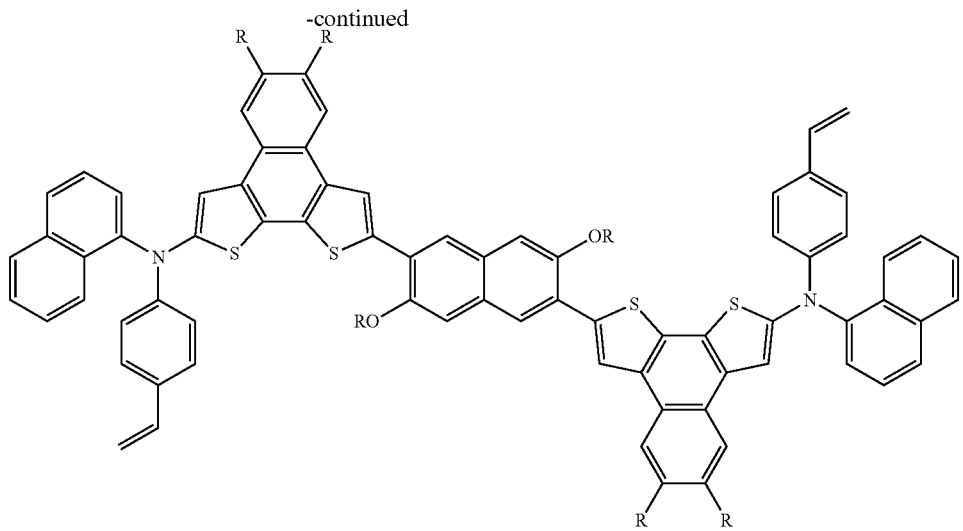
In another embodiment of PLX-4 according to formula (IV), wherein Ar² is biphenyl and each of R¹², R¹³ and R¹⁴ is hydrogen, the hole transporting compound can be synthesized, for example, as follows.
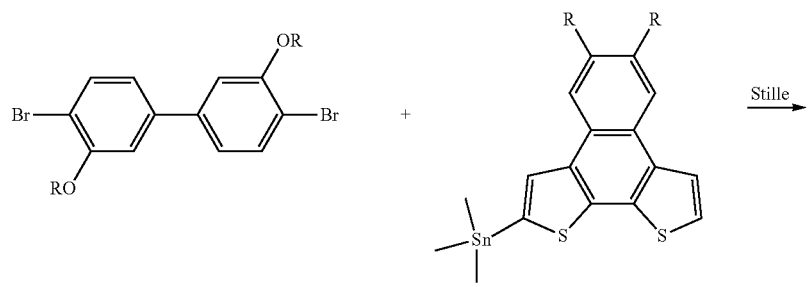
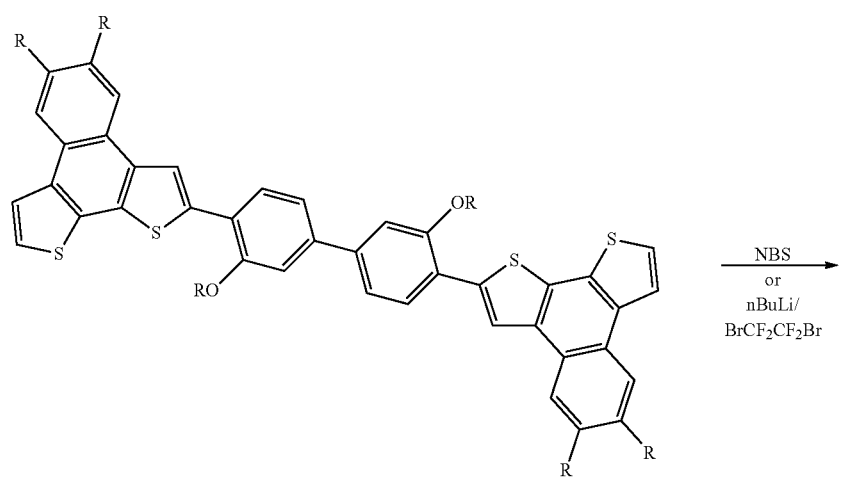

-continued
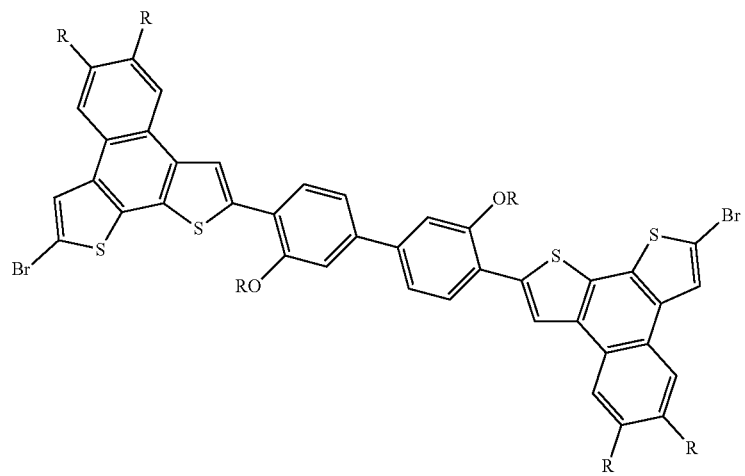
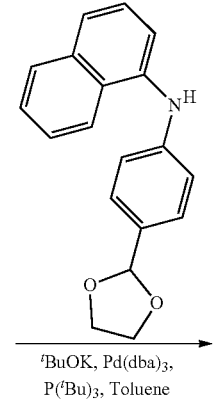
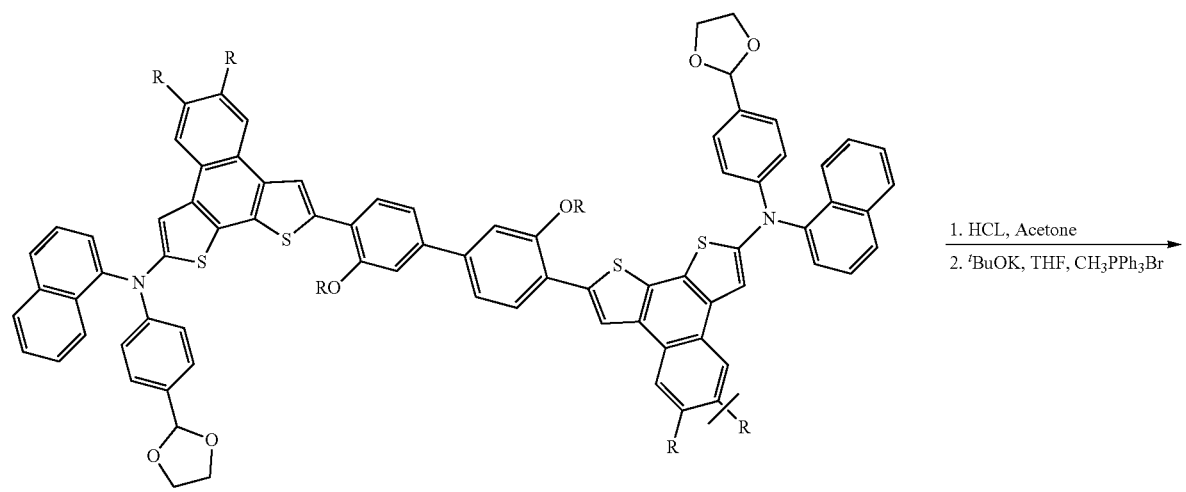
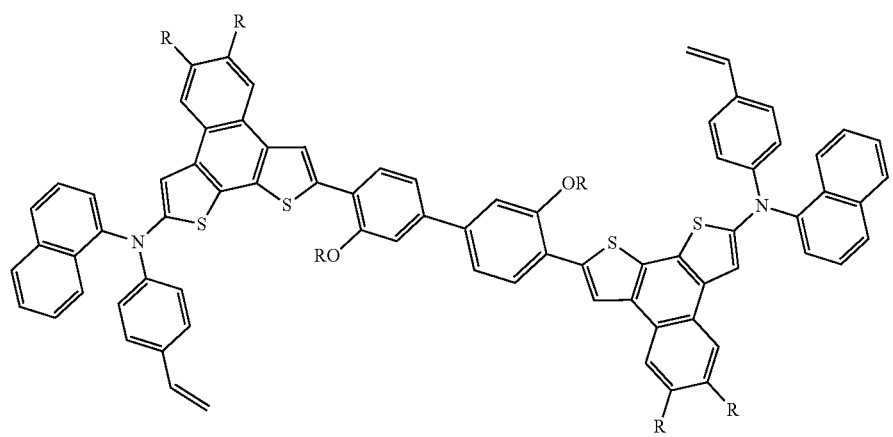

5. Synthesis of PLX-5

PLX-5 hole transporting compound can be synthesized according to, for example, the following steps: linking at least two heteroatom moiety to at least four aryl or heteroaryl moieties in a linear fashion, wherein each heteroatom is connected to two neighboring aryl or heteroaryl moieties; ring-closing to form two heterorings comprising said heteroatoms to form a hole transporting core, each heterering is fused with the two neighboring aryl or heteroaryl moieties; functioning the hole transporting core with arylamine groups; and optionally forming one or more intractability groups on either the hole transporting core or the arylamine groups via deprotection.

In one embodiment, the aryl or heteroaryl moieties include phenyl and thiophene.

In one embodiment, the heteroatom moiety is S, O, NR, $CR_2$, $SiR_2$ or $GeR_2$, and wherein each R is an optionally substituted alkyl, aryl, heteroalkyl, heteroaryl, or vinyl group.

For example, PLX-5 hole transporting compound can be synthesized according to Scheme 1.

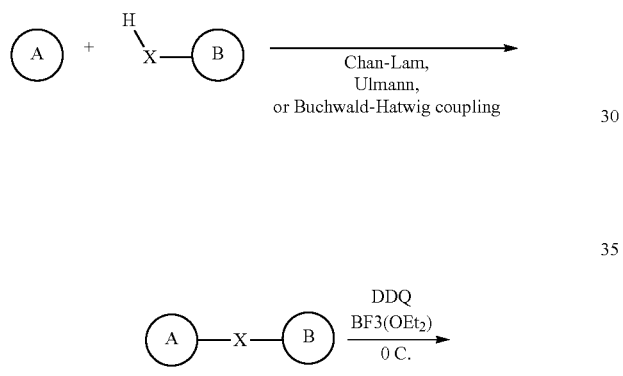

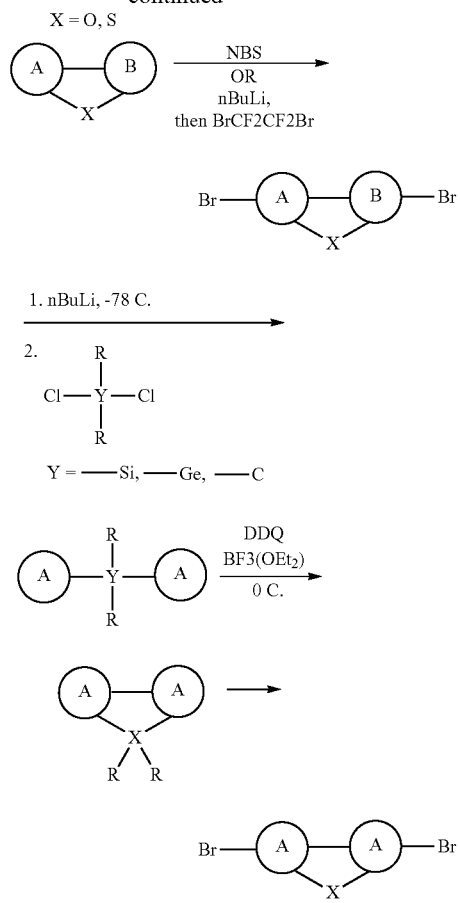

In one embodiment of PLX-5 according to formula (VI), wherein $X^2$ is O and each of $R^{15}$ and $R^{16}$ is hydrogen, the hole transporting compound can be synthesized, for example, as follows.

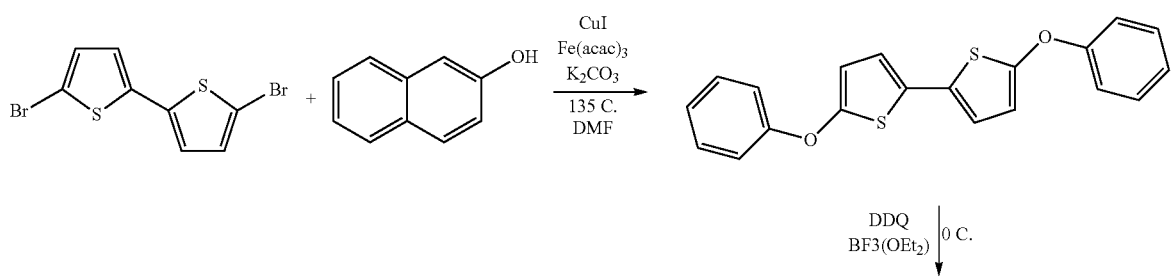

-continued
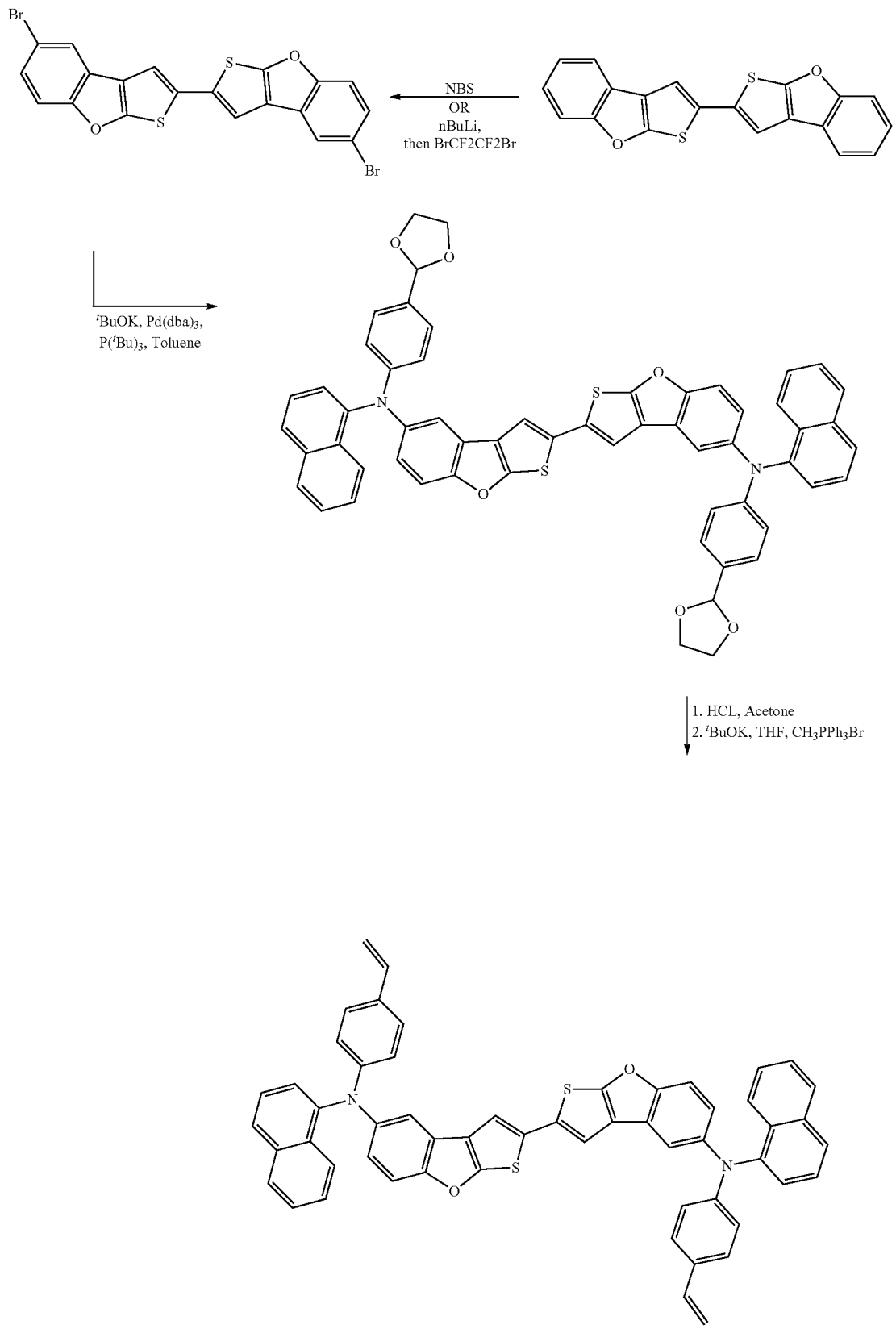

In one embodiment of PLX-5 according to formula (VII), wherein $X^3$ is O and each of $R^{17}$ and $R^{18}$ is hydrogen, the hole transporting compound can be synthesized, for example, as follows.
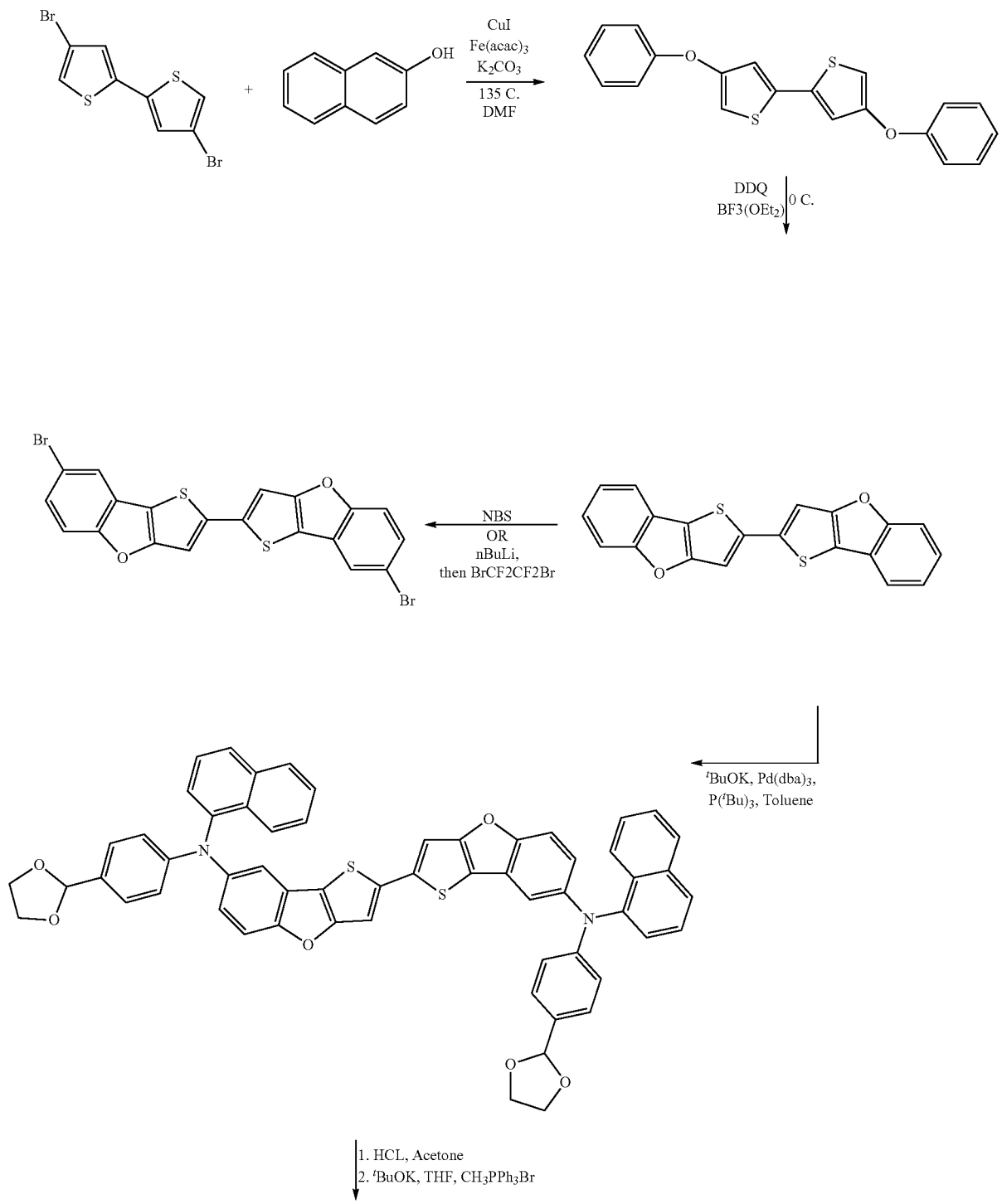

-continued

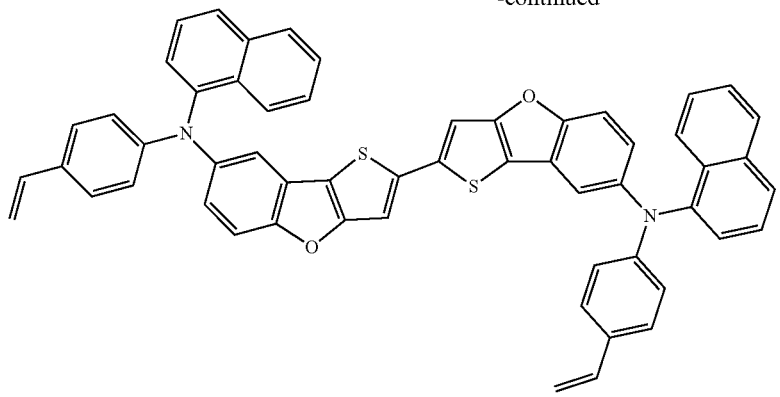

Further, PLX-5 hole transporting compound can also be synthesized according to, for example, the following steps: linking at least four aryl or heteroaryl moieties in a linear fashion, wherein at least two of said aryl or heteroaryl moieties comprise substituent groups; ring-closing to form a hole transporting core comprising two fuse-ring moieties, each fuse-ring moiety comprises at least three rings fused together; functioning the hole transporting core with arylamine groups; and optionally forming one or more intractability groups on either the hole transporting core or the arylamine groups via deprotection.

In one embodiment, the aryl or heteroaryl moieties include phenyl and thiophene.

For example, PLX-5 hole transporting compound can be synthesized according to Scheme 4.

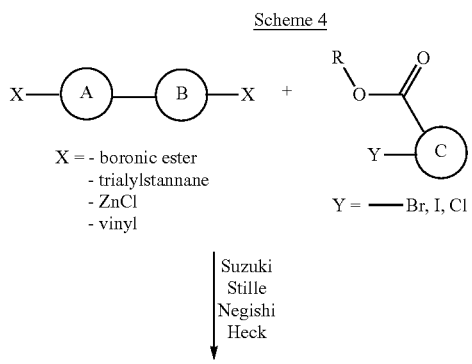

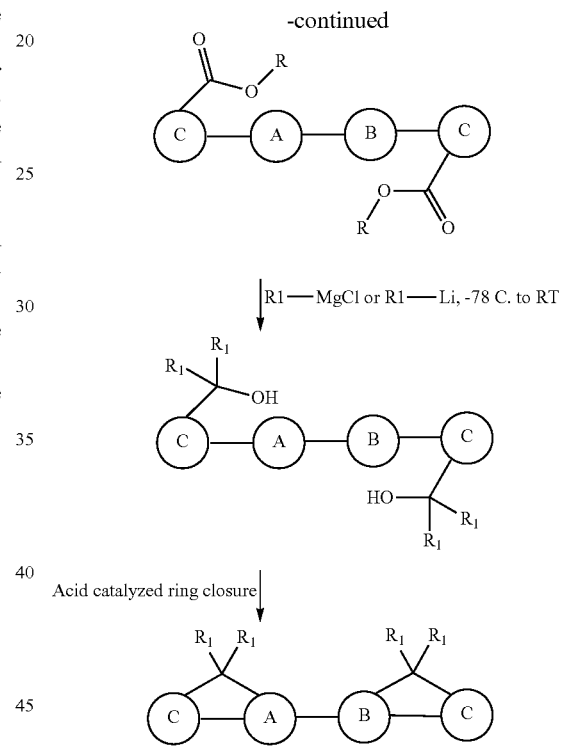

In one embodiment of PLX-5 according to formula (VII), wherein $X^3$ is $CR_2$ and each of $R^{17}$ and $R^{18}$ is hydrogen, the hole transporting compound can be synthesized, for example, as follows.

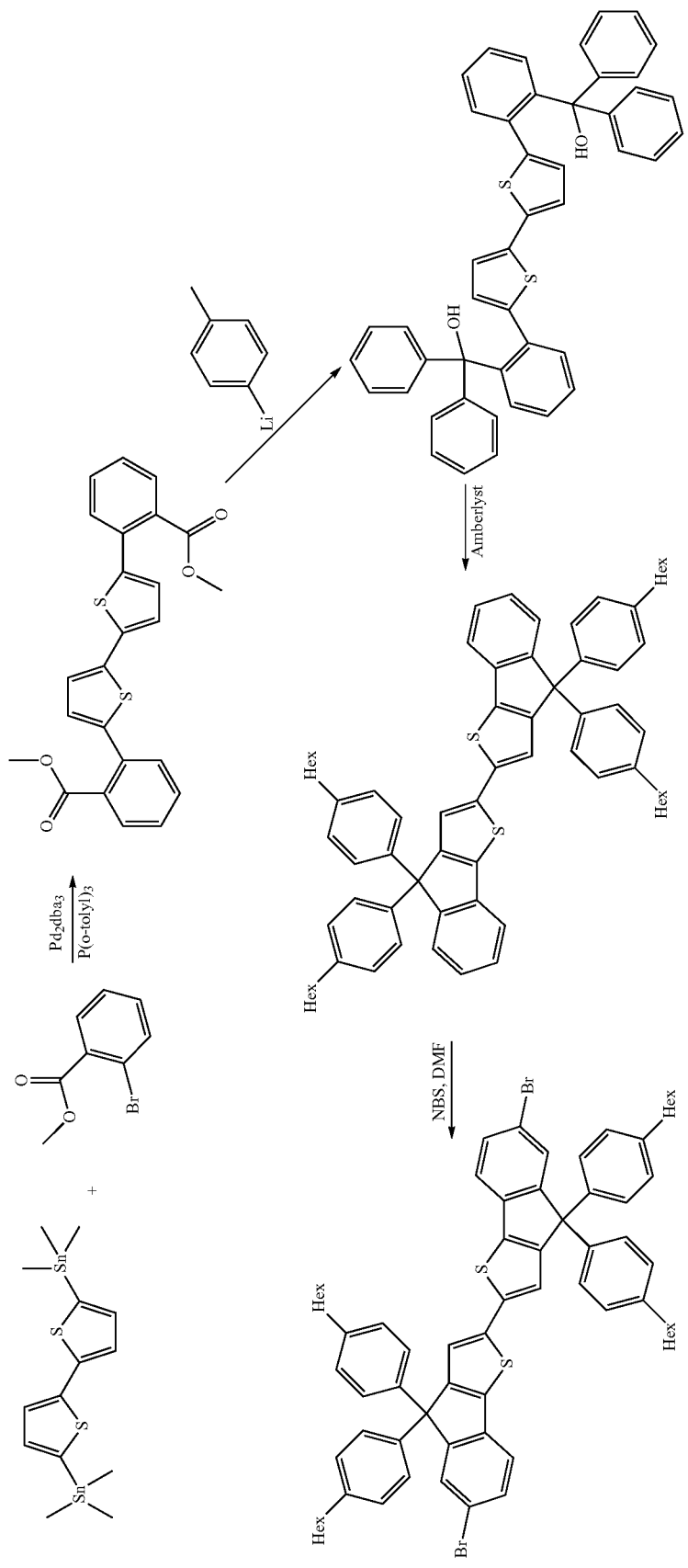

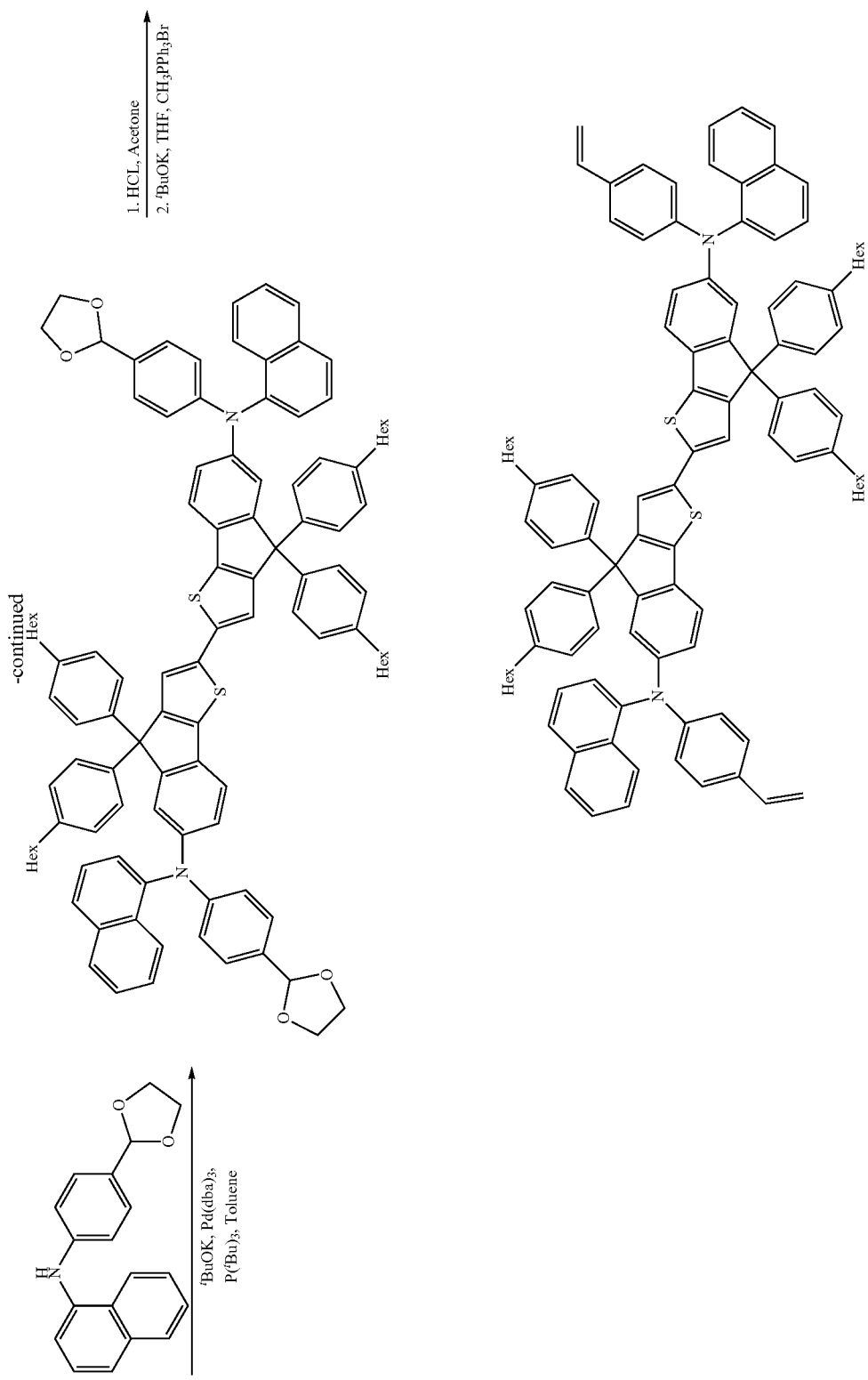

In one embodiment of PLX-5 according to formula (VIII), wherein $X^4$ is $CR_2$ and each of $R^{19}$ and $R^{20}$ is hydrogen, the hole transporting compound can be synthesized, for example, as follows.

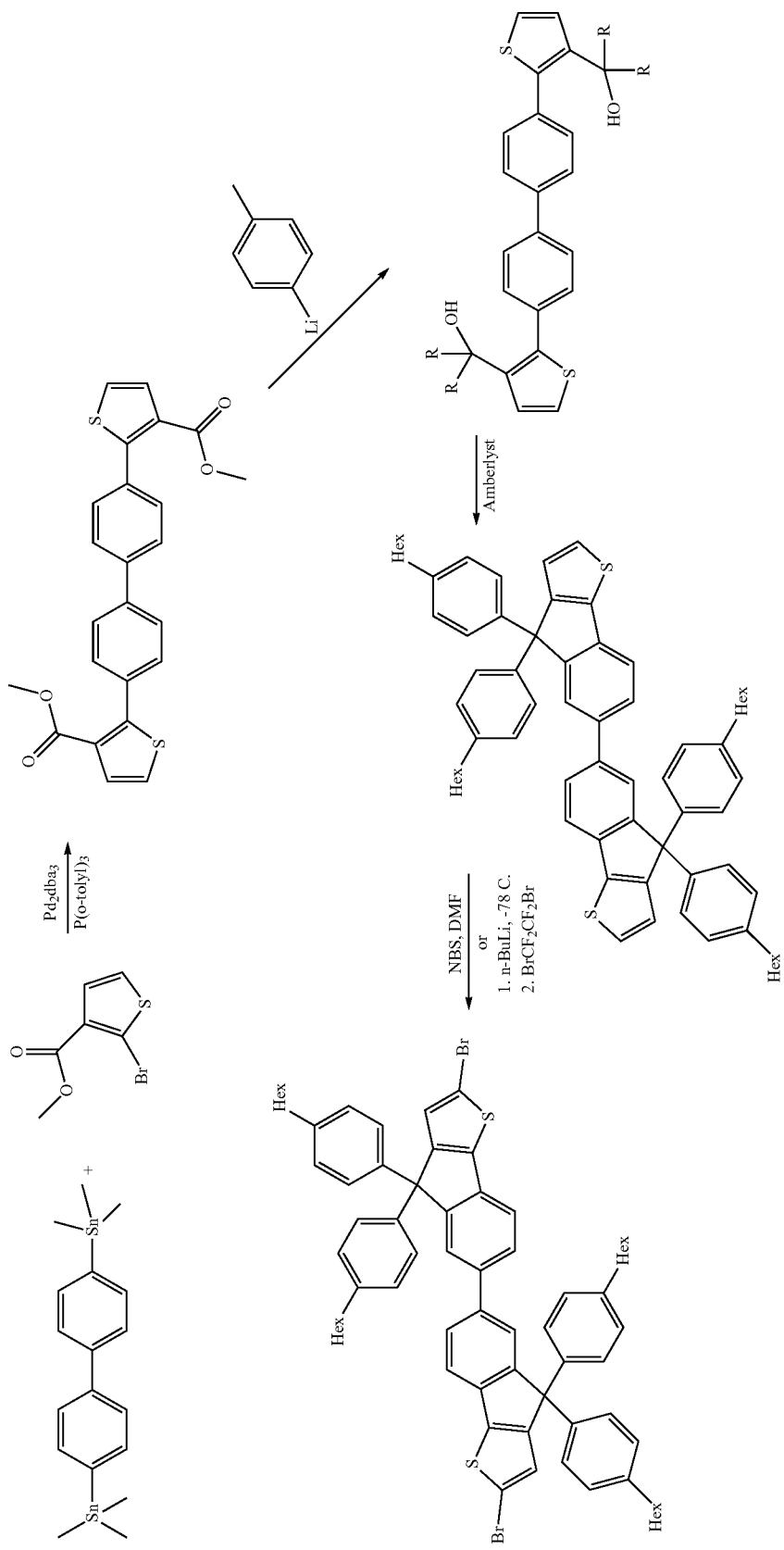

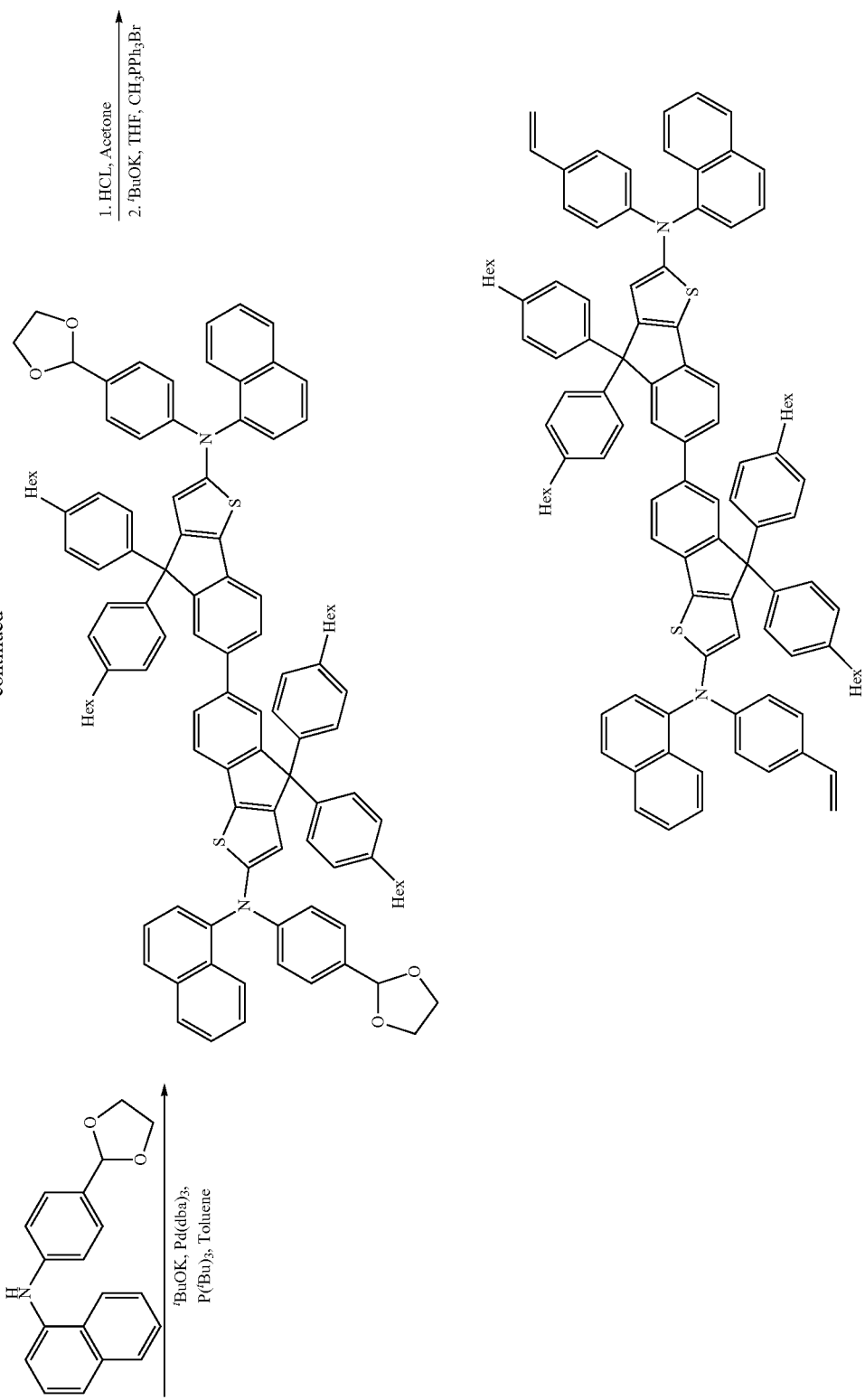

6. Synthesis of PLX-6

PLX-6 hole transporting compound can be synthesized according to, for example, the following steps: linking at least two heteroatom moieties to at least three aryl or heteroaryl moieties to form a structure of alternating heteroatoms and aryl or heteroaryl moieties; ring-closing to form at least two heterorings comprising said heteroatoms, said heterorings are fused with said aryl or heteroaryl moieties to form a hole transporting core comprising at least six rings fused together; functioning the hole transporting core with arylamine groups; and optionally forming one or more intractability groups on either the hole transporting core or the arylamine groups via deprotection.

In one embodiment, the aryl or heteroaryl moieties include phenyl and naphthyl. In another embodiment, the aryl or heteroaryl moieties include thiophene and naphthyl. In a further embodiment, the aryl or heteroaryl moieties include phenyl and

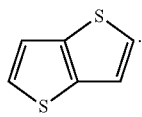

In one embodiment, the heteroatom moiety is S, O, NR, $CR_2$, $SiR_2$ or $GeR_2$, and wherein each R is an optionally substituted alkyl, aryl, heteroalkyl, heteroaryl, or vinyl group.

For example, PLX-6 hole transporting compound can be synthesized according to Schemes 5 and 6.

Scheme 5
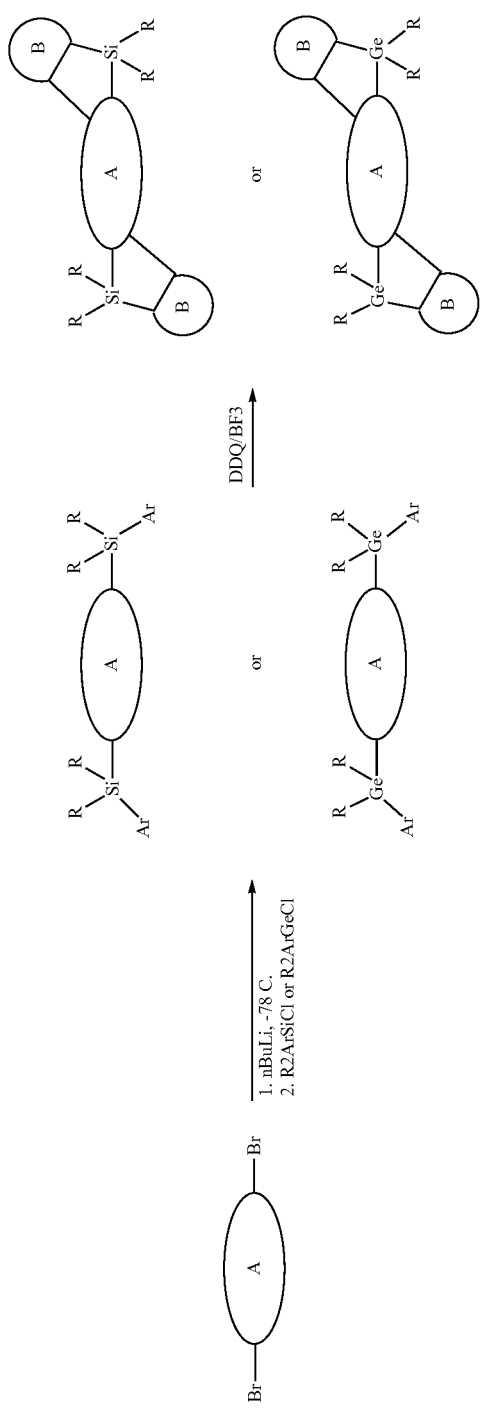

Scheme 6
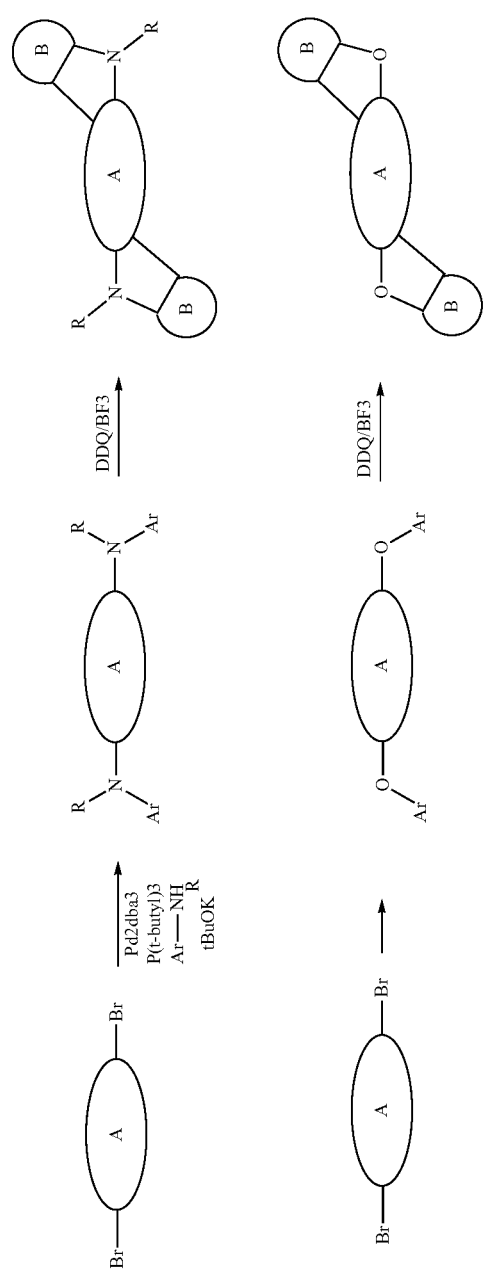

In one embodiment of PLX-6 according to formula (X), wherein $X^5$ is $SiR_2$ and each of $R^{21}$ and $R^{22}$ is hydrogen, the hole transporting compound can be synthesized, for example, as follows.
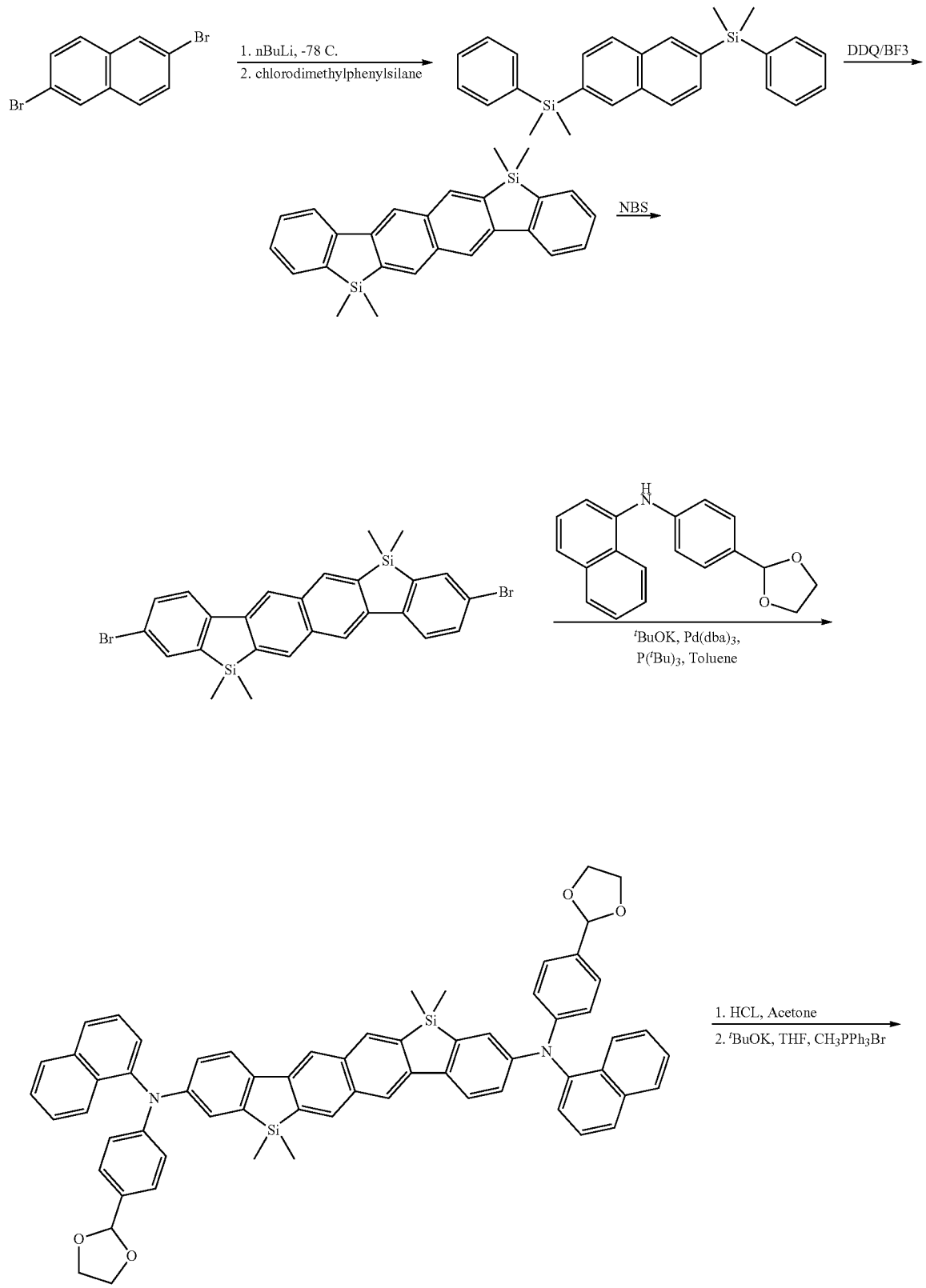

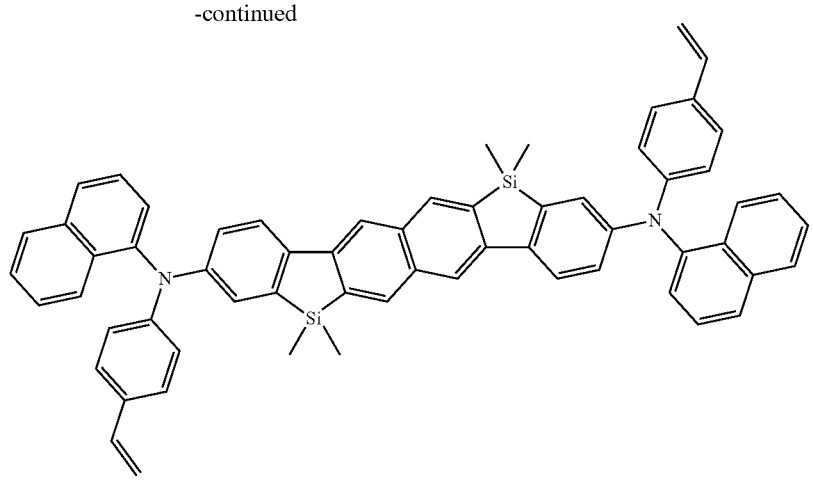
In another embodiment of PLX-6 according to formula (X), wherein $X^5$ is $GeR_2$ and each of $R^{21}$ and $R^{22}$ is hydrogen, the hole transporting compound can be synthesized, for example, as follows.
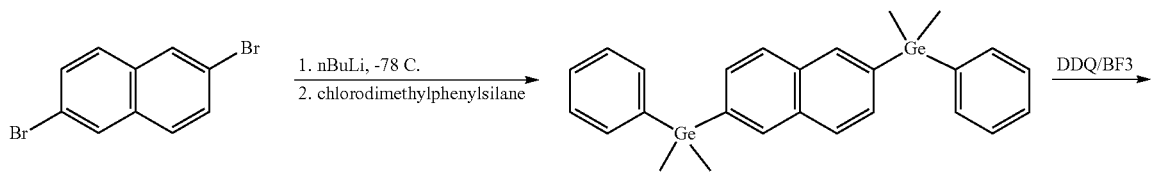
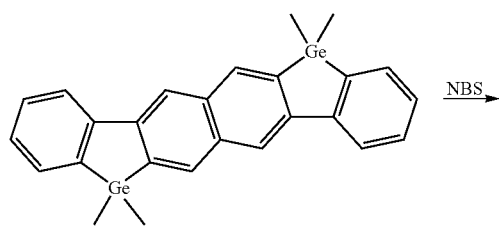
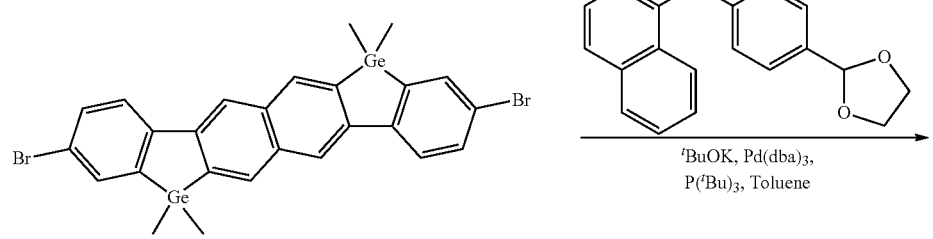

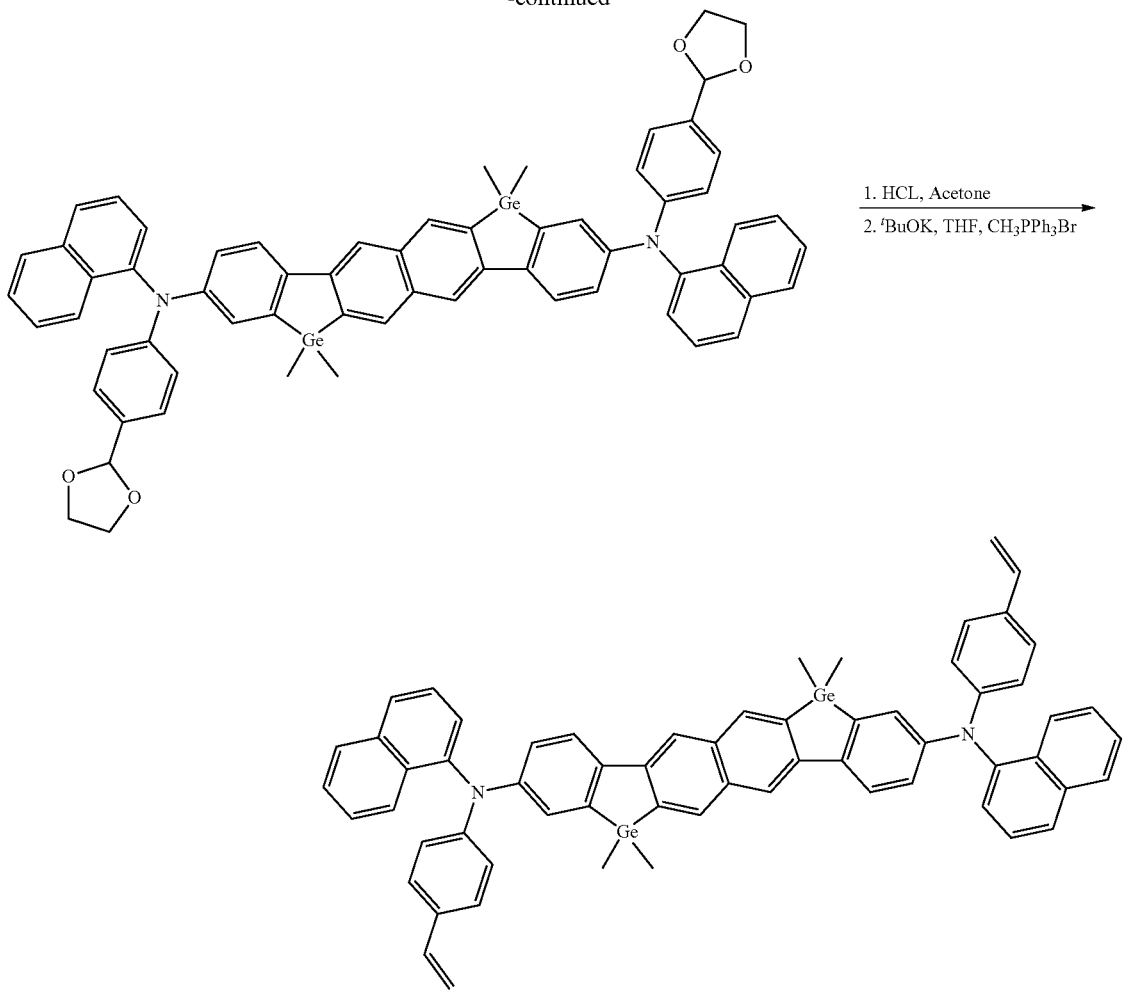
In a further embodiment of PLX-6 according to formula (XI), wherein $X^6$ is $SiR_2$ and each of $R^{23}$ and $R^{24}$ is hydrogen, the hole transporting compound can be synthesized, for example, as follows.
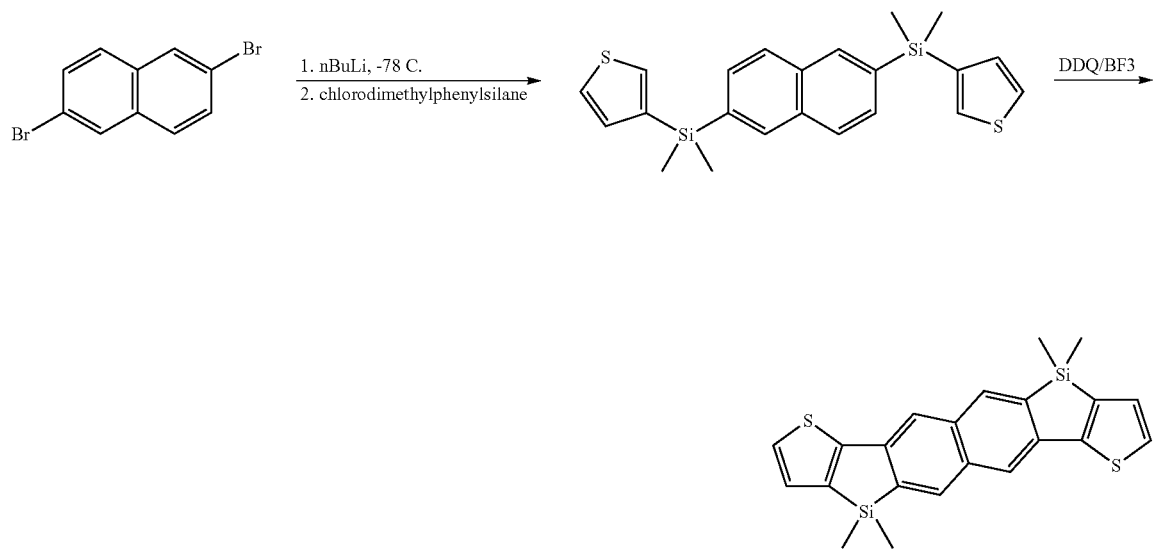

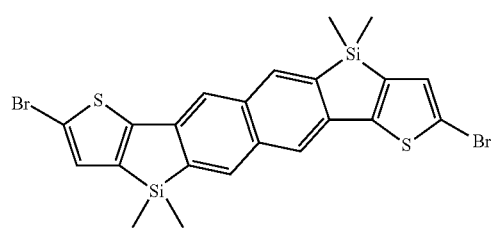
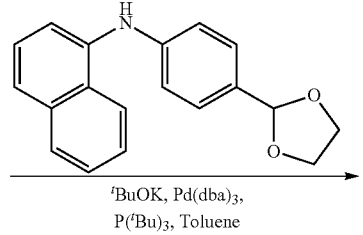
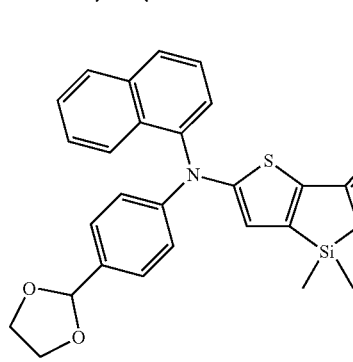
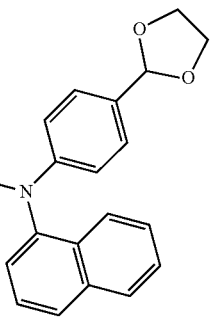
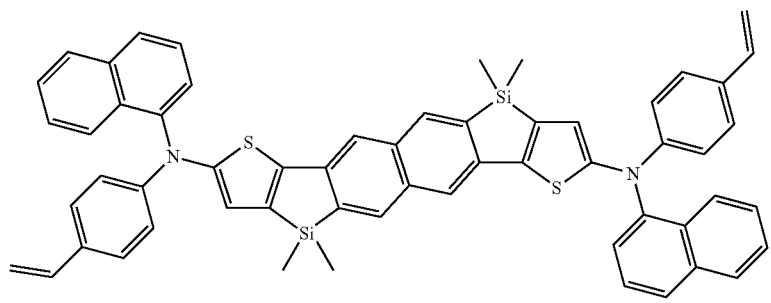
In an additional embodiment of PLX-6 according to formula (XII), wherein $X^7$ is $SiR_2$ and each of $R^{25}$ and $R^{26}$ is hydrogen, the hole transporting compound can be synthesized, for example, as follows.
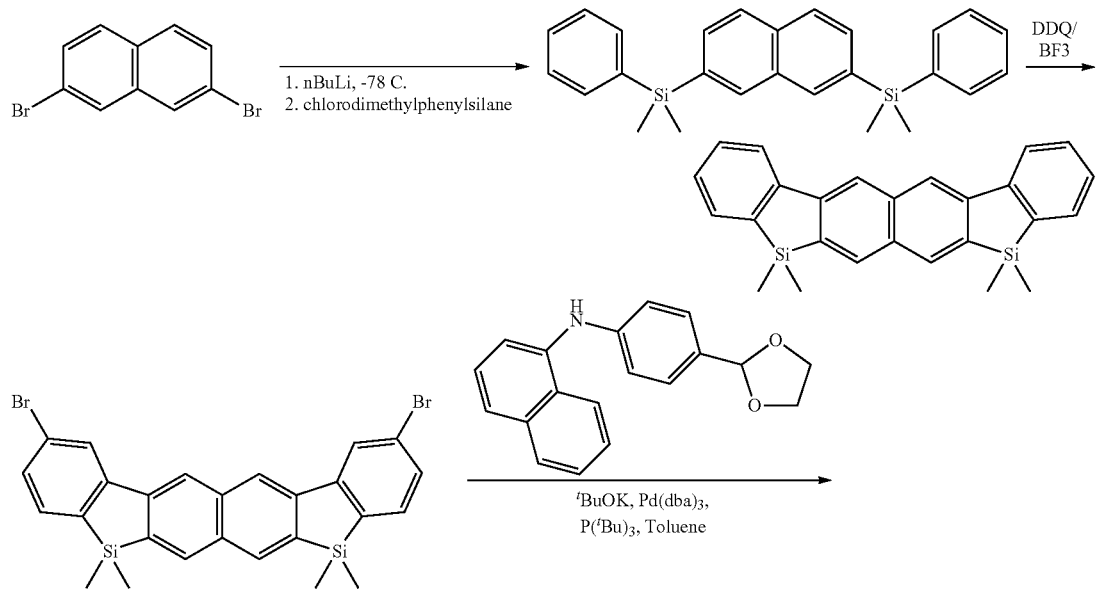

-continued
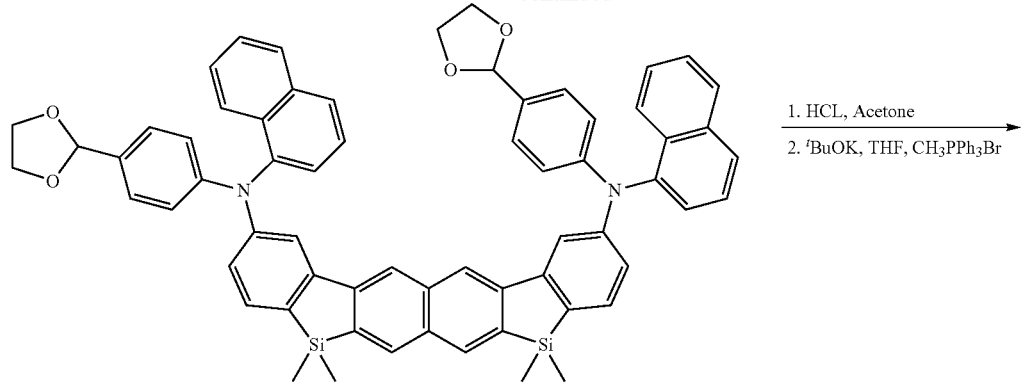
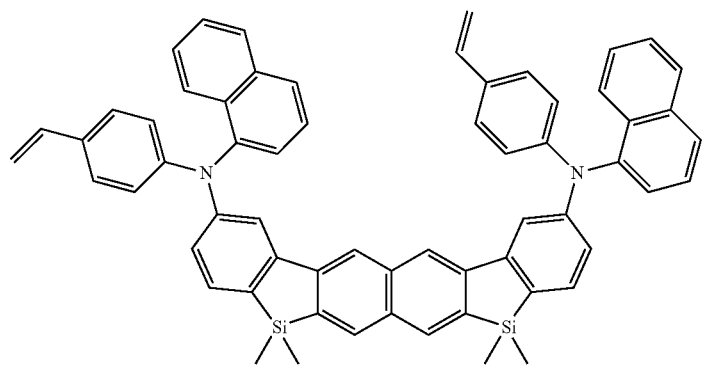
In yet another embodiment of PLX-6 according to formula (XIII), wherein $X^8$ is $CR_2$ and each of $R^{27}$ is hydrogen, the hole transporting compound can be synthesized, for example, as follows.
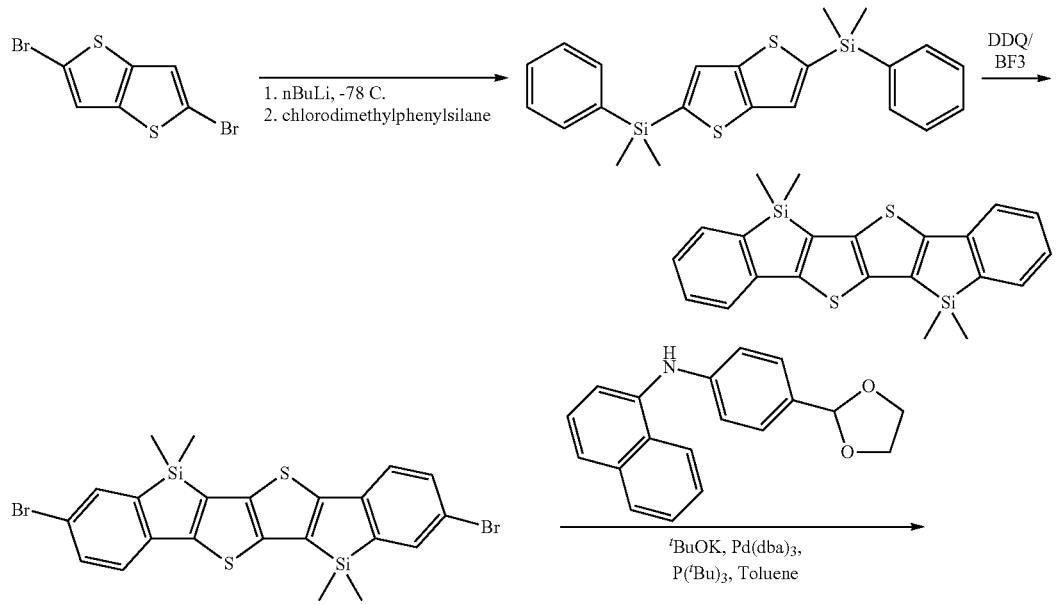

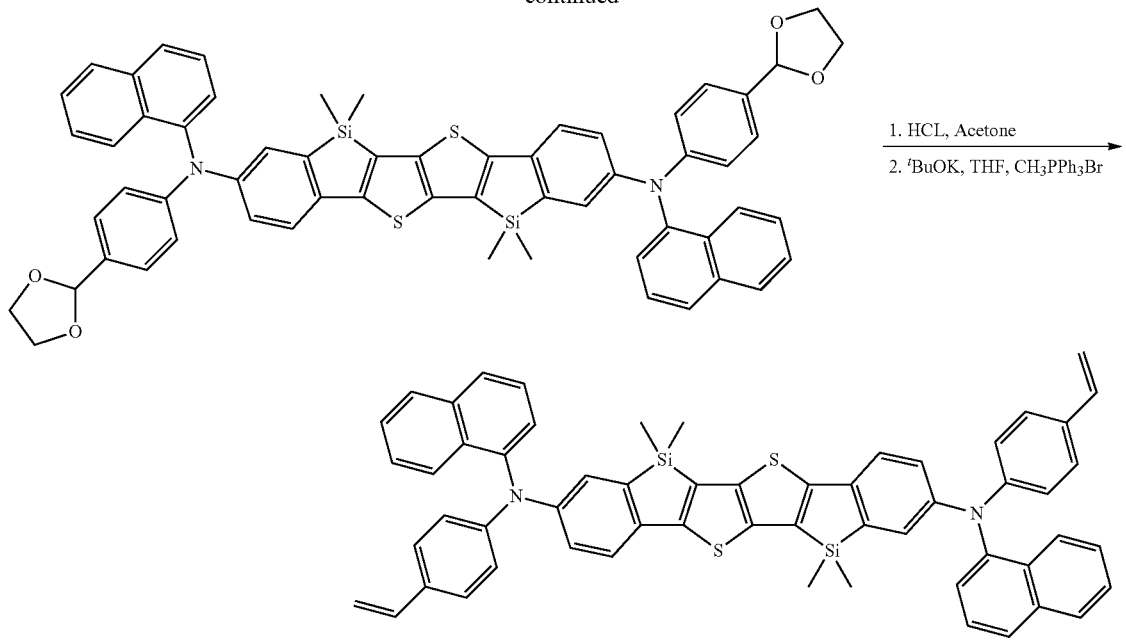

7. Synthesis of PLX-7

PLX-7 hole transporting compound can be synthesized according to, for example, the following steps: linking a first heteroatom moiety to at least two aryl or heteroaryl moieties to form an intermediate; ring-closing by reacting the intermediate with a second heteroatom moiety to form a heteroring comprising both the first heteroatom and the second heteroatom, said heteroring is fused with said aryl or heteroaryl moieties to form a hole transporting core comprising at least three rings fused together; functioning the hole transporting core with arylamine groups; and optionally forming one or more intractability groups on either the hole transporting core or the arylamine groups via deprotection.

In one embodiment, the aryl or heteroaryl moiety is phenyl.

In one embodiment, the first heteroatom moiety is S, O, NR, CR$_2$, SiR$_2$ or GeR$_2$, and wherein each R is an optionally substituted alkyl, aryl, heteroalkyl, heteroaryl, or vinyl group.

In one embodiment, the second heteroatom moiety is S, O, NR, CR$_2$, SiR$_2$ or GeR$_2$, and wherein each R is an optionally substituted alkyl, aryl, heteroalkyl, heteroaryl, or vinyl group.

In one embodiment according to formula (XIV), wherein X$^9$ is NR, X$^{10}$ is SiR$_2$, and each of R$^{28}$ is hydrogen, the core of the PLX-7 hole transporting compound can be synthesized, for example, as follows.

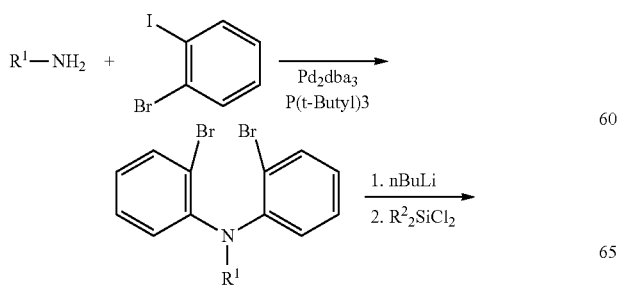

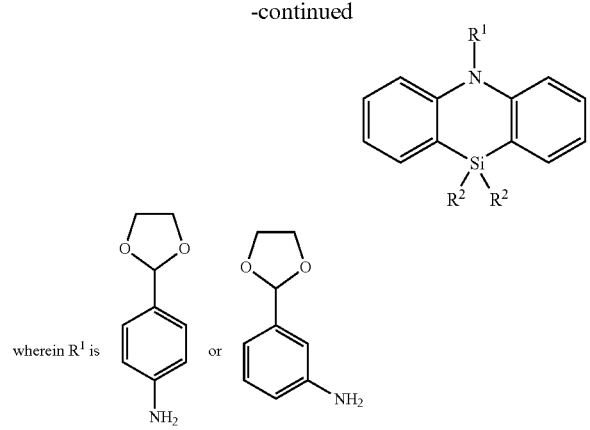

wherein R$^1$ is

In another embodiment according to formula (XIV), wherein X$^9$ is NR, X$^{10}$ is GeR$_2$, and each of R$^{28}$ is hydrogen, the core of the PLX-7 hole transporting compound can be synthesized, for example, as follows.

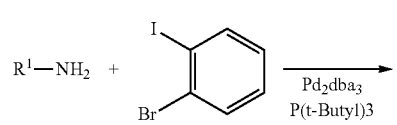

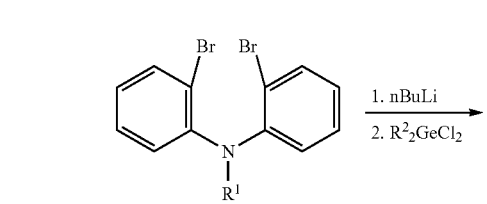

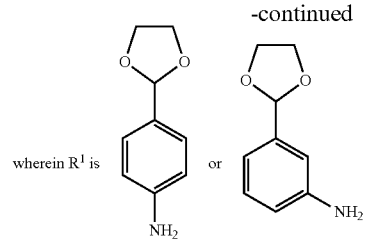

wherein R¹ is

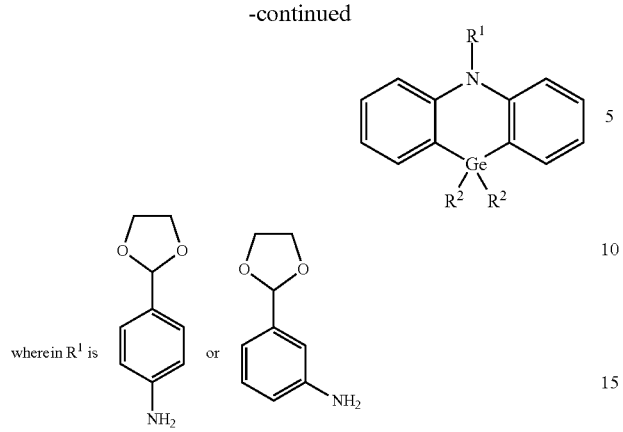

In a further embodiment according to formula (XIV), wherein $X^9$ is NR, $X^{10}$ is $CR_2$, and each of $R^{28}$ is hydrogen, the core of the PLX-7 hole transporting compound can be synthesized, for example, as follows.

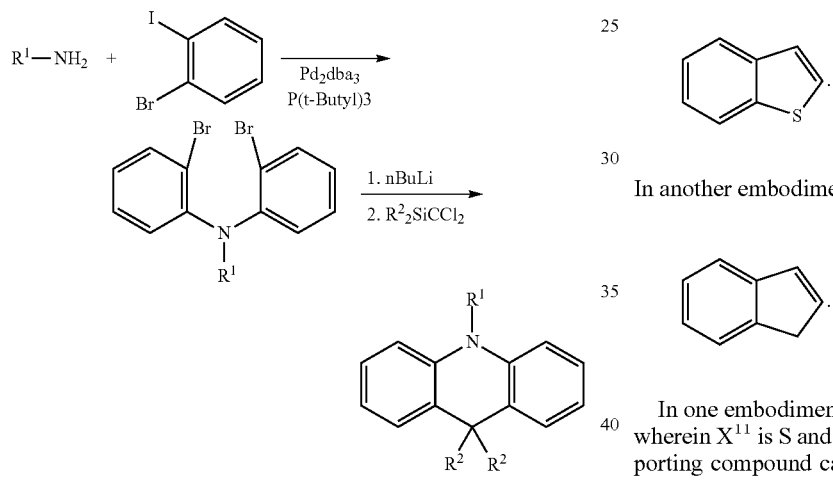

8. Synthesis of PLX-8

PLX-8 hole transporting compound can be synthesized according to, for example, the following steps: linking three fused-ring moieties together; ring-closing to fuse the three fused-ring moieties together and to form a hole transporting core comprising at least seven rings fused together in a star fashion; functioning the hole transporting core with arylamine groups; and optionally forming one or more intractability groups on either the hole transporting core or the arylamine groups via deprotection.

In one embodiment, the fused-ring moiety is

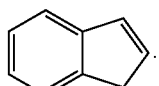

In another embodiment, the fused-ring moiety is

In one embodiment of PLX-8 according to formula (XV), wherein $X^{11}$ is S and each of $R^{29}$ is hydrogen, the hole transporting compound can be synthesized, for example, as follows.

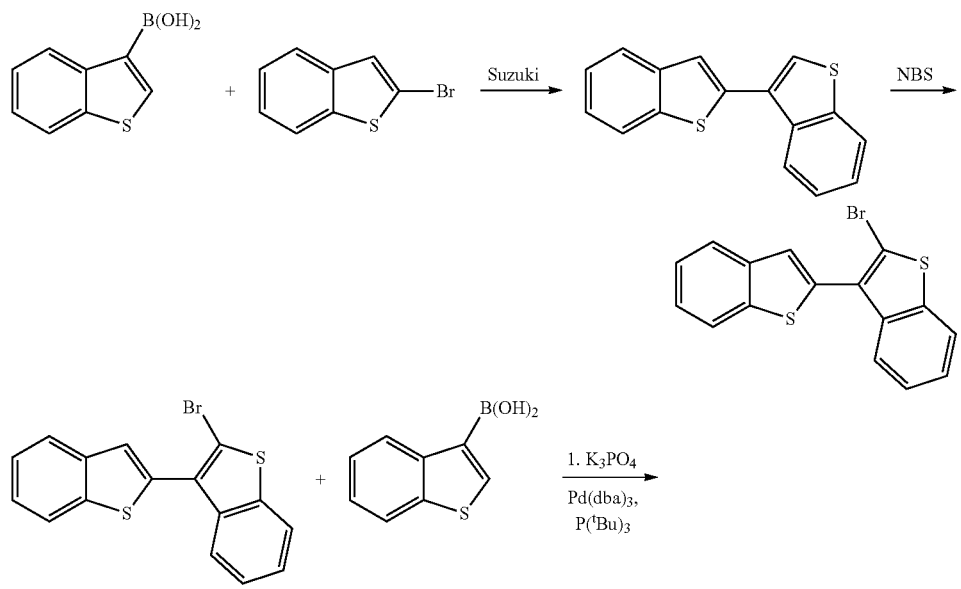

-continued
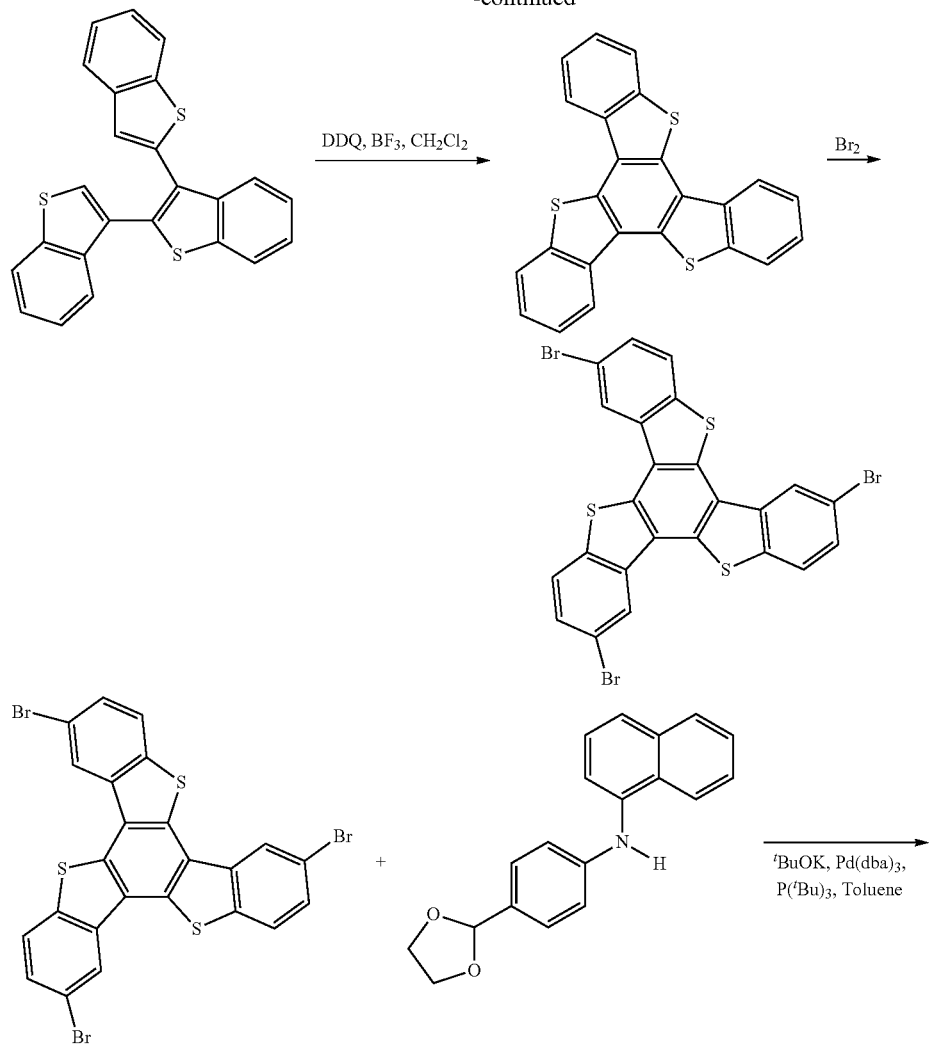
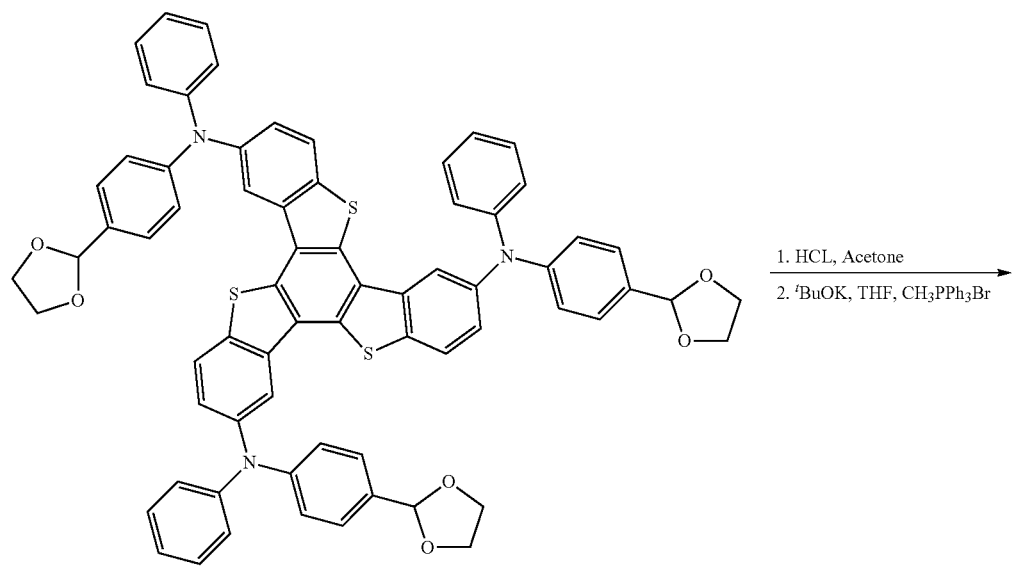

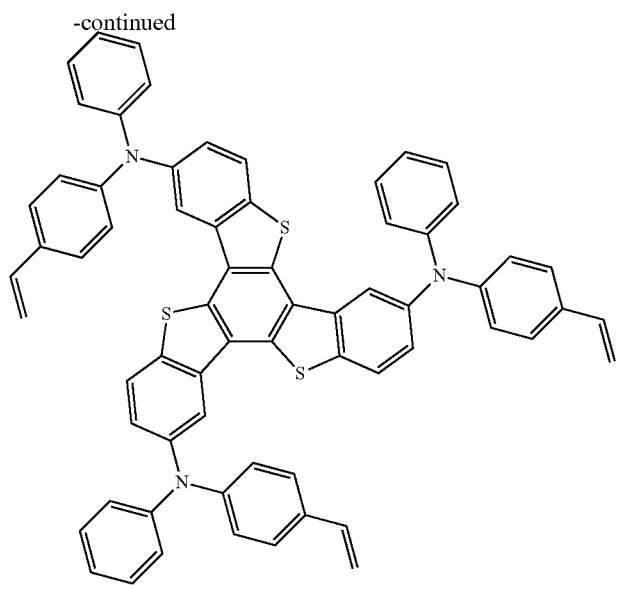
In another embodiment of PLX-8 according to formula (XV), wherein $X^{11}$ is $CR_2$ and each of $R^{29}$ is hydrogen, the hole transporting compound can be synthesized, for example, as follows.
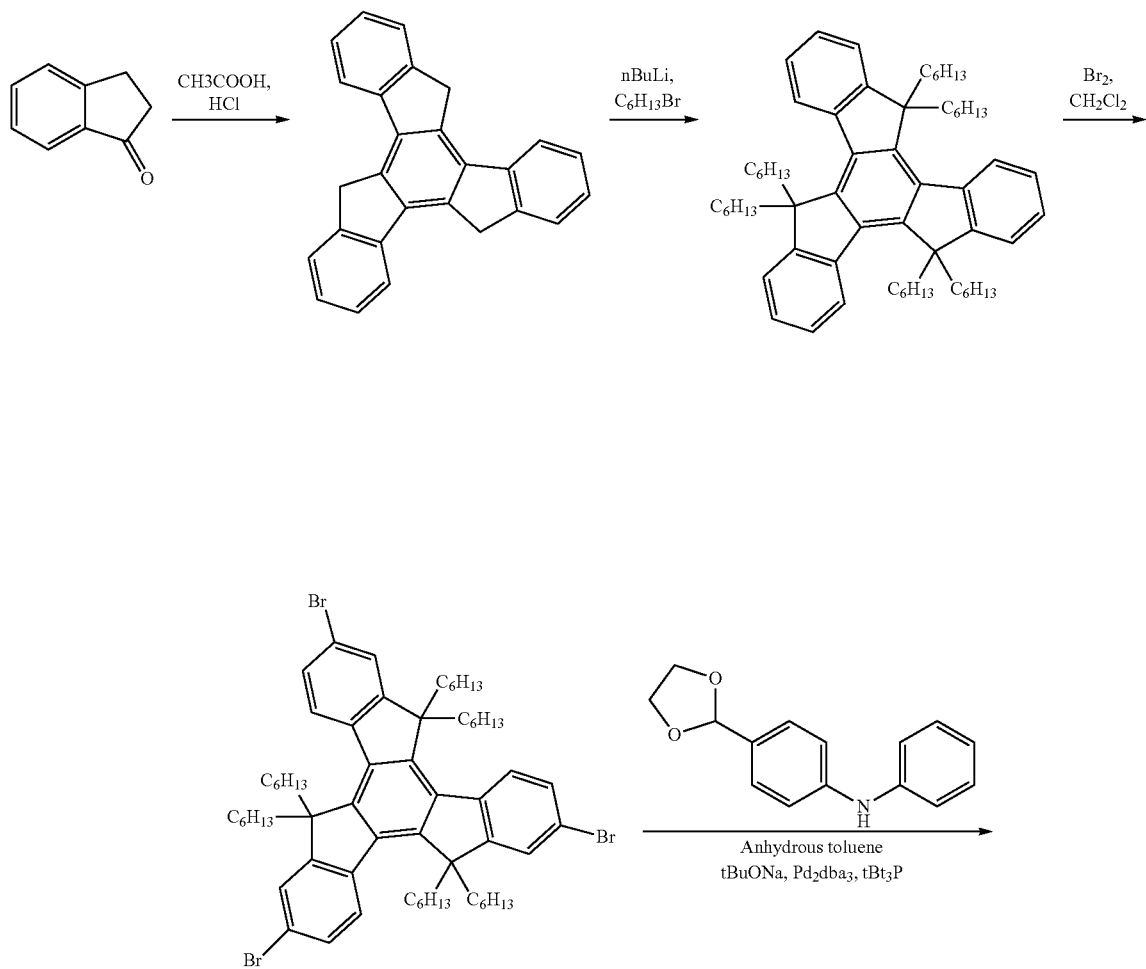

-continued
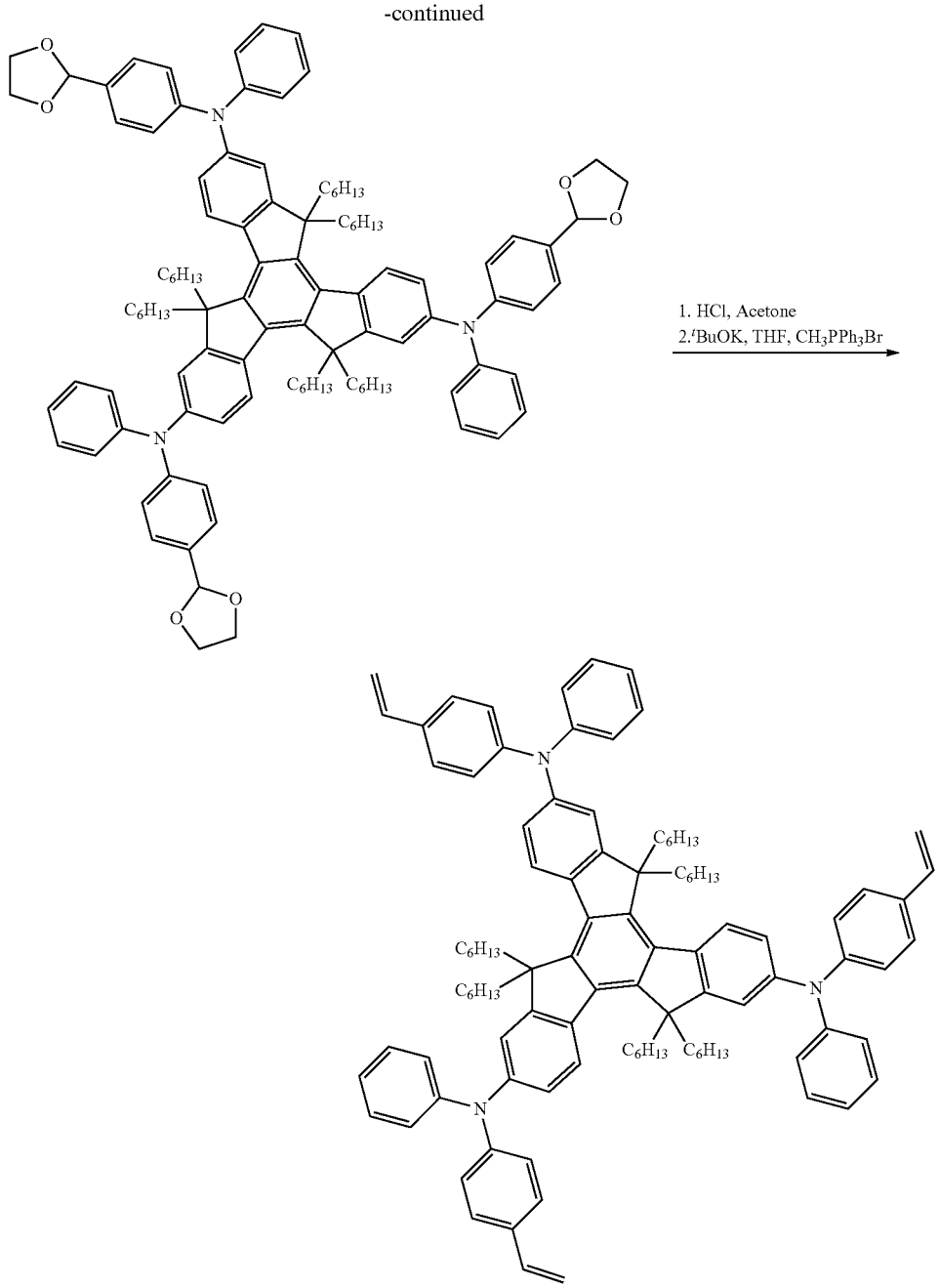
9. Synthesis of PLX-9
In one embodiment of PLX-9 according to formula (XVI), wherein $X^{12}$ is O, $R^{30}$ is phenyl, and each of $R^{31}$ and $R^{32}$ is hydrogen, the hole transporting compound can be synthesized, for example, as follows.
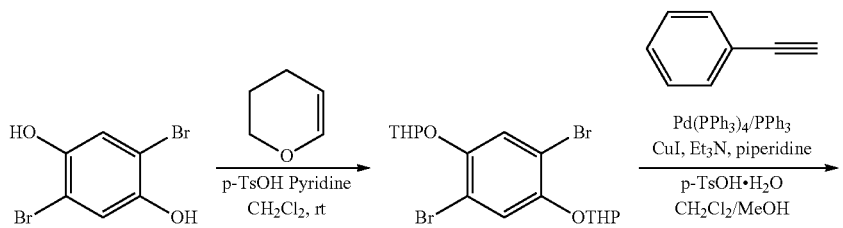

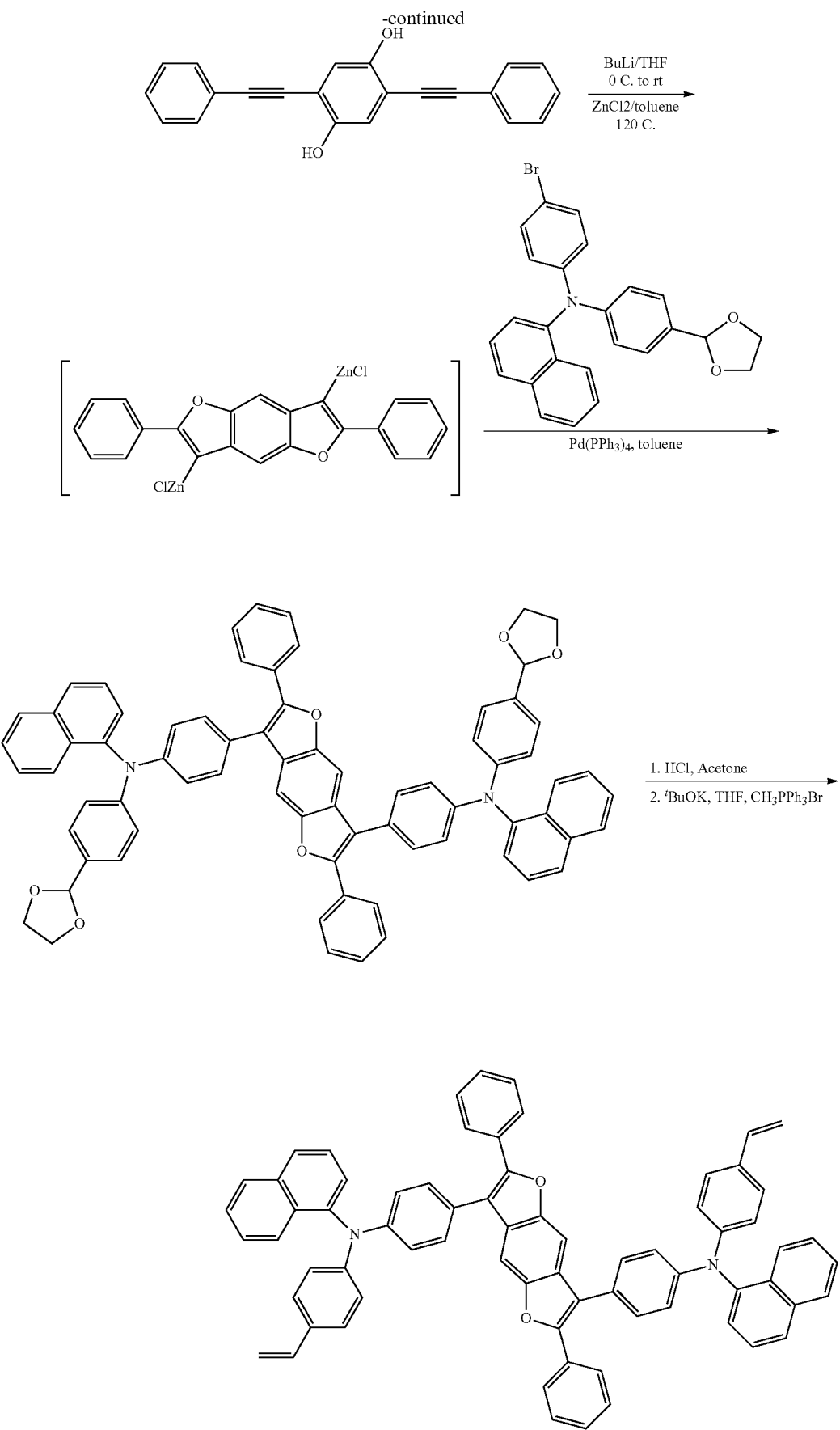

10. Synthesis of PLX-10
In one embodiment of PLX-10 according to formula (XVII), wherein $X^{13}$ is NR, each of $R^{33}$ and $R^{34}$ is hydrogen, the hole transporting compound can be synthesized, for example, as follows.
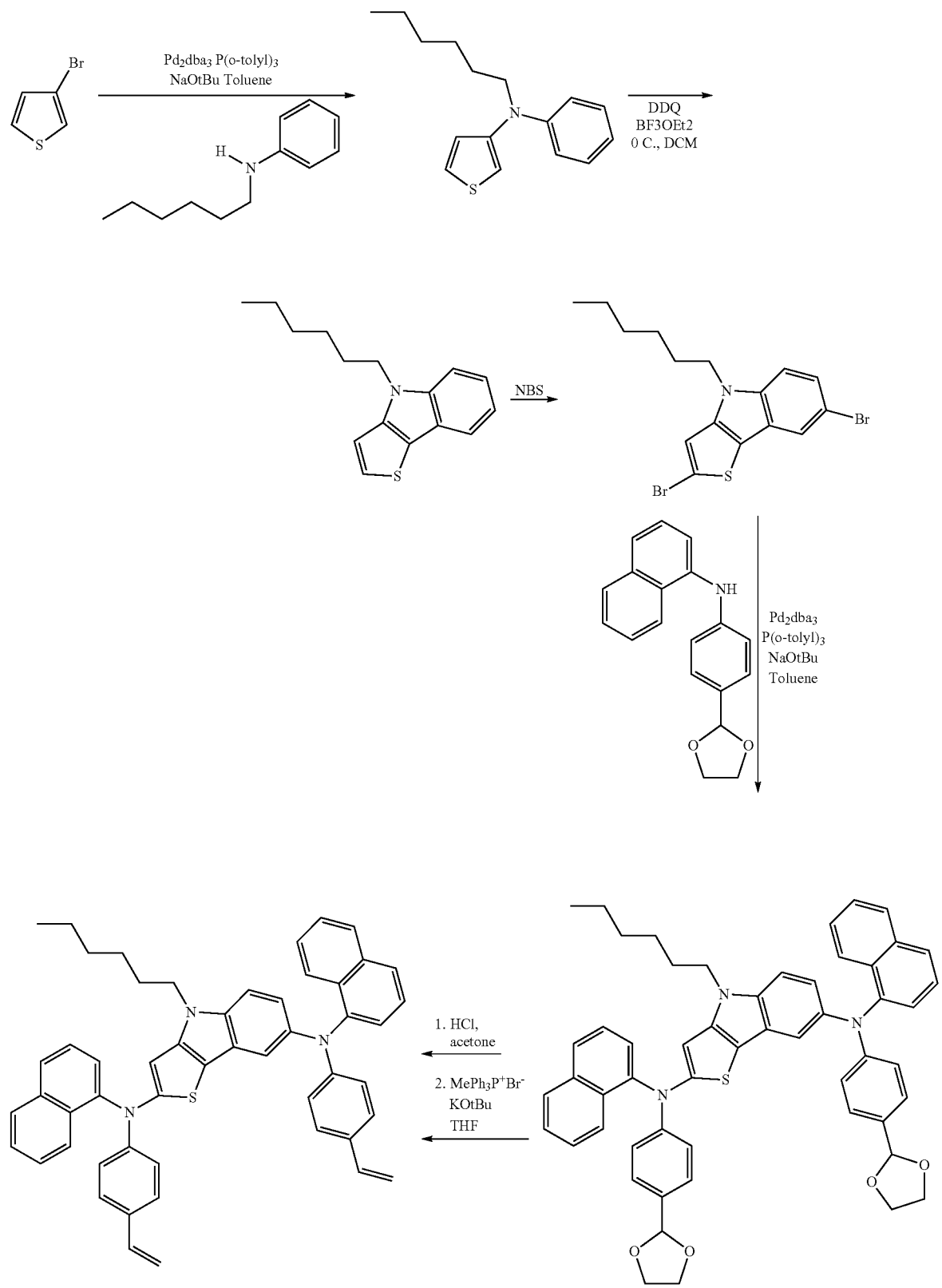

In one embodiment of PLX-10 according to formula (XVII), wherein $X^{13}$ is $SiR_2$, each of $R^{33}$ and $R^{34}$ is hydrogen, the hole transporting compound can be synthesized, for example, as follows.
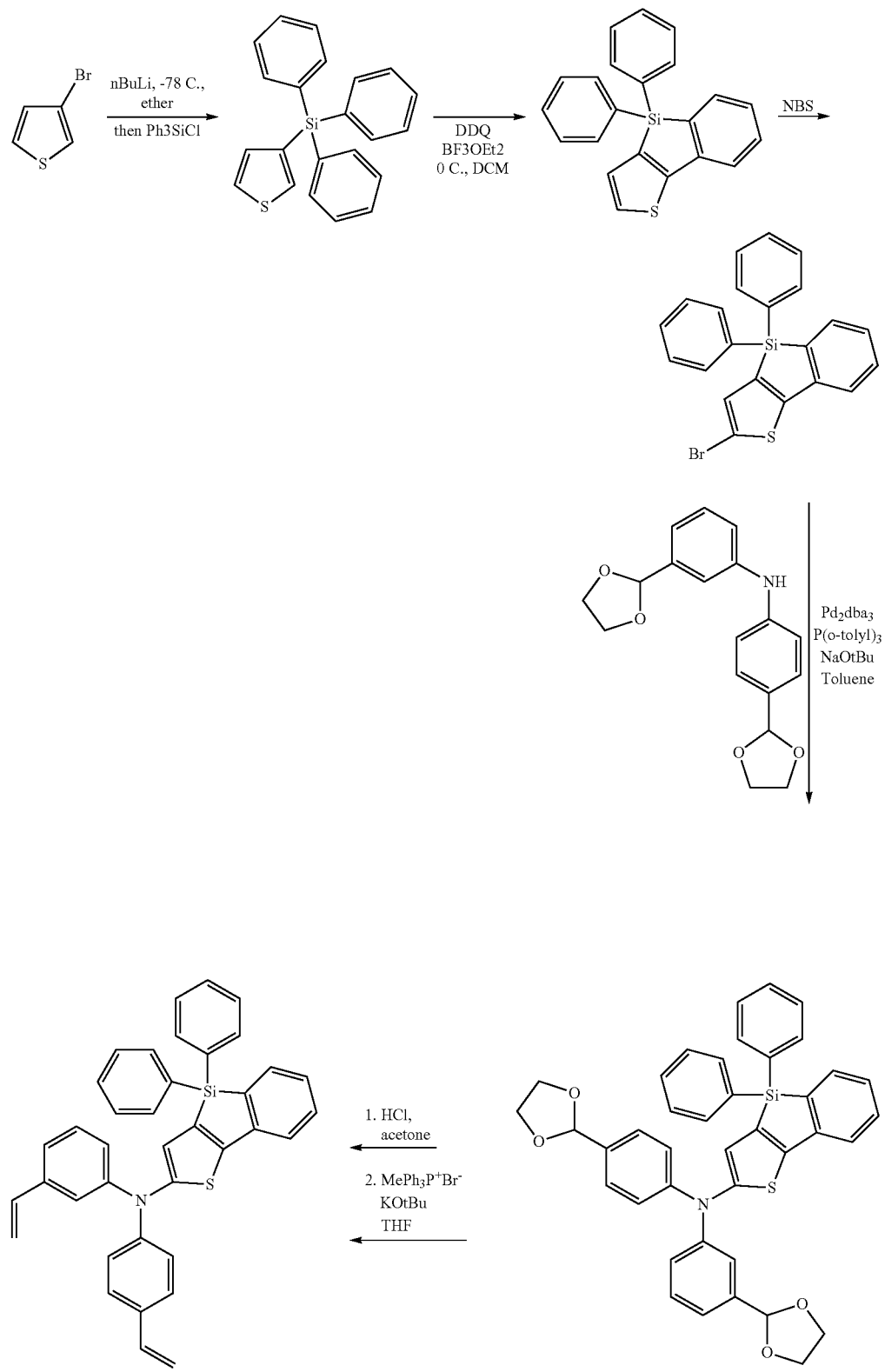

11. Synthesis of PLX-12
In one embodiment of PLX-12 according to formula (XIX), wherein $X^{15}$ is C≡C, each of $R^{37}$, $R^{38}$ and $R^{39}$ is hydrogen, the hole transporting compound can be synthesized, for example, as follows.
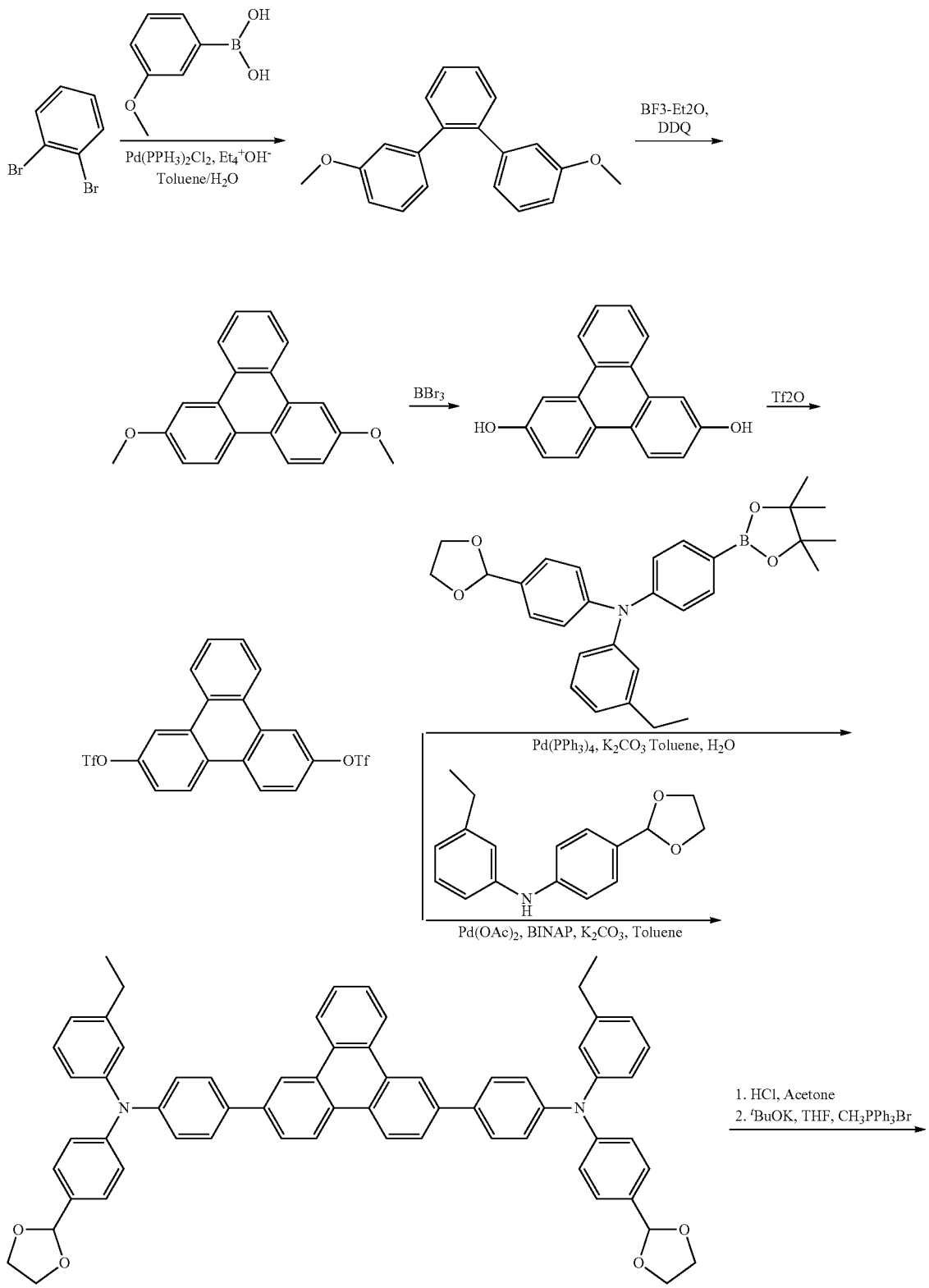

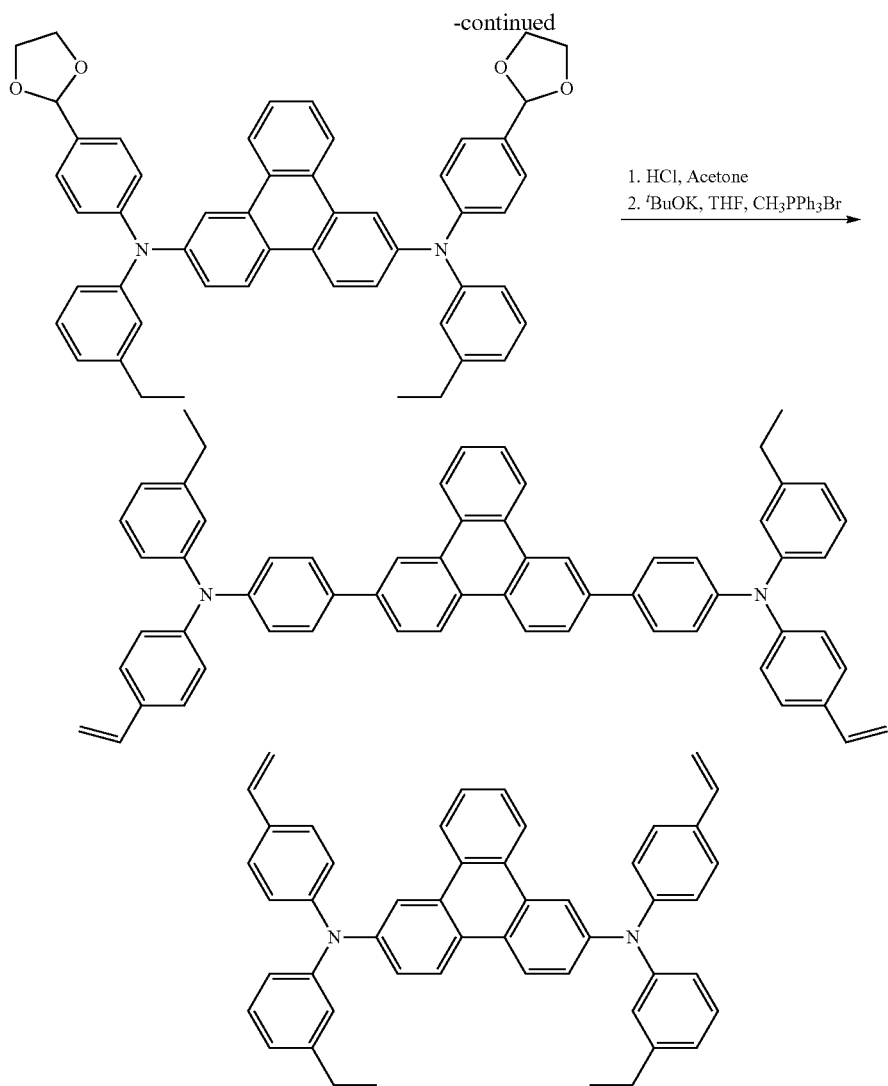
In one embodiment of PLX-12 according to formula (XIX), wherein $X^{15}$ is S, $R^{37}$ is branched alkyl, each of $R^{38}$ and $R^{39}$ is hydrogen, the hole transporting compound can be synthesized, for example, as follows.
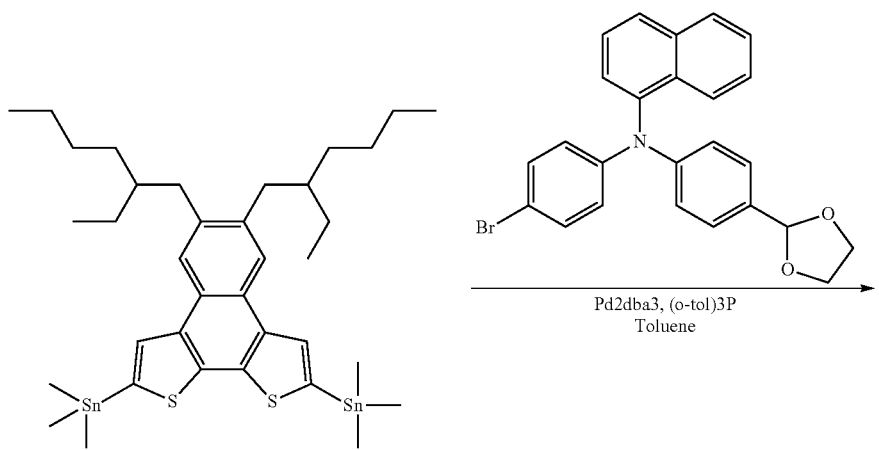

125
-continued
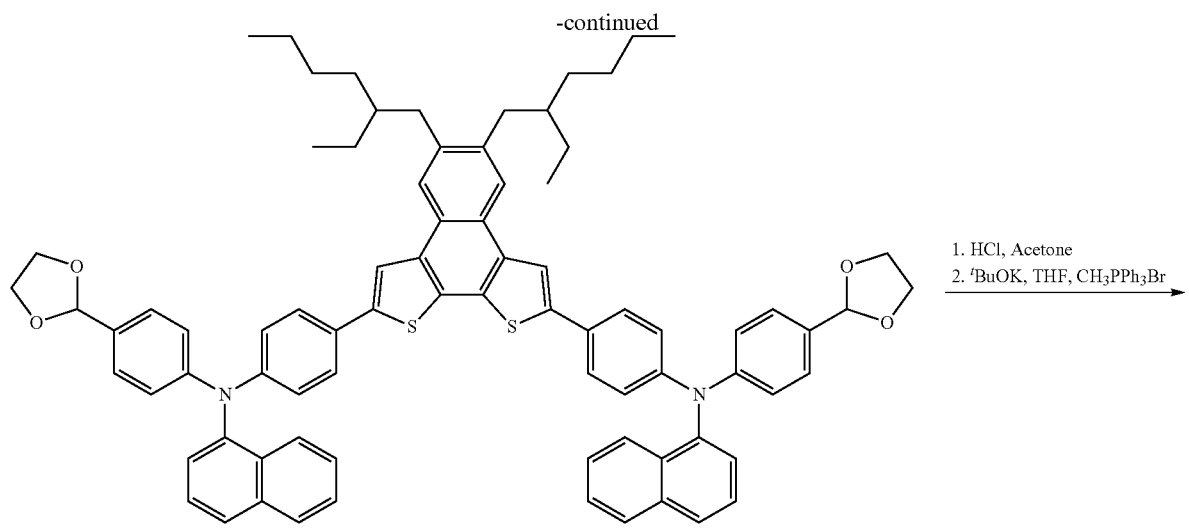
1. HCl, Acetone
2. $^t$BuOK, THF, CH$_3$PPh$_3$Br
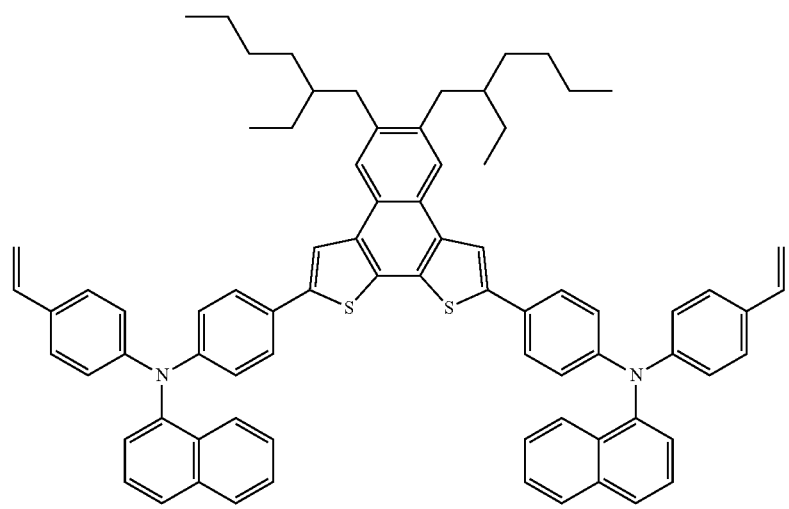
12. Synthesis of PLX-13
In one embodiment of PLX-13 according to formula (XX), wherein L is alkyl, each of $R^{40}$ and $R^{41}$ is hydrogen, the hole transporting compound can be synthesized, for example, as follows.
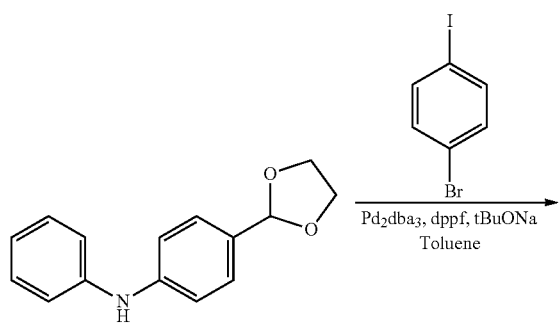
Pd$_2$dba$_3$, dppf, tBuONa
Toluene -continued
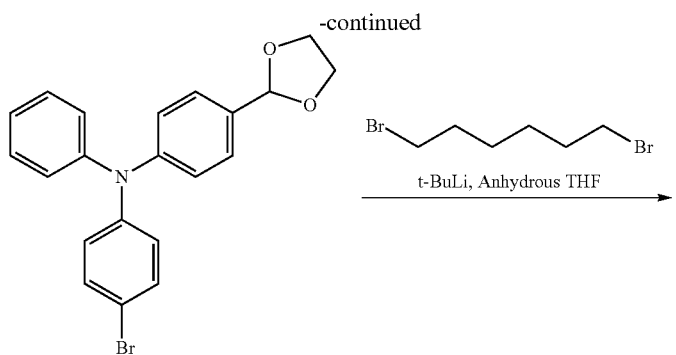
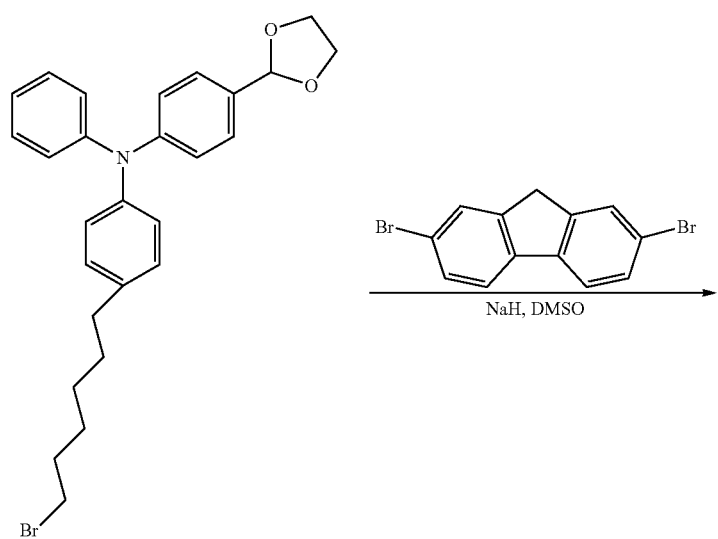
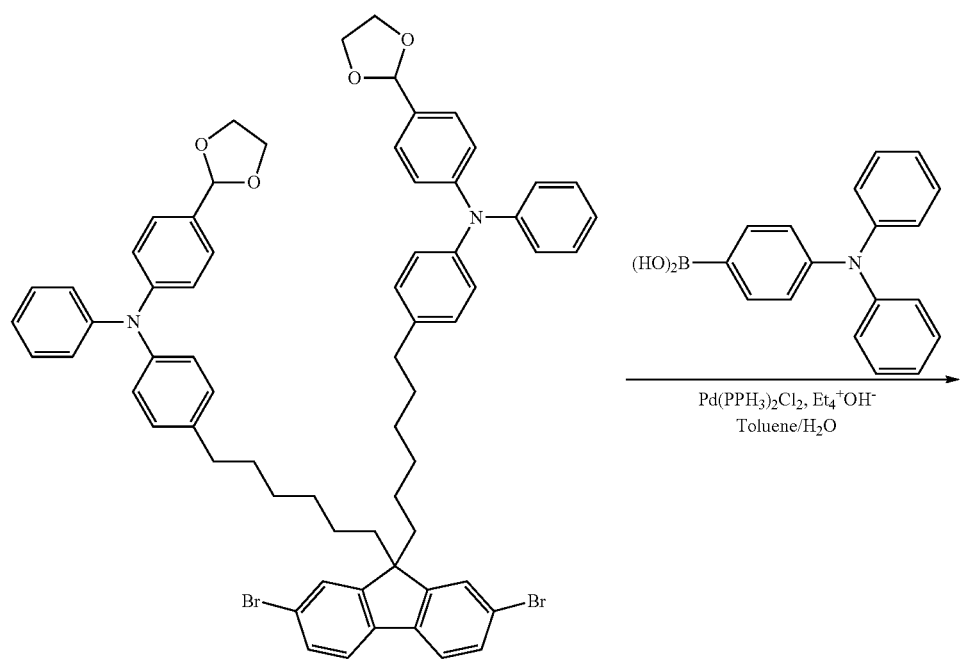

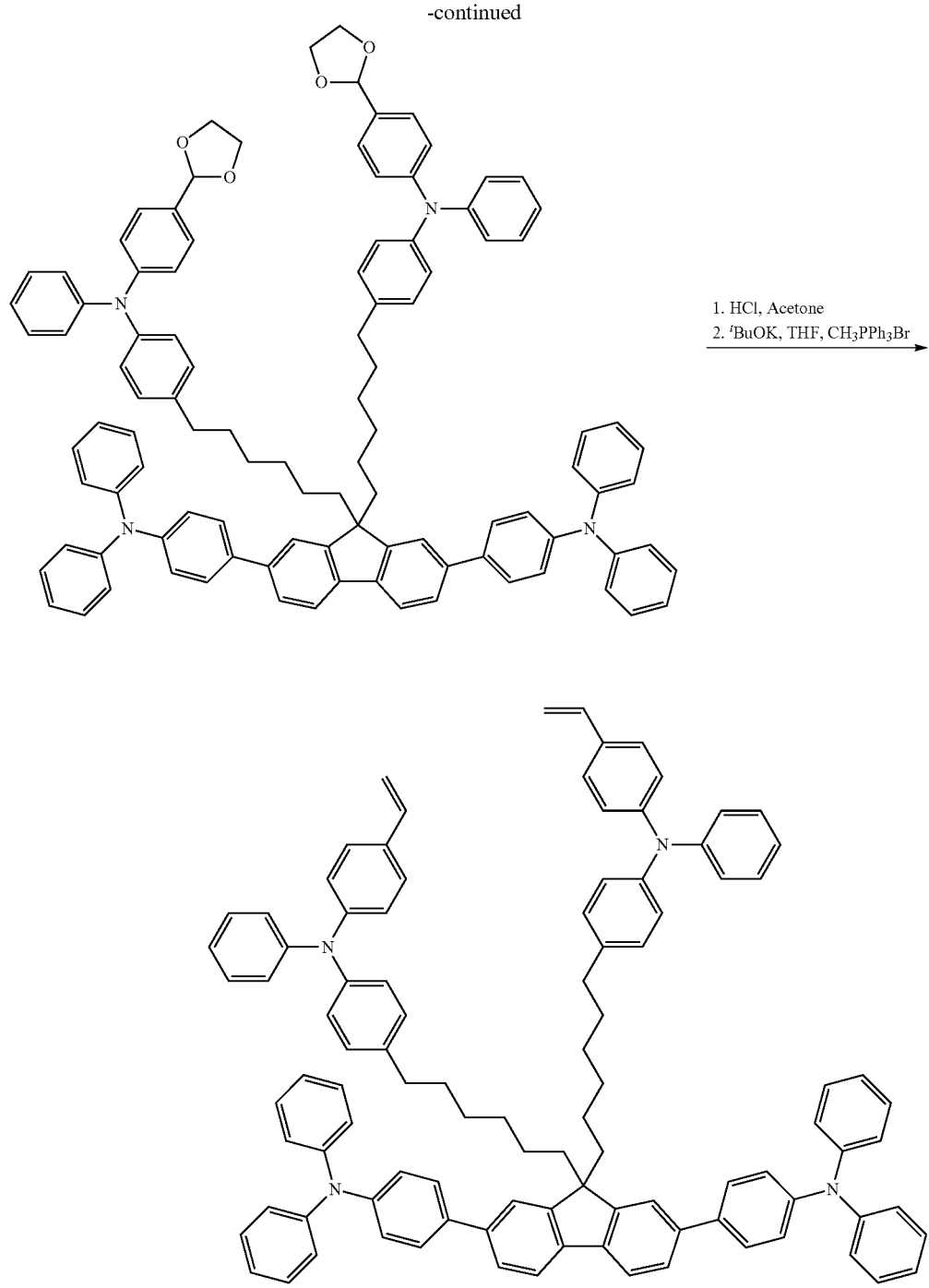
13. Synthesis of PLX-14
In one embodiment of PLX-14 according to formula (XXII), wherein $X^{17}$ is $SiR_2$, the hole transporting compound can be synthesized, for example, as follows.
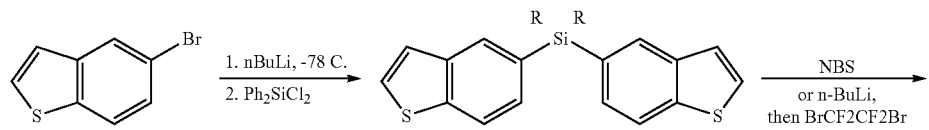

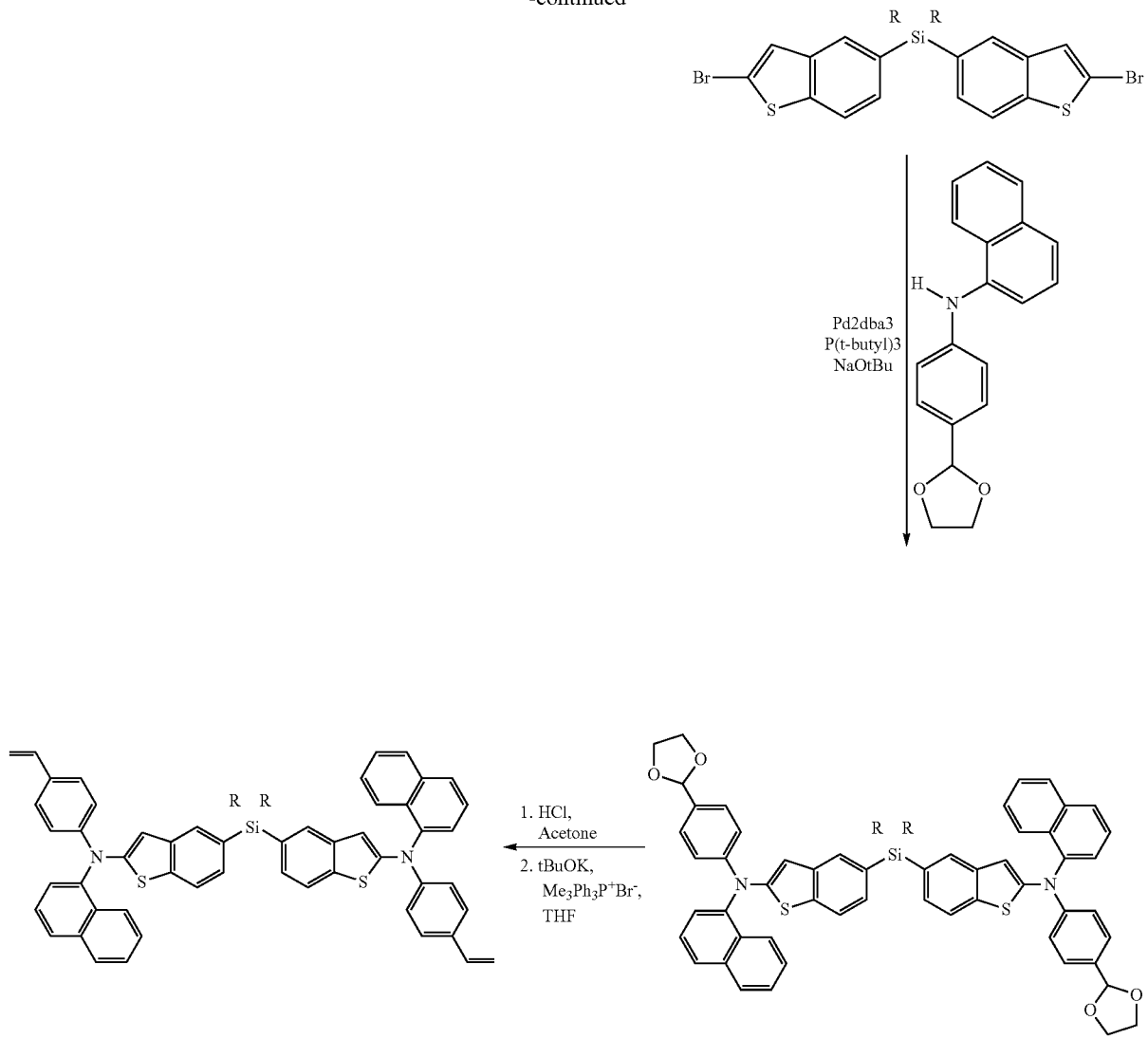
In another embodiment of PLX-14 according to formula (XXII), wherein $X^{17}$ is NR (R is aryl), the hole transporting compound can be synthesized, for example, as follows.
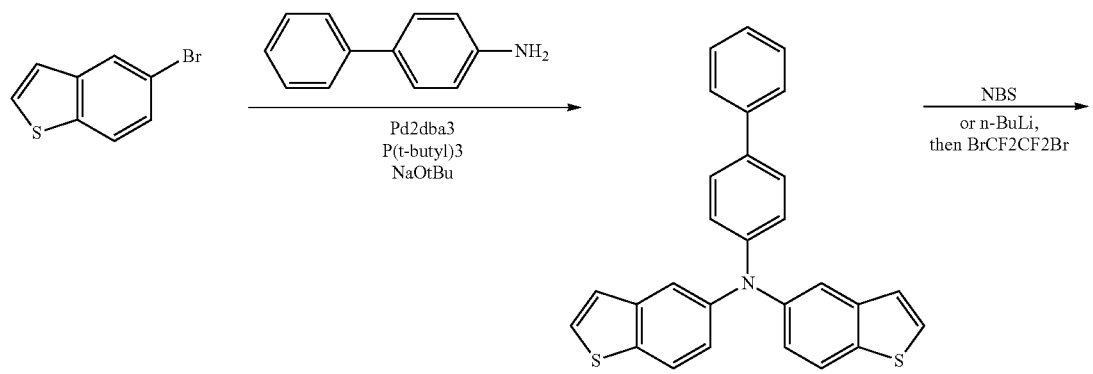

-continued
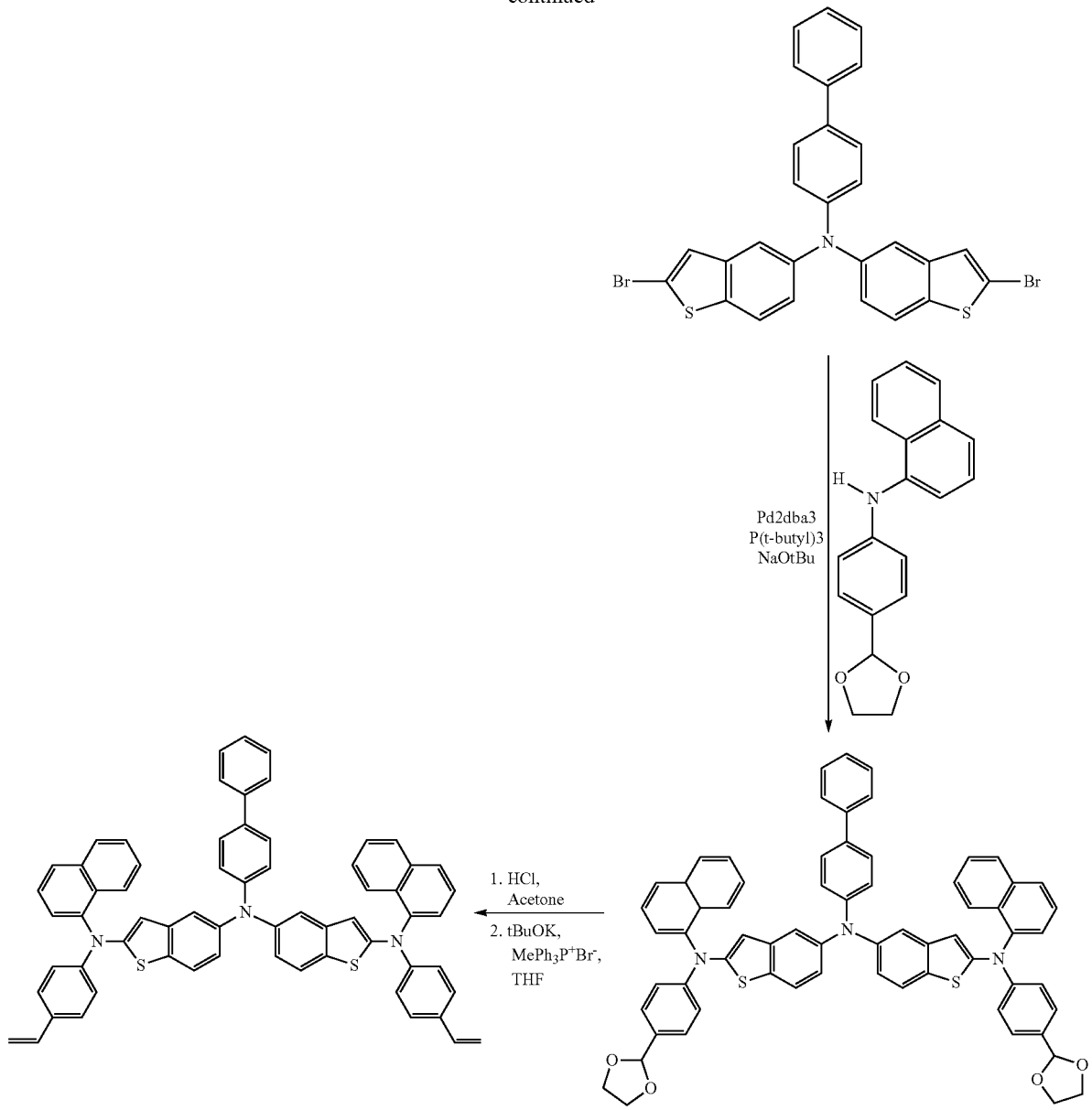
In a further embodiment of PLX-14 according to formula (XXII), wherein $X^{17}$ is NR (R is aryl), the hole transporting compound can be synthesized, for example, as follows.
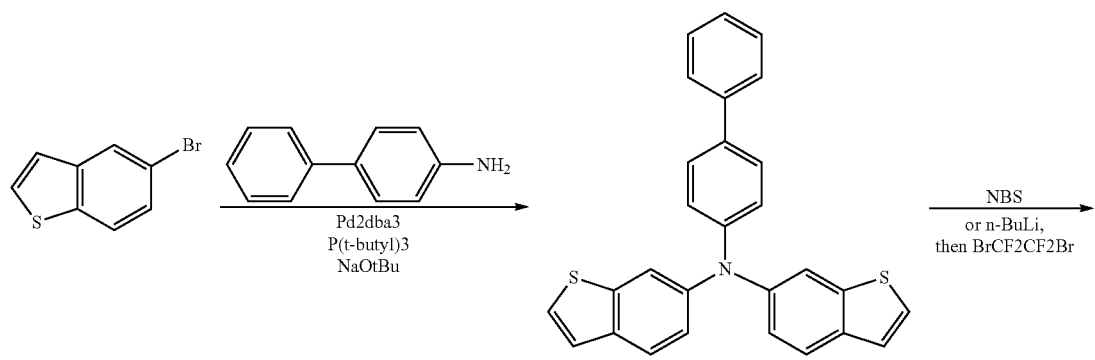

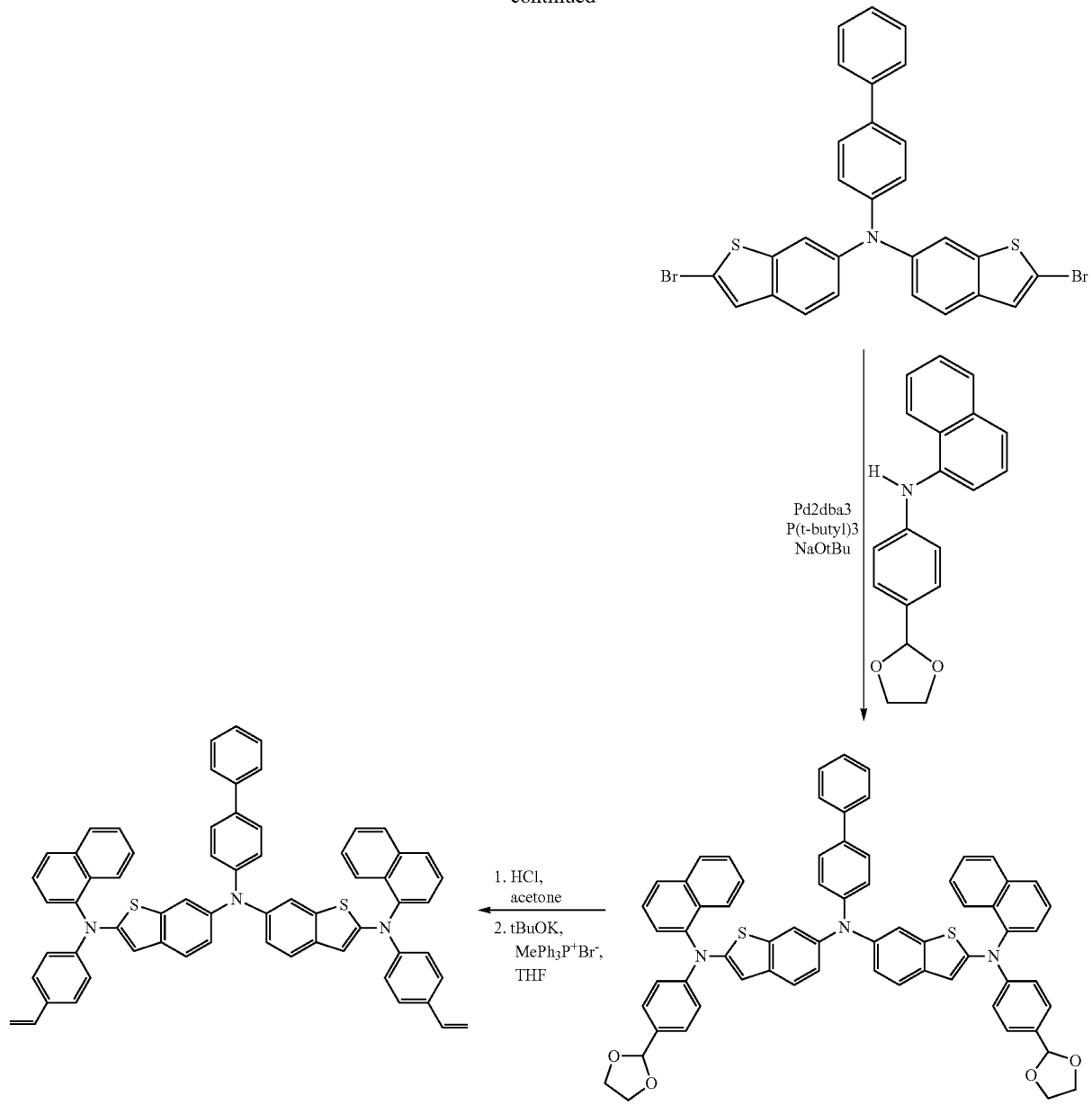
In an additional embodiment of PLX-14 according to formula (XXII), wherein $X^{17}$ is NR(R is aryl), the hole transporting compound can be synthesized, for example, as follows.

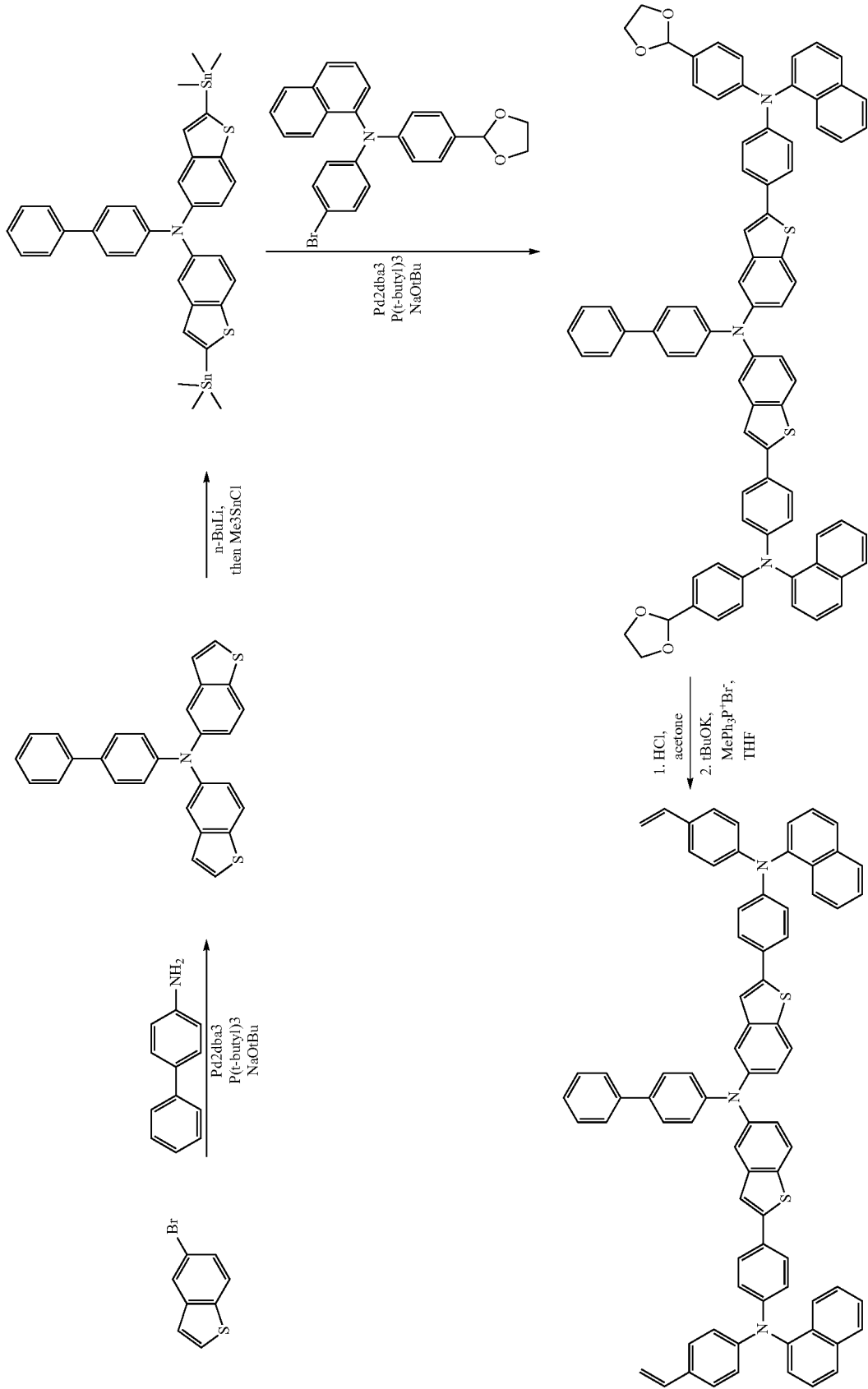

14. Synthesis of PLX-15

In one embodiment of PLX-15 according to formula (XXIII), the hole transporting compound can be synthesized, for example, as follows.

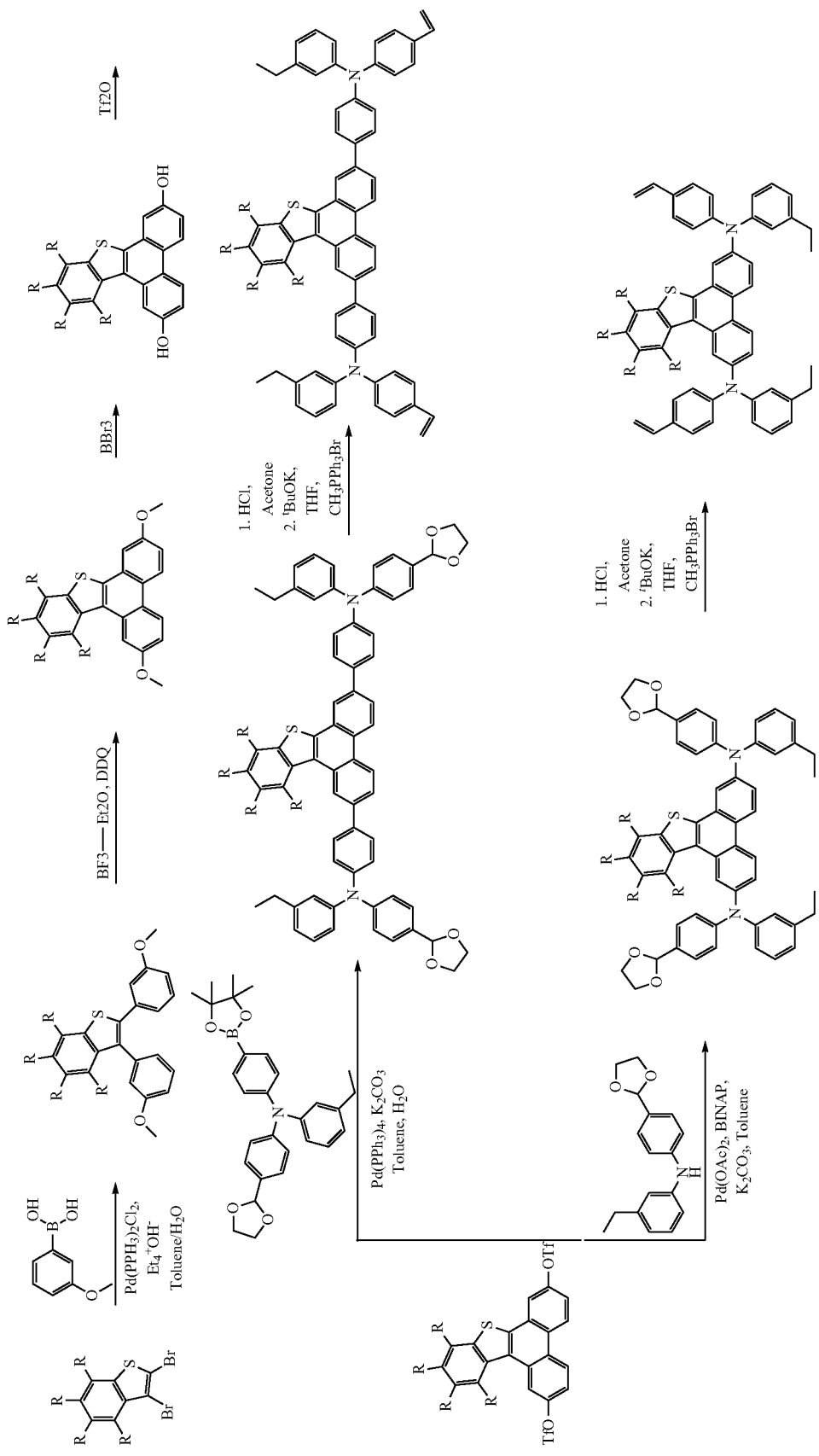

15. Synthesis of PLX-16
In one embodiment of PLX-16 according to formula (XXIV), the hole transporting compound can be synthesized, for example, as follows.
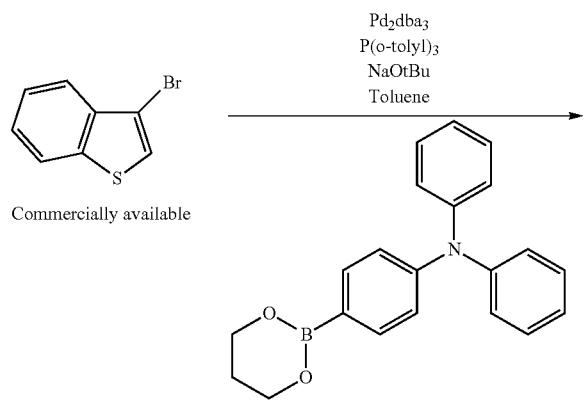
Commercially available
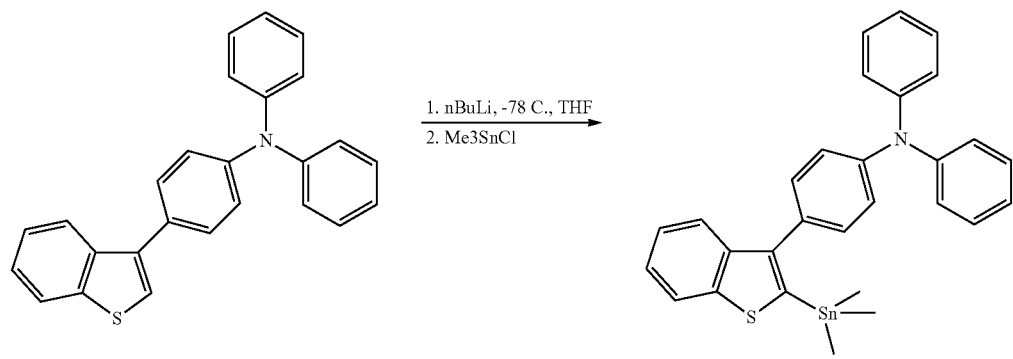
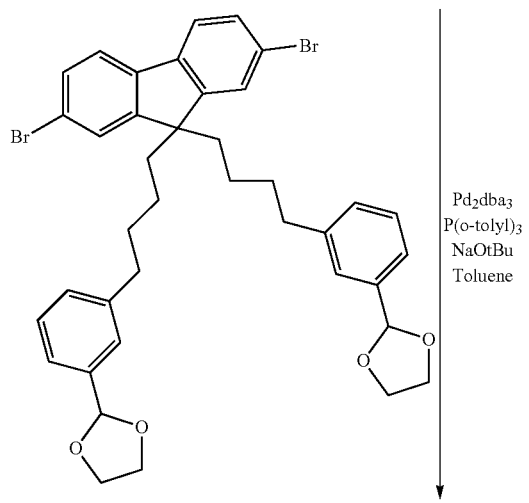

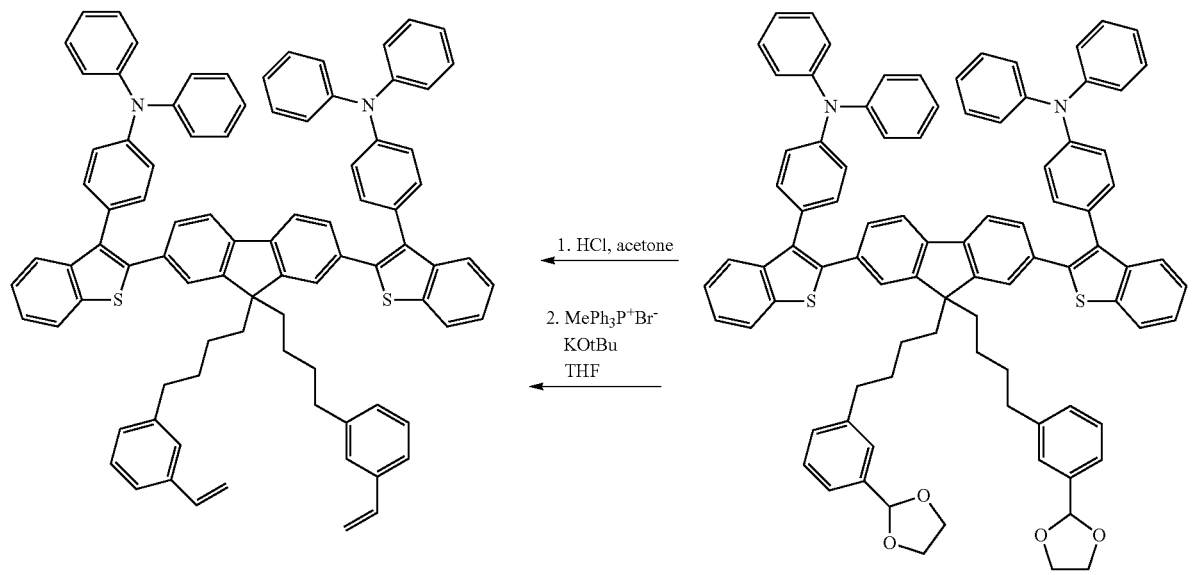 [SMILES: C=Cc1cccc(CCCCC2(CCCCc3cccc(C=C)c3)c3cc(-c4sc5ccccc5c4-c4ccc(N(c5ccccc5)c5ccccc5)cc4)ccc3-c3ccc(-c4sc5ccccc5c4-c4ccc(N(c5ccccc5)c5ccccc5)cc4)cc32)c1 ; c1ccc(N(c2ccccc2)c2ccc(-c3c(-c4ccc5c(c4)C(CCCCc4cccc(C6OCCO6)c4)(CCCCc4cccc(C6OCCO6)c4)c4cc(-c6sc7ccccc7c6-c6ccc(N(c7ccccc7)c7ccccc7)cc6)ccc4-5)sc4ccccc34)cc2)cc1]
In another embodiment of PLX-16 according to formula (XXIV), the hole transporting compound can be synthesized, for example, as follows.
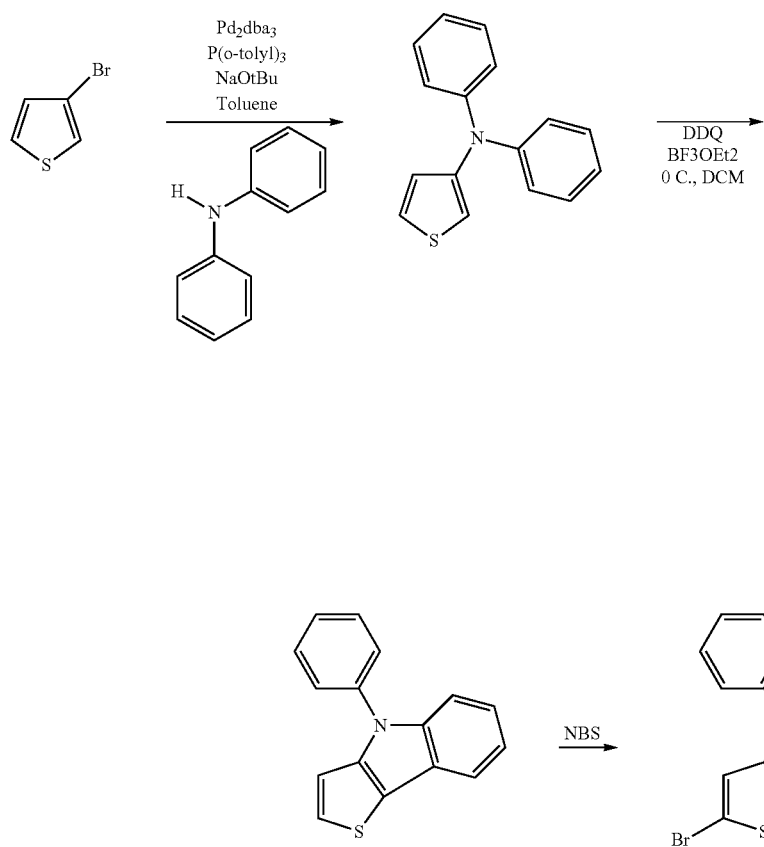

-continued

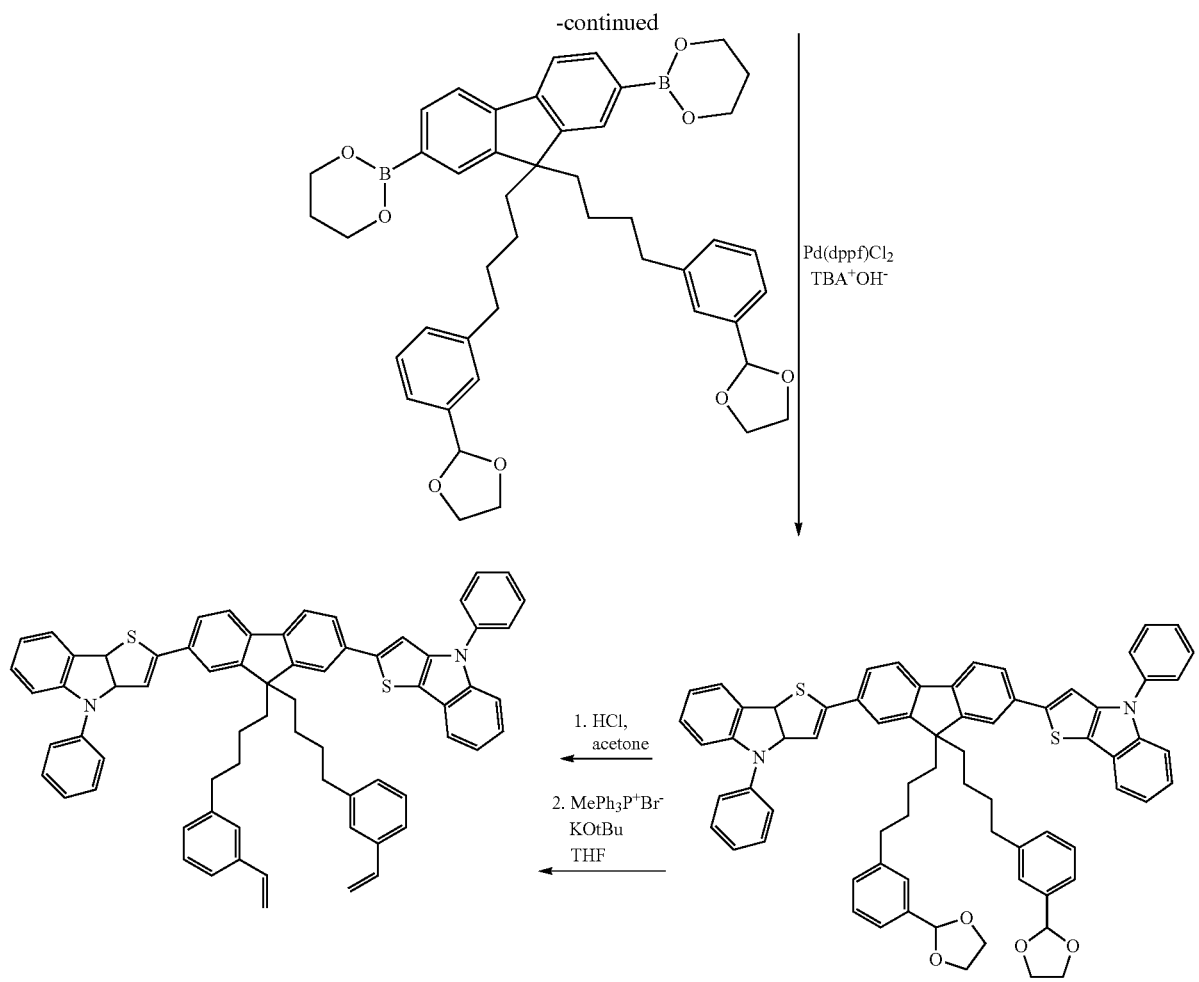

The hole transport formulations, mixtures, and compounds described herein can be further processed into inks, films, and devices.

Molecular Weight

In addition, the molecular weight (g/mol) for the hole transport compound can be adapted for an application. The molecular weight can be, for example, about 5,000 g/mol or less, or about 4,000 g/mol or less, or about 3,000 g/mol or less, or about 2,000 g/mol or less, or about 1,000 g/mol or less. In one embodiment, the compound's molecular weight is about 400 g/mol to about 5,000 g/mol, or about 400 g/mol to about 2,000 g/mol. In one embodiment, the compound's molecular weight is about 2,000 g/mol to about 5,000 g/mol. The molecular weight can be greater than, for example, about 250 g/mol, or greater than about 400 g/mol.

Exclusion of Polymer Before Crosslinking

In one embodiment, the composition described here can be free or substantially free of polymeric materials before crosslinking. For example, the composition can be free or substantially free of materials having a molecular weight of more than 5,000 g/mole or more, or free of materials having a molecular weight of more than 10,000 g/mol. The composition, before crosslinking, can comprise only materials having lower molecular weights such as below 5,000 g/mol, or below 2,000 g/mole, or below 1,000 g/mol. The amount of polymer can be less than 1 wt. %, or less than 0.1 wt. %, or less than 0.01 wt. %, for example.

Inks and Solvent System

The compositions described herein can be used in solid or can be formulated into liquid form as inks. Hence, in one embodiment, the composition further comprises a solvent system to form an ink. Solvent systems are known. See, for example, WO 2010/093592 (Cheon et al.).

The solid content of the ink can be adapted for a particular application. In one embodiment, the composition further comprises a solvent system to form an ink, wherein the solid content of the ink is at least 0.1 w/w % of solvent, or at least 0.3 w/w % of the solvent, or at least 1 w/w % of solvent.

The solvent system can comprise one solvent, two solvents, or three or more solvents (e.g., solvent blends can be used). Organic solvents can be used. In one embodiment, the solvent system comprises toluene as solvent.

Solvents can include aromatic hydrocarbons in the neutral and oxidized forms. Solvents such as tetrahydrofuran, chloroform, or aromatic hydrocarbons in the neutral and oxidized forms can be used. Additional solvents include tetrahydrofuran, chloroform, alkylated benzenes, halogenated benzenes, NMP, DMF, DMAc, DMSO, methyl ethyl ketone, cyclohexanone, chloroform, dichloromethane, acetone, THF, dioxanes, ethyl acetate, ethyl benzoate, ethylene carbonate, propylene carbonate, or combinations thereof.

For environmental compliance, one or more nonhalogenated solvents may be selected. Halogenated solvents can be substantially or totally excluded (e.g., used in less than 10%, or less than 5%, or less than 1%, or less than 0.1% by volume of total solvent carrier). In weighing such additional factors, it may be helpful to consult references such as, for example, Cheremisnoff, N. P., *Industrial Solvents Handbook, 2$^{nd}$* Ed. (Marcel Dekker, New York, 2003); Ash, M, *Handbook of Solvents, 2$^{nd}$* Ed. (Syapse Information Resources, 2003); Wypych, G., *Handbook of Solvents (Chemical)* (Noyes Publications, 2000); Hansen, C. M., Durkee, J. and Kontogeorgis, G, *Hanson Solubility Parameters: A User's Handbook* (Taylor and Francis, 2007); all of which are incorporated by reference in their entireties.

Solvents to be considered may include ethers (optionally substituted with C1-C10 alkyl chains) such as anisole, ethoxybenzene, dimethoxy benzenes and glycol ethers, such as: ethylene glycol diethers such as 1,2-dimethoxy ethane, 1,2-diethoxy ethane, 1,2-dibutoxy ethane; diethylene glycol diethers such as diethylene glycol dimethyl ether, diethylene glycol diethyl ether; propylene glycol diethers such as propylene glycol dimethyl ether, propylene glycol diethyl ether, propylene glycol dibutyl ether; dipropylene glycol diethers such as dipropylene glycol dimethyl ether, dipropylene glycol diethyl ether, dipropylene glycol dibutyl ether; also, higher analogs (tri- and tetra-) of the ethylene glycol and propylene glycol ethers mentioned above.

Still other solvents can be considered, such as ethylene glycol monoether acetates and propylene glycol monoether acetates, wherein the ether can be selected, for example, from: methyl, ethyl, n-propyl, iso-propyl, n-butyl, sec-butyl, tert-butyl, cyclohexyl. Also, higher glycol ether analogs of above list such as di-, tri- and tetra-. Examples include, but are not limited to, propylene glycol methyl ether acetate, 2-ethoxyethyl acetate, 2-butoxyethyl acetate.

Yet other possible solvents include aliphatic and aromatic ketones such as acetonyl acetone, methyl isobutyl ketone, methyl isobutenyl ketone, 2-hexanone, 2-pentanone, acetophenone, ethyl phenyl ketone, cyclohexanone, cyclopentanone.

Additional possible solvents include N,N-dimethyl formamide, N,N-dimethyl acetamide, N-methylpyrrolidone, dimethyl sulfoxide, tetramethylene sulfoxide, acetonitrile, benzonitrile, ethylene carbonate, propylene carbonate, and the like.

Other examples include cyclic ethers such as, for example, tetrahydropyran (THP). Solvent can be used such that polymerization of the solvent can be avoided. Another example is methoxyproprionitrile.

The one or more solvents can be used in varying proportions to improve the ink characteristics such as substrate wettability, ease of solvent removal, viscosity, surface tension, and jettability.

Alternatively, it may be useful to select more than one solvent, for example, a first solvent and a second solvent. In one example, the solutes can have a higher solubility in the first solvent than in the second solvent. The hole transporting compound can also have a higher solubility in the second solvent than in the first solvent. The solvent can be selected such that the first solvent can be removed at a faster rate than the second solvent in a drying step.

In one embodiment, the ink composition further comprises an additive. The additive can be, for example, a shrinkage reducer, stabilizer, or activator. The additive can also be, for example, a radical scavenger, initiator, deforming agent, wetting agent, or surfactant.

Reacted and Dried Form of Compositions

Also described herein are compositions, wherein the reactive compositions are not reacted, partially reacted or fully reacted. For example, in one embodiment, the intractable groups are polymerizable groups, and the polymerizable groups are reacted. In one embodiment, a composition is prepared by reaction of the intractability groups of the first and second compound of the compositions described herein.

The compositions can be converted into films by methods known in the art. Hence, in one embodiment, the intractable groups are polymerizable groups, and the polymerizable groups are reacted, and the composition is in the form of a thin film.

Methods of Forming Films

Coated substrates can be formed. One or more layers of film can be added to a preexisting film or substrate. For example, another embodiment provides a method comprising: providing a substrate comprising a hole injection layer, coating the substrate with at least one ink comprising at least one hole transport material comprising intractability groups to form a coated substrate, heating the coated substrate. The hole transport material can comprise one or more of the compositions described herein.

In one embodiment, the ink is subjected to pre-crosslinking before coating the ink on the substrate. In one embodiment, the ink is subjected to thermal pre-crosslinking before coating the ink on the substrate. In one embodiment, the ink is subjected to thermal pre-crosslinking to form a gel before coating the ink on the substrate. In one embodiment, the ink is subjected to thermal pre-crosslinking at at least 150° C. to form a gel before coating the ink on the substrate. In one embodiment, the ink is subjected to UV light pre-crosslinking before coating the ink on the substrate.

In one embodiment, the ink is not subjected to pre-crosslinking before coating the ink on the substrate.

In one embodiment, the coated substrate is subjected to UV light to induce pre-crosslinking before heating the coated substrate.

In one embodiment, the coated substrate is heated to at least 200° C. In one embodiment, the coated substrate is heated to at least 250° C.

The quality of the film can be examined by optical microscopy, looking for film defects, formation of aggregates and beads, dewetting of the film, and pinholes.

In one embodiment, which is comparative, after heating, the coated substrate shows films with beads formed on the top layer interspersed with the area of the lower film where the top hole transport layer film has dewetted (in the optical microscope).

In one embodiment, after heating, the coated substrate shows defect free, smooth and continuous films conforming and wetting well on the lower lying hole injection layer (in the optical microscope).

Films can be evaluated at both low and high magnifications to isolate the presence of both large and small scale defects and ensure an overall smooth continuous coating.

The film formation can be carried out by methods known in the art including drop coating, spin coating, ink jet printing, slot die coating, nozzle printing, screen printing, and the like.

Characterizing Films

In one embodiment, after heating the coated substrate is stable to toluene solvent wash so that retains at least 90% of the initial thickness before the wash. In one embodiment, after heating the coated substrate is stable to toluene solvent wash so that retains at least 95% of the initial thickness before the wash.

In one embodiment, after heating the coated substrate is stable to immersion in toluene for 5-10 minutes so that it retains at least 90% of the initial thickness before wash and does not show an increase in the thickness beyond 110% of the initial thickness.

In one embodiment, after heating the coated substrate is stable to immersion in toluene for 5-10 minutes so that it retains at least 95% of the initial thickness before wash and does not show an increase in the thickness beyond 105% of the initial thickness.

The film quality (smoothness) can be evaluated by atomic force microscopy, and films can show an rms roughness of 5 nm or below. The AFM micrographs can help to ensure good film quality at the nanoscale and also helps in understanding film morphology and its effect on device performance.

On the films deposited on the substrates, other measurements can be performed such as AC2 can be used to measure the HOMO energy of films. Absorption measurements (UV-VIS) can be done to calculate the bandgap of the hole transport material. The LUMO can be estimated by subtracting the band gap from the HOMO. Also photoluminescence measurements can be done on the hole transport films to study their emission characteristics.

In one embodiment, the coating of the coated substrate shows a Tg of less than 200° C., or less than 150° C.

Substrate and Hole Injection Layer

Solution processing for OLED fabrication is known in the art. Orthogonal solubility principles can be used. In particular, the hole transport compounds and formulations can be applied on top of a hole injection layer (HIL) material or film. The hole injection layers can be materials soluble in water or organic solvents. Solution process can provide depositing materials from a liquid medium, including solutions, dispersions, emulsions, or other forms.

In one embodiment, the hole injection layer is an aqueous hole injection layer. For example, the HIL layer material can be soluble in water.

In one embodiment, the hole injection layer is a non-aqueous hole injection layer. For example, the HIL layer material can be soluble in organic solvent.

In one embodiment, the hole injection layer comprises a polymer. In one embodiment, the hole injection layer comprises a conjugated polymer. In one embodiment, the hole injection layer comprises a polythiophene. In one embodiment, the hole injection layer comprises a polythiophene comprising at least one alkoxy substituent. In one embodiment, the hole injection layer comprises a sulfonated polythiophene. In one embodiment, the hole injection layer comprises a polymeric arylamine. In one embodiment, the hole injection layer comprises a regioregular polythiophene. In one embodiment, the hole injection layer comprises a conjugated polymer which is soluble in water. In one embodiment, the hole injection layer comprises a conjugated polymer which is soluble in organic solvent.

For example, hole injection layers are described in the following US Patent Publications (assignee: Plextronics): 2006/0078761; 2008/0248313; 2009/0256117; 2009/0230361; 2010/0108954; 20100292399; 2010/0072462; 2010/0109000; 2011/0147725, which are all hereby incorporated by reference in their entireties.

Examples of aqueous hole injection layers are described in 2008/0248313 (Seshadri et al.)

Examples of non-aqueous hole injection layers are described in 2006/0078761 and 2009/0256117 (Seshadri et al.). For example, the HIL can be based on a 3,4-disubstituted polythiophene including a poly(3,4-dialkoxythiophene).

OLED devices are also fabricated with emitting layers and other layers known in the art of OLED devices. In one embodiment, the method further comprises the step of coating an emitting layer on the coated substrate.

In one embodiment, the ink comprises at least two hole transport materials comprising intractability groups. In one embodiment, the ink comprises at least two hole transport materials each comprising a different intractability group. The two different intractability groups can be adapted to function together during film formation. For example, one might react at a lower temperature, and one might react at a higher temperature. In general, one tries to have all or as many as possible of the intractability groups to react.

Device Fabrication and Characterization

Devices can be fabricated by methods known in the art and can be characterized by methods known in the art.

An organic light emitting diode (OLED) can comprise a series of layers including, for example,
 ITO: Transparent anode, typically
 HIL: Hole injection layer to facilitate charge injection
 HTL: Hole transport layer which carries charges
 EML: Emissive layer where light is emitted
 HBL: Hole blocking layer to prevent charge leakage
 ETL: Electron transport layer to facilitate charge injection
 Cathode Layers can be supported by substrates including flexible, or rigid, or organic, or inorganic substrates.

Additional examples of layers and devices, and related methods of making, testing, and using, can be found in, for example, US Patent Publication Nos. 2005/0184287; 2006/0032528; 2008/0286566; 2009/0159877; 2010/0187500; 2010/0187510; 2010/0207109; 2010/0213446; 2010/0244665; WO 07076146; WO 07079103; WO 07120143; WO 07145979; WO 08024378; WO 08024379; WO 08024380; WO 08106210; WO 08150872; WO 08150943; WO 09018009; WO 09052085; WO 09055532; WO 09067419; WO 09097377; WO 09140570.

Applications

Hole transport materials can be used in a variety of electronic devices including organic electronic devices such as, for example, OLED, OPV, and OFET OLEDs can be used in, for example, display or lighting applications. They can be used in layers for hole injection and/or hole transport. Other applications are described in, for example, (1) *Highly Efficient OLEDS with Phosphorescent Materials* (Ed. H. Yerrin), 2008, Wiley-VCH, (2) *Organic Light Emitting Devices: Synthesis, Properties, and Applications* (Eds. Mullen, Scherf), 2006, (3) *Organic Light Emitting Methods and Devices*, (Li and Meng), 2007, CRC. See also Shirota et al., *Chem. Rev.*, 2007, 107, 953-1010 for OLEDs, OPVs, OFETs, and other applications.

WORKING EXAMPLES

Figure 2:
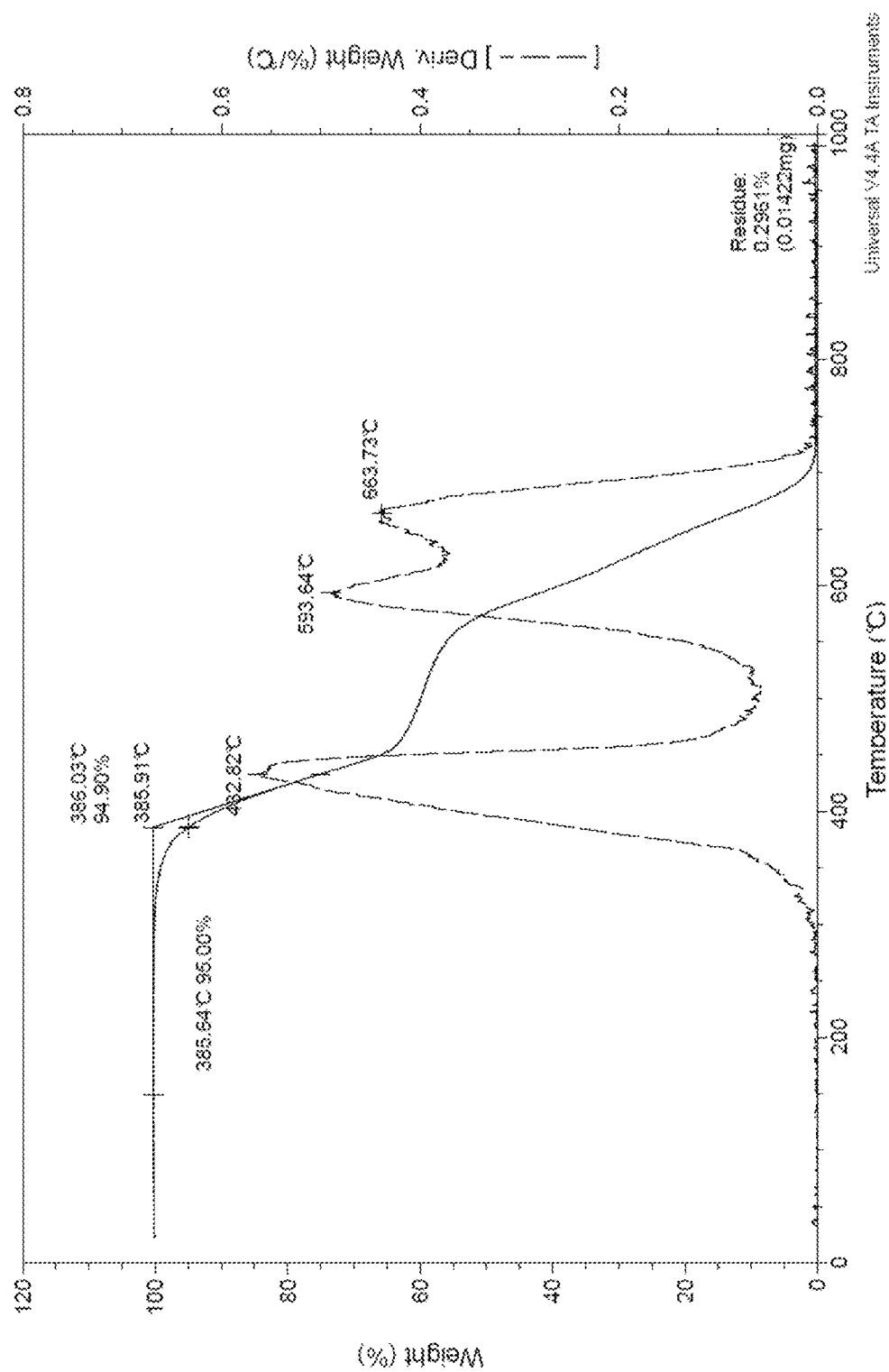
FIG. 2 shows TGA data of an exemplary embodiment of the hole transporting compounds described herein.
Figure 3:
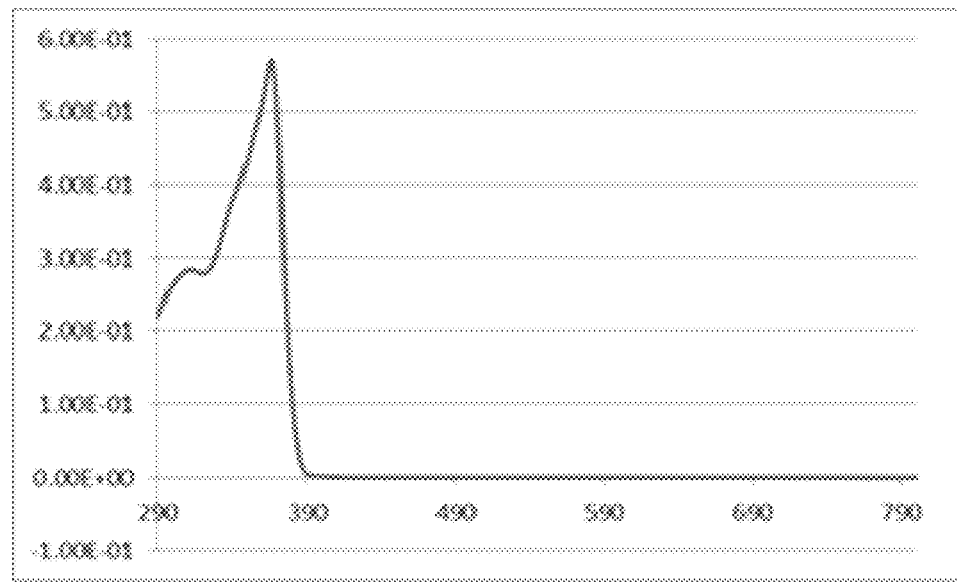
FIG. 3 shows UV-Vis and PL absorption spectra of an exemplary embodiment of the hole transporting compounds described herein.
Figure 3:
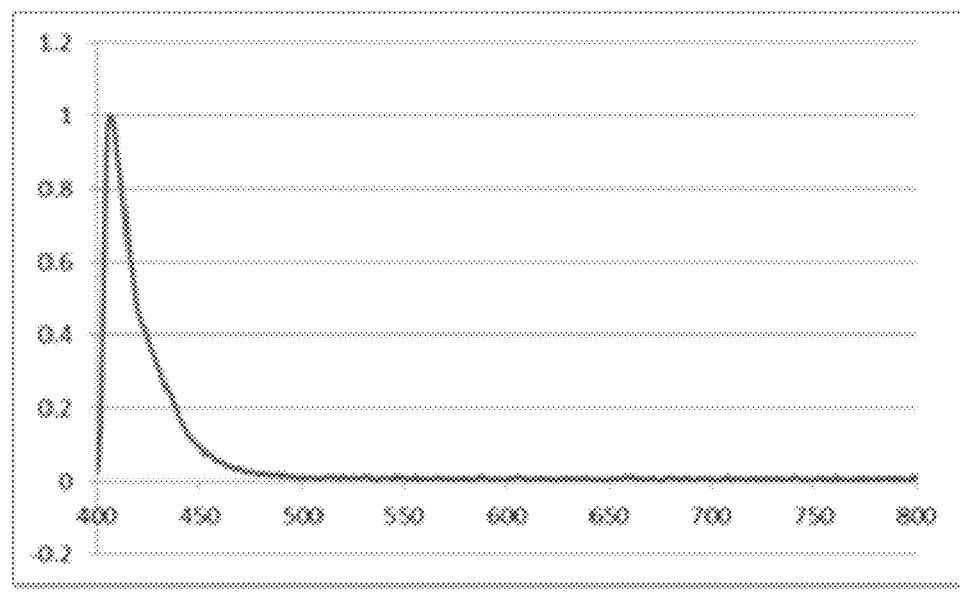

An exemplary hole transporting compound was synthesized according to the below scheme. The DSC and TGA data and UV-Vis and PL absorption spectra of the hole transporting compound are shown in FIGS. 1-3. The arylamine groups of this compound may be substituted with one or more intractability groups.

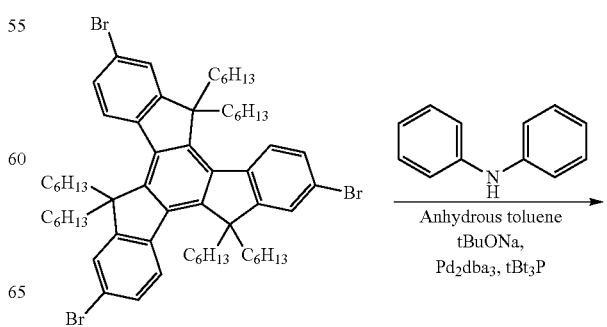

153

-continued

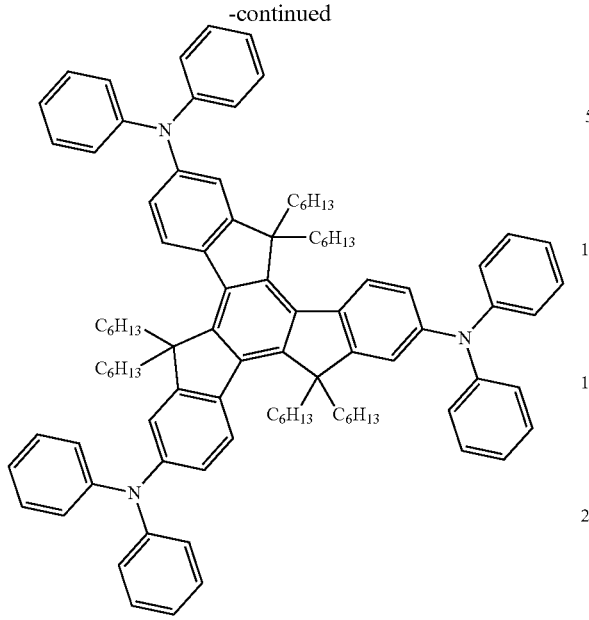

ADDITIONAL EMBODIMENTS

In additional embodiments below, aditional AA groups can be incorporated into the structures in some cases.

Part II

Additional Embodiments

Additional embodiments are provided in the following non-limiting descriptions and illustrative working examples. The description below is organized using the same PLX organizational theme for structural cores, as described above, but using suffixes. Hence, for example, PLX-1-A below supplements PLX-1, above; PLX-3-A supplements PLX-3 above; and the like.

As in above, the compounds can be functionalized with intractability groups or polymerizable groups, and can also be functionalized with one or more arylamine groups. In at least some cases, compounds are designed as known in the art to have a high triplet energy. Triplet energy can be measured or calculated by methods known in the art.

PLX-1-A

Supplementing the description here for PLX-1 compounds, an additional, related embodiment can be called PLX-1-A represented by:

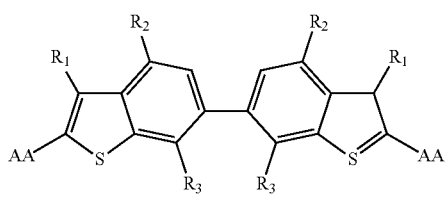

wherein the AA and R groups are as described for PLX-1 compounds. In other words, the $X^1$ in PLX-1 is nothing, a blank. No heteroatom $X^1$ is present in PLX-1-A.

154

A working example is provided:

Synthesis of 6,6'-bibenzo[b]thiophene

6,6'-bibenzo[b]thiophene

Procedures:

A clean and dry three-neck round bottom flask equipped with a reflux condenser and magnetic stir bar was placed charged with 6-bromobenzo[b]thiophene (16.00 g, 0.0751 mol), Pd$_2$dba$_3$ (3.44 g, 0.0038 mol), and tri(o-tolyl)phosphine (4.57 g, 0.0150 mol) were added to the flask. The reaction flask was placed under vacuum. Purged anhydrous toluene (700 mL) was added by cannula. The reaction flask was again purged with nitrogen for 30 minutes. Bis(tributyltin) (21.78 g, 0.0375 mol) was added via syringe, after which five nitrogen—vacuum purging cycles were carried out. The reaction was then placed in a heating mantle which was preheated to 110° C. The reaction was heated for 36 hours and then allowed to cool to room temperature. The reaction solution was filtered through a bed of Celite, washing thoroughly with MTBE. The filtrate was worked up with DI H$_2$0 and MTBE, collecting the organic layer. Solvent was removed by rotary evaporation, and the crude mixture was placed on the vacuum line which initiated crystallization of the product. The solids were filtered off, washed with methanol, collected, and placed under vacuum. Product obtained: 3.89 g.

Synthesis of 2,2'-dibromo-6,6'-bibenzo[b]thiophene

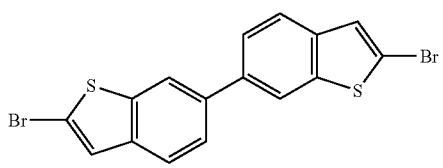

2,2'-dibromo-6,6'-bibenzo[b]thiophene

Procedures:

A clean and dry three-neck round bottom flask was equipped with a magnetic stir bar and low temperature thermometer. This flask was charged with 6,6'-bibenzo[b]thiophene (0.50 g, 0.0019 mol) under nitrogen. Anhydrous tetrahydrofuran (50 mL) was then added via syringe. The reaction flask was then placed into an isopropanol/dry ice bath until a temperature of less than negative 65° C. was achieved. At this point, n-butyllithium solution (titrated at 2.27M in hexanes, 2.48 mL, 0.0056 mol) was then added slowly drop-wise, maintaining the current temperature. Following addition, the reaction was allowed to stir for approximately 30 minutes before slowly warming to room temperature by removal of cold bath. Once at room temperature, the flask was placed back into the cold bath until a temperature of negative 68° C. was again achieved. Dibromotetrafluoroethane (0.90 mL, 0.0075 mol) was then added slowly dropwise, maintaining the current temperature. Following this addition, the flask was again removed from the cold bath, and allowed to slowly warm to room temperature. The reaction was quenched by adding isopropanol (5 mL) by syringe. The reaction was worked up with deionized water and methyl tert-butyl ether. The organic layer was collected and dried over anhydrous magnesium sulfate. The solids were removed by vacuum filtration. The filtrate was collected and solvent was removed by rotary evaporation. The resulting crude material was triturated in methanol at room temperature for two hours after which the solids were collected by vacuum filtration was washed with methanol. This provided product of sufficient purity to take onto the next reaction step. Product obtained: 3.10 g.

Synthesis of 2,2'-bis((4-(1,3-dioxolan-2-yl)phenyl)([1,1'-biphenyl]-4-yl)methyl)-6,6'-bibenzo[b]thiophene

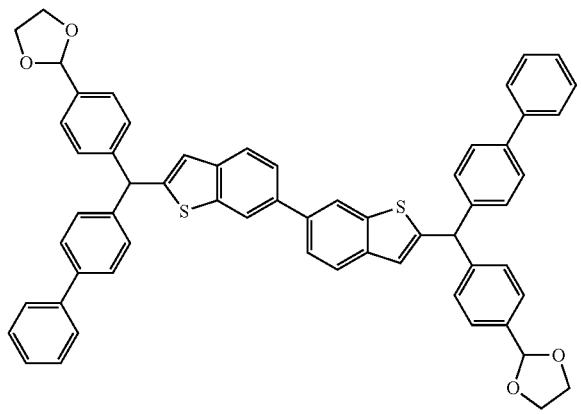

2,2'-bis((4-(1,3-dioxolan-2-yl)phenyl)([1,1'-biphenyl]-4-yl)methyl)-6,6'-bibenzo[b]thiophene Procedures:

In a clean and dry three-neck flask equipped with magnetic stir bar and reflux condenser was added 2,2'-dibromo-6,6'-bibenzo[b]thiophene (3.10 g, 0.0073 mol) and N-(4-(1,3-dioxolan-2-yl)phenyl)-[1,1'-biphenyl]-4-amine (5.80 g, 0.0183 mol). Anhydrous toluene (250 mL) was then added, and the reaction solution was purged with inert gas flow for 30 minutes. Sodium tert-butoxide (2.11 g, 0.0219 mol) and Pd$_2$dba$_3$ (0.27 g, 0.0003 mol) were then added, followed by the addition of tri-tert-butylphosphine (0.18 g, 0.0009 mol) in toluene solution (5 mL). The reaction was heated to reflux. When reaction completion was confirmed by thin-layer chromatography, the reaction was cooled to room temperature and filtered through a bed of celite and triethylamine treated silica gel, washing thoroughly with MTBE and ethyl acetate. Solvent was removed from filtrate by rotary evaporation and the crude solids were dried under vacuum. Trituration from acetone/methanol yielded TLC clean product. NMR and HPLC showed some evidence of isomerization, however the material was taken onto the next step. Product obtained: 3.93 g.

Dehalogenation of 2,2'-bis((4-(1,3-dioxolan-2-yl)phenyl)([1,1'-biphenyl]-4-yl)methyl)-6,6'-bibenzo[b]thiophene Procedures:

A three-neck round bottom flask was equipped with a reflux condenser, magnetic stir bar, and charged with 2,2'-bis((4-(1,3-dioxolan-2-yl)phenyl)([1,1'-biphenyl]-4-yl)methyl)-6,6'-bibenzo[b]thiophene (3.93 g, 0.0044 mol). Anhydrous tetrahydrofuran (250 mL) was added to the reaction flask by cannula. Triethylamine (6.2 mL) was added by syringe, followed by formic acid (1.5 mL). The reaction solution was purged with strong nitrogen flow for 30 minutes, after which palladium II acetate (0.12 g, 0.0005 mol) and tritertbutylphosphine (0.18 g, 0.0009 mol) (in 5 mL anhydrous toluene as solution) were added. The reaction was heated to reflux for two hours. After refluxing, the reaction was cooled to room temperature and worked up with MTBE and DI H$_2$O until neutral. The organic fraction was collected and filtered through a celite/silica gel (triethylamine treated) plug. Solvent was removed from the filtrate by rotary evaporation. The resulting crude material was placed under vacuum and taken on to the subsequent dehalogenation step.

Dehalogenation of 2,2'-bis((4-(1,3-dioxolan-2-yl)phenyl)([1,1'-biphenyl]-4-yl)methyl)-6,6'-bibenzo[b]thiophene Procedures:

A three-neck round bottom flask was equipped with a reflux condenser, magnetic stir bar, and charged with 2,2'-bis((4-(1,3-dioxolan-2-yl)phenyl)([1,1'-biphenyl]-4-yl)methyl)-6,6'-bibenzo[b]thiophene (3.93 g, 0.0044 mol). Anhydrous tetrahydrofuran (250 mL) was added to the reaction flask by cannula. Triethylamine (6.2 mL) was added by syringe, followed by formic acid (1.5 mL). The reaction solution was purged with strong nitrogen flow for 30 minutes, after which palladium II acetate (0.12 g, 0.0005 mol) and tritertbutylphosphine (0.18 g, 0.0009 mol) (in 5 mL anhydrous toluene as solution) were added. The reaction was heated to reflux for two hours. After refluxing, the reaction was cooled to room temperature and worked up with MTBE and DI H$_2$O until neutral. The organic fraction was collected and filtered through a celite/silica gel (triethylamine treated) plug. Solvent was removed from the filtrate by rotary evaporation. The resulting crude material was placed under vacuum and taken on to the next reaction step.

Synthesis of 4,4'-([6,6'-bibenzo[b]thiophene]-2,2'-diylbis([1,1'-biphenyl]-4-ylazanediyl)dibenzaldehyde

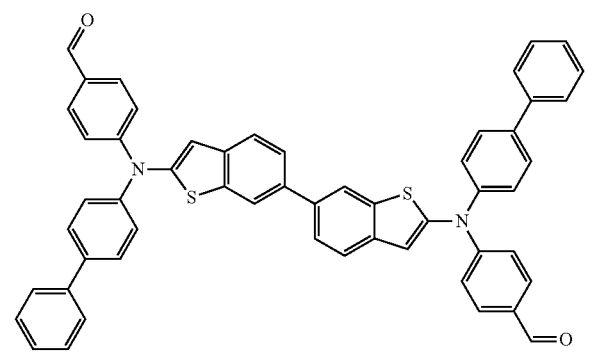

4,4'-([6,6'-bibenzo[b]thiophene]-2,2'-diylbis([1,1'-biphenyl]-4-ylazanediyl))dibenzaldehyde Procedures:

To a single-neck round bottom flask containing 2,2'-bis((4-(1,3-dioxolan-2-yl)phenyl)([1,1'-biphenyl]-4-yl)methyl)-6,6'-bibenzo[b]thiophene (3.93 g, 0.0044 mol), chloroform (500 mL) and a magnetic stir bar were added. Hydrochloric acid solution (2.0M, 5 mL) was added slowly dropwise. The reaction was allowed to stir for 30 minutes. A TLC plate was taken and showed that the reaction had finally completed. The solution was worked up with deionized water until neutral. The organic fraction was collected and filtered through a celite/silica gel (triethylamine treated) plug. Solvent was removed from the filtrate by rotary evaporation. The resulting crude material was purified trituration using acetone and methanol which provided pure product. Product obtained: 2.75 g.

Synthesis of N2,N2'-di([1,1'-biphenyl]-4-yl)-N2,N2'-bis(4-vinylphenyl)-[6,6'-bibenzo[b]thiophene]-2,2'-diamine

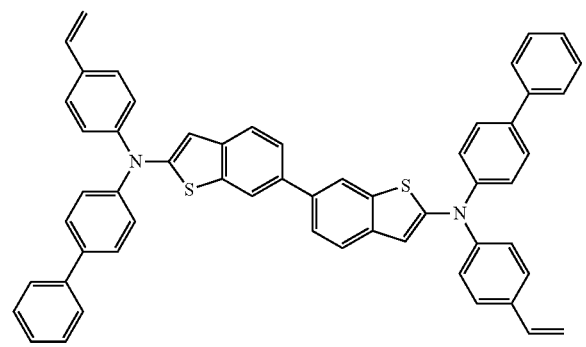

N²N²'-di([1,1'-biphenyl]-4-yl)-N²N²'-bis(4-vinylphenyl)-[6,6'-bibenzo[b]thiophene]-2,2'-diamine Procedures:

A three-neck round bottom flask was charged with methyltriphenylphosphonium bromide (4.25 g, 0.0119 mol) and anhydrous tetrahydrofuran (130 mL) was added via cannula. Stirring was initiated, and potassium tert-butoxide (1.37 g, 0.0122 mol) was added manually. This solution was allowed to stir for ten minutes before an anhydrous solution of 4,4'-([6,6'-bibenzo[b]thiophene]-2,2'-diylbis([1,1'-biphenyl]-4-ylazanediyl))dibenzaldehyde (2.75 g, 0.0034 mol) in tetrahydrofuran (20 mL) was added slowly, dropwise via syringe. The reaction was allowed to stir for thirty minutes before reaction completion was confirmed by thin-layer chromatography. The reaction solution was filtered through a bed of celite and silica gel treated with triethylamine, washing thoroughly with tetrahydrofuran. The filtrate was removed of solvent by rotary evaporation and the resulting crude material was placed under vacuum. The crude material was further purified by chromatography on silica gel using hexane/chloroform as an eluent. Precipitation from a minimum amount of toluene into methanol provided pure product. Product obtained: 1.75 g.

$\delta_H$ (300 MHz, CDCl$_3$) 5.22 (2H, d) 5.70 (2H, d) 6.70 (2H, m) 6.86 (2H, s) 7.20-7.48 (18H, m) 7.50-7.64 (12H, m) 7.89 (2H, s)

PLX-3-A

Supplementing the description here for PLX-3 compounds, additional, related embodiments can be called PLX-3-A and can be represented by

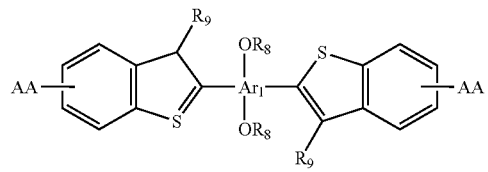

2,2'-((((2,5-dibromo-1,4-phenylene)bis(oxy))bis(butane-4,1-diyl))bis(3,1-phenylene))bis(1,3-dioxolane) Synthesis

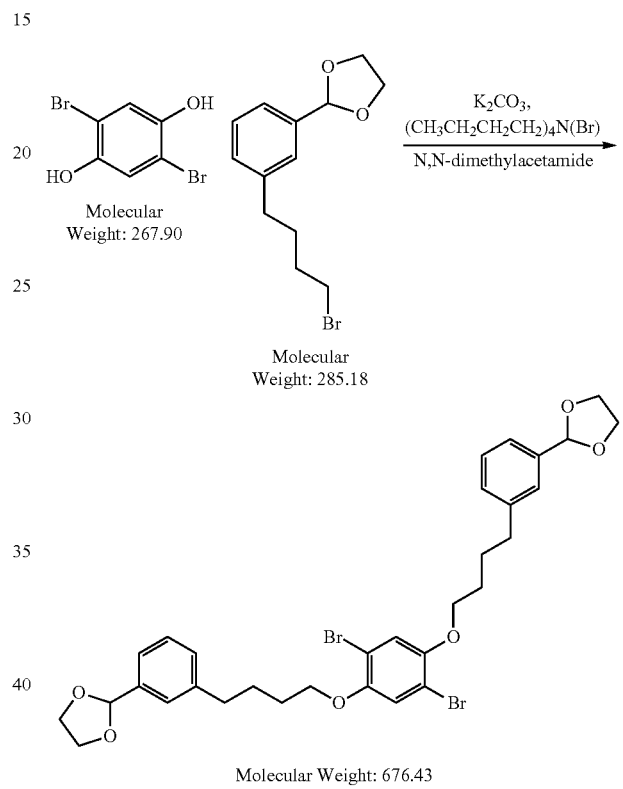

Procedure:

A 500 mL three-neck round bottom flask equipped with a reflux condenser and thermometer was charged with 2,5-dibromohydroquinone (7.08 g, 0.0264 mol) and 2-(3-(4-bromobutyl)phenyl)-1,3-dioxolane (18.1 g, 0.0636 mol). Anhydrous N,N-dimethylacetamide (261 mL) was added via syringe. All solids were dissolved with stirring to give a pale yellow solution. Potassium carbonate (10.9 g, 0.0786 mol) was then added followed by tetrabutylammonium bromide (1.4 g, 0.0043 mol). The reaction was heated to 100° C. and stirred overnight at that temperature. The solution turned orange then maroon then black as it was heated. Reaction completion was monitored via TLC and HPLC. Upon completion, the reaction was cooled to room temperature and deionized water (125 mL) was added to the reaction solution leading to precipitation of some solids. More MTBE (250 mL) and deionized water (125 mL) were added then the mixture was transferred to a 2 L separatory funnel. As some undissolved solids remained, chloroform (200 mL) was added to dissolve them. The organic and aqueous layers were separated. The aqueous layer was back-extracted with chloroform (2×400 mL). The combined organic layers were washed with deionized water (3×1.4 L). Solvents were removed via rotary evaporation and after drying under vacuum, the product was obtained as a solid. The product was purified by trituration with methanol (once) and hexane (twice), leading to 15.5 g product. Product purity was confirmed via HPLC. Product characterization was confirmed via $^1$H NMR.

2-(2,5-bis(4-(3-(1,3-dioxolan-2-yl)phenyl)butoxy)-4-(6-(phenyl(m-tolyl)amino)benzo[b]thiophen-2-yl)phenyl)-N-phenyl-N-(m-tolyl)benzo[b]thiophen-5-amine Synthesis was degassed via a strong nitrogen flow overnight. The N-phenyl-N-(m-tolyl)-2-(trimethylstannyl)benzo[b]thiophen-6-amine solution was further degassed via five vacuum-nitrogen cycles then transferred to the 200 mL Schlenk flask via syringe. This solution was purged via a strong nitrogen flow for 45 minutes, after which Pd$_2$dba$_3$ (0.7029 g, 0.0008 mol) was added. Solution was maroon in color. The reaction was heated to 85° C. After 2 hours, reaction completion was monitored via TLC and HPLC. Both indicated that the reaction was complete. The reaction solution was permitted to cool to room temperature. The reaction solution was filtered through a celite/silica gel plug, washing

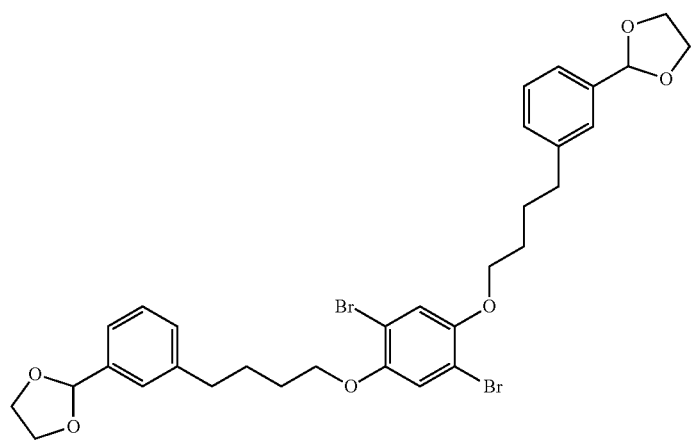

Molecular Weight: 676.43

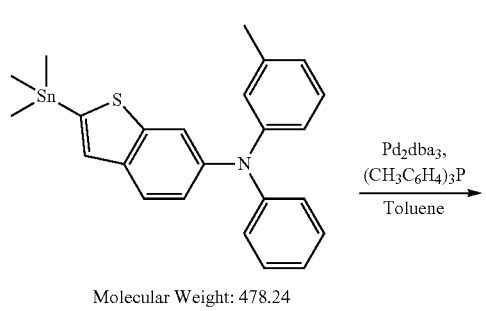

Molecular Weight: 478.24

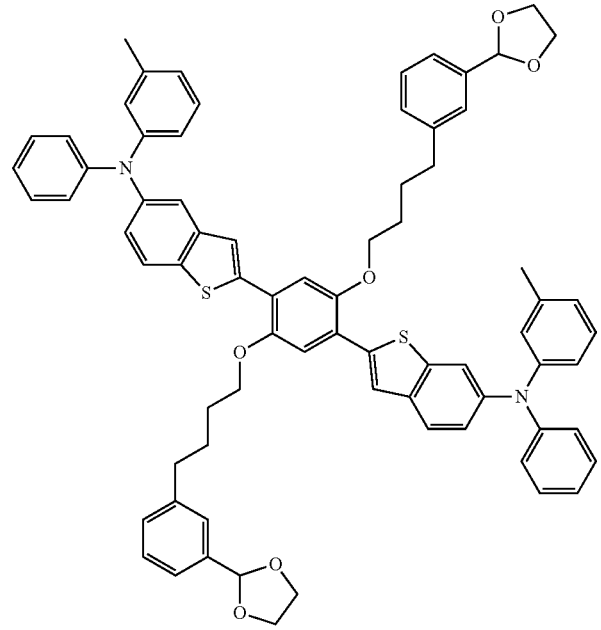

Molecular Weight: 1145.47

Procedure:

A 200 mL Schlenk flask was charged with 2,2'-((((2,5-dibromo-1,4-phenylene)bis(oxy))bis(butane-4,1-diyl))bis(3,1-phenylene))bis(1,3-dioxolane) (3.0 g, 0.0045 mol) and tri-(o-tolyl)phosphine (0.58 g, 0.0019 mol). N-phenyl-N-(m-tolyl)-2-(trimethylstannyl)benzo[b]thiophen-6-amine (4.7 g, 0.0098 mol) was dissolved in anhydrous toluene (50 mL) that thoroughly with a 2% triethylamine/ethyl acetate solution (900 mL). After removing solvents via rotary evaporation and drying under vacuum, 6.29 g product was obtained. The product was purified via flash chromatography (dry load, silica gel). The product was eluted using a gradient from 100% hexane to 100% ethyl acetate. After removing solvents via rotary evaporation and drying under vacuum, 4.07 g product was obtained. Product characterization was confirmed via ¹H NMR. Product purity was confirmed via HPLC.

Dehalogenation of 2-(2,5-bis(4-(3-(1,3-dioxolan-2-yl)phenyl)butoxy)-4-(6-(phenyl(m-tolyl)amino)benzo[b]thiophen-2-yl)phenyl)-N-phenyl-N-(m-tolyl)benzo thiophen-5-amine (Run Twice)

Procedure:

In a 500 mL single-neck round bottom flask, 2-(2,5-bis(4-(3-(1,3-dioxolan-2-yl)phenyl)butoxy)-4-(6-(phenyl(m-tolyl)amino)benzo[b]thiophen-2-yl)phenyl)-N-phenyl-N-(m-tolyl)benzo[b]thiophen-5-amine (4.07 g, 0.0036 mol) was dissolved in anhydrous THF (60 mL). This solution was transferred via syringe to a 2 L three-neck round bottom flask equipped with a reflux condenser and thermometer. Solution was pink in color. Triethylamine (5.0 mL, 0.036 mol) was added via syringe. Formic acid (1.5 mL, 0.040 mol) was added dropwise via syringe. The solution was then purged via a strong nitrogen flow for 45 minutes, after which Pd(OAc)₂ (0.1 g, 0.0006 mol) and tBu₃P (0.2 g, 0.0008 mol, in 2 mL anhydrous toluene) were added. The reaction was heated to 65° C. and left to stir at this temperature for 2 hours after which it was cooled to room temperature.

The reaction solution was filtered through a celite/silica gel plug, washing thoroughly with a 2% triethylamine/ethyl acetate solution (800 mL). The filtrate from the celite/silica gel plug was transferred to a 2 L separatory funnel and deionized water was added (600 mL). NaCl was added to break up the emulsion that formed, allowing separation of the organic and aqueous layers. The organic layer was extracted with deionized water (3×600 mL). NaCl was added to break up the emulsion that found each time. After removing solvents via rotary evaporation and drying under vacuum, 3.92 g product was obtained. The dehalogenation procedure was repeated a second time to yield 3.98 g product.

3,3'-(((2,5-bis(5-(phenyl(m-tolyl)amino)benzo[b]thiophen-2-yl)-1,4-phenylene)bis(oxy))bis(butane-4,1-diyl))dibenzaldehyde Synthesis

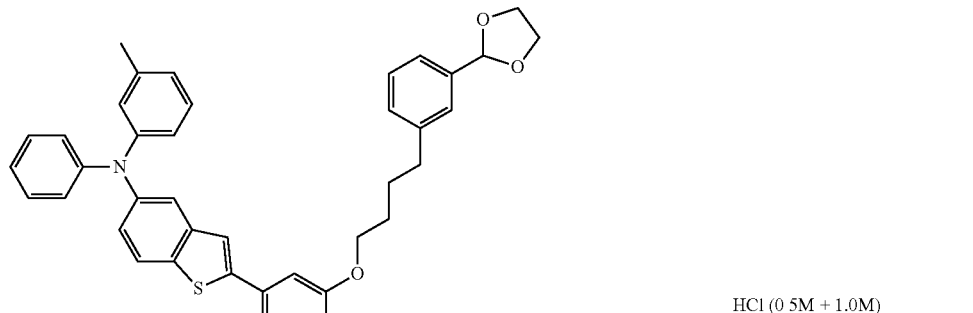

Molecular Weight: 1145.47

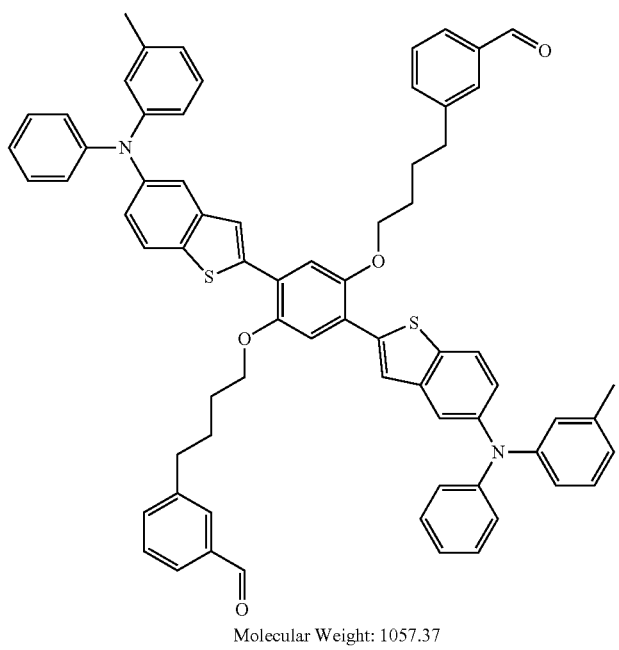

Molecular Weight: 1057.37

Procedure:

2-(2,5-bis(4-(3-(1,3-dioxolan-2-yl)phenyl)butoxy)-4-(6-(phenyl(m-tolyl)amino)benzo[b]thiophen-2-yl)phenyl)-N-phenyl-N-(m-tolyl)benzo[b]thiophen-5-amine (4.0 g, 0.0035 mol) was dissolved in THF (250 mL) in a 1 L single-neck round bottom flask. Solution was peach in color. Aqueous hydrochloric acid solution (3.4 mL, 0.5M) was added dropwise. The reaction was stirred at room temperature for 1 hour, after which reaction completion was monitored via $^1$H NMR. It indicated that the reaction was complete. Deionized water (200 mL) was added to the 1 L single-neck round bottom flask to quench the reaction. The mixture was transferred to a 2 L separatory funnel, along with more ethyl acetate (500 mL) and deionized water (300 mL). NaCl was added to break up the emulsion that formed, allowing separation of the organic and aqueous layers. The aqueous layer was back-extracted with ethyl acetate (2×250 mL). The organic layer was then washed with deionized water (3×700 mL). Again, NaCl was added to break up the emulsion that formed, allowing separation of the organic and aqueous layers. After removing solvents via rotary evaporation and drying under vacuum, 3.68 g product was obtained. The product was purified via flash chromatography (dry load, silica gel). The product was eluted using a gradient from 100% hexane to 100% ethyl acetate. After removing solvents via rotary evaporation and drying under vacuum, 1.00 g product was obtained. Product characterization was confirmed via $^1$H NMR.

2,2'-(2,5-bis(4-(3-vinylphenyl)butoxy)-1,4-phenylene)bis(N-phenyl-N-(m-tolyl)benzo[b]thiophen-5-amine) Synthesis

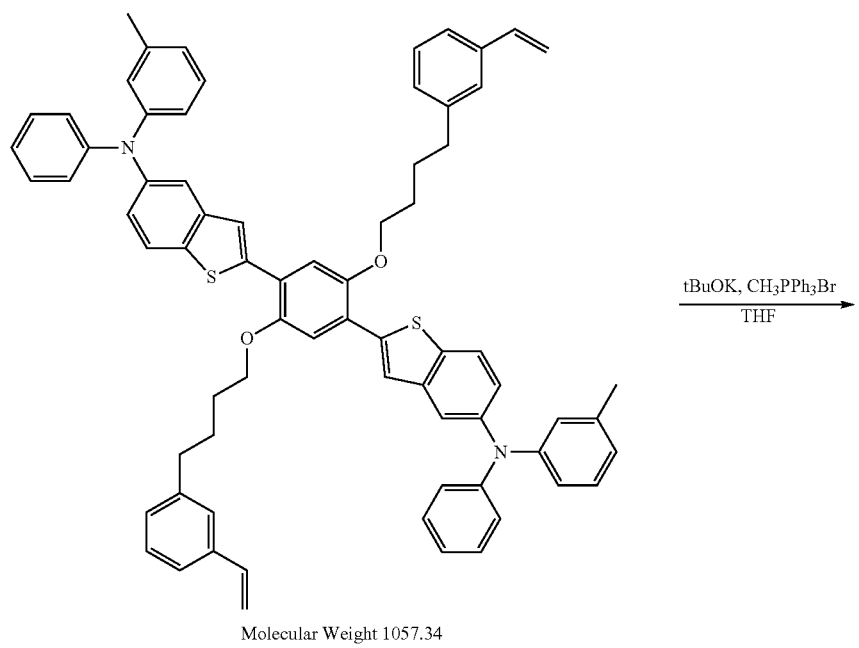

Molecular Weight 1057.34

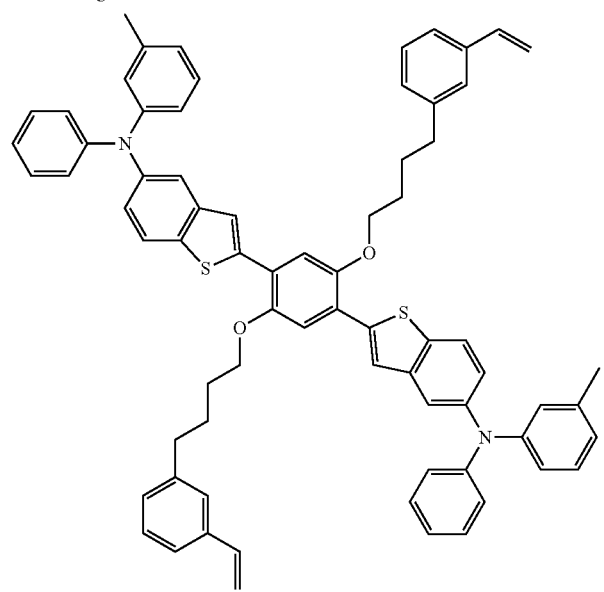

Molecular Weight 1053.42

Procedure:

In a 250 mL single-neck round bottom flask, 3,3'-(((2,5-bis(5-(phenyl(m-tolyl)amino)benzo[b]thiophen-2-yl)-1,4-phenylene)bis(oxy))bis(butane-4,1-diyl))dibenzaldehyde (1 g, 0.002 mol) was dissolved in anhydrous THF (10 mL). This solution was degassed via five vacuum-nitrogen cycles. Methyltriphenylphosphonium bromide (2.3 g, 0.0063 mol) was added to a 250 mL three-neck round bottom flask then anhydrous THF (20 mL) was added via syringe. This solution was stirred at room temperature for 5 minutes. Next, potassium tert-butoxide was added (1.1 g, 0.0094 mol). Solution turned yellow. Aluminum foil was placed around the 250 mL three-neck round bottom flask. The solution was stirred at room temperature for 10 minutes, then the 3,3'-(((2,5-bis(5-(phenyl(m-tolyl)amino)benzo[b]thiophen-2-yl)-1,4-phenylene)bis(oxy))bis(butane-4,1-diyl))dibenzaldehyde solution was added dropwise via syringe. Solution turned orange. After 1 hour, reaction completion was monitored via TLC and $^1$H NMR. Both indicated that it was complete.

The reaction solution was filtered through a celite/silica gel plug, washing thoroughly with a 2% triethylamine/ethyl acetate solution (900 mL). After removing solvents via rotary evaporation and drying under vacuum, 3.15 g product was obtained.

The product was purified via flash chromatography (dry load, silica gel). The product was eluted using a gradient from 100% hexane to 100% ethyl acetate. After removing solvents via rotary evaporation and drying under vacuum, 1.38 g product was obtained.

The product was further purified by dissolution in THF (7 mL) with stirring. This solution was added dropwise via glass pipette into methanol (200 mL, pre-chilled in an ice-water bath). The precipitated product was stirred in the chilled methanol for 15 minutes, and then filtered through a Buchner funnel. After vacuum drying, 1.27 g of product obtained. Product purity was confirmed via HPLC. Product characterization was confirmed via $^1$H NMR. $^1$H NMR (300 MHz, (CD$_3$)$_2$CO) 1.9 (m, 8H), 2.25 (s, 6H), 2.7 (t, 4H), 4.25 (t, 4H), 5.1-5.2 (d, 2H), 5.7-5.8 (d, 2H), 6.6-6.75 (q, 2H), 6.85-7.35 (m, 28H), 7.4-7.55 (d, 4H), 7.8-7.85 (d, 2H).

PLX-3-B 2,2'-(2,5-bis(octyloxy)-1,4-phenylene)dithiophene Synthesis

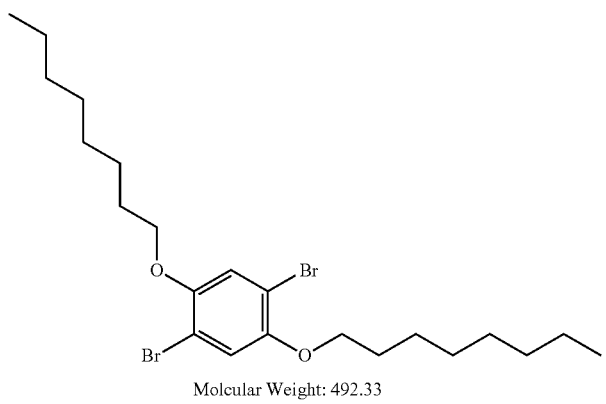

Molcular Weight: 492.33

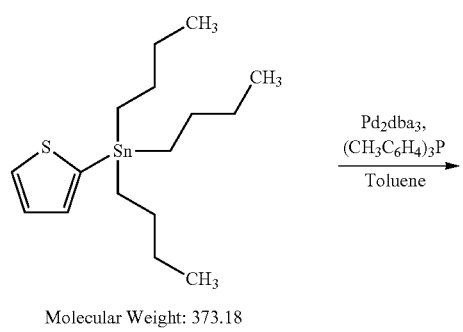

Molecular Weight: 373.18

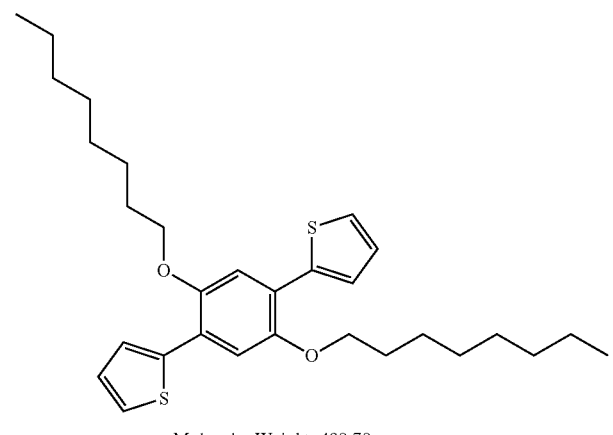

Molecular Weight: 498.78

Procedure:

In a glovebox, a 100 mL Schlenk flask was charged with dioctyloxydibromobenzene (20 g, 0.040 mol), Pd$_2$dba$_3$ (4 g, 0.004 mol), and tri(o-tolyl)phosphine (5.0 g, 0.016 mmol). 2-(tributylstannyl)thiophene (60.0 g, 0.163 mol) was added outside the glovebox via syringe. Anhydrous toluene (500 mL), degassed via a strong nitrogen flow overnight, was added via syringe. All solids dissolved with stirring. Solution turned dark maroon. This solution was degassed via five vacuum-nitrogen cycles, and then placed in an oil bath preheated to 100° C. Reaction completion was monitored via TLC and $^1$H NMR. Both indicated that it was complete within 3 hours, after which it was permitted to cool to room temperature.

The reaction solution was filtered through a celite/silica gel plug, washing thoroughly with hexane (550 mL), a 2% ethyl acetate/hexane solution (400 mL), and a 5% ethyl acetate/ hexane solution (200 mL). The filtrate from the celite/silica gel plug was nearly evaporated, at which point, methanol (200 mL) was added to precipitate the product. The precipitated product was filtered through a Buchner funnel following overnight refrigeration and dried under vacuum.

5,5'-(2,5-bis(octyloxy)-1,4-phenylene)bis(2-bromothiophene) Synthesis

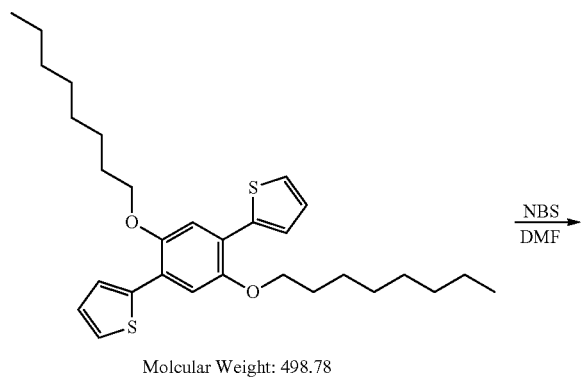

Molcular Weight: 498.78

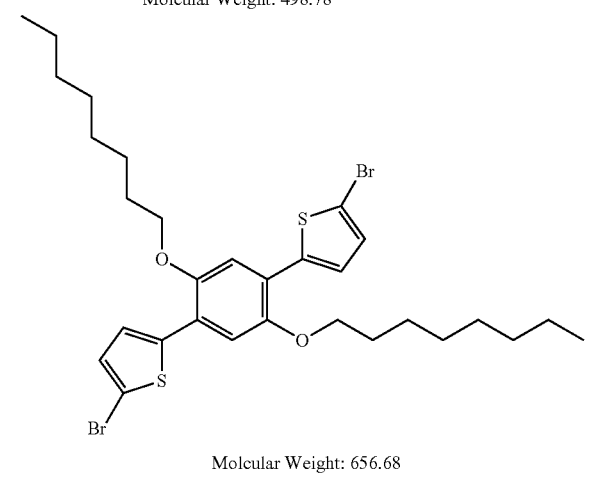

Molcular Weight: 656.68

Procedure:

A 500 mL three-neck round bottom flask equipped with a thermometer was charged with CRGG-04-065 (6.15 g, 0.0123 mol). Anhydrous THF (124 mL) was added via syringe, followed by drop-wise addition of acetic acid (12.5 mL) via syringe. All solids dissolved with stirring. Solution was clear in color. This solution was cooled to 0° C. via ice-water bath, and then permitted to stir at this temperature for 15 minutes. NBS (4.40 g, 0.0247 mol) was added and the reaction was permitted to stir at 0° C. for another 15 minutes. Reaction completion was monitored via TLC and $^1$H NMR. Both indicated that it was complete within 15 minutes. It is important to note that the product precipitated from the solution.

Deionized water (200 mL) was added to the flask in order to quench the reaction. This mixture was transferred to a 1-L separatory funnel, and then ethyl acetate (300 mL) and deionized water (200 mL) were added. Additional ethyl acetate (300 mL) and NaCl were added to break up the emulsion that formed, allowing separation of the organic and aqueous layers. The aqueous layer was back-extracted with ethyl acetate (2×250 mL). The organic layer was washed with deionized water (2×1 L). After removing solvents via rotary evaporation and drying under vacuum, 8.11 g product was obtained. Product characterization was confirmed via $^1$H NMR.

The product was further purified by dissolution in THF with stirring and light heating via heat gun. This solution was added dropwise via a glass pipette into methanol (600 mL, pre-chilled in an ice-water bath). The precipitated product was stirred in the chilled methanol for 25 minutes, and then filtered through a Buchner funnel. After drying under vacuum, 7.62 g product was obtained.

5,5'-(2,5-bis(octyloxy)-1,4-phenylene)bis(N-(4-(1,3-dioxolan-2-yl)phenyl)-N-([1,1'-biphenyl]-4-yl)thiophen-2-amine) Synthesis

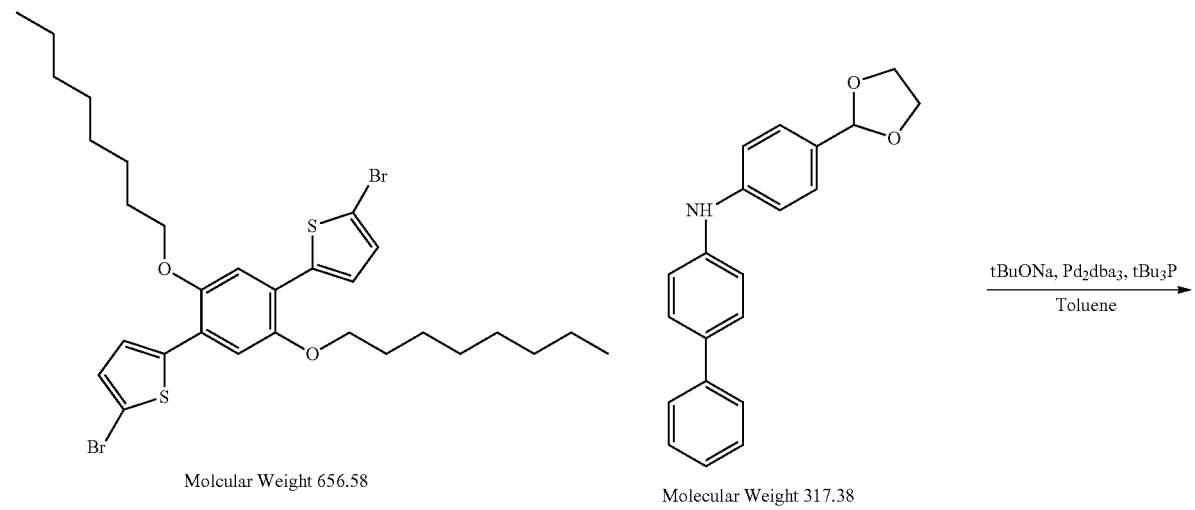

-continued

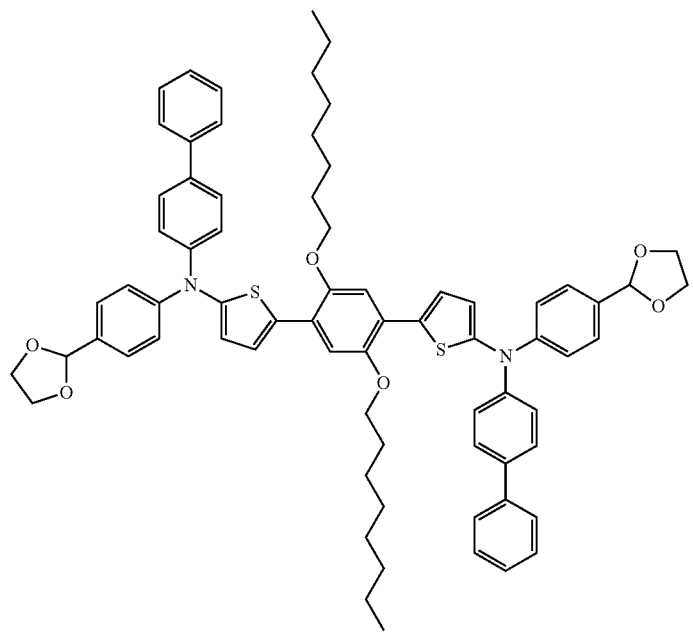

Molecular Weigh 1129.51

Procedure:

A 250 mL three-neck round bottom flask equipped with a reflux condenser was charged with 5,5'-(2,5-bis(octyloxy)-1,4-phenylene)bis(2-bromothiophene) (3.1 g, 0.0048 mol) and N-(4-(1,3-dioxolan-2-yl)phenyl)-[1,1'-biphenyl]-4-amine (3.33 g, 0.0105 mol). Anhydrous toluene (130 mL) was added via syringe. Not all solids dissolved, even with stirring and light heating via heat gun. Solution, with the solids in it, was tan in color. This solution was degassed via a strong nitrogen flow for 45 minutes, after which tBuONa (1.38 g, 0.0144 mol) and $Pd_2dba_3$ (0.2 g, 0.0002 mol) were added. Then, $tBu_3P$ (0.1 g, 0.0006 mol) dissolved in anhydrous toluene (3 mL) was added dropwise via syringe. The reaction was heated to 80° C. overnight. The next morning, reaction completion was monitored via TLC. It indicated that the reaction was complete, after which it was permitted to cool to room temperature.

The solution was filtered through a celite/silica gel plug, washing thoroughly with a 2% triethylamine/ethyl acetate solution (1.3 L). The filtrate from the celite/silica gel plug was nearly evaporated, at which point, the product precipitated from solution. The precipitated product was filtered through a Buchner funnel. After vacuum drying, 3.93 g product was obtained.

Dehalogenation of 5,5'-(2,5-bis(octyloxy)-1,4-phenylene)bis(N-(4-(1,3-dioxolan-2-yl)phenyl)-N-([1,1'-biphenyl]-4-yl)thiophen-2-amine) (Run Twice)

Procedure:

A 500 mL three-neck round bottom flask equipped with a reflux condenser was charged with 5,5'-(2,5-bis(octyloxy)-1,4-phenylene)bis(N-(4-(1,3-dioxolan-2-yl)phenyl)-N-([1,1'-biphenyl]-4-yl)thiophen-2-amine) (3.9 g, 0.0035 mol). Anhydrous THF (160 mL) was added via syringe. Solids did not all dissolve, even with the additional anhydrous THF and stirring.

Solution was yellow in color. Triethylamine (5.0 mL, 0.036 mol) then formic acid (1.40 mL, 0.0371 mol) were added drop-wise via syringe. This solution was purged via a strong nitrogen flow for 45 minutes. It turned a more peach color. Then, $Pd(OAc)_2$ (0.08 g, 0.0004 mol) and $tBu_3P$ (0.1 g, 0.0006 mol, in 2 mL anhydrous toluene) were added. The reaction was heated to 70° C. After 2 hours, it was permitted to cool to room temperature.

The solution was filtered through a celite/silica gel plug, washing thoroughly with a 2% triethylamine/ethyl acetate solution (1 L). After removing solvents via rotary evaporation and drying under vacuum, 3.98 g of product was obtained.

The dehalogenation procedure was repeated a second time to yield 3.98 g product.

4,4'((5,5'-(2,5-bis(octyloxy)-1,4-phenylene)bis(thiophene-5,2-diyl))bis([1,1'-biphenyl]-4-yla-zanediyl))dibenzaldehyde Synthesis

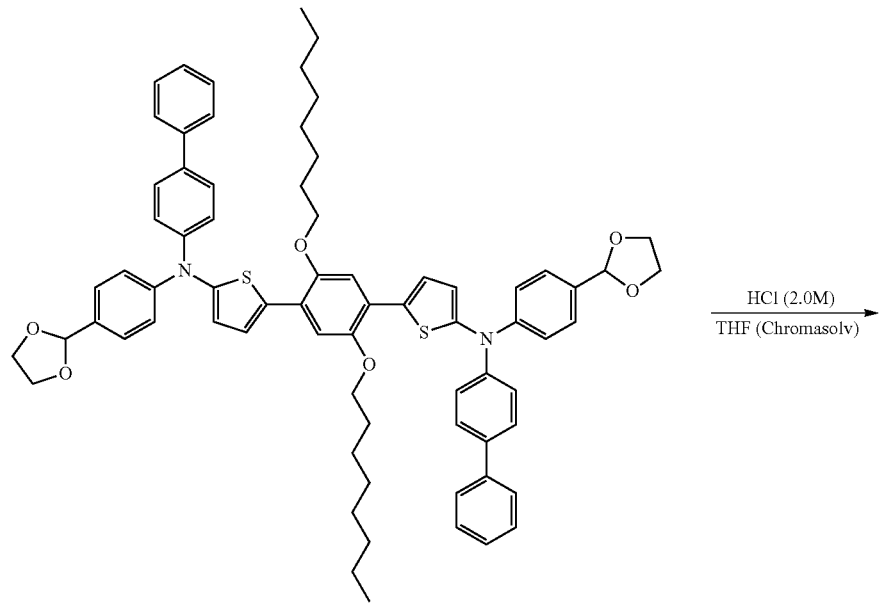

Molecular Weight: 1129.51

HCl (2.0M) / THF (Chromasolv)

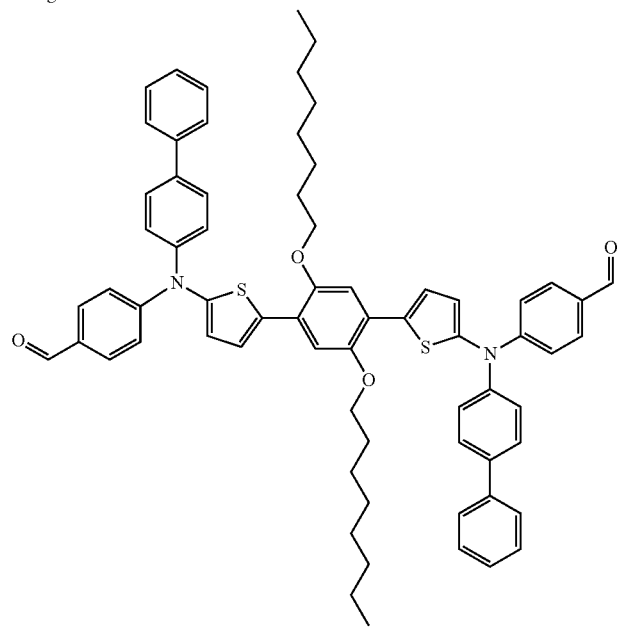

Molecular Weight: 1041.4

Procedure:

In a 1 L single-neck round bottom flask, 5,5'-(2,5-bis(octyloxy)-1,4-phenylene)bis(N-(4-(1,3-dioxolan-2-yl)phenyl)-N-([1,1'-biphenyl]-4-yl)thiophen-2-amine) was dissolved in THF (584 mL) via syringe. All solids dissolved with stirring. Solution was brown-orange in color. Aqueous hydrochloric acid solution (1.0 mL, 2.0M), was added dropwise via syringe. This solution was permitted to stir for 15 minutes, after which reaction completion was monitored via $^1$H NMR. It indicated that the reaction was not complete. Additional aqueous hydrochloric acid solution (1.0 mL, 2.0M) was added dropwise via syringe and the reaction was permitted to stir for another 15 minutes. Once again, reaction completion was monitored via $^1$H NMR. It indicated that the reaction was complete.

The mixture was transferred to a 2 L separatory funnel, along with deionized water basified with triethylamine (500 mL) and MTBE (500 mL). After separation, the aqueous layer was back-extracted with MTBE (1×400 mL). The organic layer was washed with deionized water (3×1.5 L). After removing solvents via rotary evaporation and drying under vacuum, 3.62 g product was obtained.

5,5'(2,5-bis(octyloxy)-1,4-phenylene)bis(N-([1,1'-biphenyl]-4-yl)-N-(4-vinylphenyl)thiophen-2-amine) Synthesis

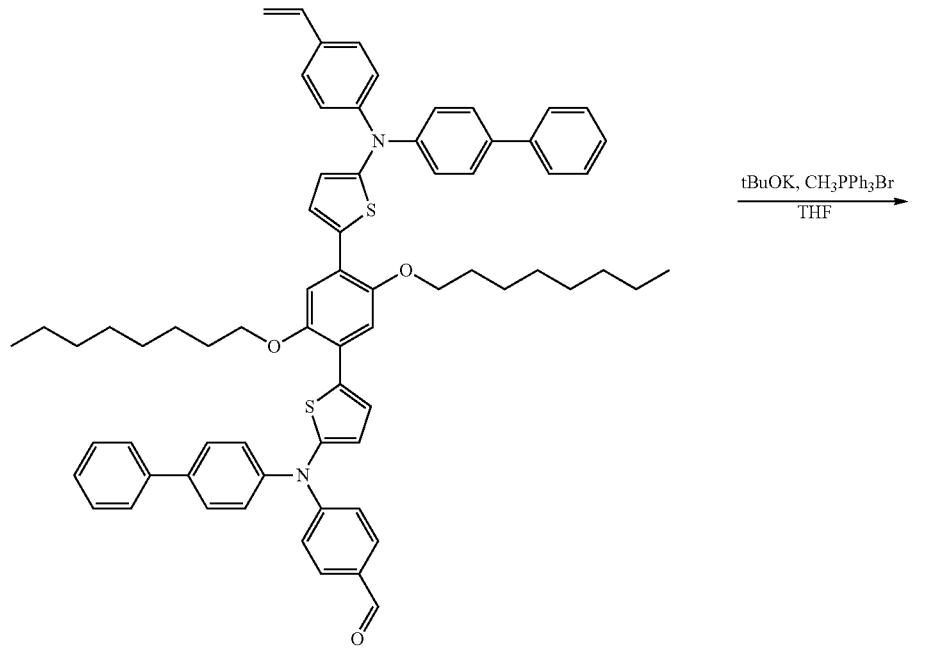

Molecular Weight 1041.41

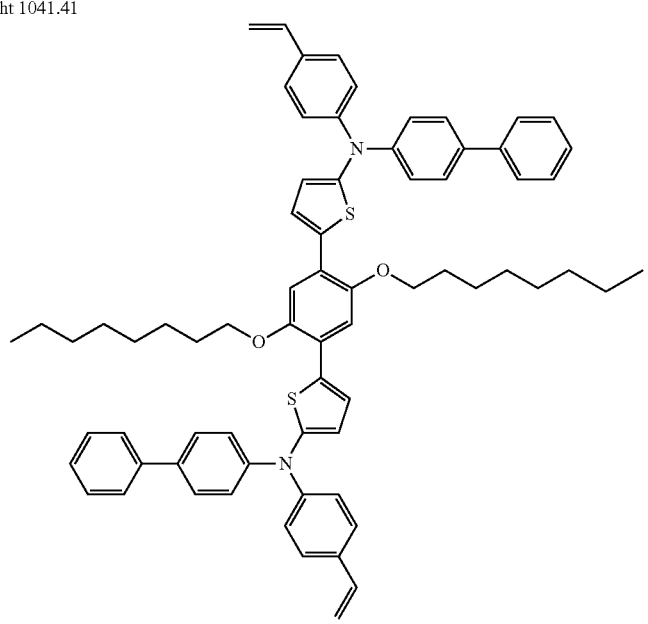

Molecular Weight 1037.46

Procedure:

4,4'((5,5'-(2,5-bis(octyloxy)-1,4-phenylene)bis(thiophene-5,2-diyl))bis([1,1'-biphenyl]-4-ylazanediyl))dibenzaldehyde was dissolved in anhydrous THF (100 mL). All solids dissolved with stirring. Solution was bright red in color. A 500 mL three-neck round bottom flask equipped with an addition funnel was charged with methyltriphenylphosphonium bromide (3.79 g, 0.0104 mol). Anhydrous THF (100 mL) was added via syringe. This solution was permitted to stir for 5 minutes, and then potassium tert-butoxide (1.22 g, 0.0109 mol) was added. Aluminum foil was placed around the 500 mL three-neck round bottom flask. Solution turned yellow. The 4,4'((5,5'-(2,5-bis(octyloxy)-1,4-phenylene)bis(thiophene-5,2-diyl))bis([1,1'-biphenyl]-4-ylazanediyl)) dibenzaldehyde solution was transferred to the addition funnel via cannula, then added dropwise to the flask. 1 hour into the reaction, reaction completion was monitored via TLC. It indicated that the reaction was complete.

The reaction solution was filtered through a celite/silica gel plug, washing thoroughly with a 2% triethylamine/ethyl acetate solution (1.5 L). After removing solvents via rotary evaporation and drying under vacuum, 5.57 g product was obtained.

The product was purified via flash chromatography (dry load, silica gel). The product was eluted using a gradient from 100% hexane to 100% ethyl acetate. TLC indicated some impurities remained.

The TLC impure product was dissolved in THF (20 mL) via syringe. This solution was added dropwise via glass pipette into methanol (500 mL, pre-chilled in an ice-water bath). The precipitated product was stirred in the chilled methanol for 15 minutes, and then filtered through a Buchner funnel. The precipitated product was transferred to a 500 mL single-neck round bottom flask and purified by trituration with hexane (200 mL). The product was filtered through a Buchner funnel while the solution was still hot. After drying under vacuum, 2.29 g product was obtained. Product purity was confirmed via HPLC. Product characterization was confirmed via $^1$H NMR. $^1$H NMR (300 MHz, (CD$_3$)$_2$CO) 0.82 (t, 6H), 1.12-1.33 (m, 16H), 1.39-1.51 (m, 4H), 1.72-1.89 (m, 4H), 4.0 (t, 4H), 5.1-5.2 (d, 2H), 5.6-5.75 (d, 2H), 6.6-6.8 (q, 2H), 7.0-7.6 (m, 32H).

PLX-3-C-2

N-phenyl-N-(m-tolyl)thiophen-2-amine Synthesis

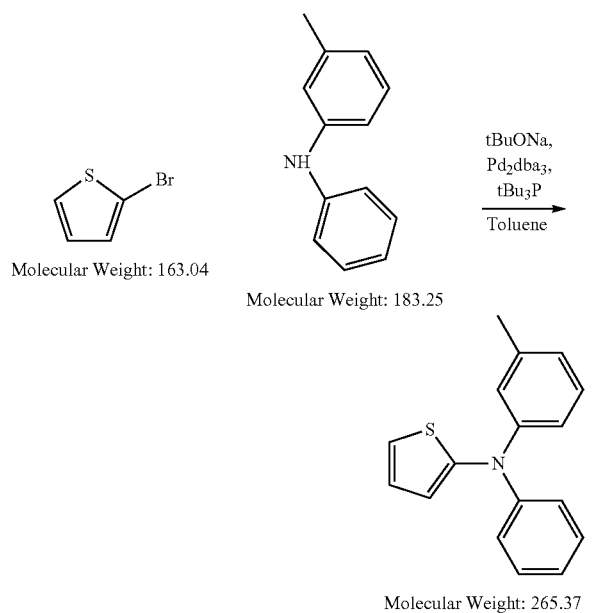

Procedure:

A 1 L three-neck round bottom flask equipped with a reflux condenser and thermometer was charged with 2-bromothiophene (8.05 g, 0.0494 mol) and 3-methyl-N-phenylaniline (10.9 g, 0.0593 mol). Anhydrous toluene (500 mL) was added via cannula. All solids dissolved. Solution was red in color. This solution was purged via a strong nitrogen flow for 1 hour, after which tBuONa (7.15 g, 0.0744 mol) and Pd$_2$dba$_3$ (1.1 g, 0.0012 mol) were added. Then, tBu$_3$P (0.81 g, 0.0040 mol) dissolved in anhydrous toluene (3 mL) was added dropwise via syringe. The reaction was heated to 80° C. overnight. Reaction completion was then monitored via TLC, GC-MS, and HPLC. All indicated that the reaction was complete, and the reaction was permitted to cool to room temperature.

The reaction solution was filtered through a celite/silica gel plug, rinsing thoroughly with a 2% triethylamine/ethyl acetate solution (1 L), 2% triethylamine/toluene solution (500 mL), and 2% triethylamine/chloroform solution. After removing solvents via rotary evaporation and drying under vacuum, 17.02 g product was obtained.

The product was purified via flash chromatography (wet load (ethyl acetate (5 mL)), silica gel). The product was eluted with 2% triethylamine/hexane solution (4 L). After removing solvents via rotary evaporation and drying under vacuum, 10.13 g product was obtained. Product purity was confirmed via HPLC.

5-bromo-N-phenyl-N-(m-tolyl)thiophen-2-amine Synthesis

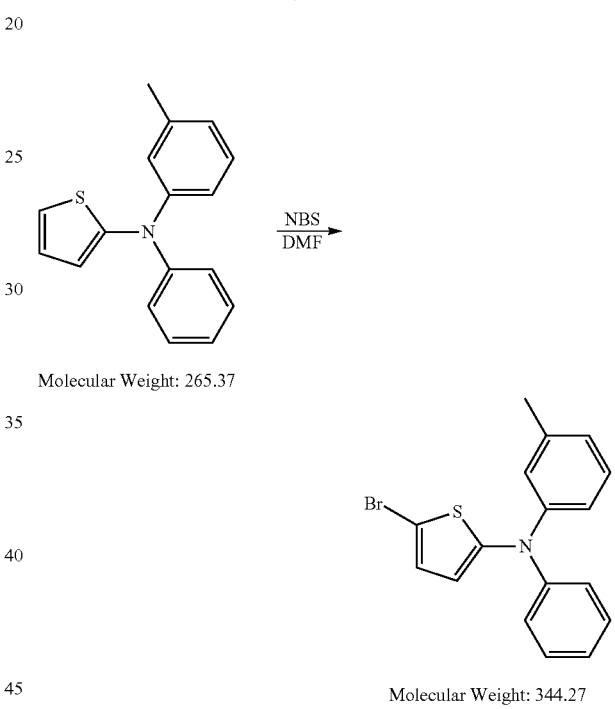

Procedure:

In a 150 mL single-neck round bottom flask, N-phenyl-N-(m-tolyl)thiophen-2-amine (9.29 g, 0.0350 mol) was dissolved in anhydrous DMF (345 mL). Solution was pinkish red in color. This solution was transferred to a 500 mL three-neck round bottom flask equipped with a thermometer via cannula. The solution was chilled to 0° C. via an ice-water bath and permitted to stir at 0° C. for 20 minutes. Solution became pale yellow in color. NBS (6.24 g, 0.0351 mol) was added then the solution was permitted to stir at 0° C. for an additional 30 minutes. Reaction completion was monitored via GC-MS. It indicated the presence of some starting material, di-brominated product, and the desired mono-brominated product (major peak). Deionized water (100 mL) was added to the flask to quench the reaction.

The reaction solution was transferred to a 2 L separatory funnel then deionized water (250 mL) and MTBE (250 mL) were added. After separation of the organic and aqueous layers, the aqueous layer was back-extracted with MTBE (2×200 mL). The organic layer was washed with deionized water (3×500 mL). After removing solvents via rotary evaporation and drying under vacuum, 10.96 g product was obtained.

The product was purified via column chromatography (wet load (hexanes (6 mL)), silica gel). The product was eluted using a gradient from 100% hexane to 100% ethyl acetate. TLC pure fractions were collected and further analyzed via GC-MS. Product obtained: 9.1 g.

N-phenyl-N-(m-tolyl)-5-(trimethylstannyl)thiophen-2-amine Synthesis

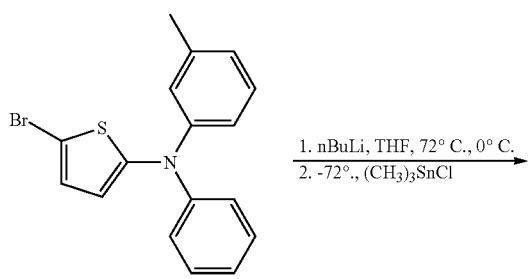

Molecular Weight: 344.27

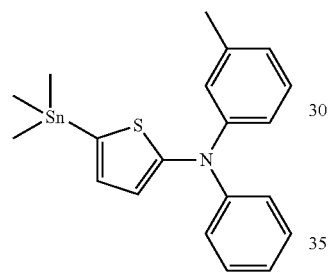

Molecular Weight: 428.18

Procedure:

In a 500 mL single-neck round bottom flask, 5-bromo-N-phenyl-N-(m-tolyl)thiophen-2-amine (3.54 g, 0.0103 mol) was dissolved in anhydrous THF (205 mL) that was purged overnight via a strong nitrogen flow. Solution was clear in color. This solution was degassed via five vacuum-nitrogen cycles, then transferred via cannula to a 1 L three-neck round bottom flask equipped with an addition funnel and thermometer. The solution was degassed once again via five vacuum-nitrogen cycles, and then chilled to −78° C. via a dry ice-isopropanol bath. Once the solution reached −78° C., tert-butyllithium solution (13 mL, 1.7M in pentane) was transferred to the addition funnel via syringe and added drop-wise to the flask. The solution was stirred at −78° C. for 30 minutes before being permitted to warm up to 0° C. Solution turned from yellow to an orange-pink color as it was warmed up. Once the solution reached 0° C., it was chilled it back to −78° C. via the dry ice-isopropanol bath. Once the solution reached −78° C. once again, trimethyltin chloride (22 mL, 1.0M in THF) was transferred to the addition funnel via syringe and added drop-wise to the flask. The solution was stirred at −78° C. for 30 minutes, then permitted to warm up to room temperature overnight. Reaction completion was monitored via GC-MS and HPLC.

The reaction solution was transferred to a 2 L separatory funnel then MTBE (300 mL) and deionized water (300 mL) were added. After separation of the organic and aqueous layers, the aqueous layer was back-extracted with MTBE (150 mL). The organic layer was washed with deionized water (3×700 mL). After removing solvents via rotary evaporation and drying under vacuum, 4.31 g product was obtained.

5,5'-(2,5-bis(4-(3-(1,3-dioxolan-2-yl)phenyl)butoxy)-1,4-phenylene)bis(N-phenyl-N-(m-tolyl)thiophen-2-amine) Synthesis

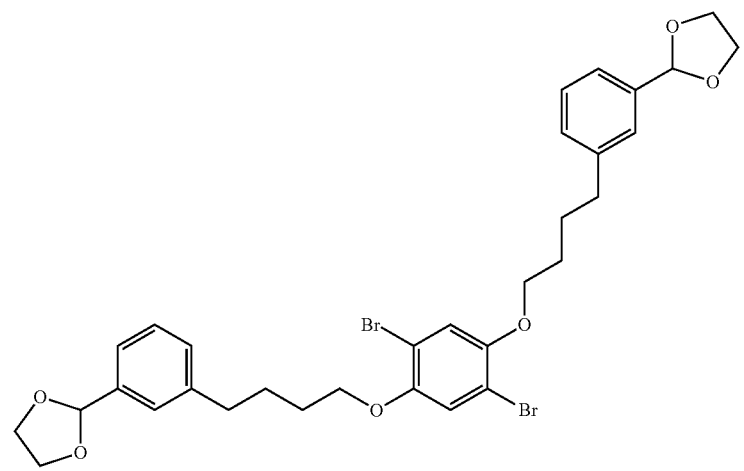

Molecular Weight: 676.43

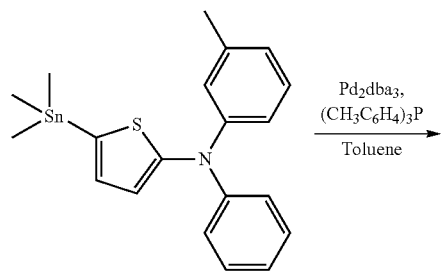

Molecular Weight: 428.18

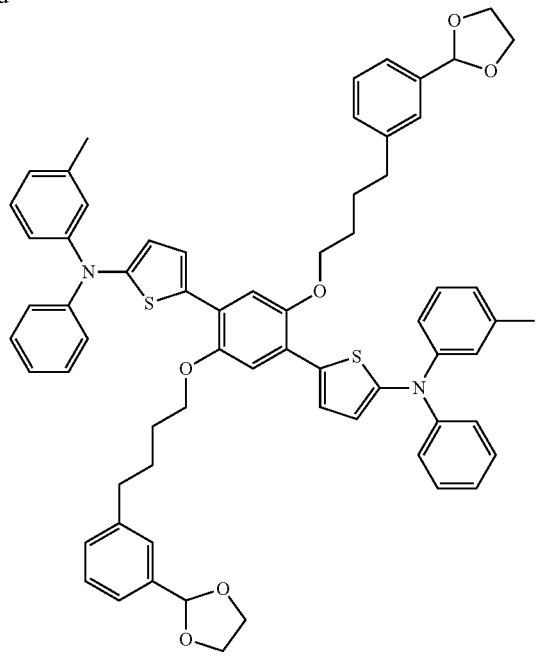

Molecular Weight 1045.35

Procedure:

A 100 mL Schlenk flask was charged with 2,2'-((((2,5-dibromo-1,4-phenylene)bis(oxy))bis(butane-4,1-diyl))bis(3,1-phenylene))bis(1,3-dioxolane) (1.5 g, 0.0022 mol) and tri-(o-tolyl)phosphine (0.30 g, 0.0010 mol). In a 500 mL single-neck round bottom flask, dissolved N-phenyl-N-(m-tolyl)-5-(trimethylstannyl)thiophen-2-amine (4.31 g, 0.0101 mol) in anhydrous toluene (22 mL) that was purged overnight via a strong nitrogen flow. The 2,2'-((((2,5-dibromo-1,4-phenylene)bis(oxy))bis(butane-4,1-diyl))bis(3,1-phenylene))bis(1,3-dioxolane) solution was degassed via five vacuum-nitrogen cycles, then transferred to the 100 mL Schlenk flask via syringe. Pd$_2$dba$_3$ (0.2 g, 0.0002 mol) was then added. Solution was maroon in color. The reaction was heated to 85° C. After 2 hours, reaction completion was monitored via TLC. As the reaction was not complete, additional tri-(o-tolyl)phosphine (0.2 g, 0.0007 mol) and Pd$_2$dba$_3$ (0.2 g, 0.0002 mol) were added and the reaction was continued overnight.

After permitting it to cool to room temperature, the reaction solution was filtered through a celite/silica gel plug, washing thoroughly with a 2% triethylamine/ethyl acetate solution (100 mL). After removing solvents via rotary evaporation and drying under vacuum, the product was obtained as a solid.

The product was purified via column chromatography (wet load (ethyl acetate (11 mL)), silica gel). The product was eluted using a gradient from 2% triethylamine in hexane to 2% triethylamine in ethyl acetate. After removing solvents via rotary evaporation and drying under vacuum, 1.95 g product was obtained. Product purity was confirmed via HPLC. Product characterization was confirmed via $^1$H NMR.

Dehalogenation of 5,5'-(2,5-bis(4-(3-(1,3-dioxolan-2-yl)phenyl)butoxy)-1,4-phenylene)bis(N-phenyl-N-(m-tolyl)thiophen-2-amine) (Run Twice)

Procedure:

In a 500 mL single-neck round bottom flask 5,5'-(2,5-bis(4-(3-(1,3-dioxolan-2-yl)phenyl)butoxy)-1,4-phenylene)bis(N-phenyl-N-(m-tolyl)thiophen-2-amine) (3.5 g, 0.0033 mol) was dissolved in anhydrous toluene (33 mL). The solution was transferred to a 250 mL three-neck round bottom flask equipped with a reflux condenser and thermometer. Solution was red in color. Triethylamine (4.6 mL, 0.033 mol) was added via syringe. Formic acid (1.2 mL, 0.032 mol) was added dropwise via syringe. This solution was purged via a strong nitrogen flow for 45 minutes, after which Pd(OAc)$_2$ (0.1 g, 0.0006 mol) and tBu$_3$P (0.2 g, 0.0010 mol, in 3 mL anhydrous toluene) were added. The reaction was heated to 100° C. and left to stir at this temperature for 4 hours, after which it was permitted to cool to room temperature.

The reaction solution was filtered through a celite/silica gel plug treated with a 2% triethylamine/ethyl acetate solution (700 mL). The filtrate from the celite/silica gel plug was transferred to a 2 L separatory funnel then deionized water (700 mL) was added. The organic layer was washed with deionized water (2×600 mL). NaCl was added to break up the emulsion that formed, allowing separation of the organic and aqueous layers. After removing solvents via rotary evaporation and drying under vacuum, 3.45 g product was obtained.

The dehalogenation procedure was repeated a second time to yield 3.33 g final product.

3,3'-(((2,5-bis(5-(phenyl(m-tolyl)amino)thiophen-2-yl)-1,4-phenylene)bis(oxy))bis(butane-4,1-diyl)) dibenzaldehyde Synthesis

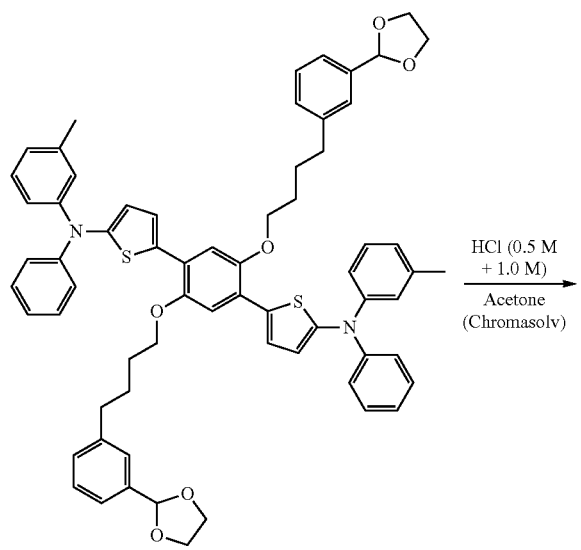

Molecular Weight 1045.35

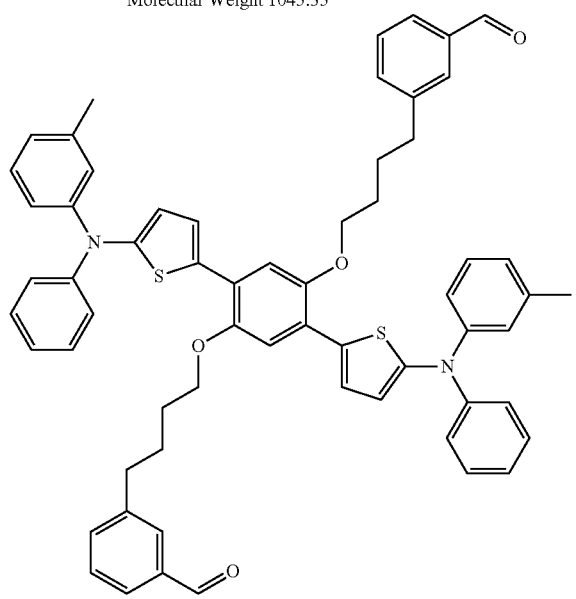

Molecular Weight: 957.23

Procedure:

In a 500 mL single-neck round bottom flask, 5,5'(2,5-bis(4-(3-(1,3-dioxolan-2-yl)phenyl)butoxy)-1,4-phenylene)bis(N-phenyl-N-(m-tolyl)thiophen-2-amine) was dissolved (3.3 g, 0.0032 mol) in acetone (531 mL) via syringe. This solution was transferred to a 1 L single-neck round bottom flask. Solution was dark brown in color. Aqueous hydrochloric acid solution (0.8 mL, 0.5M) was added dropwise via syringe. The solution was then permitted to stir at room temperature for 30 minutes. As both TLC and $^1$H NMR indicated that the reaction was not yet complete, additional aqueous hydrochloric acid solution (0.8 mL, 0.5M) was added dropwise via syringe. This solution was permitted to stir at room temperature for an additional 30 minutes. Reaction completion was then monitored, once again, via TLC and $^1$H NMR. Both indicated that it was still not yet complete. Additional, more concentrated aqueous hydrochloric acid solution (0.2 mL, 1.0M) was added drop-wise via syringe. Again, the solution was permitted to stir at room temperature for an additional 30 minutes. Reaction completion was then monitored, once again, via $^1$H NMR. It indicated that the reaction was almost complete. A final addition of aqueous hydrochloric acid solution (0.3 mL, 1.0M) was made via syringe. 30 minutes later, $^1$H NMR indicated that the reaction was complete. Deionized water (200 mL) was added to the flask to quench the reaction and the mixture was permitted to stir for 10 minutes.

The mixture was transferred to a 2 L separatory funnel, along with MTBE (500 mL) and deionized water (300 mL). NaCl was added to break up the emulsion that formed, allowing separation of the organic and aqueous layers. The aqueous layer was back-extracted with MTBE (300 mL). The organic layer was washed with deionized water (3×400 mL). NaCl was again added to break up the emulsion that formed, allowing separation of the organic and aqueous layers. After removing solvents via rotary evaporation and drying under vacuum, 5.44 g product was obtained.

The product was purified via flash chromatography (wet load (ethyl acetate (13 mL)), silica gel). The product was eluted using a gradient from 2% triethylamine in hexane to 2% triethylamine in ethyl acetate. After removing solvents via rotary evaporation and drying under vacuum, 1.01 g product was obtained.

The product was further purified by dissolution in ethyl acetate (6 mL) and THF (6 mL) with extensive stirring. This solution was added dropwise via a glass pipette into methanol (200 mL, pre-chilled in the refrigerator). The precipitated product was permitted to stir in the chilled methanol for 15 minutes, and then filtered through a Buchner funnel. Solvents were removed via rotary evaporation and dried on a vacuum line. Product obtained: 0.76 g. Product purity was confirmed via HPLC. Product characterization was confirmed via $^1$H NMR.

5,5'-(2,5-bis(4-(3-vinylphenyl)butoxy)-1,4-phenylene)bis(N-phenyl-N-(m-tolyl)thiophen-2-amine) Synthesis

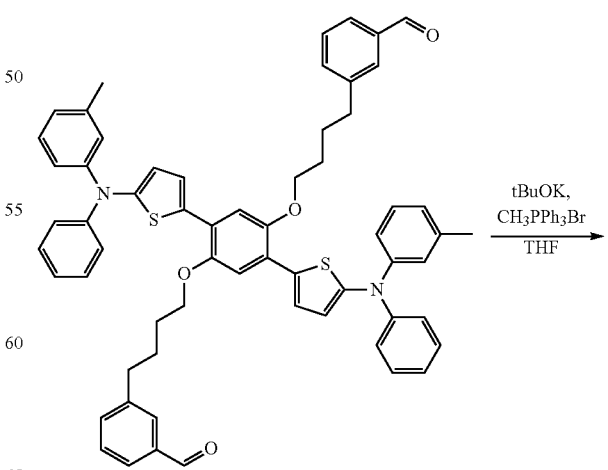

Molecular Weight: 957.23

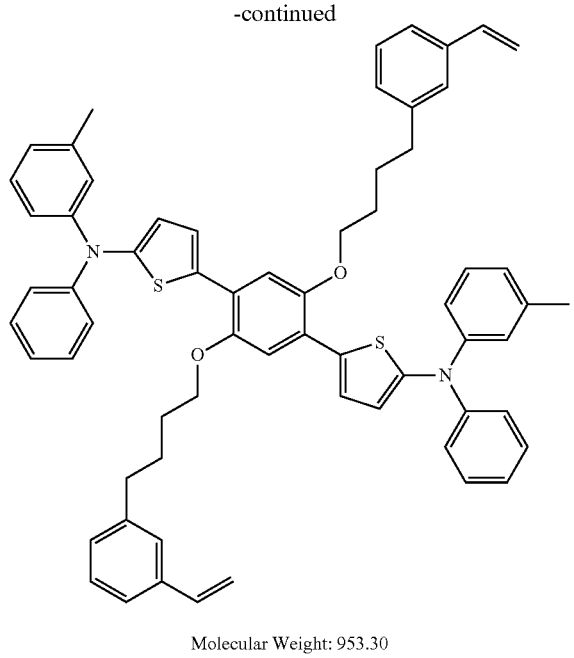

Molecular Weight: 953.30

Procedure:

3,3'-(((2,5-bis(5-(phenyl(m-tolyl)amino)thiophen-2-yl)-1,4-phenylene)bis(oxy))bis(butane-4,1-diyl))dibenzaldehyde (0.8 g, 0.001 mol) was dissolved in anhydrous THF (8 mL) via syringe. Solution was pink-red in color. A 100 mL three-neck round bottom flask was charged with methyltriphenylphosphonium bromide (0.9 g, 0.003 mol) then anhydrous THF (16 mL) via syringe. Next, tBuOK (0.32 g, 0.0029 mol) was added. Solution turned yellow. Aluminum foil was placed around the 100 mL three-neck round bottom flask. The solution was permitted to stir at room temperature for 5 minutes, then the 3,3'-(((2,5-bis(5-(phenyl(m-tolyl)amino)thiophen-2-yl)-1,4-phenylene)bis(oxy))bis(butane-4,1-diyl))dibenzaldehyde solution was added drop-wise to the flask via syringe. After 1 hour, reaction completion was monitored via TLC and $^1$H NMR. Both indicated that it was complete.

The reaction solution was filtered through a celite/silica gel plug treated with 2% triethylamine/ethyl acetate solution (250 mL). After removing solvents via rotary evaporation and drying under vacuum, 1.08 g product was obtained.

The product was purified via flash chromatography (wet load (ethyl acetate (7 mL)). The product was eluted using a gradient from 100% hexane to 100% ethyl acetate. After removing solvents via rotary evaporation and drying under vacuum, 0.62 g purified product was obtained. Product purity was confirmed via HPLC. Product characterization was confirmed via $^1$H NMR. $^1$H NMR (300 MHz, (CD$_3$)$_2$CO) 1.85 (m, 8H), 2.25 (s, 6H), 2.6 (t, 4H), 4.15 (t, 4H), 5.1-5.2 (d, 2H), 5.7-5.8 (d, 2H), 6.6-6.75 (m, 4H), 6.85-7.35 (m, 27H), 7.5 (d, 2H).

PLX-3D 2,5-dibromo-4-(octyloxy)phenol Synthesis

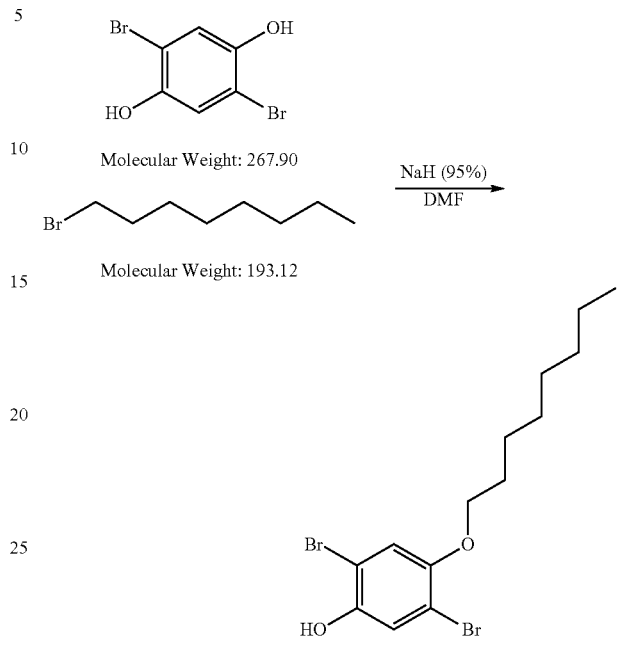

Procedure:

A 2 L three-neck round bottom flask equipped with an addition funnel, thermometer, and bubbler was charged with sodium hydride (2.6 g, 0.11 mmol). The flask was placed in an ice-water bath and anhydrous DMF (300 mL) was added via syringe. In a 500 mL single-neck round bottom flask, dissolved 2,5-dibromohydroquinone (20.1 g, 0.0750 mol) in anhydrous DMF (300 mL) via syringe with stirring. Solution was peach in color. This solution was transferred to the addition funnel via cannula, and then added drop-wise to the flask. Solution turned yellow. The solution was permitted to stir for 30 minutes in the ice-water bath before being permitted to warm to room temperature. Solution turned a bit more orange. In a 500 mL single-neck round bottom flask, 1-bromooctane (14.1 g, 0.0746 mol) was dissolved in anhydrous DMF via syringe. Solution was clear in color. This solution was transferred to the addition funnel via cannula, and then added dropwise to the flask. The addition funnel was quickly swapped for a reflux condenser. The reaction was heated to 80° C. and continued overnight, after which it was cooled to room temperature. Reaction completion was monitored via TLC and GC-MS.

The reaction solution was transferred to a 2 L separatory funnel, along with aqueous hydrochloric acid solution (950 mL, 1.0M) and ethyl acetate (950 mL). After separation of the organic and aqueous layers, the aqueous layer was back-extracted with ethyl acetate (3×600 mL). The organic layer was washed with deionized water (2×2.1 L). After removing solvents via rotary evaporation and drying under vacuum, 29.89 g product was obtained. The product was purified via manual chromatography (dry load, silica gel). The product was eluted using a gradient from 100% hexane to 100% ethyl acetate. After removing solvents via rotary evaporation and drying under vacuum, 10.59 g of product was obtained. Product characterization and purity were confirmed via GC-MS and HPLC.

2-(3-(4-(2,5-dibromo-4-(octyloxy)phenoxy)butyl)phenyl)-1,3-dioxolane Synthesis

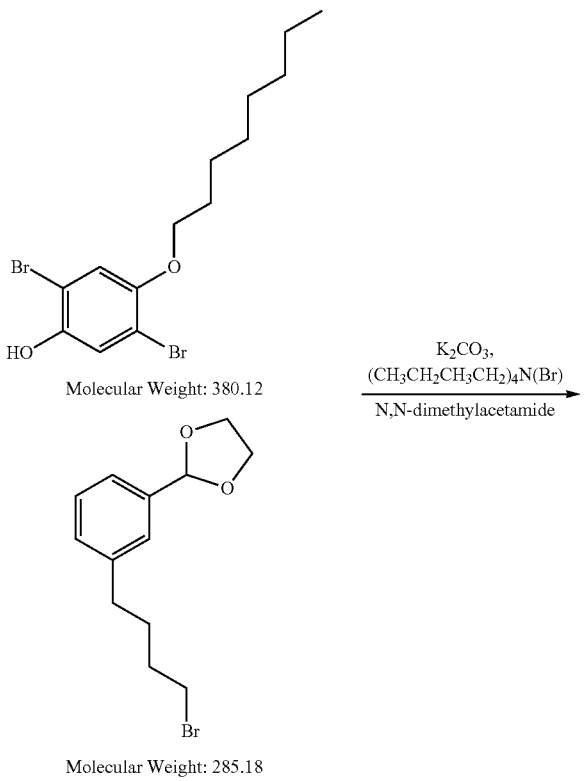

Procedure:

A 500 mL single-neck round bottom flask was charged with 2,5-dibromo-4-(octyloxy)phenol (10.6 g, 0.0279 mol) and anhydrous N,N-dimethylacetamide (220 mL). This solution, dark purplish black in color, was transferred via cannula to a 500 mL three-neck round bottom flask equipped with a reflux condensor and thermometer. 2-(3-(4-bromobutyl)phenyl)-1,3-dioxolane (9.55 g, 0.0335 mol), potassium carbonate (5.86 g, 0.0424 mol), and tetrabutylammonium bromide (0.98 g, 0.0030 mol) were then added. The reaction was heated to 85° C. and continued overnight, after which it was permitted to cool to room temperature. Reaction completion was monitored via TLC and HPLC.

The reaction solution was transferred to a 2 L separatory funnel along with ethyl acetate (250 mL) and deionized water (250 mL). After separation of organic and aqueous layers, the aqueous layer was back-extracted with ethyl acetate (2×200 mL). The organic layers were washed with deionized water (3×500 mL). NaCl was added to break up the emulsion that formed, allowing separation of the organic and aqueous layers. After removing solvents via rotary evaporation and drying under vacuum, 15.88 g product was obtained.

The product was purified via manual chromatography (dry load, silica gel). The product was eluted using a gradient from 2% triethylamine/hexane solution to a 2% triethylamine/8% ethyl acetate/90% hexane solution. After removing solvents via rotary evaporation and drying under vacuum, 13.05 g product was obtained. Product purity was confirmed via HPLC. Product characterization was confirmed via $^1$H NMR.

N-(naphthalen-1-yl)-N-phenylthiophen-2-amine Synthesis

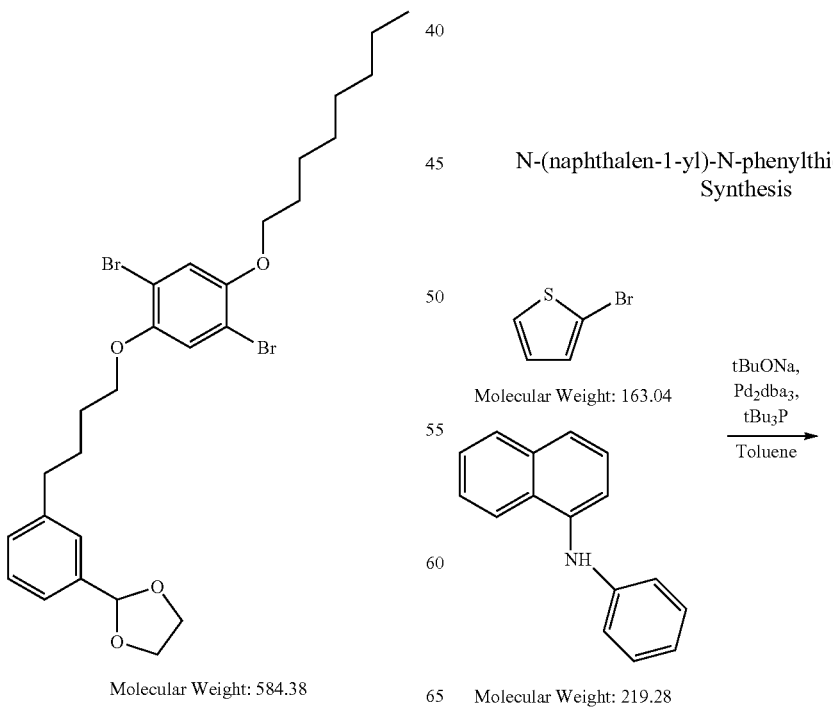

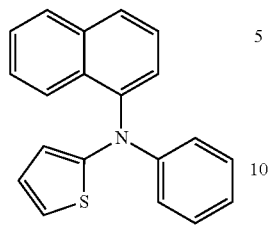

Molecular Weight: 301.40

Procedure:

A 2 L three-neck round bottom flask equipped with a reflux condenser and thermometer was charged with 2-bromothiophene (15.0 g, 0.0921 mol) and N-phenyl-1-naphthylamine (24.8 g, 0.113 mol). Anhydrous toluene (1 L) was added via cannula. All solids dissolved. Solution was red in color. The solution was purged via a strong nitrogen flow for 30 minutes, after which tBuONa (14.0 g, 0.145 mol) and Pd$_2$dba$_3$ (1.8 g, 0.0020 mol) were added. Then, tBu$_3$P (1.4 g, 0.0067 mol) dissolved in anhydrous toluene (2 mL) was added dropwise via syringe. The reaction was heated to 80° C. After 2 hours, reaction completion was monitored via GC-MS, indicating that the reaction was complete. The reaction was then permitted to cool to room temperature.

The reaction solution was filtered through a celite/silica gel plug, washing thoroughly with a 2% triethylamine/ethyl acetate solution (2 L). The filtrate from the celite/silica gel plug was nearly evaporated, at which point, triethylamine and celite were added to prepare a dry load for manual column chromatography.

The product was purified via manual chromatography (silica gel). The product was eluted using a gradient from 100% hexane to 8% ethyl acetate/hexane. After removing solvents via rotary evaporation and drying under vacuum, 17.53 g product was obtained. Product purity was confirmed via HPLC. Product characterization and purity was confirmed via GC-MS.

N-(naphthalen-1-yl)-N-phenyl-5-(trimethylstannyl)thiophen-2-amine Synthesis

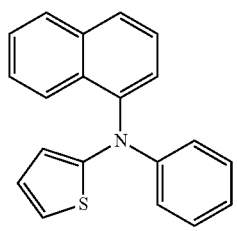

Molecular Weight: 301.40

1. nBuLi, THF, -68° C. 0° C.
2. -68° C., (CH$_3$)$_3$SnCl

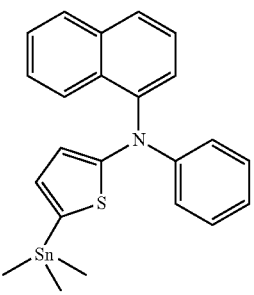

Molecular Weight: 464.21

Procedure:

In a 500 mL single-neck round bottom flask, N-(naphthalen-1-yl)-N-phenylthiophen-2-amine (16.5 g, 0.0546 mol) was dissolved in anhydrous THF (550 mL, dried over sodium) via cannula. This solution was transferred via cannula to a 2 L three-neck round bottom flask equipped with a thermometer and addition funnel. The solution was chilled to −78° C. via dry ice-isopropanol bath. Solution was light yellow in color. Once the solution reached −78° C., n-butyllithium solution (47 mL, 2.4M in hexane (titrated)) was added dropwise via syringe. Solution turned pink-red. The solution was permitted to stir at −78° C. for 30 minutes before being permitted to up to 0° C. At this point, solution became maroon in color. Once the solution reached 0° C., it was cooled back to −78° C. via dry ice-isopropanol bath. Two aliquots were withdrawn from the reaction and quenched in separate vials (pre-cooled to −78° C.) with, respectively, 1,2-dibromotetrafluoroethane for GC-MS analysis and trimethyltin chloride for HPLC analysis. Both confirmed completion of lithiation reaction. Trimethyltin chloride (110 mL, 0.1M in THF) was transferred to the addition funnel via syringe, then added dropwise to the flask. This solution was permitted to stir at −78° C. for 30 minutes, and then was permitted to warm up to room temperature overnight. Reaction completion was monitored via HPLC.

The reaction solution was transferred to a 2 L separatory funnel along with MTBE (500 mL) and deionized water (500 mL). After separation of the organic and aqueous layers, the aqueous layer was back-extracted with MTBE (1×200 mL). The organic layer was washed with deionized water (3×700 mL). After removing solvents via rotary evaporation and drying under vacuum, 31.65 g product was obtained. Product purity was determined via HPLC.

5,5'-(2-(4-(3-(1,3-dioxolan-2-yl)phenyl)butoxy)-5-(octyloxy)-1,4-phenylene)bis(N-(naphthalen-1-yl)-N-phenylthiophen-2-amine) Synthesis

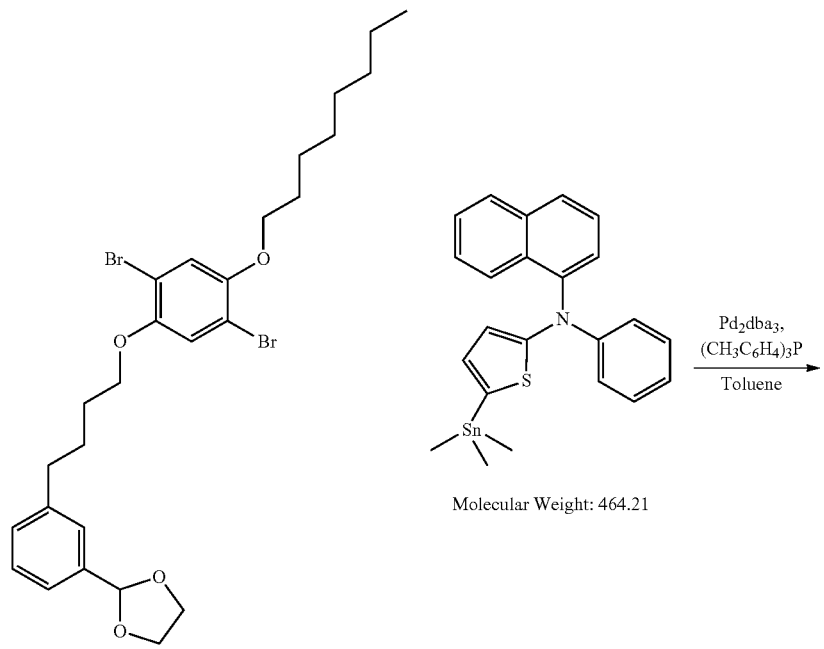

Molecular Weight 584.38

Molecular Weight: 464.21

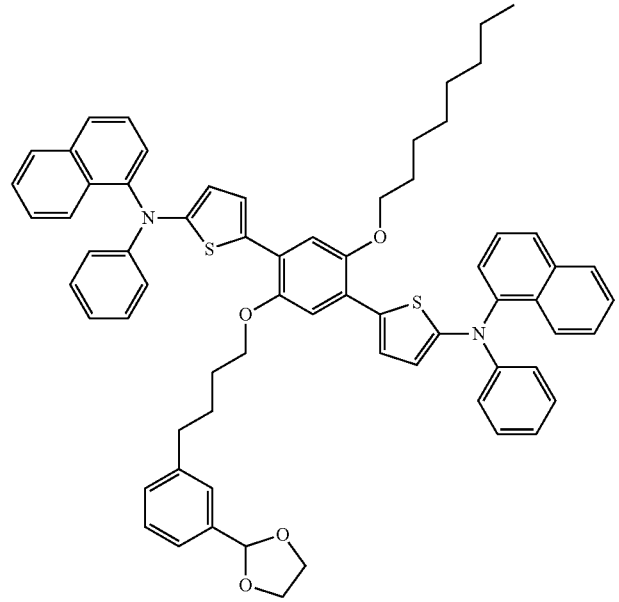

Molecular Weight 1025.37

Procedure:

In a 40 mL pre-cleaned vial equipped with a magnetic stir bar, 2-(3-(4-(2,5-dibromo-4-(octyloxy)phenoxy)butyl)phenyl)-1,3-dioxolane (7.04 g, 0.0120 mol) was dissolved in anhydrous toluene (20 mL) that was purged overnight via a strong nitrogen flow. Similarly, in another 40 mL pre-cleaned vial equipped with a magnetic stir bar, N-(naphthalen-1-yl)-N-phenyl-5-(trimethylstannyl)thiophen-2-amine (17.7 g, 0.0381 mol) was dissolved in anhydrous toluene (20 mL). These solutions were transferred to a 500 mL Schlenk flask via syringe. Additional anhydrous toluene (90 mL) was added to the 500 mL Schlenk flask via syringe. This solution was degassed via five vacuum-nitrogen cycles, and then purged via a strong nitrogen flow for 1 hour. Next, tri(o-tolyl)phosphine (1.5 g, 0.0050 mol) and Pd$_2$dba$_3$ (1.6 g, 0.0018 mol) were added. The solution was degassed via another five vacuum-nitrogen cycles. Solution was dark black/maroon in color. The reaction was heated to 90° C. continued overnight. Reaction completion was monitored via HPLC, indicating a complete reaction. It was then permitted to cool to room temperature.

The reaction solution was filtered through a celite/silica gel plug, washing thoroughly with a 2% triethylamine/ethyl acetate solution. After removing solvents via rotary evaporation and drying under vacuum, 21.2 g crude product was obtained.

The product was purified via manual chromatography (dry load, silica gel). The product was eluted using a gradient from 2% triethylamine/hexane solution to a 2% triethylamine/ethyl acetate solution. The solvents were nearly evaporated, at which point, hexanes (200 mL) was added to precipitate the product. The precipitated product was filtered through a Buchner funnel following overnight refrigeration. After vacuum drying, 10.09 g purified product was obtained. Product purity was confirmed via HPLC.

Dehalogenation of 5,5'-(2-(4-(3-(1,3-dioxolan-2-yl)phenyl)butoxy)-5-(octyloxy)-1,4-phenylene)bis(N-(naphthalen-1-yl)-N-phenylthiophen-2-amine) (Run Twice)

Procedure:

A 500 mL three-neck round bottom flask equipped with a reflux condenser and thermometer was charged with 5,5'-(2-(4-(3-(1,3-dioxolan-2-yl)phenyl)butoxy)-5-(octyloxy)-1,4-phenylene)bis(N-(naphthalen-1-yl)-N-phenylthiophen-2-amine) (9.9 g, 0.0096 mol). Anhydrous toluene (100 mL) was added via syringe. Solution was pink-red in color. Next, triethylamine (14.00 mL, 0.1004 mol) was added via syringe followed by formic acid (3.50 mL, 0.0928 mol), added dropwise via syringe. This solution was purged via a strong nitrogen flow, after which Pd(OAc)$_2$ (0.39 g, 0.0017 mol) and tBu$_3$P (0.45 g, 0.0022 mol, in 2 mL anhydrous toluene) were added. The reaction was heated to 100° C. and left to stir at this temperature for 2 hours, after which it was permitted to cool to room temperature.

The reaction solution was filtered through a celite/silica gel plug, washing thoroughly with a 2% triethylamine/toluene solution (850 mL). The filtrate from the celite/silica gel plug was transferred to a 2 L separatory funnel and deionized water (500 mL) was added. After separation of the organic and aqueous layers, the organic layer was washed with deionized water (4×500 mL). After removing solvents via rotary evaporation and drying under vacuum, 10.5 g product was obtained.

The dehalogenation procedure was repeated a second time to yield 11.85 g product. The product was purified via manual chromatography (dry load, silica gel). The product was eluted using a gradient from 2% triethylamine/hexane solution to a 2% triethylamine/chloroform solution due to solubility issues. After removing solvents via rotary evaporation and drying under vacuum, 9.21 g product was obtained.

3-(4-(2,5-bis(5-(naphthalen-1-yl(phenyl)amino)thiophen-2-yl)-4-(octyloxy)phenoxy)butyl)benzaldehyde Synthesis

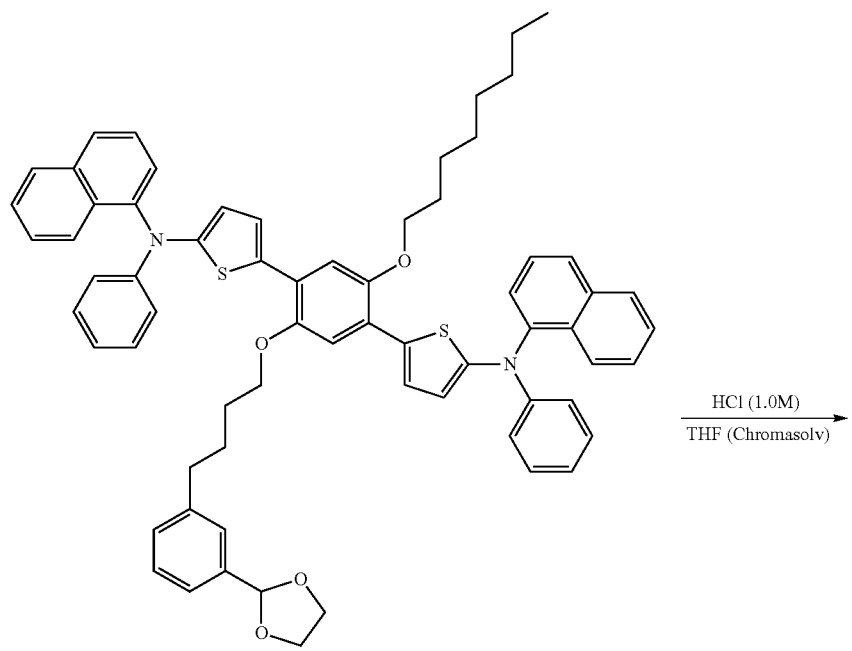

Molecular Weight 1025.37

-continued

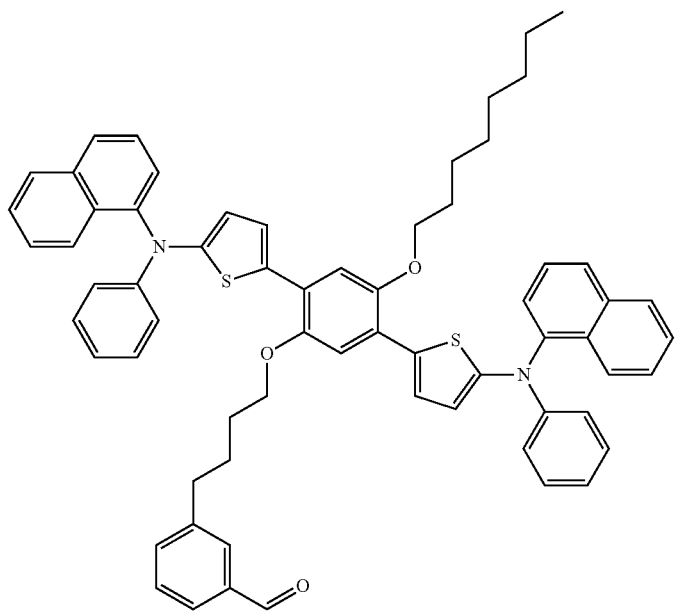

Molecular Weight 981.31

Procedure:

In a 500 mL single-neck round bottom flask, 5,5'-(2-(4-(3-(1,3-dioxolan-2-yl)phenyl)butoxy)-5-(octyloxy)-1,4-phenylene)bis(N-(naphthalen-1-yl)-N-phenylthiophen-2-amine) (9 g, 0.009 mol) was dissolved in THF (300 mL) via syringe. All solids dissolved with stirring. Solution was red in color. Aqueous hydrochloric acid solution (1.1 mL, 1.0M) was added drop-wise via syringe. Solution became more maroon in color. The solution was permitted to stir at room temperature for 1 hour, at which point reaction completion was monitored via $^1$H NMR. It indicated that the reaction was not yet complete. Additional aqueous hydrochloric acid solution (1.1 mL, 1.0M) was added dropwise via syringe. The solution was permitted to stir at room temperature for an additional 30 minutes, at which point reaction completion was once again monitored via $^1$H NMR. It indicated that the reaction was not yet complete. Additional aqueous hydrochloric acid solution (1.1 mL, 1.0M) was added dropwise via syringe. The solution was permitted to stir at room temperature for an additional 30 minutes, at which point reaction completion was once again monitored via $^1$H NMR. It indicated the presence of just a small amount of protected aldehyde so a final addition of aqueous hydrochloric acid solution (0.55 mL, 1.0M) was made dropwise via syringe followed by another hour of stirring at room temperature. Reaction completion was then, once again, monitored via $^1$H NMR. It indicated that the reaction was complete. Deionized water (100 mL) was added to the flask to quench the reaction.

This mixture was transferred to a 1 L separatory funnel along with deionized water (200 mL). Additional MTBE (200 mL) and NaCl were added to break up the emulsion that formed, allowing separation of the organic and aqueous layers. The aqueous layer was back-extracted with MTBE (200 mL). The organic layer was washed with deionized water (3×600 mL). NaCl was added to break up the emulsion that formed, allowing separation of the organic and aqueous layers. After removing solvents via rotary evaporation and drying under vacuum, 8.29 g product was obtained.

5,5'-(2-(octyloxy)-5-(4-(3-vinylphenyl)butoxy)-1,4-phenylene)bis(N-(naphthalen-1-yl)-N-phenylthiophen-2-amine) Synthesis

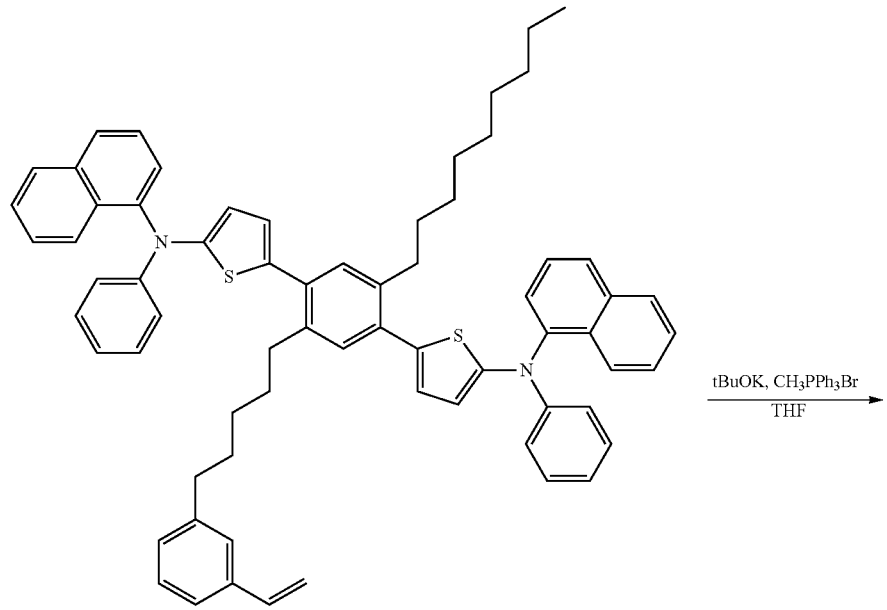

Molecular Weight: 981.31

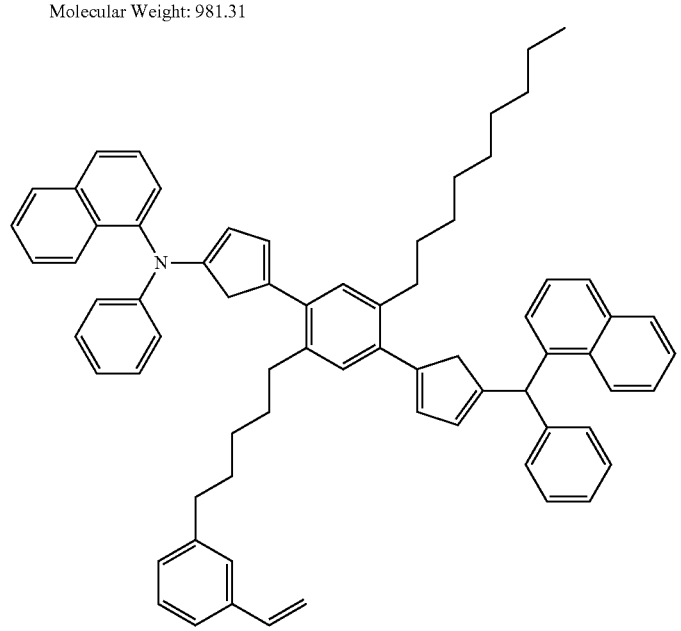

Molecular Weight 979.34

Procedure:

In a 500 mL single-neck round bottom flask, 3-(4-(2,5-bis(5-(naphthalen-1-yl(phenyl)amino)thiophen-2-yl)-4-(octyloxy)phenoxy)butyl)benzaldehyde (7.8 g, 0.0079 mol) was dissolved in anhydrous THF (80 mL) via syringe. Solution was maroon in color. This solution was degassed via five vacuum-nitrogen cycles. A 500 mL three-neck round bottom flask equipped with an addition funnel was charged with methyltriphenylphosphonium bromide (4.37 g, 0.0122 mol) and anhydrous THF (120 mL) via syringe. The solution was permitted to stir at room temperature for 5 minutes. Next, tBuOK (1.63 g, 0.0145 mol) was added. Solution turned yellow. Aluminum foil was placed around the 500 mL three-neck round bottom flask. The solution was permitted to stir at room temperature for 10 minutes, after which the 3-(4-(2,5-bis(5-(naphthalen-1-yl(phenyl)amino)thiophen-2-yl)-4-(octyloxy)phenoxy)butyl)benzaldehyde solution was transferred to the addition funnel and added dropwise to the flask. After 2 hours, reaction completion was monitored via TLC and $^1$H NMR. Both indicated that the reaction was complete.

The reaction solution was filtered through a celite/silica gel plug, washing thoroughly with THF (750 mL). The product was purified via manual chromatography (dry load, silica gel). The product was eluted using a gradient from 100% hexane to 100% ethyl acetate to 100% THF due to solubility issues. After vacuum drying, two product fractions were obtained: a higher purity fraction (1.61 g) and an impure fraction (7.56 g). The higher purity product was further purified by dissolution in THF (10 mL). This solution was added dropwise via a glass pipette into methanol (125 mL, pre-chilled in an ice-water bath). The precipitated product was permitted to stir in the chilled methanol for 15 minutes, and then filtered through a Buchner funnel. Product obtained after vacuum drying: 1.48 g. Product purity was confirmed via HPLC. Product characterization was confirmed via $^1$H NMR. The impure fraction was further purified via recrystallization from a toluene/methanol mixture. After filtration and vacuum drying, 1.97 g of product was obtained (3.45 g total). Product purity was confirmed via HPLC. Product characterization was confirmed via NMR. $^1$H NMR (300 MHz, (CD$_3$)$_2$CO) 0.85 (t, 3H), 1.15-1.35 (m, 8H), 1.35-1.45 (m, 2H), 1.6-1.8 (m, 6H), 2.5-2.6 (m, 2H), 4.05 (m, 4H), 5.1-5.2 (d, 1H), 5.7-5.8 (d, 1H), 6.6-6.75 (m, 3H), 6.85-7.1 (m, 7H), 7.1-7.3 (m, 9H), 7.4-7.6 (m, 10H), 7.85-8.1 (m, 6H).

PLX-7-E

Synthesis of 10-hexyl-10H-phenothiazine

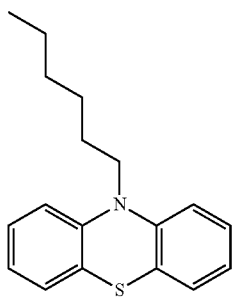 [SMILES: CCCCCCN1c2ccccc2Sc2ccccc21]

Procedures:
To a clean, dry round bottom flask was added sodium hydride (7.74 g, 0.3062 mol). The reaction flask was equipped with a reflux condenser and a bubbler was added to one neck of the flask to allow any rapid gas formation to escape the system and was placed in an ice water bath. Anhydrous N,N-dimethylformamide (300 mL) was added to the reaction flask via cannula. A solution of phenothiazine (40.68 g, 0.2041 mol) in anhydrous DMF (150 mL) was prepared and then added to the reaction flask slowly, drop-wise. Following the addition, the reaction was allowed to stir for an additional thirty minutes, after which the reaction was removed from the ice water bath and warmed to room temperature. A solution of 1-bromohexane (0.2450 mol) in anhydrous DMF (50 mL) was added to the reaction flask slowly, drop-wise. Then reaction was then heated to 80 C for one hour, and then monitored via thin-layer chromatography. Upon the confirmation of reaction completion, the reaction was cooled to room temperature. The resulting solution was worked up with methyl tert-butyl ether (600 mL) and deionized water (5×200 mL). The organic fraction was collected and dried over anhydrous magnesium sulfate. Solids were removed by vacuum filtration and solvent by rotary evaporation. The resulting oil was placed under vacuum. A column plug was used to further purify the mixture (5% ethyl acetate/hexane). The solvent was removed by rotary evaporation. The resulting oil was characterized by $^1$H-NMR spectroscopy. Product obtained: 54.36 g.

Synthesis of 3,7-dibromo-10-hexyl-10H-phenothiazine

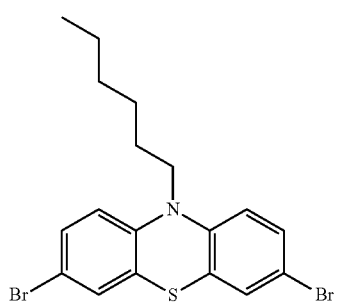 [SMILES: CCCCCCN1c2ccc(Br)cc2Sc2cc(Br)ccc21]

Procedures:
A round bottom flask was charged with 10-hexyl-10H-phenothiazine (54.36 g, 0.1918 mol) and N,N-dimethylformamide (DMF, 800 mL). The reaction vessel was placed in an ice/water bath and cooled to a temperature of 0° C. N-bromo-succinimide (NBS, 75.10 g, 0.4219 mol) was added portion-wise with vigorous stirring. Reaction progress and completion was monitored via thin-layer chromatography. Once complete, the reaction solution was worked up with methyl tert-butyl ether (1000 mL) and deionized water (4×250 mL). The organic fraction was dried over anhydrous magnesium sulfate. Solids were removed by vacuum filtration and solvent was removed from the filtrate by rotary evaporation. Further purification was carried out by chromatography on silica gel using 5% ethyl acetate/hexane as an eluent. This provided $^1$H-NMR pure product.

Synthesis of N3,N7-bis(4-(1,3-dioxolan-2-yl)phenyl)-N3,N7-di([1,1'-biphenyl]-4-yl)-10-hexyl-10H-phenothiazine-3,7-diamine

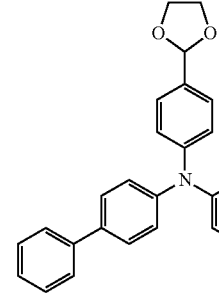

Procedures:
To an oven-dried three-neck round-bottom flask under nitrogen, were added anhydrous toluene (500 mL), 3,7-dibromo-10-hexyl-10H-phenothiazine (6.32 g, 0.0143 mol), and N-(4-(1,3-dioxolan-2-yl)phenyl)-[1,1'-biphenyl]-4-amine (10.00 g, 0.0315 mol). After the reaction mixture was degassed with strong nitrogen flow for thirty minutes, sodium tert-butoxide (4.13 g, 0.0430 mol), tris(dibenzylideneacetone)dipalladium(0) (Pd$_2$dba$_3$, 1.05 g, 0.0011 mol), and tri-tert-butyl phosphine (0.70 g, 0.0034 mol, in 5 mL toluene) were added. The reaction mixture was heated to reflux. Reaction completion confirmed by thin-layer chromatography, and upon completion, was cooled to room temperature. The reaction solution was filtered through a Celite/silica gel (triethylamine treated) plug, washing thoroughly with ethyl acetate. Solvent was removed from the filtrate by rotary evaporation. Further purification was carried out by chromatography on silica gel using ethyl acetate/hexane as an eluent. The product was precipitated from ethyl acetate (5 mL) in methanol (50 mL), which provided $^1$H-NMR pure material.

Dehalogenation of N3,N7-bis(4-(1,3-dioxolan-2-yl)phenyl)-N3,N7-di([1,1'-biphenyl]-4-yl)-10-hexyl-10H-phenothiazine-3,7-diamine (Run Twice)

Procedures:

A 1 L three-neck round bottom flask equipped with a reflux condenser was charged with N3,N7-bis(4-(1,3-dioxolan-2-yl)phenyl)-N3,N7-di([1,1'-biphenyl]-4-yl)-10-hexyl-10H-phenothiazine-3,7-diamine (15.1 g, 0.0165 mol). Anhydrous THF (120 mL) was added via syringe. Solids all dissolved with stirring. Triethylamine (23.00 mL, 0.1650 mol) was added via syringe. Formic acid (6.000 mL, 0.1590 mol) was added dropwise via syringe. The solution was then purged via a strong nitrogen flow for 30 minutes, after which Pd(OAc)$_2$ (0.42 g, 0.0019 mol) and tBu$_3$P (0.61 g, 0.0030 mol, in 4 mL anhydrous THF) were added. The reaction was heated to 100° C. and left to stir at this temperature for 2 hours. The reaction was then cooled to room temperature.

The reaction solution was filtered through a celite/silica gel plug, washing thoroughly with ethyl acetate (1.5 L). Solvents were removed via rotary evaporation, and then the product was further dried under vacuum. Product obtained: 17.44 g. The dehalogenation procedure was repeated a second time to yield 15.83 g product.

Purification was carried out via manual chromatography (dry load, silica gel treated with a 2% triethylamine/hexane solution). The manual column was run with a gradient from 10% ethyl acetate/hexane to 100% ethyl acetate. Product obtained: 7.58 g. Product characterization was confirmed via $^1$H NMR.

4,4'-((10-hexyl-10H-phenothiazine-3,7-diyl)bis([1,1'-biphenyl]-4-ylazanediyl))dibenzaldehyde Synthesis

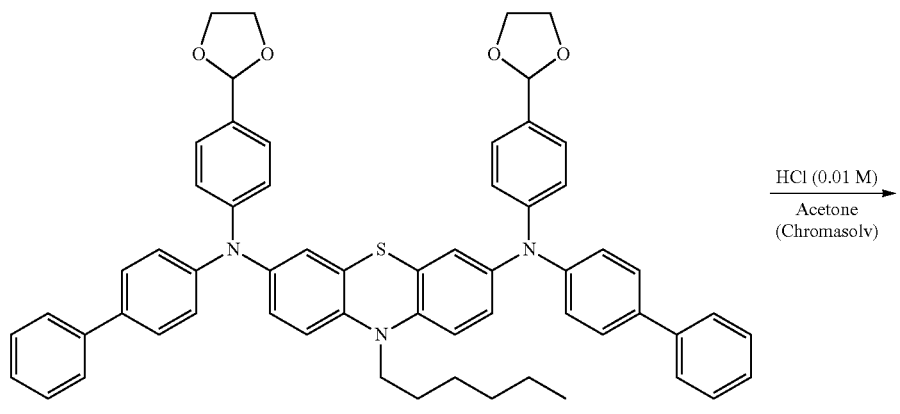

Molecular Weight: 914.16

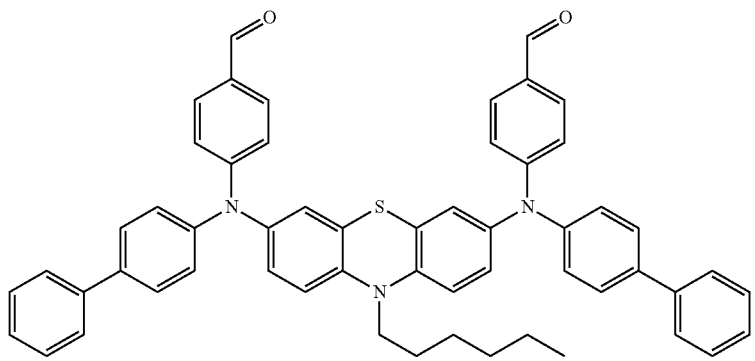

Molecular Weight: 826.06

Procedures:

N3,N7-bis(4-(1,3-dioxolan-2-yl)phenyl)-N3,N7-di([1,1'-biphenyl]-4-yl)-10-hexyl-10H-phenothiazine-3,7-diamine (7.6 g, 0.0083 mol) was dissolved in acetone (250 mL) in a 1 L single-neck round bottom flask. Note that all solids did not dissolve, even with vigorous stirring via stir plate and slight heating via heat gun. The solution was transferred to a 1 L three-neck round bottom flask equipped with an addition funnel, then aqueous hydrochloric acid solution (170 mL, 0.01M) was added dropwise via the addition funnel. After 30 minutes reaction, reaction completion was monitored via TLC and $^1$H NMR. Both indicated that it was complete.

In order to quench the reaction, deionized water basified with triethylamine (300 mL) was added to the 1 L three-neck round bottom flask. Solvents were removed via rotary evaporation, and then additional deionized water basified with triethylamine (500 mL) was added. The solution was filtered through a Buchner funnel and the product was washed with deionized water (200 mL). The product was then dried under vacuum. Product obtained: 13.5 g. Product characterization was confirmed via $^1$H NMR.

N3,N7-di([1,1'-biphenyl]-4-yl)-10-hexyl-N3,N7-bis(4-vinylphenyl)-10H-phenothiazine-3,7-diamine Synthesis equipped with an addition funnel, followed by anhydrous THF (285 mL) via syringe. The solution was stirred at room temperature, then potassium tert-butoxide was added (2.04 g, 0.0182 mol). Solution turned yellow. Aluminum foil was placed around the 1 L three-neck round bottom flask, after which the 4,4'-((10-hexyl-10H-phenothiazine-3,7-diyl)bis([1,1'-biphenyl]-4-ylazanediyl))dibenzaldehyde solution was transferred to the addition funnel via cannula and added to the flask dropwise. 1 hour later, reaction completion was monitored via TLC. It indicated that the reaction was complete.

The reaction solution was filtered through a celite/silica gel plug, washing thoroughly with ethyl acetate (1 L). Solvents were removed via rotary evaporation, and then the product was dried under vacuum. Product obtained: 7.79 g.

Purification was carried out via flash chromatography (dry load, silica gel). The product was eluted with a gradient from 100% hexanes to 5% ethyl acetate/hexanes. TLC pure fractions were collected and solvents were removed via rotary evaporation. The product was then dried under vacuum. Product obtained: 3.29 g.

In a 500 mL single-neck round bottom flask, the product was dissolved in toluene (13 mL) and chlorobenzene (18 mL) with stirring. Methanol (275 mL, pre-chilled in an ice-water bath) was slowly added and the solution was stirred for 30

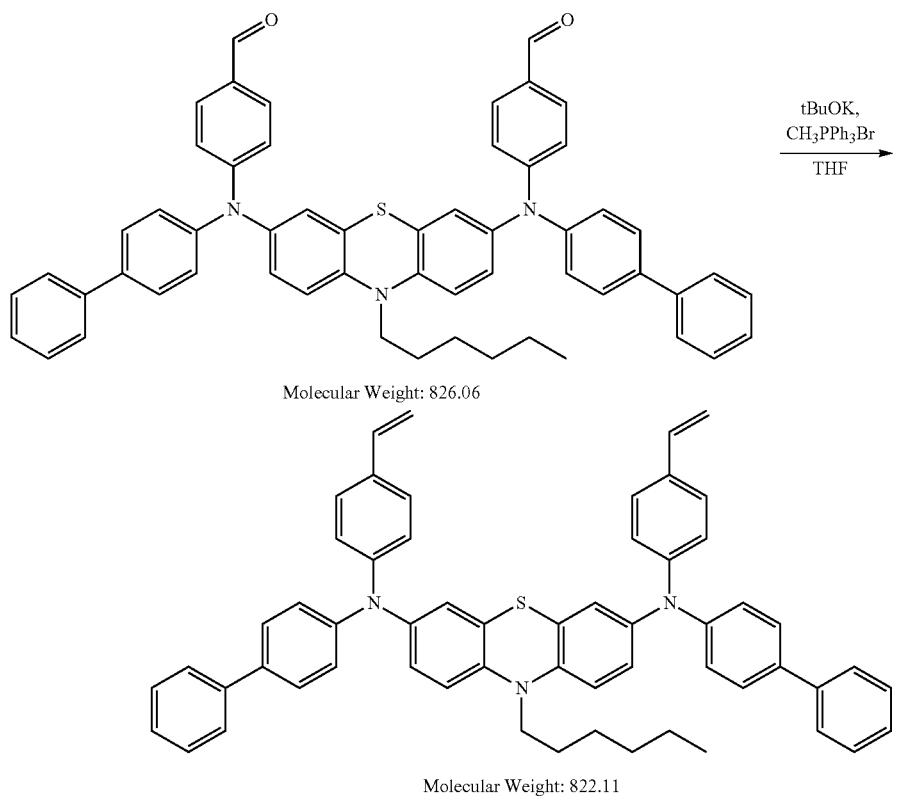

Procedures:

In a 500 mL single-neck round bottom flask, 4,4'-((10-hexyl-10H-phenothiazine-3,7-diyl)bis([1,1'-biphenyl]-4-ylazanediyl))dibenzaldehyde (4.7 g, 0.0057 mol) was dissolved in anhydrous THF (121 mL). Solids all dissolved with stirring. Methyltriphenylphosphonium bromide (6.12 g, 0.0171 mol) was added to a 1 L three-neck round bottom flask minutes. The precipitated solids were filtered through a Buchner funnel, and then dried under vacuum leading to 2.45 g product. Product purity was confirmed via HPLC. Product characterization was confirmed via $^1$H NMR. $^1$H NMR (300 MHz, $C_6D_4Cl_2$) 0.8-0.9 (t, 3H), 1.1-1.3 (m, 4H), 1.3-1.5 (m, 3H), 1.7-1.9 (m, 2H), 3.7-3.9 (s, 2H), 5.1-5.2 (d, 2H), 5.6-5.7 (d, 2H), 6.6-6.7 (q, 2H), 6.8-6.9 (d, 2H), 6.9-7.6 (m, 36H).

PLX-8-A

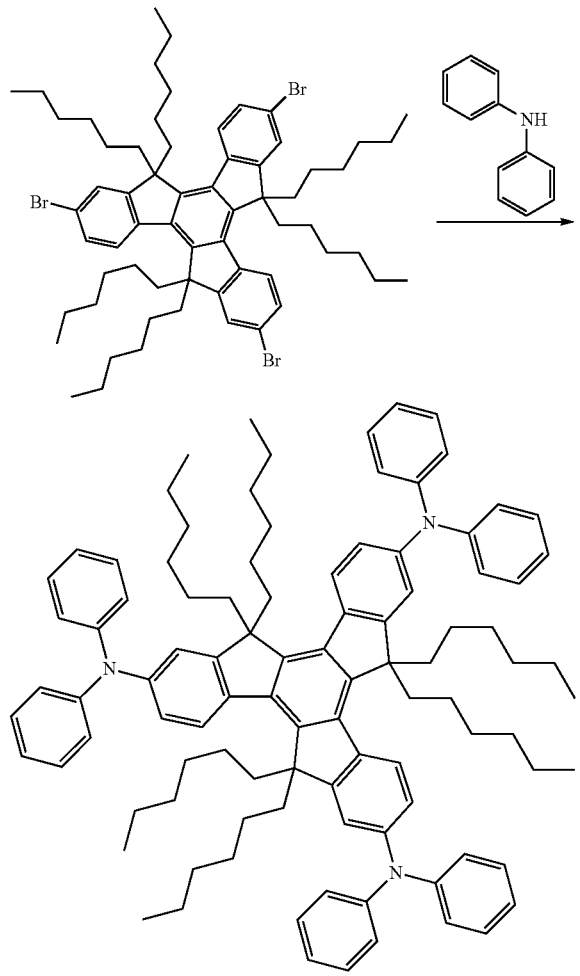

Prepared clean oven dried 500 mL 3 neck round bottom flask, stir bar, and matching coil condenser by cooling and purging with $N_{2(g)}$. Charged reaction vessel with 1.3 g (0.0012 mol) 2,7,12-tribromo-5,5,10,10,15,15-hexahexyl-10,15-dihydro-5H-diindeno[1,2-a: 1',2'-c]fluorene and 0.731 g (0.0043 mol) diphenylamine. Dissolved reagents with ~250 mL dry Toluene via cannula. Purged mixture with $N_{2(g)}$ for 20 minutes. Weighed 0.519 g (0.0054 mol) sodium tert-butoxide and 0.1 g (~0.0001 mol) $Pd_2dba_3$ together in disposable vial then added quickly to reaction mixture with glass funnel. Dissolved 0.07 g (~0.0003 mol) tri-tert-butyl phosphine in 6 mL dry Toluene and added to reaction mixture via Luer lock syringe. Heated reaction to reflux with heating mantle (~30% on variac) while stirring at 500 R.P.M. Allowed reaction to reflux for 4 hours then monitored progress of reaction with thin layer chromatography. TLC confirmed reaction completion. Heating mantle was removed and mixture was allowed to cool to room temperature. Prepared a large fitted glass filter funnel with celite, coarse silica gel (60-200 µm), and filter paper. Filtered reaction mixture through plug and washed with EtOAc until TLC showed minimal spotting. Solvents were removed via rotary evaporation. The crude was washed in methanol to remove excess diphenylamine. Ran manual column chromatography and collected similarly pure fractions. Solvents were via rotary evaporation. Pure material was redissolved in dichloromethane and precipitated in ice-cold HPLC grade methanol. Final mass of pure product was 1.38 g. NMR confirmed the presence of desired product: 5,5,10,10,15,15-hexahexyl-$N^2,N^2,N^7,N^7,N^{12},N^{12}$-hexaphenyl-10,15-dihydro-5H-diindeno[1,2-a:1',2'-c]fluorene-2,7,12-triamine.

PLX-8-B

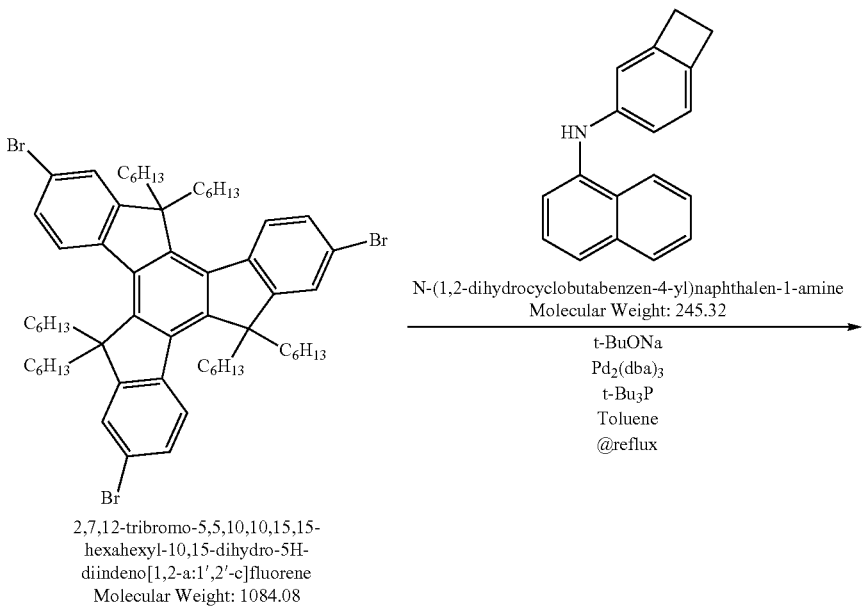

-continued

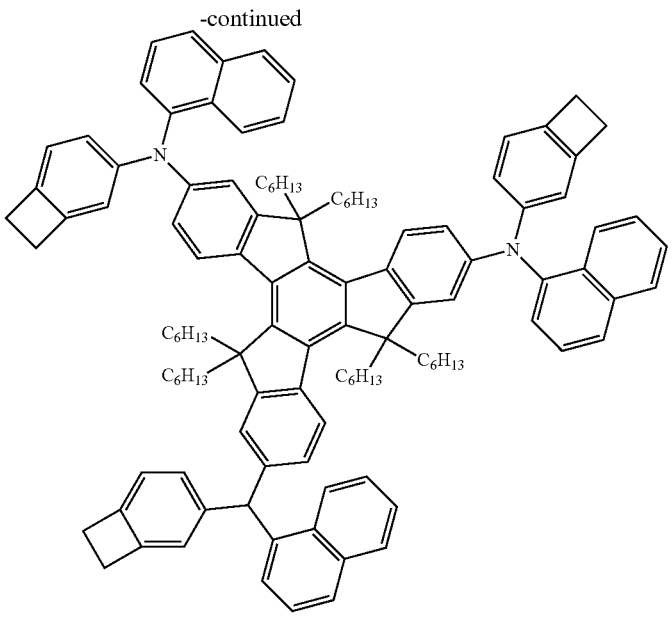

N2,N7,N12-tris(1,2-dihydrocyclobutabenzen-4-yl)-5,5,10,10,15,15-hexahexyl-
N2,N7,N12-tri(naphthalen-1-yl)-10,15-dihydro-5H-diindeno[1,2-a:1',2'-c]fluorene-
2,7,12-triamine
Molecular Weight: 1577.30

Procedure:

Degassed ~250 mL anhydrous Toluene with $N_{2(g)}$. Prepared clean oven dried 250 mL 2 neck round bottom flask, stir bar, and matching spiral condenser by cooling and purging with $N_{2(g)}$. Charged reaction vessel with 2.005 g (0.00185 mol) 2,7,12-tribromo-5,5,10,10,15,15-hexahexyl-10,15-dihydro-5H-diindeno[1,2-a:1',2'-c]fluorene and 1.584 g (0.00646 mol) N-(1,2-dihydrocyclobutabenzen-4-yl)naphthalen-1-amine while under inert atmosphere. Dissolved reagents with ~150 mL dry Toluene via cannula. Purged mixture with $N_{2(g)}$ for 15 minutes. Weighed 0.7995 g (0.00832 mol) tBuONa, 0.1045 g (0.000114 mol) $Pd_2(dba)_3$, and 0.0696 (0.000344 mol) $tBu_3P$ in septa vial and dissolved in ~10 mL dry Toluene and added to reaction mixture via Luer lock syringe. Heated reaction to reflux with heating mantle (~30% on variac) while stirring at 360 R.P.M. Monitored progress of reaction with thin layer chromatography every hour. When TLC confirmed the reaction was complete, heating mantle was removed, and mixture was allowed to cool.

Prepared large fritted glass filter with celite, coarse silica gel (60-200 μm), and filter paper on top. Filtered reaction mixture through plug and washed with ~1.0 L EtOAc. Continued flushing with solvent until TLC of filtrate shows all of N2,N7,N12-tris(1,2-dihydrocyclobutabenzen-4-yl)-5,5,10,10,15,15-hexahexyl-N2,N7,N12-tri(naphthalen-1-yl)-10,15-dihydro-5H-diindeno[1,2-a:1',2'-c]fluorene-2,7,12-triamine is through. Removed solvents with rotary evaporator to a volume of ~20 mL. Precipitated the 20 mL of solution in 800 mL of stirring cold MeOH. Vacuum filtered solid with 5.0 μm Millipore filter and rinsed with ~500 mL MeOH. Ran TLC of solid vs. filtrate. Very little product is present in filtrate. TLC of solid shows some impurity not in line with starting materials. Prepared 2 inch diameter by 18 inch long 500 mL column with ~200 g coarse silica gel slurry. Added crude product in a wet load with 100% hexanes and started flash chromatography column with 100% Hexanes. Eluted product with 10 L of 100% Hexanes. Separation from starting material was not successful however the separation of an unknown impurity from crude was. Solvent was removed via rotary evaporation in a 2 L round bottom flask to a volume small enough to transfer to a smaller tare weighed round bottom flask. Placed N2,N7,N12-tris(1,2-dihydrocyclobutabenzen-4-yl)-5,5,10,10,15,15-hexahexyl-N2,N7,N12-tri(naphthalen-1-yl)-10,15-dihydro-5H-diindeno[1,2-a:1',2'-c]fluorene-2,7,12-triamine under vacuum.

Yield of pure product=2.44 g

Dehalogenations I&II

Procedure:

Prepared clean oven dried 250 mL 2 neck round bottom flask, stir bar, and matching spiral condenser by cooling and purging with $N_{2(g)}$. Cannulated ~50 mL THF into round bottom flask containing N2,N7,N12-tris(1,2-dihydrocyclobutabenzen-4-yl)-5,5,10,10,15,15-hexahexyl-N2,N7,N12-tri(naphthalen-1-yl)-10,15-dihydro-5H-diindeno[1,2-a:1',2'-c]fluorene-2,7,12-triamine. Solution is clear, yellow. Cannulated the solution into 250 mL round bottom flask while under inert atmosphere. Repeated cannulations 2 more times to ensure all product is in solution. Added 4.0 mL $Et_3N$ (2.902 g, 0.0287 mol) to reaction vessel with Luer Lock syringe. Next 1.0 mL HCOOH (1.22 g, 0.0265 mol) was also added to the reaction vessel with a Luer Lock syringe. Purged mixture with $N_{2(g)}$ for 15 minutes. Weighed 0.0.0790 g ($3.519 \times 10^{-4}$ mol) $Pd(OAc)_2$ in disposable vial then added quickly to reaction mixture with glass funnel. Mixture is slightly orange in color. Dissolved 0.0964 g ($4.765 \times 10^{-4}$ mol)

tri-tert-butyl phosphine in 4 mL dry Toluene and added to reaction mixture via Luer lock syringe. Heated reaction to reflux with heating mantle (~20% on variac) while stirring at 400 R.P.M. After 2 hours reaction mixture had turned black. Heating mantle was removed and mixture was allowed to cool to room temperature.

Prepared large fitted glass filter with celite, coarse silica gel (60-200 μm), and filter paper on top. Filtered reaction mixture through plug and washed with 2.0 L THF until TLC of filtrate shows all product is through. Removed solvents in round bottom flask via rotary evaporation until dry and placed under vacuum.

Purification

Added ~100 mL of room temperature MeOH to the round bottom flask containing N2,N7,N12-tris(1,2-dihydrocyclobutabenzen-4-yl)-5,5,10,10,15,15-hexahexyl-N2,N7,N12-tri(naphthalen-1-yl)-10,15-dihydro-5H-diindeno[1,2-a:1',2'-c]fluorene-2,7,12-triamine and three small egg stir bars. Used a metal spatula to break large pieces of solid then began stirring. Fitted flask with rubber septum and placed contents under $N_{2(g)}$. Occasionally rinsed the sides with MeOH to remove any solid that had clung to the walls of the flask. Turned stirring to 800 r.p.m.'s and allowed to stir overnight. Vacuum filtered the cloudy grey mixture with a 5.0 μm Millipore filter. Rinsed with ~200 mL MeOH. Collected solid, dissolved with THF and Hexanes, and prepared a dry load. Used enough coarse silica gel to produce a free flowing powder when dry. Prepared column with ~200 g coarse silica gel in a slurry with Hexanes. Started column with 5% EtOAc in Hexanes. Colored bands began to move quickly through the column so the polarity was reduced to 100% Hexanes. Collected and combined fractions that share similar spots on TLC. Removed solvents via rotary evaporator and placed N2,N7,N12-tris(1,2-dihydrocyclobutabenzen-4-yl)-5,5,10,10,15,15-hexahexyl-N2,N7,N12-tri(naphthalen-1-yl)-10,15-dihydro-5H-diindeno[1,2-a:1',2'-c]fluorene-2,7,12-triamine under vacuum. Performed two more precipitations in MeOH. The first used dry HPLC grade THF as the solvent to dissolve product and 400 mL cold HPLC grade MeOH. The second used HPLC grade Acetone as the solvent and room temperature HPLC grade MeOH to precipitate. Both times after the precipitation the solid was vacuum filtered and washed with ~500 mL room temperature MeOH. The final product was collected and placed under vacuum.

Final mass of product after purification=1.79 g

PLX-8-C

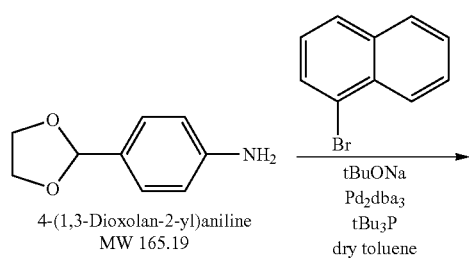

4-(1,3-Dioxolan-2-yl)aniline
MW 165.19 tBuONa
Pd₂dba₃
tBu₃P
dry toluene

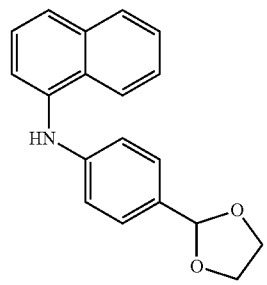

-continued

Procedure:

Prepared clean oven dried 1000 mL 2 neck round bottom flask, stir bar, and matching spiral condenser by cooling and purging with $N_{2(g)}$. Charged reaction vessel with 10.141 g (0.0490 mol, 6.852 mL) 1-bromonaphthalene and 9.573 g (0.0588 mol) 4-(1,3-Dioxolan-2-yl)aniline while under inert atmosphere. Dissolved reagents with ~500 mL dry Toluene via cannula. Purged mixture with $N_{2(g)}$ for 15 minutes. Weighed 6.942 g (0.0735 mol) sodium tert-butoxide and 0.897 g (0.0010 mol) Pd₂(dba)₃ together in disposable vial then added quickly to reaction mixture with glass funnel. Mixture is dark purple. Dissolved 0.596 g (0.0029 mol) tri-tert-butyl phosphine in 4 mL dry Toluene and added to reaction mixture via Luer lock syringe. Heated reaction to reflux with heating mantle (~30% on variac) while stirring at 500 R.P.M. Allowed reaction to reflux overnight then monitored progress of reaction with thin layer chromatography the next morning. TLC confirmed reaction is complete. Heating mantle was removed and mixture was allowed to cool to room temperature.

Prepared large fritted glass filter with celite, coarse silica gel (60-200 μm), and filter paper on top. Treated plug with 1% triethylamine (Et₃N) in 99% ethyl acetate (EtOAc). Filtered reaction mixture through plug and washed with (~3.0 L) 1% Et₃N/99% EtOAc until TLC of filtrate shows all product is through. Removed most solvents with rotary evaporator and added enough silica gel treated with ~5 mL Et₃N to prepare a dry load for column chromatography.

Prepared 500 mL 18 inch column with ~200 g coarse silica gel slurry treated with Et₃N. Added crude product in a dry load and started flash chromatography column with 99% Hexanes/1% Et₃N. Increased polarity by 2.5% with EtOAc until a polarity of 10% was reached. After 12 fractions (250 mL each) product began to elute. Several impure product fractions were collected and set aside. Ten pure product fractions total were collected and solvent was removed via rotary evaporation in a round bottom flask. Fitted flask with rubber septum and placed N-(4-(1,3-dioxolan-2-yl)phenyl)naphthalen-1-amine under vacuum.

Final mass of pure product=7.380 g.

Amination Reaction

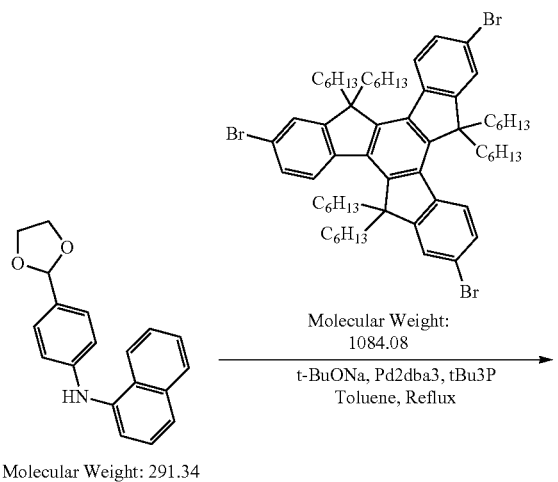

Molecular Weight: 291.34

Molecular Weight: 1084.08 t-BuONa, Pd2dba3, tBu3P
Toluene, Reflux

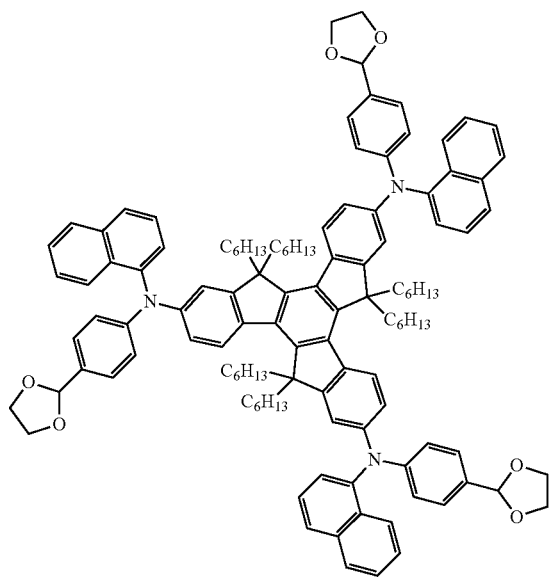

Procedure:

Prepared clean oven dried 1000 mL 2 neck round bottom flask, stir bar, and matching spiral condenser by cooling and purging with $N_{2(g)}$. Charged reaction vessel with 7.596 g (0.0070 mol) 2,7,12-tribromo-5,5,10,10,15,15-hexahexyl-10,15-dihydro-5H-diindeno[1,2-a:1',2'-c]fluorene and 7.349 g (0.0252 mol) N-(4-(1,3-dioxolan-2-yl)phenyl)naphthalen-1-amine. Dissolved reagents with ~500 mL dry Toluene via cannula. Purged mixture with $N_{2\ (g)}$ for 15 minutes. Weighed 3.030 (0.0315 mol) sodium tert-butoxide and 0.385 g (0.0004 mol) $Pd_2dba_3$ together in disposable vial then added quickly to reaction mixture with glass funnel. Mixture is dark purple. Dissolved 0.255 g (0.0013 mol) tri-tert-butyl phosphine in 6 mL dry Toluene and added to reaction mixture via Luer lock syringe. Heated reaction to reflux with heating mantle (~30% on variac) while stirring at 500 R.P.M. Allowed reaction to reflux for 4 hours then monitored progress of reaction with thin layer chromatography. TLC confirmed reaction is complete. Heating mantle was removed and mixture was allowed to cool to room temperature.

Prepared large fritted glass filter funnel with celite, coarse silica gel (60-200 μm), and filter paper. Treated plug with 1% triethylamine ($Et_3N$) in ethyl acetate (EtOAc). Filtered reaction mixture through plug and washed with (~3.0 L) 1% $Et_3N$/99% EtOAc until TLC shows all product is through. Removed solvents via rotary evaporation. The crude product was dissolved in 50 mL EtOAc and added slowly drop wise to a stirring flask of ~500 mL room temperature MeOH. Vacuum filtered the mixture using a 5.0 μm Millipore filter paper. Prepared 4 inch diameter by 12 inch long 2000 mL column with ~400 g coarse silica gel slurry treated with 2% $Et_3N$/98% Hexanes. Started flash chromatography column with 99% Hexanes/1% $Et_3N$ and increased polarity by 2.5% with EtOAc until a polarity of 10% was reached. Ran TLC on each fraction and combined fractions with similar spots. Removed solvents in round bottom flask via rotary evaporation and placed under vacuum.

Final mass of pure product=9.078 g

Dehalogenation I & II

Procedure:

Prepared clean oven dried 1000 mL 2 neck round bottom flask, stir bar, and matching spiral condenser by cooling and purging with $N_{2(g)}$. Cannulated ~100 mL THF into round bottom flask containing N2,N7,N12-tris(4-(1,3-dioxolan-2-yl)phenyl)-5,5,10,10,15,15-hexahexyl-N2,N7,N12-tri(naphthalen-1-yl)-10,15-dihydro-5H-diindeno[1,2-a:1',2'-c]fluorene-2,7,12-triamine. Solution is clear, yellow. Cannulated THF solution into 1000 mL round bottom flask while under inert atmosphere. Repeated cannulations 2 more times to ensure all solution was transferred. Added 10.183 g $Et_3N$ (13.3 mL, 0.0953 mol) to reaction vessel with 24.0 mL Luer Lock syringe. Next 3.66 g HCOOH (3.0 mL, 0.0794 mol) was added to the reaction vessel with a 5.0 mL Luer Lock syringe. Purged mixture with $N_{2\ (g)}$ for 15 minutes. Weighed 0.1859 g ($7.938 \times 10^{-4}$ mol) $Pd(OAc)_2$ in disposable vial then added quickly to reaction mixture with glass funnel. Mixture is slightly orange in color. Dissolved 0.2418 g ($1.191 \times 10^{-3}$ mol) tri-tert-butyl phosphine in 4 mL dry Toluene and added to reaction mixture via Luer lock syringe. Heated reaction to reflux with heating mantle (~20% on variac) while stirring at 500 R.P.M. After 2 hours reaction mixture had turned dark purple. Heating mantle was removed and mixture was allowed to cool to room temperature. Prepared large fritted glass filter with celite, coarse silica gel (60-200 μm), and filter paper on top. Treated plug with 1% triethylamine ($Et_3N$) in 99% ethyl acetate (EtOAc). Filtered reaction mixture through plug and washed with (~3.0 L) 1% $Et_3N$/99% EtOAc until TLC of filtrate shows all product is through. Removed solvents in round bottom flask via rotary evaporation until dry and placed under vacuum.

*Repeated Twice

Final mass of product after $2^{nd}$ dehalogenation=9.50 g

Deprotection

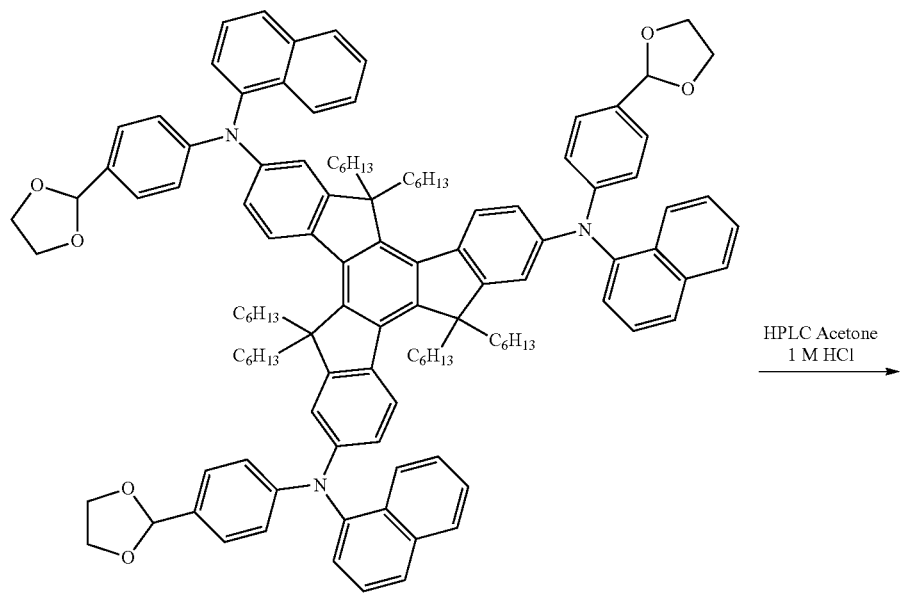

N2,N7,N12-tris(4-(1,3-dioxolan-2-yl)phenyl)-5,5,10,10,15,15-hexahexyl-N2,N7,N12-tri(naphthalen-1-yl)-10,15-dihydro-5H-diindeno[1,2-a:1',2'-c]fluorene-2,7,12-triamine HPLC Acetone
1 M HCl
⟶

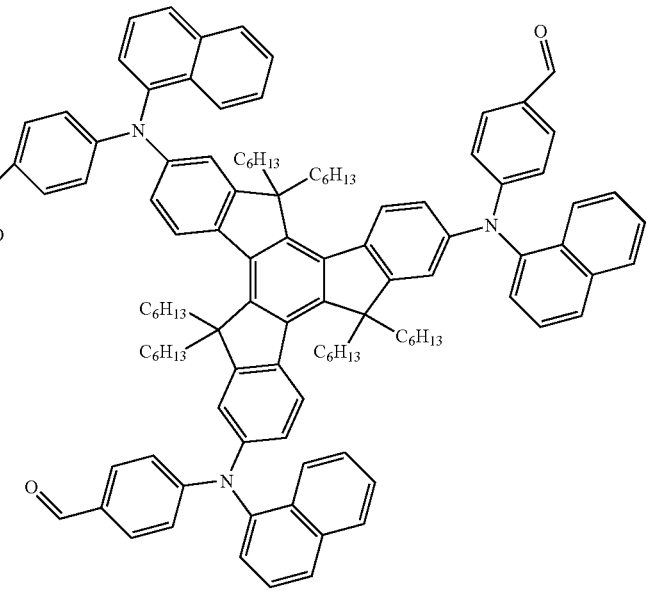

4,4',4''-(5,5,10,10,15,15-hexahexyl-10,15-dihydro-5H-diindeno[1,2-a:1',2'-c]fluorene-2,7,12-triyl)tris(naphthalen-1-ylazanediyl)tribenzaldehyde Procedure:

Prepared clean oven dried 1000 mL 2 neck (24/40) round bottom flask and magnetic stir bar by cooling and purging with $N_{2(g)}$. Dissolved N2,N7,N12-tris(4-(1,3-dioxolan-2-yl)phenyl)-5,5,10,10,15,15-hexahexyl-N2,N7,N12-tri(naphthalen-1-yl)-10,15-dihydro-5H-diindeno[1,2-a:1',2'-c]fluorene-2,7,12-triamine in 500 mL HPLC grad Acetone. Solution is clear reddish purple. Slowly added 4 mL 1 M_HCl with Luer Lock syring over the course of 5 minutes. Let solution stir. After 30 minutes TLC was run to check if the reaction had gone to completion. Reaction complete after 40 minutes. Removed solvents completely with rotary evaporator. Prepared clean dry separatory funnel. Dissolved 4,4',4''-(5,5,10,10,15,15-hexahexyl-10,15-dihydro-5H-diindeno[1,2-a:1',2'-c]fluorene-2,7,12-triyl)tris(naphthalen-1-ylazanediyl)tribenzaldehyde in EtOAc. Solution is clear purple. Added the solution to a separatory funnel. Added 300 mL D.I. water, capped, inverted 3 times, burped and let mixture settle. An emulsion formed but was easily treated with 20 mL saturated NaCl solution. Separated aqueous layer and pH=3. Repeated washes 2 more times until pH=~6. Placed organic layer in clean 1000 mL Erlenmeyer with magnetic stir bar and added MgSO$_4$ (anhydrous) until clumps of the hydrated salt no longer formed. Stirred for 5 minutes. Gravity filtered the mixture into a clean 2000 mL round bottom flask using a ground glass funnel (24/40) and fluted filter paper. Rinsed with 500 mL EtOAc. Evaporated solvents to a volume of ~200 mL via rotary evaporator then completed removal of solvents in a clean dry 500 mL round bottom flask.

Prepared 2 inch diameter by 12 inch long 500 mL chromatography column with ~80 g coarse silica gel and wrapped in aluminum foil. Prepared dry load with product dissolved in CHCl$_3$ and enough silica gel to create a free flowing powder when dry. Started column at 10% CHCl$_3$ and increased concentration by 2.5% until a concentration of 20% was reached. Once 20% was reached the concentration of CHCl$_3$ was increased by 5% until a final concentration of 40%. Monitored fractions with TLC combined like spots discarding those not containing product. The product fractions were combined in a 2 L round bottom flask for rotary evaporation and covered with aluminum foil during evaporation. Removed enough solvent to transfer into a smaller round bottom flask then finished removing solvent. Placed 4,4',4"-(5,5,10,10,15,15-hexahexyl-10,15-dihydro-5H-diindeno[1,2-a:1',2'-c]fluorene-2,7,12-triyl)tris(naphthalen-1-ylazanediyl)tribenzaldehyde under vacuum and covered in aluminum foil.

Final mass of purified product=7.730 g

Wittig Reaction

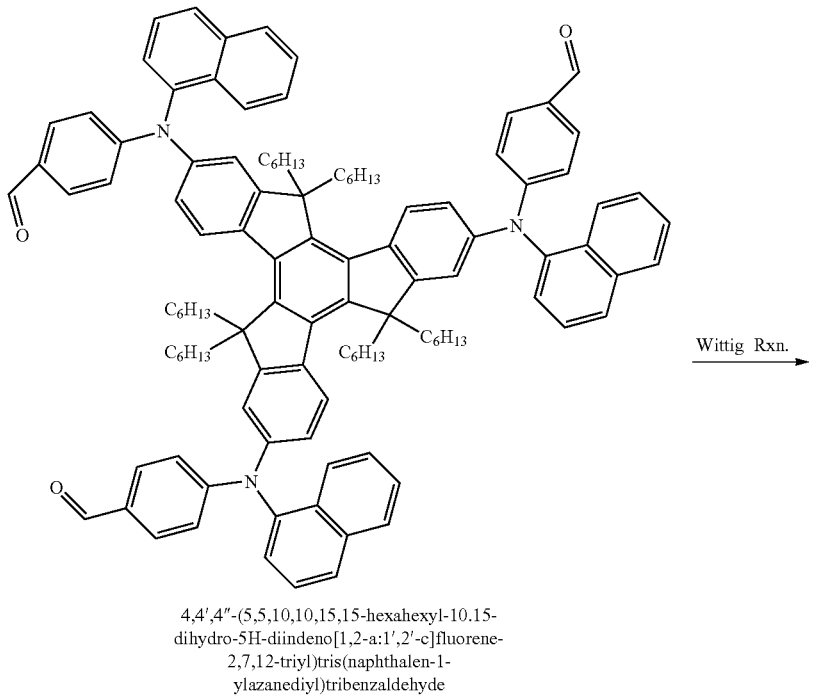

4,4',4"-(5,5,10,10,15,15-hexahexyl-10.15-dihydro-5H-diindeno[1,2-a:1',2'-c]fluorene-2,7,12-triyl)tris(naphthalen-1-ylazanediyl)tribenzaldehyde

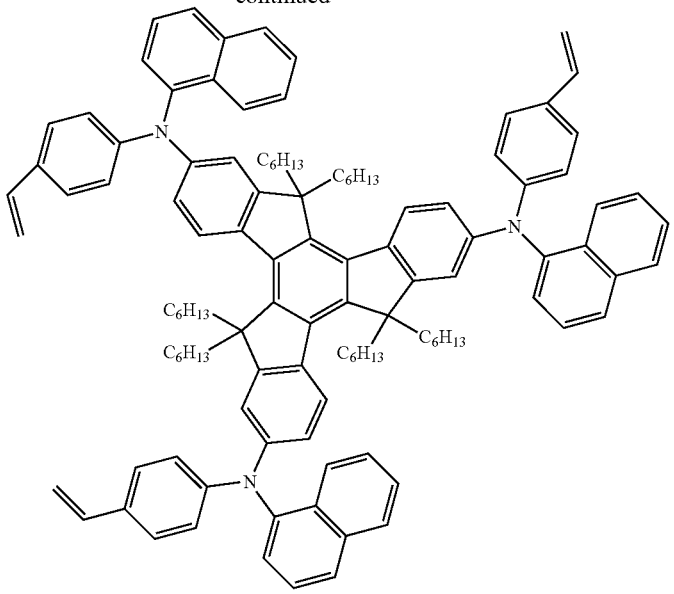

5,5,10,10,15,15-hexahexyl-N2,N7,N12-tri(naphthalen-1-yl)-N2,N7,N12-
tris(4-vinylphenyl)-10,15-dihydro-5H-diindeno[1,2-a:1',2'-c]fluorene-
2,7,12-triamine Synthesis of 5,5,10,10,15,15-hexahexyl-N2,N7,N12-tri(naphthalen-1-yl)-N2,N7,N12-tris(4-vinylphenyl)-10,15-dihydro-5H-diindeno[1,2-a:1',2'-c]fluorene-2,7,12-triamine Prepared clean oven dried 1000 mL 3 neck (24/40) round bottom flask with stir bar and 100 mL addition funnel by cooling/purging with $N_{2(g)}$. Purged an open 1.0 L bottle of dry THF with $N_{2(g)}$ for 15 minutes. Added 7.7727 g (0.0220 mol) triphenylmethylbromide and 2.6029 g (0.0227 mol) to the round bottom flask while under an inert atmosphere. Cannulated ~400 mL THF into the round bottom flask and began stirring. Wrapped the 1000 mL flask with aluminum foil. Cannulated ~100 mL THF into a flask containing 4,4',4''-(5,5,10,10,15,15-hexahexyl-10,15-dihydro-5H-diindeno[1,2-a:1',2'-c]fluorene-2,7,12-triyl)tris(naphthalen-1-ylazanediyl)tribenzaldehyde. Once solid was completely in solution it was cannulated into the addition funnel. Began the addition of the solution at a rate of ~3 drops/sec. After 2.5 hours the addition is complete the mixture is cloudy and orange. Ran TLC to ensure the reaction went to completion.

Prepared fritted glass filter funnel with celite, coarse silica gel, and a filter paper on top. Filtered the reaction mixture through the plug and flushed with ~2 L EtOAc. Filtrate is clear, orange. Rotovapped to dryness and placed under vacuum. Prepared a dry load for column chromatography by dissolving 5,5,10,10,15,15-hexahexyl-N2,N7,N12-tri(naphthalen-1-yl)-N2,N7,N12-tris(4-vinylphenyl)-10,15-dihydro-5H-diindeno[1,2-a:1',2'-c]fluorene-2,7,12-triamine in EtOAc and adding enough silica gel treated with $Et_3N$ so when dry it forms a free flowing powder.

Prepared a 2 inch×18 inch long 500 mL column with ~125 g coarse silica gel. One previous attempt at purification resulted in a precipitate forming in the solvent head above the dry load making it impossible to run a flash column. Cold hexane was found to help stop this from happening. ~250 mL cold hexane was flushed through the column prior to adding the dry load. Another 250 mL was poured into the column and the dry load was immediately added. Started with 100% hexane and TLC shows product immediately began to elute from the column. TLC pure product completely removed with 100% hexane with no need to increase polarity. Rotovapped pure product fractions to dryness and placed under vacuum. Dissolved product in the minimum amount of HPLC grade EtOAc. Allowed ~800 mL HPLC grade MeOH in an Erlenmeyer flask to cool in an ice bath while stirring at ~500 r.p.m. Slowly added the EtOAc/product solution to the cold MeOH with a Luer lock syringe fitted with a 22 gauge needle. An off white precipitate immediately formed. Once all the solution was precipitated, the mixture was vacuum filtered using a 5.0 μm Millipore filter. A TLC of solid vs. filtrate was run to verify the solid was indeed the desired product. The solid was collected and allowed to dry under vacuum.

Final mass of pure product=4.40 g

217
PLX-9-A
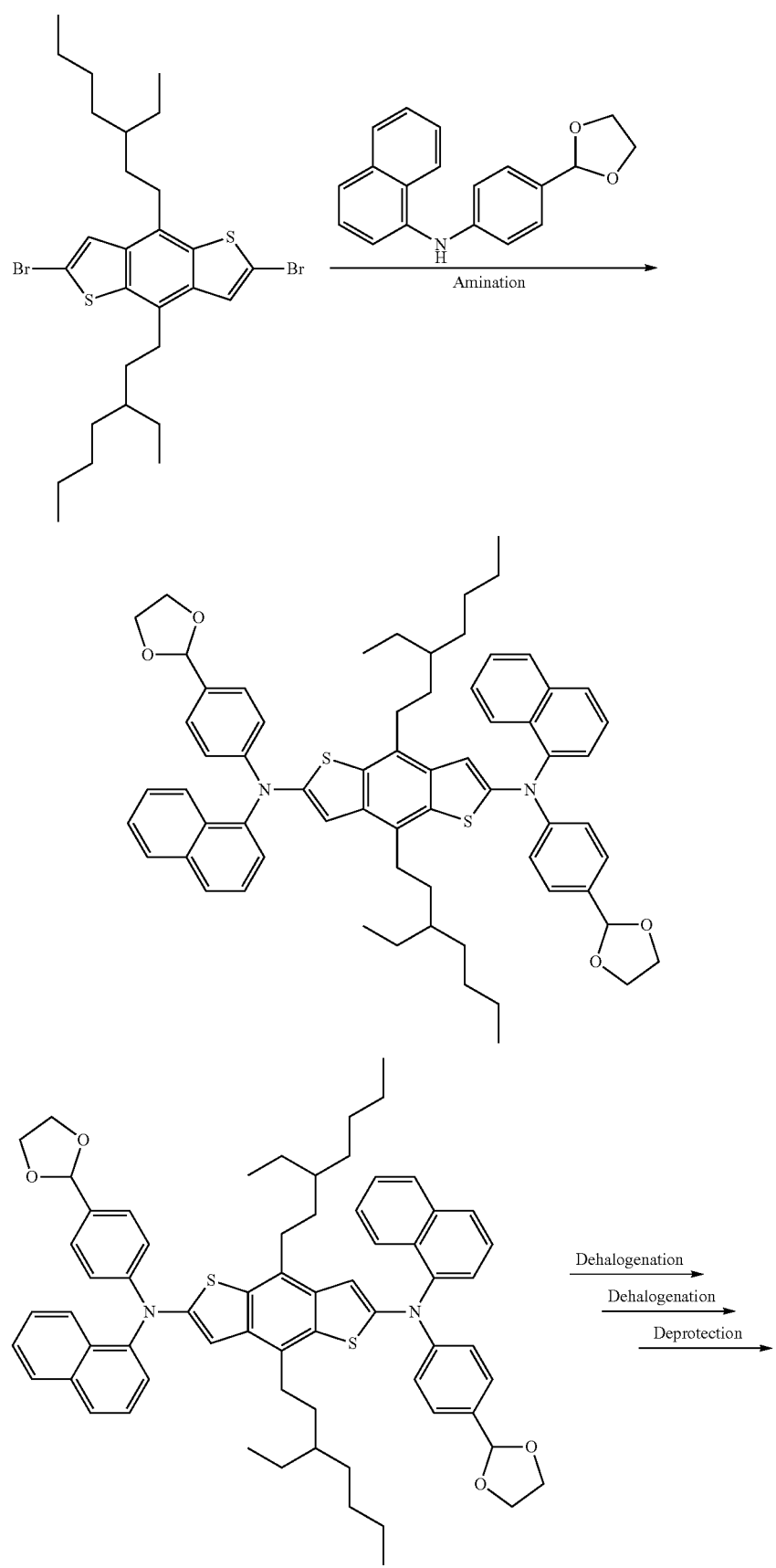

-continued
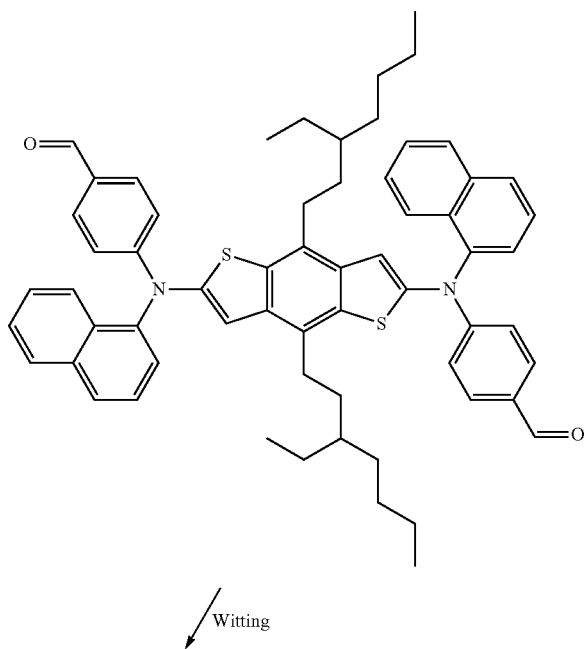
↓ Witting
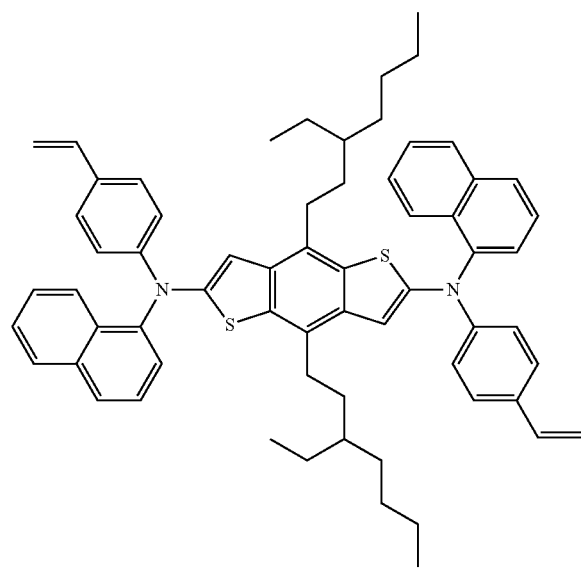
Amination

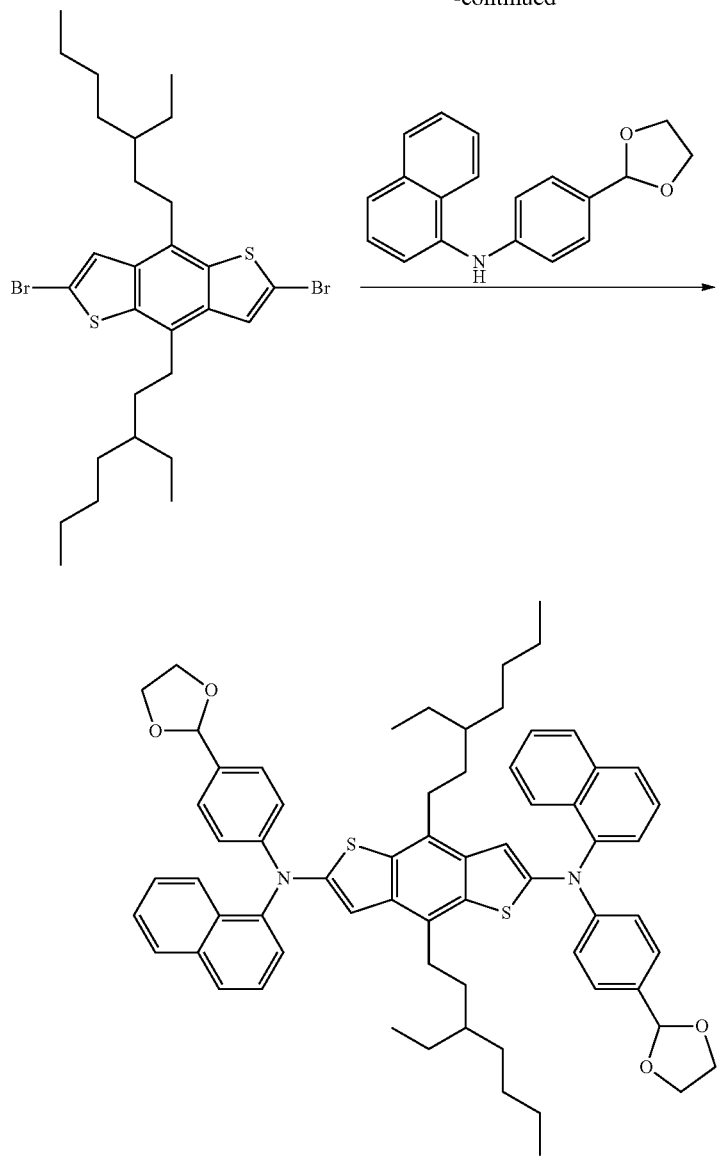

Prepared all clean, oven-dried glassware: 500 mL three-neck round-bottom flask with a magnetic stir bar, and a reflux condenser. Purged reaction vessel with $N_2$. Charged reaction flask with 1.44 g (2.4e-3 mol) of 2,6-dibromo-4,8-bis(3-ethylheptyl)benzo[1,2-b:4,5-b']dithiophene and 1.68 g (5.76e-3 mol) of N-(4-(1,3-dioxolan-2-yl)phenyl)naphthalen-1-amine. Dissolved in ~200 mL of dry toluene transferred via cannula. Purged reaction solution with nitrogen flow for 30 minutes. Added 0.692 g (7.2e-3 mol) sodium tert-butoxide. Added ~0.088 g (9.6e-5 mol) $Pd_2dba_3$. Added ~0.06 g (2.9e-4 mol) tri-tert-butyl phosphine/~5 mL dry toluene solution via syringe. Allowed reaction to reflux overnight then monitored via thin-layer chromatography. TLC confirmed reaction completion. Removed reaction from heat and allowed to cool to r.t. Prepared celite/silica gel plug and basified with 1% $Et_3N$/99% EtOAc solution. Filtered reaction solution through a Celite/silica gel plug. Adsorbed crude reaction mixture to silica gel and chromatographed at an increasing ethyl acetate/hexanes gradient. Collected similar spots on TLC and removed solvents. Separation from excess amine was not achieved, so the purified crude was refluxed in methanol and filtered. Mass of product obtained was 1.79 g. NMR indicated desired product.

Dehalogenation 1 & 2

Prepared all clean, oven-dried glassware: 500 mL three-neck round-bottom flask with a magnetic stir bar, reflux condenser. Dissolved 1.79 g (1.75e-3 mol) $N^2,N^6$-bis(4-(1,3-dioxolan-2-yl)phenyl)-4,8-bis(3-ethylheptyl)-$N^2,N^6$-di(naphthalen-1-yl)benzo[1,2-b:4,5-b']dithiophene-2,6-diamine in 200 mL dry THF. Transferred solution to reaction flask via cannulae. Added 2.91 mL triethylamine (2.1e-2 mol) via syringe. Added 0.66 mL formic acid (1.75e-2 mol) via syringe. Fuming observed. Solution was purged with $N_2$ for 30 mins. Added 0.04 g $Pd(OAc)_2$ (1.75e-4 mol) via funnel. Added 0.06 g $tBu_3P$ (~2.63e-4 mol) dissolved in 2 mL toluene via syringe. Reaction was refluxed until the solution turned black from suspended palladium. Allowed the reaction to cool and filtered through a celite/silica gel plug. Silica gel was pretreated with triethylamine in chloroform. Solvents were removed via rotary evaporation and solids went through a second dehalogenation that was carried out identically.

Deprotection

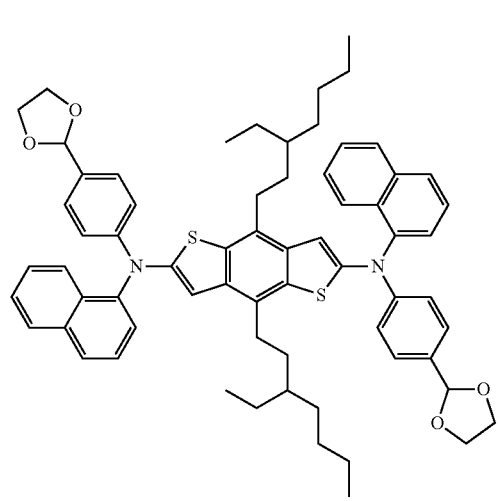

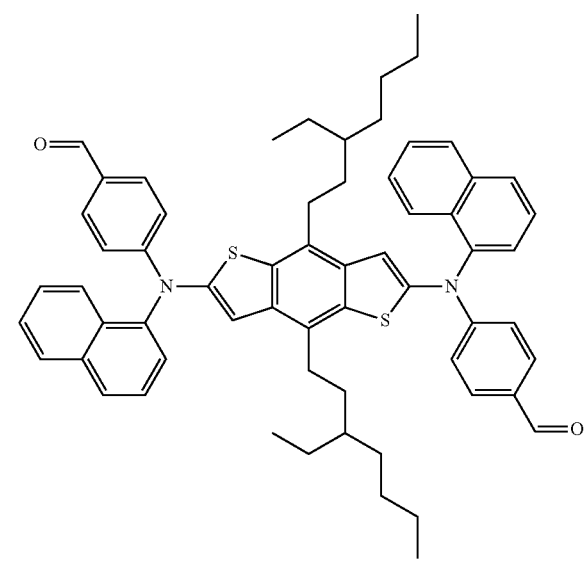

Prepared all clean, oven-dried glassware: 1000 mL three-neck round-bottom flask with a magnetic stir bar. Charged flask with 1.79 g (1.75e-3 mol) of $N^2,N^6$-bis(4-(1,3-dioxolan-2-yl)phenyl)-4,8-bis(3-ethylheptyl)-$N^2,N^6$-di(naphthalen-1-yl)benzo[1,2-b:4,5-b']dithiophene-2,6-diamine. Transferred 500 mL of dry THF to reaction flask via cannulae. Slowly added 1.4 mL 1M HCl solution dropwise to flask via syringe. As acid hit reaction solution, some precipitate was observed to form, which quickly redissolved. After ~15 mins, addition of acid was complete. Let stir for 30 mins. TLC confirmed reaction completion. Reaction not complete until after 3 hours. Reaction solution was extracted into 200 mL ethyl acetate and washed with 3×500 mL of DI $H_2O$ until aqueous fraction pH=~7. Collected organic layer and dried over $MgSO_4$. Gravity filtered off salts. Removed solvents, stored under vacuum. Crude mixture was chromatographed at increasing EtOAc/Hexanes gradient. Mass of TLC pure material was 1.47 g. NMR indicated desired product.

Wittig

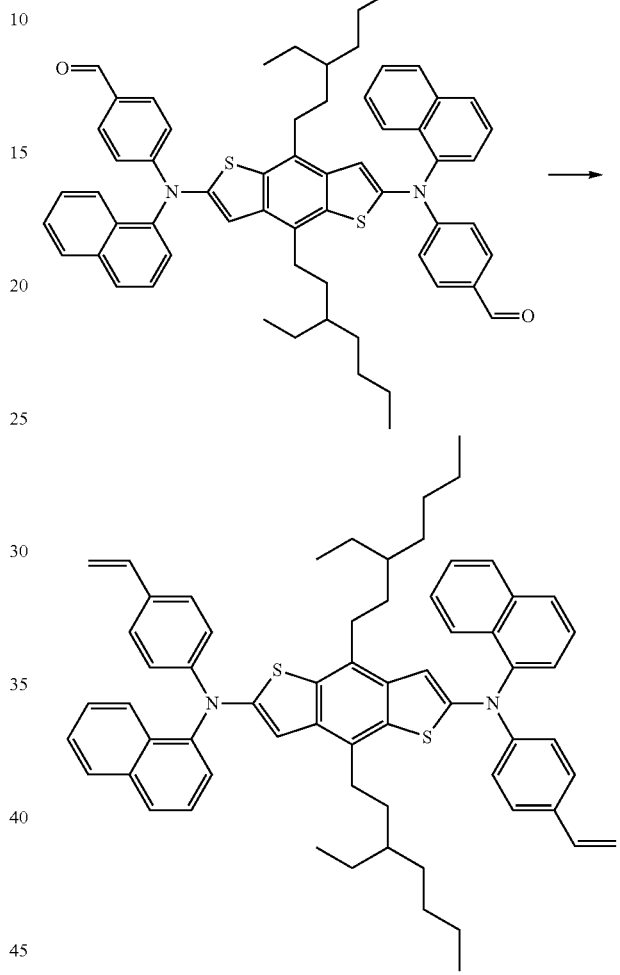

Prepared all clean, oven-dried glassware: 500 mL three-neck round-bottom flask with a magnetic stir bar, 250 mL addition funnel. Charged reaction flask with 1.8 g (5.04e-3 mol) $CH_3PPh_3Br$ via funnel. Charged reaction flask with 0.6 g (5.36e-3 mol) tBuOK via funnel. Added ~400 mL dry THF to reaction flask via cannulae, attempting to dissolve $CH_3PPh_3Br$/tBuOK. A milky-yellow suspension of ylide formed. After stirring for 15 minutes, the reaction flask was covered in foil. Dissolved 1.47 g (1.58e-3 mol) of 4,4'-((4,8-bis(3-ethylheptyl)benzo[1,2-b:4,5-b']dithiophene-2,6-diyl) bis(naphthalen-1-ylazanediyl))dibenzaldehyde in dry THF and transferred via cannula to addition funnel. The dialdehyde was added to the ylide solution dropwise at approximately 3 Hz. After adding all of the dialdehyde, the solution in the flask appeared to be more pink. Solution was allowed to stir for 15 minutes before TLC confirmed the reaction's completion. The crude mixture was filtered through a celite/silica gel plug and washed with EtOAc until no spotting observed on TLC. Solvents were removed via rotary evaporation using a temperature no higher than 40° C. The crude material was dry loaded onto a silica gel column and eluted at 1% EtOAc/99% Hexanes until product fully eluted. Similar fractions were collected and solvents removed. The TLC pure fractions were redissolved in HPLC grade ethyl acetate and precipitated into HPLC grade methanol. The solids were filtered off and dried under vacuum. Mass of solids: 1.2 g. NMR of solids confirmed the presence of desired product: 4,8-bis(3-ethylheptyl)-$N^2$,$N^6$-di(naphthalen-1-yl)-$N^2$,$N^6$-bis(4-vinylphenyl)benzo[1,2-b:4,5-b']dithiophene-2,6-diamine.

PLX-9-B

Synthesis of 2,6-dibromobenzo[1,2-b:4,5-b']dithiophene

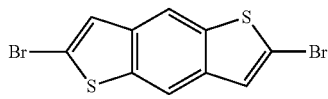 [SMILES: Brc1cc2cc3sc(Br)cc3cc2s1]

Procedures:

A clean and dry three neck round bottom flask was charged with benzo[1,2-b:4,5-b']dithiophene (5.00 g, 0.0263 mol) and anhydrous tetrahydrofuran (1 L) was then added by cannula. The reaction flask was cooled to −78° C. in a dry ice/IPA bath. Tert-butyllithium (1.7M, 46.4 mL) was then added slowly via syringe. The reaction was allowed to stir at this temperature for 30 minutes, after which was allowed to warm to 0° C. The reaction flask was cooled to −78° C. again, and 1,2-dibromotetrafluoroethane (9.5 mL, 0.0788 mol) was added via syringe. The reaction was allowed to stir at this temperature for one hour before being allowed to warm to ambient temperature. Isopropanol (10 mL) was added to quench, and the reaction poured into an erlenmeyer flask containing DI $H_2O$ (200 mL) portion-wise with vigorous stirring. MTBE (400 mL) was added to this flask, and then the solution was transferred to a separatory funnel. The organic layer was washed with DI $H_2O$ (3×200 mL), collected and dried over anhydrous magnesium sulfate. Solids were filtered off by vacuum filtration and solvent was removed from the filtrate by rotary evaporation. The resulting crude material was further purified by chromatography using ethyl acetate/hexanes as an eluent.

Synthesis of $N^2$,$N^6$-bis(4-(1,3-dioxolan-2-yl)phenyl)-N2,N6-di-m-tolylbenzo[1,2-b:4,5-b']dithiophene-2,6-diamine

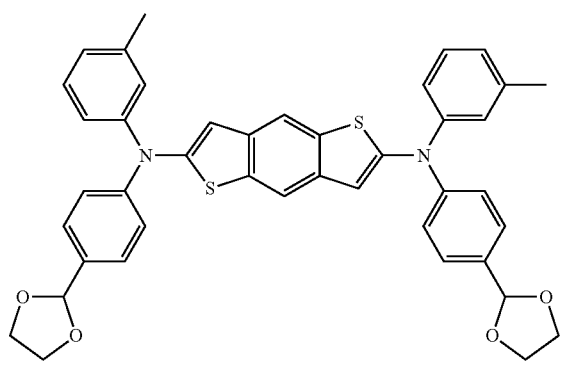 [SMILES: Cc1cccc(N(c2ccc(C3OCCO3)cc2)c2cc3cc4sc(N(c5ccc(C6OCCO6)cc5)c5cccc(C)c5)cc4cc3s2)c1]

Procedures:

In a clean and dry three neck flask equipped with magnetic stir bar and reflux condenser was added 2,6-dibromobenzo[1,2-b:4,5-b']dithiophene (1.00 g, 0.0029 mol) and N-(4-(1,3-dioxolan-2-yl)phenyl)-3-methylaniline (2.20 g, 0.0086 mol). Anhydrous toluene (100 mL) was then added, and the reaction solution was purged with inert gas flow for thirty minutes. Sodium tert-butoxide (0.83 g, 0.0086 mol) and $Pd_2dba_3$ (0.21 g, 0.00023 mol) were then added, followed by the addition of tri-tert-butylphosphine (0.14 g, 0.00069 mol) in toluene solution (5 mL). The reaction was heated to reflux. When reaction completion was confirmed by thin-layer chromatography, the reaction was cooled to room temperature and filtered through a bed of celite and triethylamine treated silica gel, washing thoroughly with ethyl acetate. Solvent was removed from filtrate by rotary evaporation and the crude solids were dried under vacuum. Purification was carried out by chromatography on silica gel using a gradient of triethylamine/ethyl acetate/hexanes as an eluent. Precipitation from a minimum amount of chloroform into methanol provided $^1$H-NMR pure product.

Yield=0.74 g

Dehalogenation of N2,N6-bis(4-(1,3-dioxolan-2-yl)phenyl)-N2,N6-di-m-tolylbenzo[1,2-b:4,5-b']dithiophene-2,6-diamine

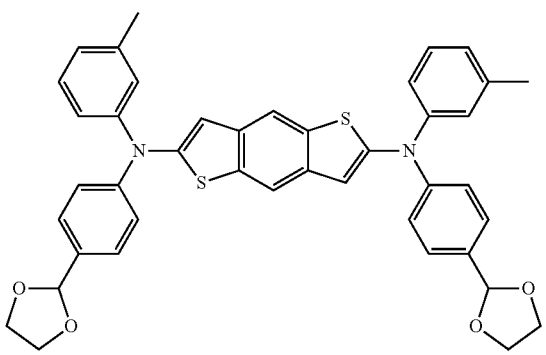 [SMILES: Cc1cccc(N(c2ccc(C3OCCO3)cc2)c2cc3cc4sc(N(c5ccc(C6OCCO6)cc5)c5cccc(C)c5)cc4cc3s2)c1]

Procedures:

A solution of N2,N6-bis(4-(1,3-dioxolan-2-yl)phenyl)-N2,N6-di-m-tolylbenzo[1,2-b:4,5-b']dithiophene-2,6-diamine (0.6 g, 0.00086 mol) in anhydrous THF (50 mL) was prepared and transferred by cannula to a clean, dry round bottom flask equipped with a reflux condenser. Triethylamine (7.3 mL) was then added via syringe. Formic acid (2 mL) was added slowly, dropwise via syringe. The reaction solution and system was then purged with an inert gas flow for thirty minutes, after which $Pd(OAc)_2$ (0.12 g) and $tBu_3P$ (0.16 g in 5 mL anhydrous toluene) were added. The reaction was heated to reflux for approximately 2 hours and then cooled to room temperature. The solution was filtered through a Celite and triethylamine treated silica gel plug, washing with excess ethyl acetate. Precipitation was carried out by dissolving product in ethyl acetate and slowly adding hexanes. Solids were collected by filtration and placed in vacuum drying oven to be carried on to the next dehalogenation reaction.

Dehalogenation of N2,N6-bis(4-(1,3-dioxolan-2-yl)phenyl)-N2,N6-di-m-tolylbenzo[1,2-b:4,5-b']dithiophene-2,6-diamine Procedures:

A solution of singly dehalogenated N2,N6-bis(4-(1,3-dioxolan-2-yl)phenyl)-N2,N6-di-m-tolylbenzo[1,2-b:4,5-b']dithiophene-2,6-diamine (0.6 g, 0.00086 mol) in anhydrous THF (50 mL) was prepared and transferred by cannula to a clean, dry round bottom flask equipped with a reflux condenser. Triethylamine (7.3 mL) was then added via syringe. Formic acid (2 mL) was added slowly, dropwise via syringe. The reaction solution and system was then purged with an inert gas flow for thirty minutes, after which $Pd(OAc)_2$ (0.12 g) and $tBu_3P$ (0.16 g in 5 mL anhydrous toluene) were added. The reaction was heated to reflux for approximately 2 hours and then cooled to room temperature. The solution was filtered through a Celite and triethylamine treated silica gel plug, washing with excess ethyl acetate. Precipitation was carried out by dissolving product in ethyl acetate and slowly adding hexanes. Solids were collected by filtration and placed in vacuum drying oven to be carried on to the deprotection reaction.

Synthesis of 4,4'-(benzo[1,2-b:4,5-b']dithiophene-2,6-diylbis(m-tolylazanediyl))dibenzaldehyde

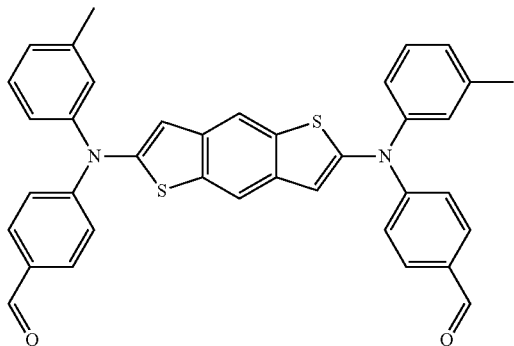 [SMILES: Cc1cccc(N(c2ccc(C=O)cc2)c2cc3cc4sc(N(c5ccc(C=O)cc5)c5cccc(C)c5)cc4cc3s2)c1]

Procedures:

To a single-neck round bottom flask containing doubly dehalogenated N2,N6-bis(4-(1,3-dioxolan-2-yl)phenyl)-N2,N6-di-m-tolylbenzo[1,2-b:4,5-b']dithiophene-2,6-diamine (0.4 g, 0.00057 mol), acetone (400 mL) and a magnetic stir bar were added. Hydrochloric acid solution (1.0M, 1.0 mL) was added slowly drop-wise. The reaction was allowed to stir for 30 minutes. A TLC plate was taken and showed that the reaction had finally completed. The solution was worked up with methyl tert-butyl ether and deionized water until neutral. The organic fraction was collected and dried over anhydrous magnesium sulfate. The solids were separated by vacuum filtration, and the solvent was removed from the filtrate by rotary evaporation. Product was purified by dissolution with tetrahydrofuran and precipitation with hexanes followed by filtration. Yield=0.200 g

Synthesis of N2,N6-di-m-tolyl-N2,N6-bis(4-vinylphenyl)benzo[1,2-b:4,5-b']dithiophene-2,6-diamine

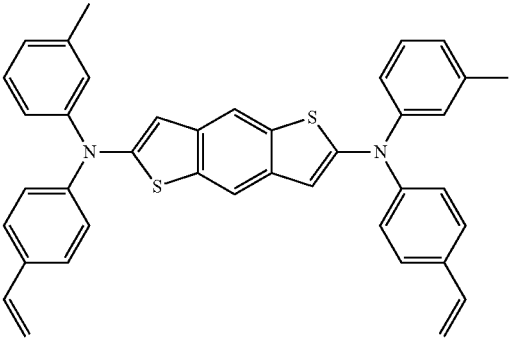 [SMILES: C=Cc1ccc(N(c2cccc(C)c2)c2cc3cc4sc(N(c5ccc(C=C)cc5)c5cccc(C)c5)cc4cc3s2)cc1]

Procedures:

A three-neck round bottom flask was charged with methyltriphenylphosphonium bromide (1.31 g, 0.0037 mol) and anhydrous tetrahydrofuran (100 mL) was added via cannula. Stirring was initiated, and potassium tert-butoxide (0.42 g, 0.0038 mol) was added manually. This solution was allowed to stir for ten minutes before an anhydrous solution of 4,4'-(benzo[1,2-b:4,5-b']dithiophene-2,6-diylbis(m-tolylazanediyl))dibenzaldehyde (0.74 g, 0.0012 mol) in tetrahydrofuran (30 mL) was added slowly, dropwise via syringe. The reaction was allowed to stir for thirty minutes before reaction completion was confirmed by thin-layer chromatography. The reaction solution was filtered through a bed of celite and silica gel (triethylamine treated), washing thoroughly with tetrahydrofuran. The filtrate was removed of solvent by rotary evaporation and the resulting crude material was placed under vacuum. The crude material was further purified by chromatography on silica gel using ethyl acetate/hexane as an eluent. Precipitation from a minimum amount of ethyl acetate into methanol provided $^1$H-NMR pure product. Yield=0.300 g

PLX-9-D

Synthesis of 4,8-diphenylbenzo[1,2-b:4,5-b']dithiophene

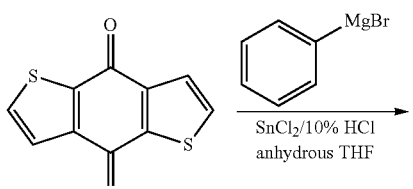

Molecular Weight: 220.27

Synthesis of 2,6-dibromo-4,8-diphenylbenzo[1,2-b:4,5-b']dithiophene

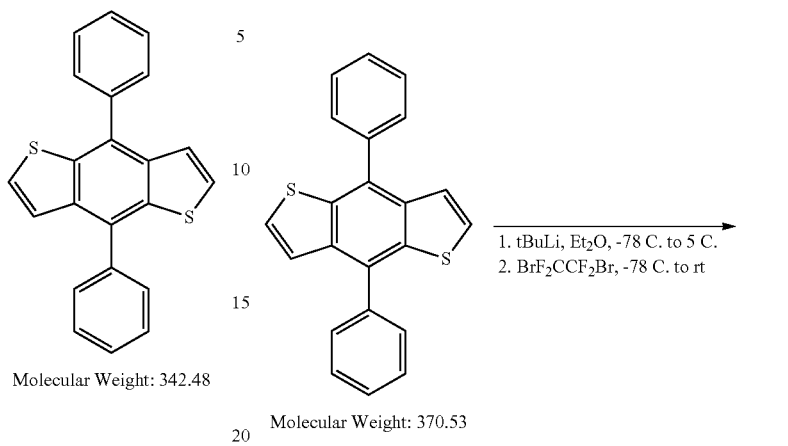

Molecular Weight: 342.48

Molecular Weight: 370.53

1. tBuLi, Et$_2$O, -78 C. to 5 C.
2. BrF$_2$CCF$_2$Br, -78 C. to rt

Molecular Weight: 500.27

Procedures:

To a clean, dry 500 mL 3N-RBF equipped with a reflux condenser and magnetic stir bar, was added 4,8-Dihydrobenzo[1,2-b:4,5-b']dithiophen-4,8-dione (2.00 g, 9 mmol) and dissolved in anhydrous tetrahydrofuran (225 mL) under nitrogen. A solution of hydrochloric acid (10%) containing tin (II) chloride dihydrate (8.19 g, 43.2 mmol) was prepared and kept stirring until needed. The reaction flask was placed in an ice bath to chill. Phenylmagnesium bromide solution (36.3 mL) was added to the flask via 50 mL syringe. The reaction vessel was removed from the ice bath and subsequently heated to reflux for 1 hour. The reaction solution underwent color changes from clear to orange to dark amber. The reaction was monitored via GC-MS by mini-workup with tin(II)chloride/10% hydrochloric acid. GC-MS indicated some starting material still present. Once it was confirmed complete, the reaction was removed from heat and allowed to cool to room temperature in a water bath. Next, hydrochloric acid (10%, 40 mL)/tin (II) chloride dihydrate (30.05 g) solution was added via syringe. Solids slowly formed in solution and then quickly dissolved. The solution color changed from red to clear. The reaction was heated to reflux again for an additional 2 hours and then allowed to cool to room temperature overnight. The next day, THF was removed by rotary evaporation and dissolved in 300 mL of ethyl acetate. At this point solids precipitated out of solution. The ethyl acetate solution was washed three times with 200 mL. Solids were filtered through a Buchner funnel and the organic layer was dried over magnesium sulfate. Organic layer was again filtered and evaporated. The product was dissolved into 25 mL of acetone and precipitated into 250 mL of methanol. Solid product was filtered through a Buchner funnel and dried in a vacuum oven. The unknown solids collected during the extraction were impure product formation. $^1$H NMR indicates pure product from the precipitation. Product obtained: 4.60 g.

Procedures:

To a clean, dry 100 mL 3N-RBF equipped with a low temperature thermometer and magnetic stir bar was added 4,8-diphenylbenzo[1,2-b:4,5-b']dithiophene (0.25 g, 0.7 mmol) and dissolved into 75 mL of anhydrous THF via cannula. The reaction flask was then placed into a dry ice/acetone bath until a temperature of less than -70° C. was reached. Tert-butyllithium solution (1.2 mL) was added to the reaction slowly, drop-wise via syringe and allowed to stir for 30 minutes. Upon the addition of tert-butyllithium, the solution changed color from clear to orange. The reaction was warmed to 5° C. and then placed back in the dry ice/acetone bath to chill back down to less than -70° C. Dibromotetrafluoroethane (0.76 g, 29 mmol) was added dropwise via syringe and allowed to stir for 30 minutes. The reaction was allowed to warm to room temperature. TLC indicated the reaction was complete. The reaction was then quenched with 10 mL of deionized water via syringe. THF was removed by rotary evaporation. The crude product was dissolved in 200 mL of hot chloroform and washed three times with 150 mL of deionized water. The organic layer was collected, dried over magnesium sulfate, and filtered through a gravity filter. GC-MS and $^1$H NMR both indicate clean product. Product obtained: 0.15 g.

231

Synthesis of N2,N6,4,8-tetraphenyl-N2,N6-di-m-tolylbenzo[1,2-b:4,5-b']dithiophene-2,6-diamine

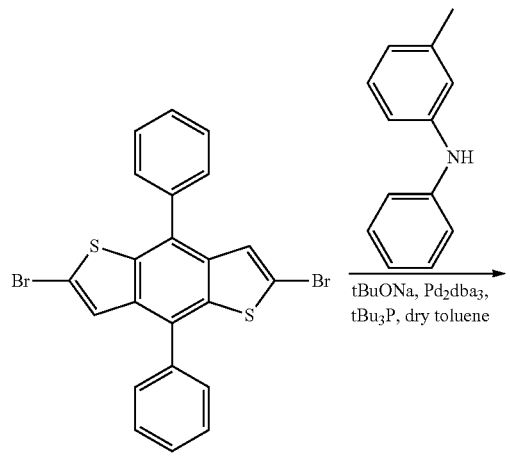

Molecular Weight: 500.27

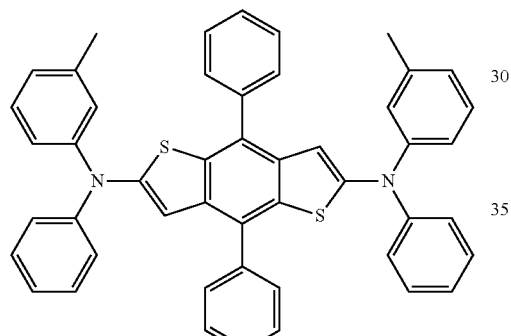

Molecular Weight 704.94

Procedures:

To a clean, dry 100 mL 3N-RBF equipped with a reflux condenser and a magnetic stir bar, 2,6-dibromo-4,8-diphenyl-benzo[1,2-b:4,5-b']dithiophene (0.15 g, 0.3 mmol) was added and dissolved into 35 mL of anhydrous toluene via syringe. The flask was heated by a heat gun while stirring to dissolve the starting material. 3-methyldiphenylamine (0.13 mL) was added to the reaction via syringe. The reaction vessel was purged with a strong nitrogen flow for 30 minutes. Sodium tert-butoxide (0.09 g,), Pd$_2$dba$_3$ (0.03 g), tri-tert-butylphosphine (0.02 g) in anhydrous toluene (6 mL) were added all at once. The reaction was heated to reflux for three hours. TLC indicated the reaction was complete. The reaction was removed from heat and allowed to cool to room temperature. The reaction solution was filtered through a celite/silica gel plug and washed with chloroform. Solution was evaporated and dried under vacuum for 30 minutes. Next, 50 mL of methanol was added to the dry product and allowed to stir while being heated by a heat gun. The solids were filtered through a gravity filter and allowed to dry. A precipitation was attempted from chloroform into methanol with no success. Therefore, the product was sublimed. Product obtained: 0.06 g

232

PLX-9-E

Synthesis of 2,6-dibromo-4,8-bis(3-ethylheptyl)benzo[1,2-b:4,5-b']dithiophene

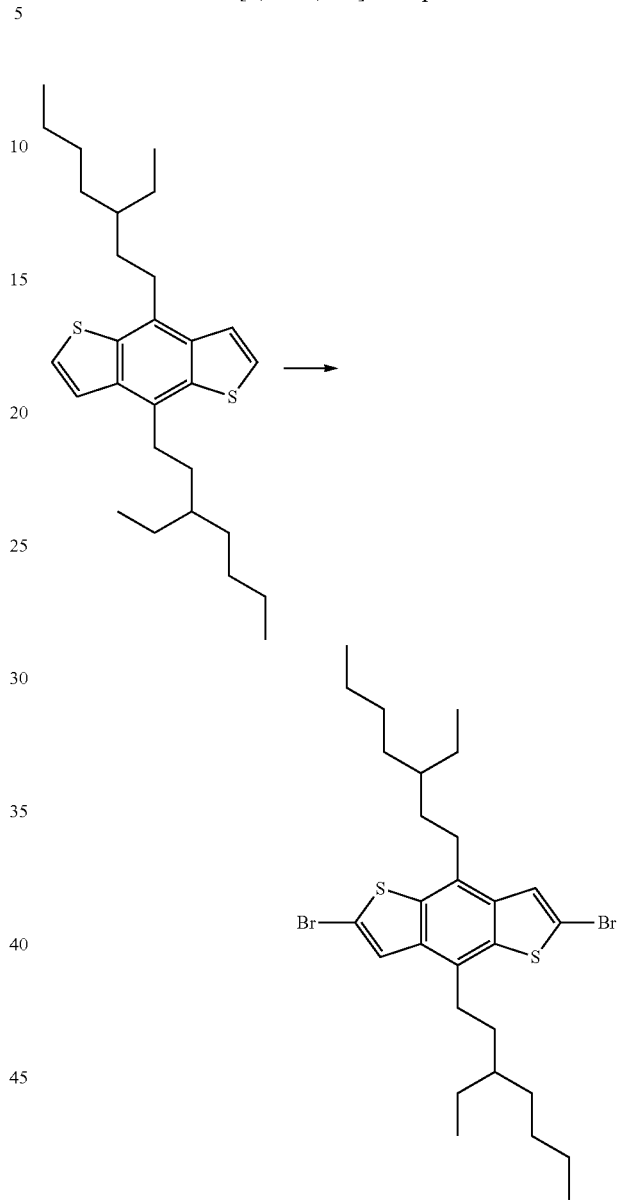

Procedures:

To a clean, dry 100 mL 3N-RBF equipped with a low temperature thermometer and magnetic stir bar was added 4,8-bis(3-ethylheptyl)benzo[1,2-b:4,5-b']dithiophene (0.25 g, 0.6 mmol) and dissolved into 75 mL of anhydrous THF via cannula. The reaction flask was then placed into a dry ice/acetone bath until a temperature of less than −70° C. was reached. Tert-butyllithium solution (1.2 mL) was added to the reaction slowly, drop-wise via syringe and allowed to stir for 30 minutes. Upon the addition of tert-butyllithium, the solution changed color from clear to orange. The reaction was warmed to 5° C. and then placed back in the dry ice/acetone bath to chill back down to less than −70° C. Dibromotetrafluoroethane (0.76 g, 29 mmol) was added dropwise via syringe and allowed to stir for 30 minutes. The reaction was allowed to warm to room temperature. TLC indicated the reaction was complete. The reaction was then quenched with 10 mL of deionized water via syringe. THF was removed by rotary evaporation. The crude product was dissolved in 200 mL of hot chloroform and washed three times with 150 mL of deionized water. The organic layer was collected, dried over magnesium sulfate, and filtered through a gravity filter. TLC indicated clean product. Product obtained: 0.15 g.

Synthesis of 4,8-bis(3-ethylheptyl)-N2,N6-diphenyl-N2,N6-di-m-tolylbenzo[1,2-b:4,5-b']dithiophene-2,6-diamine

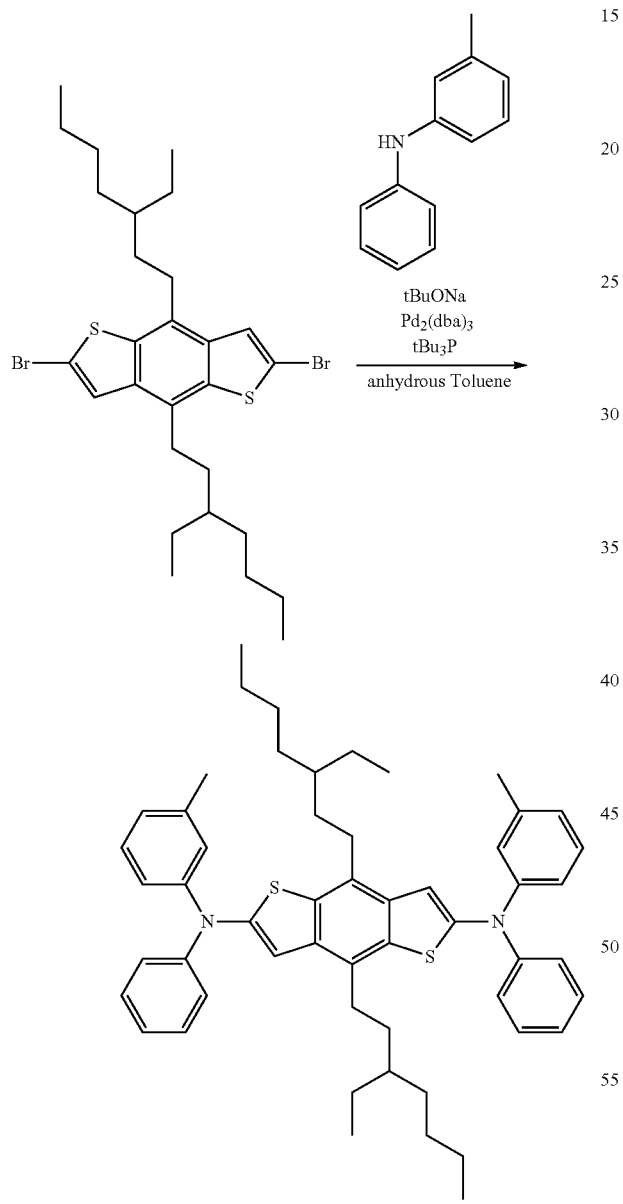

Procedures:

To a clean, dry 100 mL 3N-RBF, equipped with a reflux condenser and a magnetic stir bar, 2,6-dibromo-4,8-bis(3-ethylheptyl)benzo[1,2-b:4,5-b']dithiophene (0.50 g, 0.9 mmol) was added and dissolved into 60 mL of anhydrous toluene. 3-methydiphenylamine (0.4 mL, 2.1 mmol) was added to the reaction flask and the solution was purged with a strong nitrogen flow for 30 minutes. Sodium tert-butoxide (0.25 g, 2.6 mmol), Pd$_2$dba$_3$ (0.07 g, 0.07 mmol), tri-tert-butylphosphine (0.05 g, 0.21 mmol) in anhydrous toluene (8 mL) were added all at once. The reaction was heated to reflux for 2 hours. TLC indicated that reaction had gone to completion and the reaction flask was removed from heat to allow it to cool to room temperature. Once cooled, the reaction solution was filtered through a celite/silica gel plug and washed thoroughly with acetone. Product solution was evaporated using a rotary evaporator and placed on the vacuum line to dry for 30 minutes. Product was dissolved and silica gel was added to form a dry load for flash chromatography use. 1.5% ethyl acetate/hexane solution was used as the eluent; however, no separation was achieved. The product was evaporated and dissolved in a minimum amount of acetone and precipitated into −70° C. methanol with vigorous stirring. Solid product was filtered through a Buchner funnel and placed in the vacuum oven to dry. $^1$H NMR indicates removal of 3-methydiphenylamine. Therefore, the product was moved onto testing. Product obtained: 0.43 g

PLX-9-F

Synthesis of 4,8-di-m-tolylbenzo[1,2-b:4,5-b']dithiophene

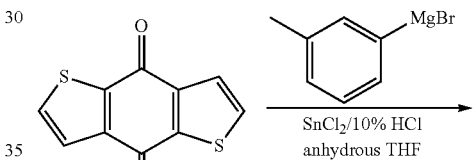

Molecular Weight: 220.27

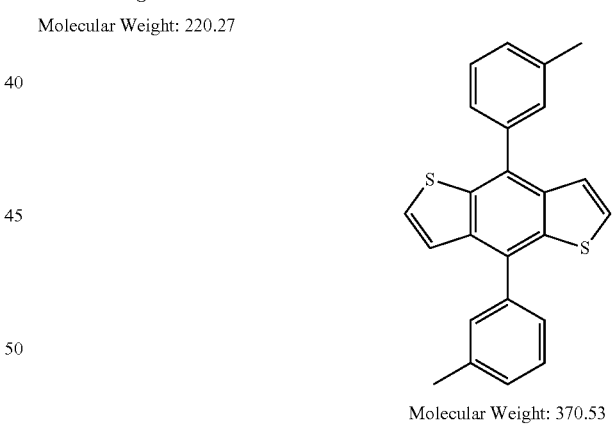

Molecular Weight: 370.53

Procedures:

To a clean, dry 500 mL 3N-RBF equipped with a reflux condenser and magnetic stir bar, was added 4,8-Dihydrobenzo[1,2-b:4,5-b']dithiophen-4,8-dione (2.00 g, 9 mmol) and dissolved in anhydrous tetrahydrofuran (225 mL) under nitrogen. A solution of hydrochloric acid (10%) containing tin (II) chloride dihydrate (8.19 g, 43.2 mmol) was prepared and kept stirring until needed. The reaction flask was placed in an ice bath to chill. Phenylmagnesium bromide solution (36.3 mL) was added to the flask via 50 mL syringe. The reaction vessel was removed from the ice bath and subsequently heated to reflux for 1 hour. The reaction solution underwent color changes from clear to orange to dark amber.

The reaction was monitored via GC-MS by mini-workup with tin(II)chloride/10% hydrochloric acid. GC-MS indicated some starting material still present. Once it was confirmed complete, the reaction was removed from heat and allowed to cool to room temperature in a water bath. Next, hydrochloric acid (10%, 40 mL)/tin (II) chloride dihydrate (30.05 g) solution was added via syringe. Solids slowly formed in solution and then quickly dissolved. The solution color changed from red to clear. The reaction was heated to reflux again for an additional 2 hours and then allowed to cool to room temperature overnight. The next day, THF was removed by rotary evaporation and dissolved in 300 mL of ethyl acetate. At this point solids precipitated out of solution. The ethyl acetate solution was washed three times with 200 mL. Solids were filtered through a Buchner funnel and the organic layer was dried over magnesium sulfate. Organic layer was again filtered and evaporated. The product was dissolved into 25 mL of acetone and precipitated into 250 mL of methanol. Solid product was filtered through a Buchner funnel and dried in a vacuum oven. The unknown solids collected during the extraction were impure product formation. $^1$H NMR indicates pure product from the precipitation. Product obtained: 4.60 g.

Synthesis of 2,6-dibromo-4,8-di-m-tolylbenzo[1,2-b:4,5-b']dithiophene

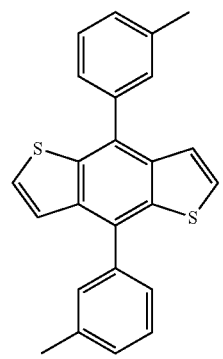

Molecular Weight: 370.53

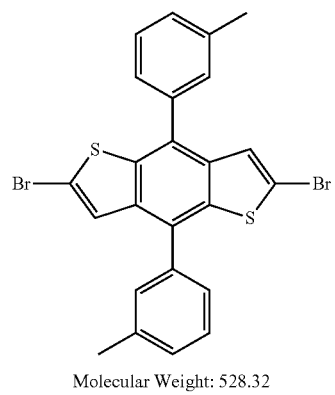

Molecular Weight: 528.32

Procedures:

To a clean, dry 100 mL 3N-RBF equipped with a low temperature thermometer and magnetic stir bar was added 4,8-di-m-tolylbenzo[1,2-b:4,5-b']dithiophene (0.25 g, 0.7 mmol) and dissolved into 75 mL of anhydrous THF via cannula. The reaction flask was then placed into a dry ice/acetone bath until a temperature of less than −70° C. was reached. Tert-butyllithium solution (1.2 mL) was added to the reaction slowly, drop-wise via syringe and allowed to stir for 30 minutes. Upon the addition of tert-butyllithium, the solution changed color from clear to orange. The reaction was warmed to 5° C. and then placed back in the dry ice/acetone bath to chill back down to less than −70° C. Dibromotetrafluoroethane (0.76 g, 29 mmol) was added dropwise via syringe and allowed to stir for 30 minutes. The reaction was allowed to warm to room temperature. TLC indicated the reaction was complete. The reaction was then quenched with 10 mL of deionized water via syringe. THF was removed by rotary evaporation. The crude product was dissolved in 200 mL of hot chloroform and washed three times with 150 mL of deionized water. The organic layer was collected, dried over magnesium sulfate, and filtered through a gravity filter. GC-MS and $^1$H NMR both indicate clean product. Product obtained 0.15 g.

Synthesis of N2,N6-bis(3-(1,3-dioxolan-2-yl)phenyl)-N2,N6,4,8-tetra-m-tolylbenzo[1,2-b:4,5-b']dithiophene-2,6-diamine

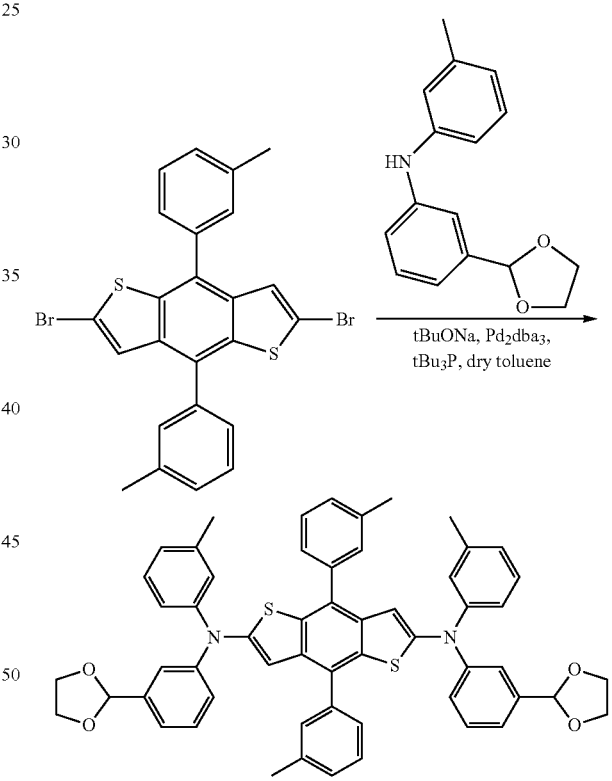

Procedures:

To a clean, dry 100 mL 3N-RBF equipped with a reflux condenser and a magnetic stir bar, 2,6-dibromo-4,8-di-m-tolylbenzo[1,2-b:4,5-b']dithiophene (0.15 g, 0.3 mmol) was added and dissolved into 35 mL of anhydrous toluene via syringe. The flask was heated by a heat gun while stirring to dissolve the starting material. 3-methyldiphenylamine (0.13 mL) was added to the reaction via syringe. The reaction vessel was purged with a strong nitrogen flow for 30 minutes. Sodium tert-butoxide (0.09 g,), Pd$_2$dba$_3$ (0.03 g), tri-tert-butylphosphine (0.02 g) in anhydrous toluene (6 mL) were added all at once. The reaction was heated to reflux for three hours. TLC indicated the reaction was complete. The reaction was removed from heat and allowed to cool to room temperature. The reaction solution was filtered through a celite/silica gel plug and washed with chloroform. Solution was evaporated and dried under vacuum for 30 minutes. Next, 50 mL of methanol was added to the dry product and allowed to stir while being heated by a heat gun. The solids were filtered through a gravity filter and allowed to dry. A precipitation was attempted from chloroform into methanol with no success. Therefore, the product was sublimed. Product obtained: 0.06 g Dehalogenation of N2,N6-bis(3-(1,3-dioxolan-2-yl)phenyl)-N2,N6,4,8-tetra-m-tolylbenzo[1,2-b:4,5-b']dithiophene-2,6-diamine Procedures:

To a clean, dry 500 mL 3N-RBF, equipped with a reflux condenser and a magnetic stir bar, was added N2,N6-bis(3-(1,3-dioxolan-2-yl)phenyl)-N2,N6,4,8-tetra-m-tolylbenzo[1,2-b:4,5-b']dithiophene-2,6-diamine (4.60 g, 5.2 mmol) and dissolved in 250 mL of anhydrous THF added via cannula. Triethylamine (7.3 mL, 52.4 mmol) was added first followed by formic acid (2.0 mL, 52.4 mmol) via syringe. The reaction was purged with a strong nitrogen flow for 30 minutes. Then, palladium (II) acetate (0.12 g, 0.5 mmol) and tri-tert-butylphosphine in toluene (0.16 g, 0.79 mmol) were added. The reaction was heated to reflux for 3 hours and then allowed to cool to room temperature overnight. The next day, the reaction solution was filtered through a celite plug and washed thoroughly with chloroform. Product solution was evaporated and then dried under vacuum. The procedure was repeated a second time.

Synthesis of 3,3'-((4,8-di-m-tolylbenzo[1,2-b:4,5-b']dithiophene-2,6-diyl)bis(m-tolylazanediyl))dibenzaldehyde

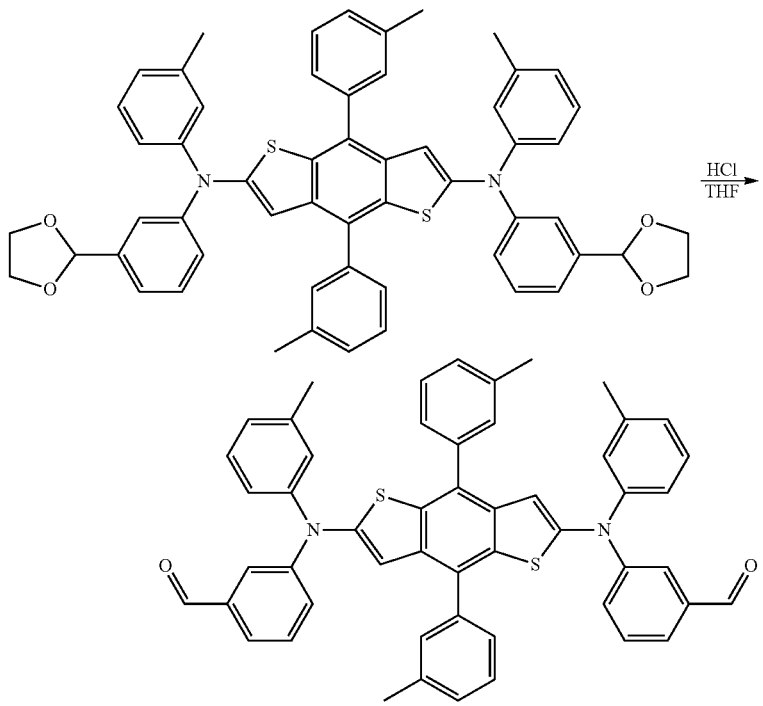

Procedures:

To a clean 1 L RBF, equipped with a stir bar and an addition funnel, N2,N6-bis(3-(1,3-dioxolan-2-yl)phenyl)-N2,N6,4,8-tetra-m-tolylbenzo[1,2-b:4,5-b']dithiophene-2,6-diamine (4.60 g, 5.2 mmol) was added and dissolved in 500 mL of a 9:1 mixture of warm TFH/chloroform. Hydrochloric acid (2.0M, 26.0 mL) was added to the addition funnel via syringe and added slowly, drop-wise, while stirring. The reaction was monitored via TLC. Once the reaction was complete, the reaction solution was poured into a separatory funnel. 300 mL of chloroform was added and washed three times with 300 mL of DI water. Organic layer was collected, dried over magnesium sulfate, filtered through a Buchner funnel, and dried in a vacuum oven. The product was wet loaded onto an auto column flash chromatography from chloroform/hexane using 5% ethyl acetate/95% hexane as an eluent. The pure product fractions were collected and evaporated by rotary evaporation. $^1$H NMR indicated clean product. Product obtained: 3.00 g.

Synthesis of N2,N6,4,8-tetra-m-tolyl-N2,N6-bis(3-vinylphenyl)benzo[1,2-b:4,5-b']dithiophene-2,6-diamine

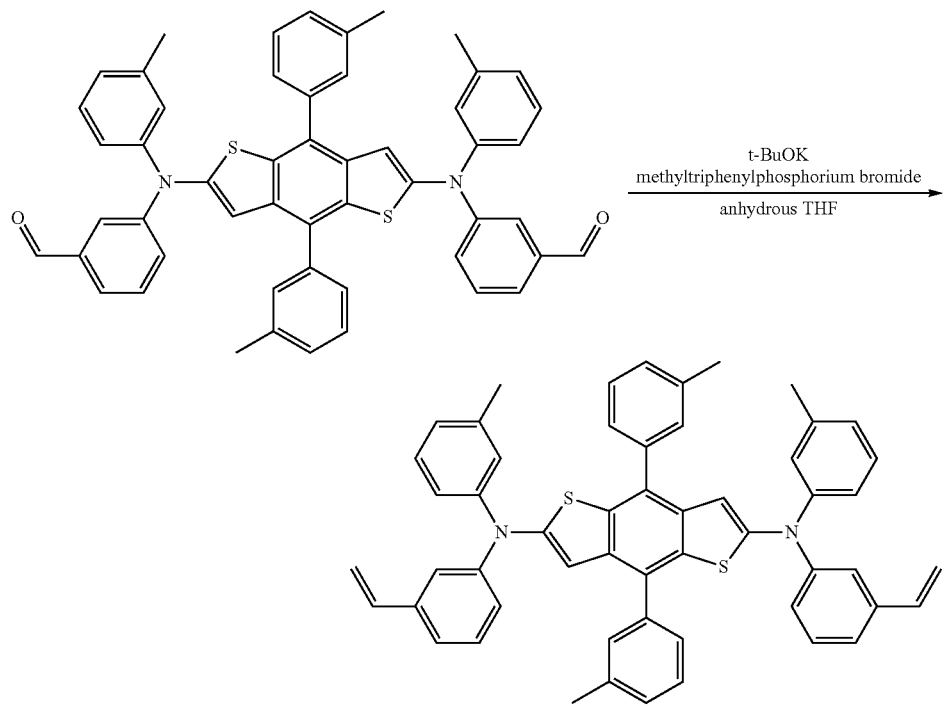

PLX-11-A

Procedures:

To a clean, dry 1 L 3N-RBF, equipped with an addition funnel and a magnetic stir bar, methyltriphenylphosphonium bromide (4.07 g, 11.4 mmol) was added and dissolved in 225 mL of anhydrous THF. Potassium tert-butoxide (1.32 g, 11.8 mmol) was added to the reaction vessel. A solution of 3,3'-((4,8-di-m-tolylbenzo[1,2-b:4,5-b']dithiophene-2,6-diyl)bis(m-tolylazanediyl))dibenzaldehyde (3.0 g, 3.8 mmol) was prepared by dissolving in 175 mL of anhydrous THF and transferred to the addition funnel via cannula. The reaction flask was covered with aluminum foil to minimize light exposure. Then, the solution in the addition funnel was added slowly, drop-wise, while vigorously stirring. After the addition was complete, the solution stirred for an additional 30 minutes before monitoring with TLC. Once the reaction was complete, the reaction solution was filtered through a celite/silica gel plug and washed thoroughly with acetone. Product solution was evaporated and dried on a vacuum line overnight covered in foil. Attempted to dissolve crude for wet load by dissolving into ethyl acetate (200 mL) and initially goes into solution but the volume is too great. The solution was reduced by rotary evaporation, but the product crashed out on the evaporator. Once dry, attempted to dissolve the product in several solvents: chloroform, THF, acetone, combinations—all with no success. The product solids were filtered through a Buchner funnel. TLC was taken of the solids versus filtrate and indicated that the solids were pure product and this wash has removed phosphine oxide. Product was dried in a vacuum oven. $^1$H NMR sample would only completely dissolve in d-DMF but showed clean product. Product obtained: 2.65 g Synthesis of 2-(4-(benzo[b]thiophen-3-yl)phenyl)-1,3-dioxolane

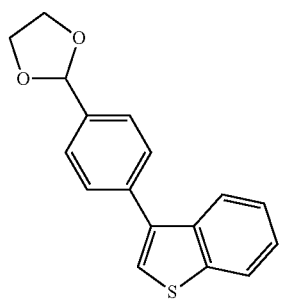

2-(4-(benzo[b]thiophen-3-yl)phenyl)-1,3-dioxolane

Procedures:

To a single-neck round bottom flask containing 2-(4-trimethylstannylphenyl)-1,3-dioxolane (70%, 7.53 g, 0.0168 mol) was added anhydrous toluene (50 mL). 3-bromothianaphthene (1.79 g, 0.0084 mol) was added via syringe, and the mixture was allowed to stir. The reaction solution was purged with strong nitrogen flow for thirty minutes, after which Pd$_2$dba$_3$ (0.39 g, 0.0004 mol) and tri(o-tolyl)phosphine (0.51 g, 0.0017 mol) were added. The reaction flask went through five vacuum, nitrogen purging cycles, and was slowly heated to a temperature of 105° C. for 12 hours. The following day the reaction was removed from heat and cooled to room temperature. Reaction solution was passed through a plug of Celite and silica gel (pretreated with triethylamine). Solvent was removed from the filtrate by rotary evaporation. The crude material was purified by chromatography on silica gel using ethyl acetate/hexane as an eluent. Product obtained: 2.0 g Synthesis of 2-(4-(2-bromobenzo[b]thiophen-3-yl)phenyl)-1,3-dioxolane

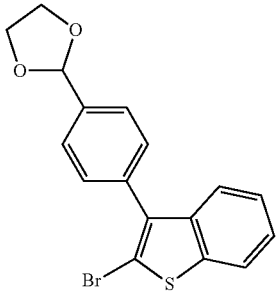

2-(4-(2-bromobenzo[b]thiophen-3-yl)phenyl)-1,3-dioxolane

Procedures:

A clean and dry three-neck round bottom flask was charged with 2-(4-(benzo[b]thiophen-3-yl)phenyl)-1,3-dioxolane (2.00 g, 0.0071 mol) and anhydrous tetrahydrofuran (380 mL) was then added by cannula. The reaction flask was cooled to −78° C. in a dry ice/isopropanol bath. Tert-butyl-lithium (1.7M, 8.5 mL) was then added slowly via syringe. The reaction was allowed to stir at this temperature for 30 minutes, after which was allowed to warm to 0° C. The reaction flask was cooled to −78° C. again, and dibromotetrafluoroethane (2 mL, 0.0177 mol) was added via syringe. The reaction was allowed to stir at this temperature for one hour before being allowed to warm to ambient temperature. Isopropanol (10 mL) was added to quench, and the reaction poured into an erlenmeyer flask containing DI H$_2$O (200 mL) portion-wise with vigorous stirring. MTBE (200 mL) was added to this flask, and then the solution was transferred to a separatory funnel. The organic layer was washed with DI H$_2$O (3×200 mL), collected and dried over anhydrous magnesium sulfate. Solids were filtered off by vacuum filtration and solvent was removed from the filtrate by rotary evaporation. The resulting crude material was further purified by chromatography using 5% ethyl acetate/2% triethylamine/hexane as an eluent. Product obtained: 1.8 g Synthesis of 4-(3-(4-(1,3-dioxolan-2-yl)phenyl)benzo[b]thiophen-2-yl)-N,N-diphenylaniline

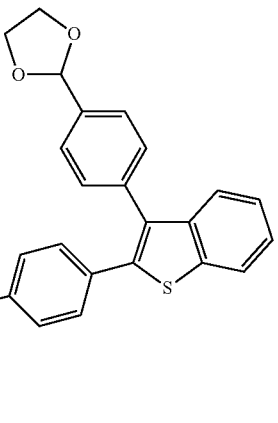

4-(3-(4-(1,3-dioxolan-2-yl)phenyl)benzol[b]thiophen-2-yl)-N,N-diphenylaniline

Procedures:

In a Schlenk flask, 2-(4-(2-bromobenzo[b]thiophen-3-yl)phenyl)-1,3-dioxolane (1.30 g, 0.0036 mol) was added with 4-(diphenylamino)phenylboronic acid pinacol ester (2.00 g, 0.0054 mol). Anhydrous toluene (120 mL) was transferred via cannula to the reaction flask. Tetraethylammonium hydroxide solution (20%, 35 mL) was then added and the solution was purged with nitrogen flow for one hour. Dichloro-bis(triphenylphosphine)palladium (0.10 g) was added and five vacuum purge cycles were carried out before heating to a temperature of 100° C. for twelve hours. The reaction was worked up with MTBE and DI H$_2$O. The organic fraction was collected and filtered through a Celite and silica gel (Et$_3$N treated) plug. Solvent was removed by rotary evaporation and the resulting crude was purified by chromatography using a hexane/ethyl acetate gradient as an eluent. The resulting pure product was characterized and taken on to the next step of the synthesis.

Dehalogenation of 4-(3-(4-(1,3-dioxolan-2-yl)phenyl)benzo[b]thiophen-2-yl)-N,N-diphenylaniline

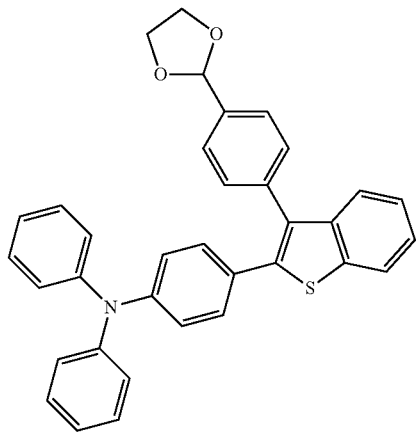

4-(3-(4-(1,3-dioxolan-2-yl)phenyl)benzo[b]thiophen-2-yl)-N,N-diphenylaniline

Procedures:

A three-neck round bottom flask was equipped with a reflux condenser, magnetic stir bar, and charged with 4-(3-(4-(1,3-dioxolan-2-yl)phenyl)benzo[b]thiophen-2-yl)-N,N-diphenylaniline (1.80 g, 0.0034 mol). Anhydrous toluene (125 mL) was added to the reaction flask by cannula. Triethylamine (5 mL) was added by syringe, followed by formic acid (1.2 mL). The reaction solution was purged with strong nitrogen flow for 30 minutes, after which palladium II acetate (0.10 g) and tri-tertbutylphosphine (0.20 g in 5 mL anhydrous toluene as solution) were added. The reaction was heated to reflux for two hours. After refluxing, the reaction was cooled to room temperature and worked up with MTBE and DI H$_2$O until neutral. The organic fraction was collected and filtered through a celite/silica gel (Et$_3$N treated) plug. Solvent was removed from the filtrate by rotary evaporation. The resulting crude material was placed on the vacuum line to be taken on to the next dehalogenation.

Dehalogenation of 4-(3-(4-(1,3-dioxolan-2-yl)phenyl)benzo[b]thiophen-2-yl)-N,N-diphenylaniline

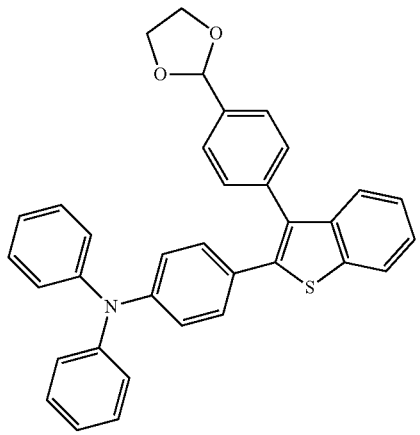

4-(3-(4-(1,3-dioxolan-2-yl)phenyl)benzo[b]thiophen-2-yl)-N,N-diphenylaniline

Procedures:

A three-neck round bottom flask was equipped with a reflux condenser, magnetic stir bar, and charged with 4-(3-(4-(1,3-dioxolan-2-yl)phenyl)benzo[b]thiophen-2-yl)-N,N-diphenylaniline (1.80 g, 0.0034 mol). Anhydrous toluene (125 mL) was added to the reaction flask by cannula. Triethylamine (5 mL) was added by syringe, followed by formic acid (1.2 mL). The reaction solution was purged with strong nitrogen flow for 30 minutes, after which palladium II acetate (0.10 g) and tri-tertbutylphosphine (0.20 g in 5 mL anhydrous toluene as solution) were added. The reaction was heated to reflux for two hours. After refluxing, the reaction was cooled to room temperature and worked up with MTBE and DI $H_2O$ until neutral. The organic fraction was collected and filtered through a celite/silica gel ($Et_3N$ treated) plug. Solvent was removed from the filtrate by rotary evaporation. The resulting crude material was placed on the vacuum line to be taken on to the next step.

Synthesis of 4-(2-(4-(diphenylamino)phenyl)benzo[b]thiophen-3-yl)benzaldehyde

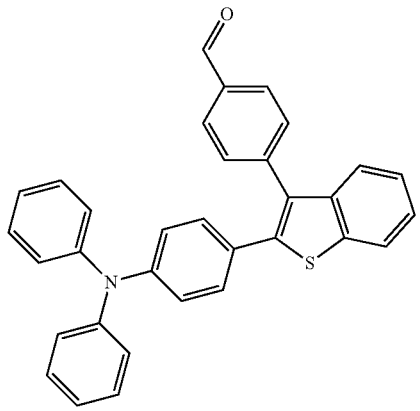

4-(2-(4-(diphenylamino)phenyl)benzo[b]thiophen-3-yl)benzaldehyde

Procedures:

To a single-neck round bottom flask containing doubly dehalogenated 4-(3-(4-(1,3-dioxolan-2-yl)phenyl)benzo[b]thiophen-2-yl)-N,N-diphenylaniline (1.8 g, 0.0034 mol), acetone (250 mL) and a magnetic stir bar were added. Hydrochloric acid solution (2.0M, 5 mL) was added slowly dropwise. After thirty minutes, reaction completion was confirmed by thin-layer chromatography. The reaction solution was placed on the rotary evaporator until a volume of 100 mL was reached. The solution was worked up with MTBE and DI $H_2O$ until neutral. The organic fraction was collected and solvent was removed by rotary evaporation. The resulting crude material was purified by column chromatography using a hexane/ethyl acetate gradient which provided $^1H$ NMR pure product. Product obtained: 1.1 g

Synthesis of N,N-diphenyl-4-(3-(4-vinylphenyl)benzo[b]thiophen-2-yl)aniline

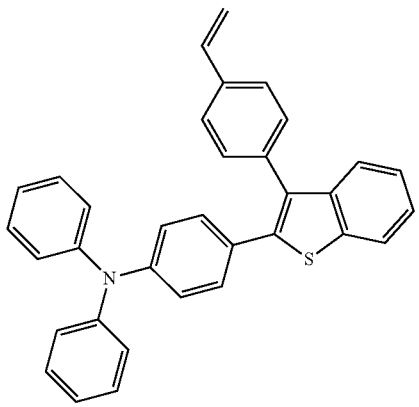

N,N-diphenyl-4-(3-(4-vinylphenyl)benzo[b]thiophen-2-yl)aniline

Procedures:

A solution of 4-(2-(4-(diphenylamino)phenyl)benzo[b]thiophen-3-yl)benzaldehyde (1.1 g, 0.0023 mol) was prepared in anhydrous tetrahydrofuran (75 mL). To a dry round bottom flask equipped with an addition funnel, methyltriphenylphosphonium bromide (1.22 g, 0.003 mol) was added. Tetrahydrofuran (75 mL) was added to this reaction flask and allowed to stir. Potassium tert-butoxide (0.40 g, 0.0035 mol) was then added. The solution of (2-(4-(diphenylamino)phenyl)benzo[b]thiophen-3-yl)benzaldehyde/THF was then transferred to the addition funnel via cannula. This solution was then added to the reaction flask from the addition funnel drop-wise. The reaction solution was allowed to stir for approximately 1 hour and completion was then monitored via thin-layer chromatography. Following confirmation of completion, the reaction solution was filtered through a celite/silica gel (treated with triethylamine) plug. Solvent was removed by rotary evaporation. And the resulting solids were placed under vacuum. Crude mixture was purified by chromatography. Precipitation from a minimum amount of ethyl acetate into methanol yielded $^1H$ NMR pure product. Product obtained: 0.7 g $\delta_H$ (300 MHz, $(CD_3)_2CO$) 5.30 (1H, d) 5.90 (1H, d) 6.78-6.91 (3H, m) 7.03-7.16 (6H, m) 7.20-7.44 (10H, m) 7.48-7.63 (3H, m) 7.98 (1H, d)

PLX-11-B

Synthesis of
4-(benzo[b]thiophen-3-yl)-N,N-diphenylaniline

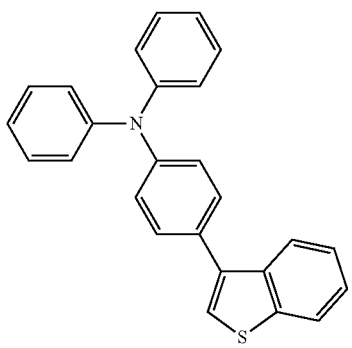

4-(benzo[b]thiophen-3-yl)-N,N-diphenylaniline

Procedures:

In a Schlenk flask, 3-bromothianaphthene (3.44 g, 0.0162 mol) was added, along with 4-(diphenylamino)phenylboronic acid pinacol ester (5.00 g, 0.0135 mol). Anhydrous toluene (450 mL) was transferred via cannula to the reaction flask. Tetraethylammonium hydroxide solution (20%, 130 mL) was then added and the solution was purged with nitrogen flow for one hour. Added dichloro-bis(triphenylphosphine)palladium (0.24 g), and carried out five vacuum purge cycles before heating to a temperature of 100° C. for twelve hours. The reaction was worked up with MTBE and DI $H_2O$. Organic fraction was collected and filtered through a Celite and silica gel ($Et_3N$ treated) plug. Solvent was removed by rotary evaporation. The resulting crude material was further purified by recrystallization from ethyl acetate/methanol three times resulting in pure product. Product obtained: 3.23 g Synthesis of N,N-diphenyl-4-(2-(trimethylstannyl)benzo[b]thiophen-3-yl)aniline

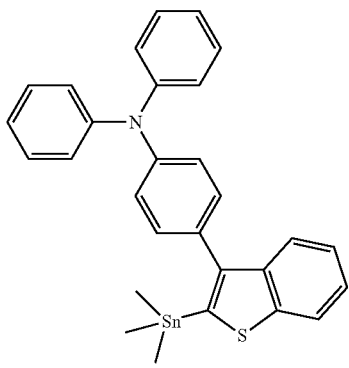

N,N-diphenyl-4-(2-(trimethylstannyl)benzo[b]thiophen-3-yl)aniline

Procedures:

In a three-neck round bottom flask, 4-(benzo[b]thiophen-3-yl)-N,N-diphenylaniline (3.23 g, 0.0086 mol) was charged. Anhydrous tetrahydrofuran (500 mL) was added via cannula. The reaction flask was placed in a dry ice/isopropanol bath until a temperature of less than negative 60° C. was achieved. At this point, tert-butyllithium solution (1.7M, 10 mL) was added to the reaction slowly dropwise via syringe, always maintaining a temperature of less than negative 60° C. After addition was complete, the reaction was allowed to stir at this temperature for one half hour, and then slowly warmed to 0 C by removing from the cold bath. After reaching 0° C., the reaction vessel was once again placed into the cold bath until a temperature of less than negative 60° C. was reached. Trimethyltin chloride solution (1.0M, 22.0 mL) was added slowly dropwise via syringe, always maintaining a temperature of less than negative 60° C. Upon completion of addition, the reaction was allowed to stir at this temperature for an additional thirty minutes. The reaction was then removed from the cold bath and allowed to warm to room temperature.

Isopropanol (20 mL) was added via syringe to quench the reaction. The solution was then worked up with MTBE and DI $H_2O$ until neutral. The organic fraction was collected and solvent was nearly removed by rotary evaporation. Acetone was added (50 mL) along with a stir bar. While the solution was being stirred vigorously, methanol (300 mL) was slowly added portion-wise until solids were observed floating in solution. The solids were filtered off and washed with methanol, collected and dried under vacuum providing pure product. Product obtained: 3.82 g Synthesis of 4-(2-(4-(1,3-dioxolan-2-yl)phenyl)benzo[b]thiophen-3-yl)-N,N-diphenylaniline

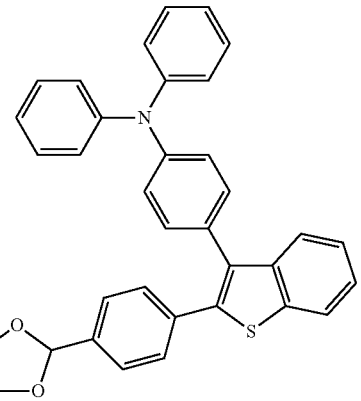

4-(2-(4-(1,3-dioxolan-2-yl)phenyl)benzo[b]thiophen-3-yl)-N,N-diphenylaniline

Procedures:

In a clean and dry Schlenk flask was added N,N-diphenyl-4-(2-(trimethylstannyl)benzo[b]thiophen-3-yl)aniline (3.82 g, 0.0071 mol) and 2-(4-bromophenyl)-1,3-dioxolane (3.24 g, 0.0141 mol). Anhydrous, nitrogen purged toluene (250 mL) was then added via cannula. The reaction solution was then purged with nitrogen flow for thirty minutes, after which $Pd_2dba_3$ (0.32 g, 0.0004 mol) and tri(o-tolyl)phosphine (0.43 g, 0.0014 mol) were added during outward nitrogen flow. The reaction flask went through five vacuum, nitrogen purging cycles, and was slowly heated to a temperature of 105° C. for twelve hours. The reaction was removed from heat and cooled to room temperature. Reaction solution was passed through a plug of Celite and silica gel (pretreated with triethylamine). Solvent was removed from the filtrate by rotary evaporation. The crude material was dissolved in a minimum amount of ethyl acetate and loaded onto a silica gel column for chromatographic separation using ethyl acetate/hexane as an eluent. This provided pure product which was subsequently characterized by $^1$H NMR. Product obtained: 1.70 g Dehalogenation of 4-(2-(4-(1,3-dioxolan-2-yl)phenyl)benzo[b]thiophen-3-yl)-N,N-diphenylaniline

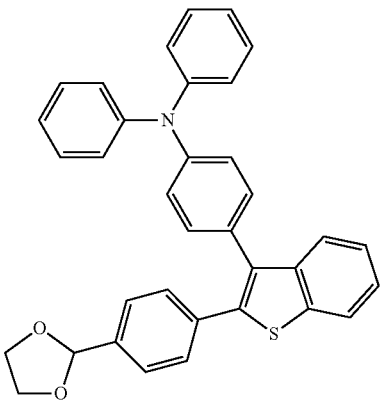

4-(2-(4-(1,3-dioxolan-2-yl)phenyl)benzo[b]thiophen-3-yl)-N,N-diphenylaniline

Procedures:

A three-neck round bottom flask was equipped with a reflux condenser, magnetic stir bar, and charged with 4-(2-(4-(1,3-dioxolan-2-yl)phenyl)benzo[b]thiophen-3-yl)-N,N-diphenylaniline (1.70 g, 0.0032 mol). Anhydrous toluene (125 mL) was added to the reaction flask by cannula. Triethylamine (3 mL) was added by syringe, followed by formic acid (0.6 mL). The reaction solution was purged with strong nitrogen flow for 30 minutes, after which palladium II acetate (0.04 g) and tri-tertbutylphosphine (0.05 g) (in 5 mL anhydrous toluene as solution) were added. The reaction was heated to reflux for two hours. After refluxing, the reaction was cooled to room temperature and worked up with MTBE and DI H$_2$O until neutral. The organic fraction was collected and filtered through a celite/silica gel (Et$_3$N treated) plug. Solvent was removed from the filtrate by rotary evaporation. The resulting crude material was dried under strong vacuum and carried onto the subsequent dehalogenation reaction.

Dehalogenation of 4-(2-(4-(1,3-dioxolan-2-yl)phenyl)benzo[b]thiophen-3-yl)-N,N-diphenylaniline Procedures:

A three-neck round bottom flask was equipped with a reflux condenser, magnetic stir bar, and charged with 4-(2-(4-(1,3-dioxolan-2-yl)phenyl)benzo[b]thiophen-3-yl)-N,N-diphenylaniline (1.70 g, 0.0032 mol). Anhydrous toluene (125 mL) was added to the reaction flask by cannula. Triethylamine (3 mL) was added by syringe, followed by formic acid (0.6 mL). The reaction solution was purged with strong nitrogen flow for 30 minutes, after which palladium II acetate (0.04 g) and tritertbutylphosphine (0.05 g) (in 5 mL anhydrous toluene as solution) were added. The reaction was heated to reflux for two hours. After refluxing, the reaction was cooled to room temperature and worked up with MTBE and DI H$_2$O until neutral. The organic fraction was collected and filtered through a celite/silica gel (Et$_3$N treated) plug. Solvent was removed from the filtrate by rotary evaporation. The resulting crude material was placed under vacuum and taken onto the next step.

Synthesis of 4-(3-(4-(diphenylamino)phenyl)benzo[b]thiophen-2-yl)benzaldehyde

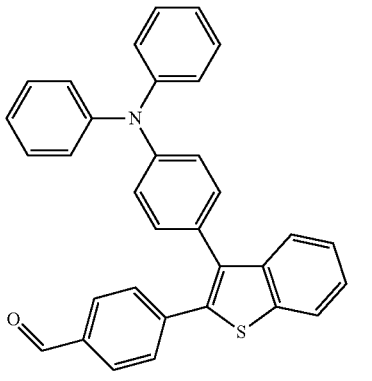

4-(3-(4-(diphenylamino)phenyl)benzo[b]thiophen-2-yl)benzaldehyde

Procedures:

To a single neck round bottom flask containing 4-(2-(4-(1,3-dioxolan-2-yl)phenyl)benzo[b]thiophen-3-yl)-N,N-diphenylaniline (1.7 g, 0.0032 mol), acetone (250 mL) and a magnetic stir bar were added. Hydrochloric acid solution (2.0 M, 5 mL) was added slowly dropwise. The reaction was allowed to stir for 30 minutes. A TLC plate was taken and showed that the reaction had finally completed. Solution was removed from the reaction by rotary evaporation until a volume of 100 mL was achieved. The solution was worked up with MTBE and DI H2O until neutral. The organic fraction was collected and solvent was removed by rotary evaporation. The resulting crude material was purified by chromatography on silica gel using an ethyl acetate/hexane gradient which provided pure product. Product obtained: 1.4 g Synthesis of N,N-diphenyl-4-(2-(4-vinylphenyl)benzo[b]thiophen-3-yl)aniline

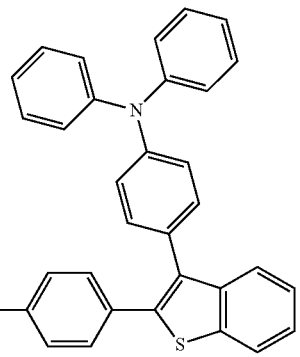

N,N-diphenyl-4-(2-(4-vinylphenyl)benzo[b]thiophen-3-yl)aniline

Procedures:

A solution of 4-(3-(4-(diphenylamino)phenyl)benzo[b]thiophen-2-yl)benzaldehyde (1.4 g, 0.0029 mol) was prepared in anhydrous THF (50 mL) in a clean, dry, and purged round bottom flask. To a dry round bottom flask equipped with an addition funnel methyltriphenylphosphonium bromide (1.82 g, 0.0051 mol) was added. Tetrahydrofuran (70 mL) was added to this reaction flask. Potassium tert-butoxide (0.59 g, 0.0052 mol) was then added to the reaction flask, and the flask was subsequently covered with aluminum foil. The solution of 4-(3-(4-(diphenylamino)phenyl)benzo[b]thiophen-2-yl)benzaldehyde/THF was then transferred to the addition funnel via cannula. This solution was then added to the reaction flask from the addition funnel dropwise. The reaction solution was allowed to stir for approximately 1 hour and completion was then confirmed via thin-layer chromatography. The reaction solution was filtered through a celite/silica gel (treated w/Et₃N) plug. Solvent was removed by rotary evaporation. The resulting crude mixture was purified by chromatography on silica gel using ethyl acetate/hexane as an eluent. Precipitation from a minimum amount of ethyl acetate into methanol provided ¹H NMR pure product. Product obtained: 1.06 g $\delta_H$ (300 MHz, CDCl$_3$) 5.28 (1H, d) 5.77 (1H, d) 6.71 (1H, m) 7.02-7.21 (10H, m) 7.26-7.37 (10H, m) 7.68 (1H, m) 7.87 (1H, m)

PLX-12-A

Stille Coupling

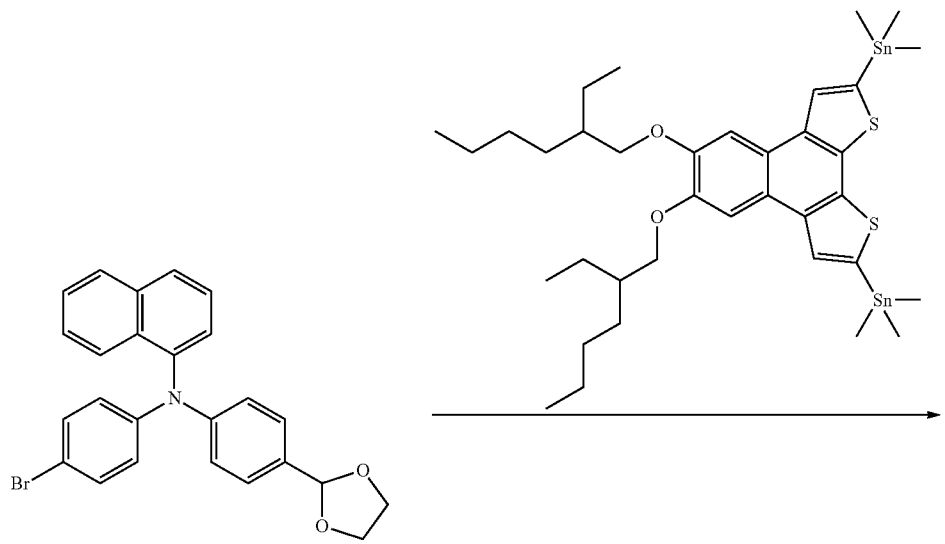

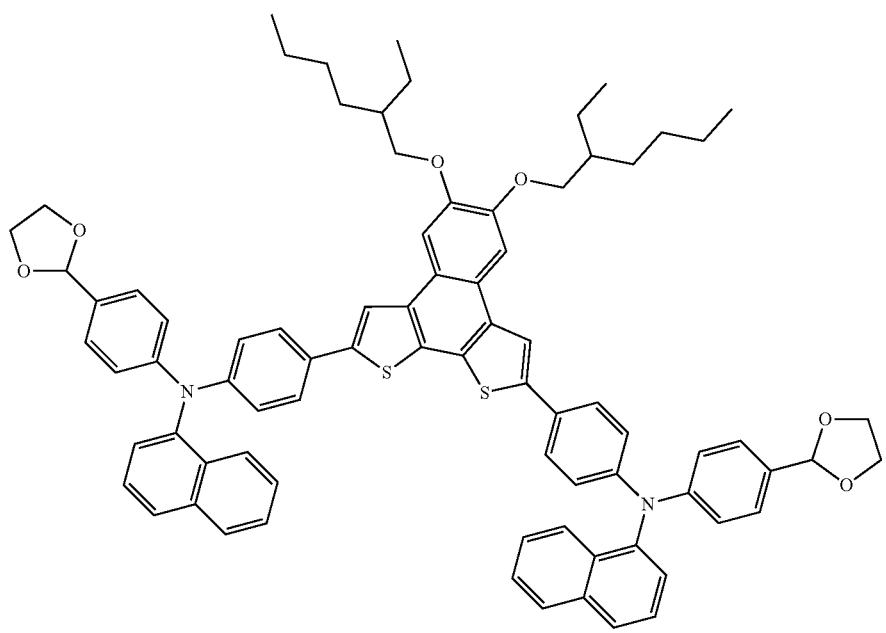

Prepared all clean, oven-dried glassware: 1000 mL three-neck round-bottom flask with a magnetic stir bar, and a reflux condenser. Purged reaction vessel with $N_2$. Via cannula, dissolved 3.48 g (4.23e-3 mol) of (5,6-bis((2-ethylhexyl)oxy)naphtho[2,1-b:3,4-b']dithiophene-2,9-diyl)bis(trimethylstannane) in dry toluene and transferred to reaction flask. Charged flask with 4.83 g (1.08e-3 mol) N-(4-(1,3-dioxolan-2-yl)phenyl)-N-(4-bromophenyl)naphthalen-1-amine.
Purged for 45 minutes with nitrogen. Charged flask with dry mix of 0.166 g (1.81e-4 mol) $Pd_2(dba)_3$ and 0.165 g (5.42e-4 mol) $(o\text{-tol})_3P$. Solution became dark red in color. Turned on water flow for reflux condenser and set variac/heating mantle to 35% output. Refluxed for 3.5 hrs. TLC confirmed reaction completion; turned heat off and allowed reaction to cool. After reaction cooled, filtered through celite/silica gel plug. Deactivated silica with triethylamine prior to filtration. Redissolved in THF and precipitated in r.t. MeOH. TLC showed that MeOH ppt. cleaned off most impurities; however, prepared crude for column chromatography. Prepared a celite dry load with $CHCl_3$/1% triethylamine, and loaded onto a manual column with 200 g deactivated silica. Immediately encountered a solubility problem. Removed top impurities and flushed column. Collected similar fractions and removed solvents. TLC showed improvement in purity. Mass of material: 3.64 g; NMR: good Dehalogenation 1&2

Prepared all clean, oven-dried glassware: 1000 mL three-neck round-bottom flask with a magnetic stir bar, reflux condenser. Purged reaction vessel with $N_2$. Dissolved 3.64 g (3.04e-3 mol) N,N'-((5,6-bis((2-ethylhexyl)oxy)naphtho[2,1-b:3,4-b']dithiophene-2,9-diyl)bis(4,1-phenylene))bis(N-(4-(1,3-dioxolan-2-yl)phenyl)naphthalen-1-amine) in 400 mL dry THF. Transferred solution to reaction flask via cannulae. Added 5.06 mL triethylamine (3.65e-2 mol) via syringe. Added 1.15 mL formic acid (3.04-2 mol) via syringe. Fuming observed. Purged with nitrogen flow for 30 mins. Added 0.07 g $Pd(OAc)_2$ (~3.04e-4 mol) via funnel. Solution turned an orange color. Added 0.09 g $tBu_3P$ (4.56e-4 mol) dissolved in 2 mL toluene via syringe. Heated to reflux for 2 hours. Solution turned black over time. Turned heat off and allowed to cool. Filtered through celite/silica gel plug. Pretreated silica with triethylamine in $CHCl_3$, then washed with 2 L of $CHCl_3$/1% triethylamine, until no spotting on TLC observed. Removed solvents, and dried under vacuum for ~2 hours.

Prepared all clean, oven-dried glassware: 1000 mL three-neck round-bottom flask with a magnetic stir bar, reflux condenser. Purged reaction vessel with $N_2$. Dissolved 3.64 g (3.04e-3 mol) N,N'-((5,6-bis((2-ethylhexyl)oxy)naphtho[2,1-b:3,4-b']dithiophene-2,9-diyl)bis(4,1-phenylene))bis(N-(4-(1,3-dioxolan-2-yl)phenyl)naphthalen-1-amine) in 400 mL dry THF. Transferred solution to reaction flask via cannulae. Added 5.06 mL triethylamine (3.65e-2 mol) via syringe. Added 1.15 mL formic acid (3.04-2 mol) via syringe. Fuming observed. Purged with nitrogen flow for 30 mins. Added 0.07 g $Pd(OAc)_2$ (~3.04e-4 mol) via funnel. Solution turned an orange color. Added 0.09 g $tBu_3P$ (4.56e-4 mol) dissolved in 2 mL toluene via syringe. Heated to reflux overnight. Solution mirrored the flask over time. Turned heat off and allowed to cool. Filtered through celite/silica gel plug. Pretreated silica with triethylamine in $CHCl_3$, then washed with 2 L of $CHCl_3$/1% triethylamine, until no spotting on TLC observed. Removed solvents, and dried under vacuum for ~2 hours. TLC is clean enough for deprotection.

Deprotection

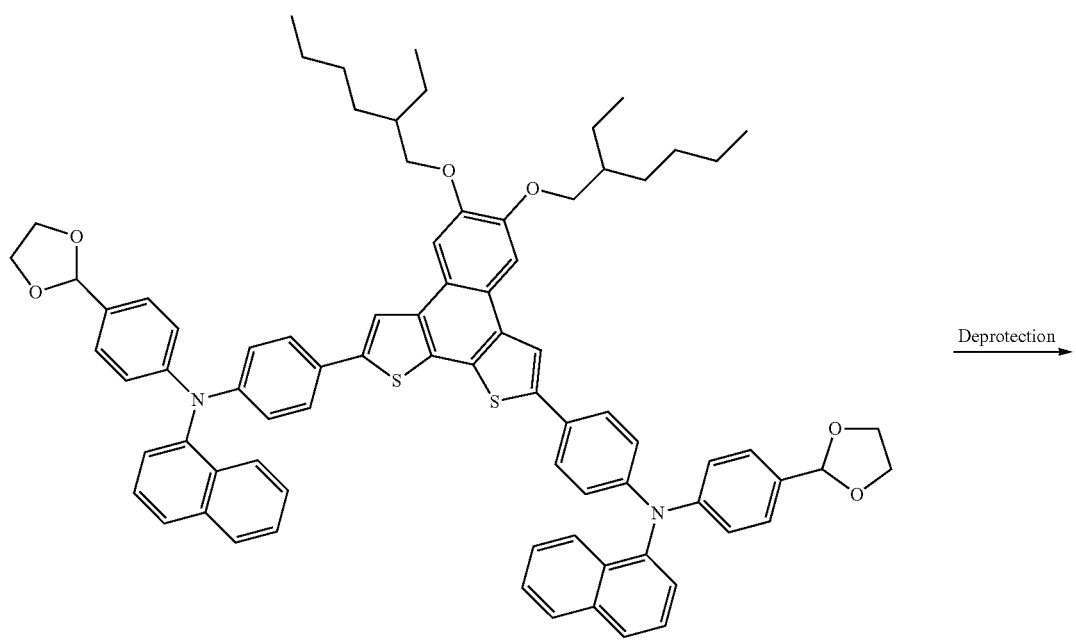

Deprotection

-continued

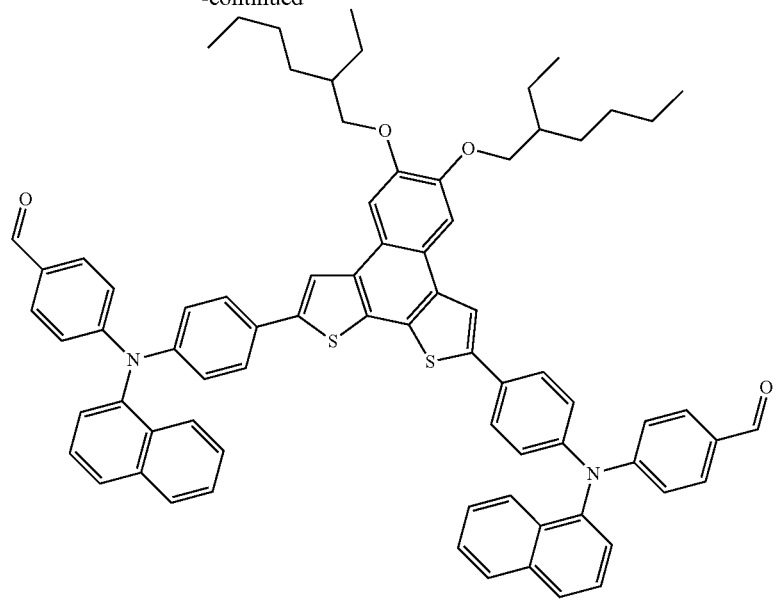

Prepared all clean, oven-dried glassware: 500 mL three-neck round-bottom flask with a magnetic stir bar. Charged flask with 3.64 g (2.97e-3 mol) of N,N'-((5,6-bis((2-ethylhexyl)oxy)naphtho[2,1-b:3,4-b']dithiophene-2,9-diyl)bis(4,1-phenylene))bis(N-(4-(1,3-dioxolan-2-yl)phenyl)naphthalen-1-amine). Transferred 200 mL of dry THF to reaction flask via cannulae. Transferred 0.593 mL 1M HCl solution dropwise to flask via syringe. After ~15 mins, addition of acid was complete, and solution had yellowed slightly. Allowed reaction to stir at room temperature for 30 minutes. TLC confirmed reaction completion. Upon confirmation of reaction completion poured reaction solution into cool water. Extracted into 200 mL chloroform. Washed with 3×500 mL portions of DI H$_2$O until aqueous fraction pH=~7. Collected the organic layer and aqueous layer. Dried organic layer using MgSO$_4$ and gravity filtered. Remove solvents via rotary evaporation. Ran manual column chromatography: Wet loaded crude at 60% Toluene/40% hexane. Eluted at 60% Toluene/40% hexane increasing to 90% Toluene/10% Hexanes, and then finally pushing out the product at 90% Toluene/5% hexanes/5% EtOAc. Mass of TLC pure: 3.07 g; NMR: good Wittig

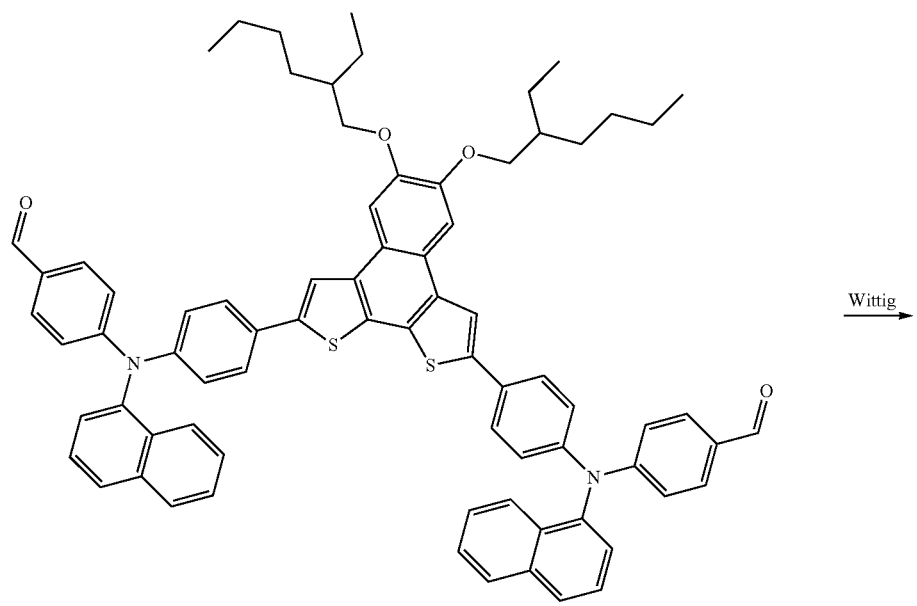

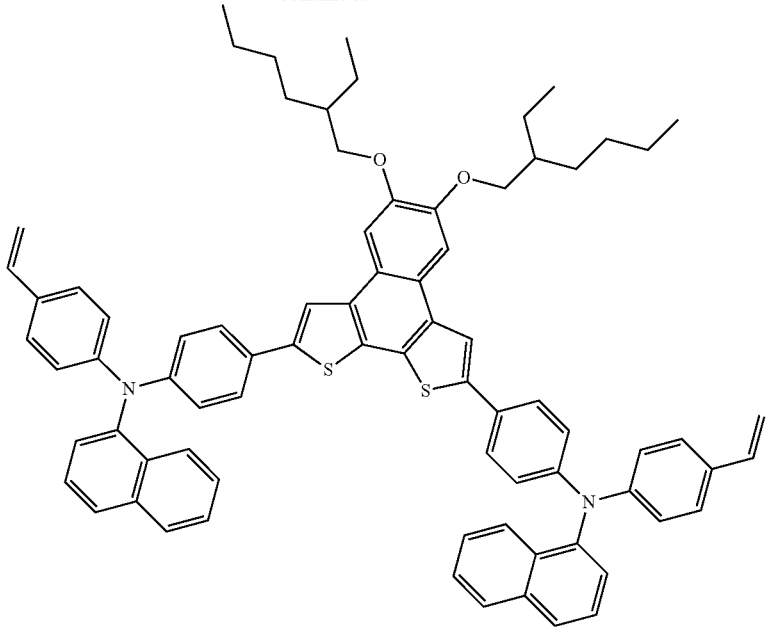

Prepared all clean, oven-dried glassware: 500 mL three-neck round-bottom flask with a magnetic stir bar, 250 mL addition funnel. Charged reaction flask with 3.1 g CH$_3$PPh$_3$Br via funnel. Charged reaction flask with 1.04 tBuOK via funnel. Added ~400 mL dry THF to reaction flask via cannulae, attempting to dissolve CH$_3$PPh$_3$Br/tBuOK. A milky, yellow suspension formed. Covered reaction flask in foil. Dissolved 3.07 g (2.7e-3 mol) of 4,4'-(((5,6-bis((2-ethylhexyl)oxy)naphtho[2,1-b:3,4-b']dithiophene-2,9-diyl)bis(4,1-phenylene))bis(naphthalen-1-ylazanediyl))dibenzaldehyde in dry THF and transferred via cannula to addition funnel. Began addition of solution of 4,4'-(((5,6-bis((2-ethylhexyl)oxy)naphtho[2,1-b:3,4-b']dithiophene-2,9-diyl)bis(4,1-phenylene))bis(naphthalen-1-ylazanediyl))dibenzaldehyde dropwise (3 Hz) to reaction flask. After addition was complete, solution had turned brick red. Reaction solution was allowed to stir for 15 minutes. TLC confirmed reaction completion. Upon confirmation of reaction completion, crude reaction solutions was run through a celite/silica gel plug. Silica gel was deactivated with triethylamine prior to filtration. The plug was washed with basified toluene and ethyl acetate. Removed solvents using a temperature no higher than 45° C. Wet loaded in 60% toluene/40% hexanes and ran chromatography using toluene/hexane gradient. Collected similar fractions. Flush contained a small amount of product. Set aside as an impure fraction. Concentrated TLC pure fractions and crashed out in 600 mL HPLC grade MeOH. Washed solids at 0° C. for 1 hr. Filtered off solids. After some time drying, transferred solids to tared amber vial. Dried under vacuum overnight. Mass of solids: 2.7 g. NMR solids: Good.

PLX-12-B

Suzuki Coupling

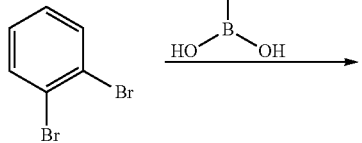

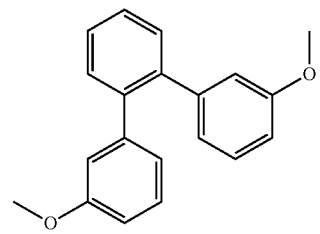

Purged 50/50 by volume mixture of Toluene and Isopropanol and a separate aqueous sodium carbonate solution for a minimum of one hour prior to reaction. Prepped clean, dry glassware: 1 L 2-neck round bottom flask, stir bar, reflux condenser. Cooled flask with N2 after removing from drying oven. Charged flask with 19.3 grams (0.127 mol) of 3-methoxyphenylboronic acid. Via syringe, charged flask with 5.1 ml (4.24e-2 mol) of 1,2-dibromobenzene. Via air-free cannula transfer, dissolved the previous compounds in 50/50 by volume Toluene/IPA. Purged reaction solution for 30 minutes with nitrogen flow. After 30 minutes, charged flask with 3.93 g (0.34e-3 mol) of Pd(PPh$_3$)$_4$. Via cannula, transferred 170 mL (~0.34 mol) of 2M sodium carbonate solution. Placed heating mantle under flask, set variac to 35%, and turned condenser water on. Refluxed reaction overnight. TLC confirmed reaction completion. Turned heat off and allowed reaction solution to cool. Poured solution into 300 mL DI water. Extracted with 500 mL EtOAc. Washed 3× with 150 mL DI water until neutral. Dried with MgSO$_4$, gravity filtered, and adsorbed to ~80 g coarse silica gel. Ran flash chromatography initially using 100% hexane as an eluent, and then increasing to a 2% EtOAc/98% Hexanes via gradient. Collected similar spots on TLC and removed solvents. Mass of TLC pure product collected=10.28 g; NMR=Good; GC/MS: 96%

Scholl Reaction

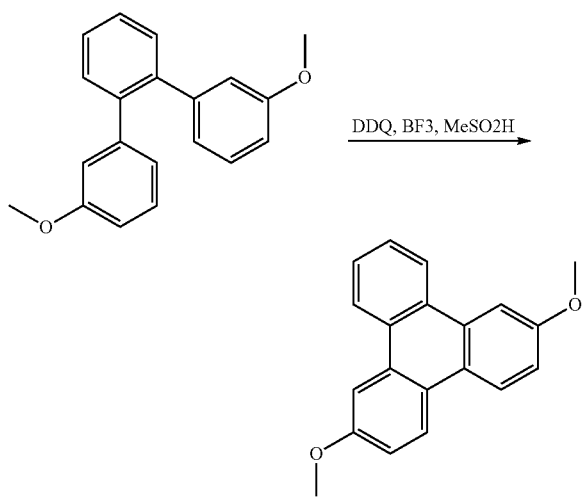

DDQ, BF3, MeSO2H

Prepped clean, dry glassware: 2 L 3-neck round bottom flask, stir bar, thermometer and adaptor. Purged with N2 after removing from drying oven until cool. Charged flask with 13 grams (4.43e-2 mol) of 3,3"-dimethoxy-1,1':2',1"-terphenyl. Via cannula transfer, dissolved in 1 L anhydrous dichloromethane. Placed reaction flask into dry ice/IPA bath and allowed to cool to negative 30 degrees Celsius. Purged reaction for 30 minutes with nitrogen flow. After 30 minutes, charged flask with 5.7 mL (8.96e-2 mol) of Boron trifluoride diethyl etherate. Portion by portion, DDQ was added to flask while maintaining temperature at −30° C. Added half of DDQ over 15 min. Reaction had turned dark blue/green. TLC indicated no reaction. Added one mL of methanesulfonic acid at −40° C. Subsequent TLC showed reaction started to proceed. Added more portions of DDQ (75% total) over 10 minutes and one more mL of methanesulfonic acid. TLC showed progression of reaction. Fluorescent spot on baseline increasing. Added remaining DDQ and remaining 0.9 mL of methanesulfonic acid. Lowered dry ice bath and allowed reaction to warm up. TLC at 15° C. showed reaction was almost complete, quenched with 21 g of ferrocene to avoid overreaction. Filtered reaction through a celite pad and rinsed with 2 L chloroform. Removed solvents via rotary evaporation. Adsorbed crude to coarse silica for chromatography. Ran flash chromatography initially using 100% hexane as an eluent, and then increasing to a 2% EtOAc/98% Hexanes gradient. Separation was not trivial. Isolated 3.6 g TLC pure. A second attempt at purification of the impure fractions led to the pure product band spontaneously crystallizing in the column. Isolated another 2.2 g TLC pure. Set aside impure fractions. Mass of TLC pure product collected=5.8 g; NMR=Good Dealkylation

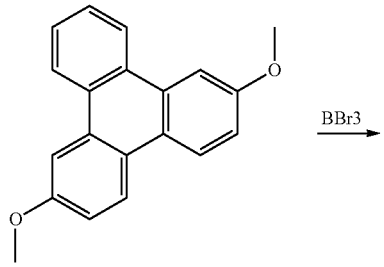

BBr3

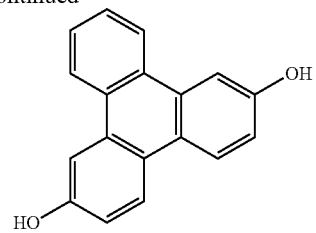

Prepped clean, oven and torch dried glassware: 1 L 3-neck round-bottom flask and stir bar. From a separate round bottom flask, transferred solution of 5.54 g (1.92e-2 mol) 2,7-dimethoxytriphenylene in 500 mL dry dichloromethane. Cooled reaction flask in ice water bath. After 30 minutes of chilling (~5° C.), began the slow addition of 1M BBr3 solution via 50 mL syringe. Fuming observed from needle tip. This was carried out with the sash 60% of the way closed. Exotherm observed (~10° C.). After addition of 40 mL of BBr3 solution, solids began to crash out of solution. Allowed to stir for 2 hrs before preliminary TLC: reaction not complete. Removed ice bath and allowed to stir overnight. TLC the next day confirmed reaction completion. Attempted aqueous extraction, however, solubility in dichloromethane was poor, and 2 L of EtOAc was required dissolve the product and to lower the density of the organic phase enough rise above the aqueous layer. Washed with 3 L of DI water until neutral. Dried over MgSO4 and filtered off hydrated salts. Removed solvents via rotary evaporation. Ran flash chromatography initially using 100% hexane as an eluent, and then increasing to a 60% EtOAc/40% Hexanes gradient. Solubility issues were encountered, but main impurity was leached off before column was flushed. Mass of almost TLC pure product: 4.93 g; NMR=good Transesterification

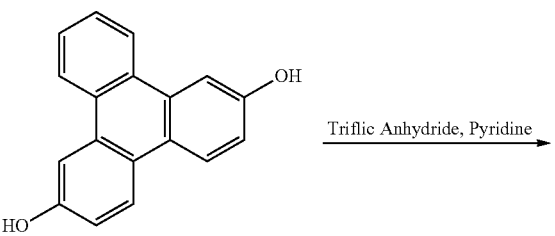

Triflic Anhydride, Pyridine

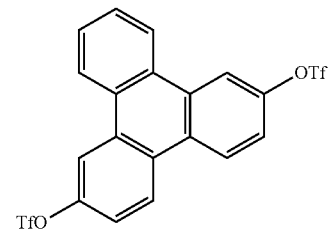

Prepped clean, oven and torch dried glassware: 1 L 3-neck round-bottom flask, stir bar, addition funnel. Charged flask with 4.68 g (1.8e-2 mol) of triphenylene-2,7-diol. Dissolved in ~50 mL pyridine via syringe. Diluted with 200 mL dry CH$_2$Cl$_2$ transferred via cannula. Charged addition funnel with 25 mL dry CH$_2$Cl$_2$ via cannula. Via syringe, charged addition funnel with 9.1 mL (5.4e-2 mol) of triflic anhydride. Waited five minutes for addition. Began addition at 3 drops per second. Fuming observed. As addition proceeded, solution changed from brownish to red and became slightly warm. Allowed to stir overnight. TLC the next day confirmed reaction completion. Extracted into 600 mL chloroform and rinsed with water until neutral. Dried over MgSO$_4$ and filtered off hydrated salts. Ran a column plug with silica gel to remove baseline salts. Washed with chloroform and removed solvents. Mass of TLC pure product: 8.88 g; NMR=good

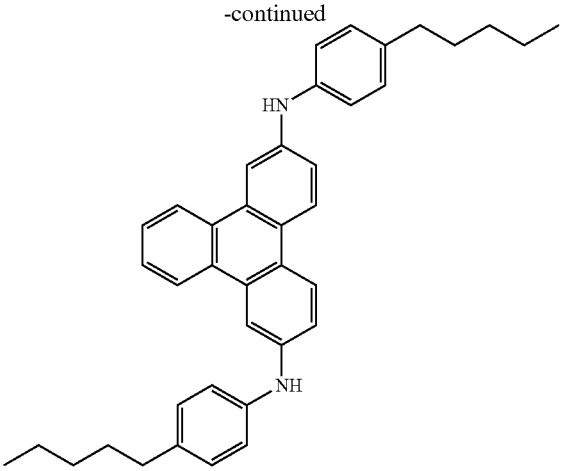

Triflate Amination

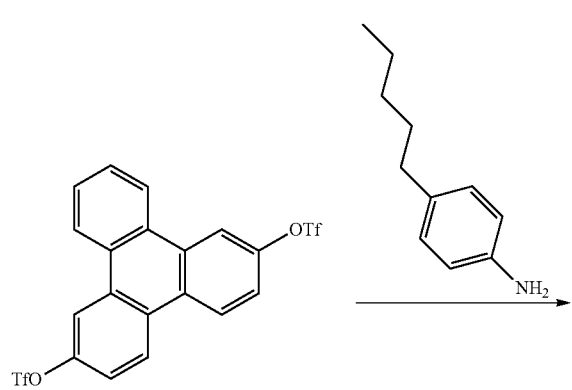

Prepped clean, oven and torch dried glassware: 1 L 3-neck round-bottom flask, stir bar, reflux condenser. Charged flask with 4 g (7.63e-3 mol) of triphenylene-2,7-diyl bis(trifluoromethanesulfonate). Transferred 700 mL anhydrous toluene via cannula. Fine crystalline suspension formed. Charged flask with 5.42 (3.05e-2 mol) 4-pentylaniline. Purged with nitrogen for 20 minutes. After purging, charged flask with 12.44 g (~3.8e-2 mol) of anhydrous cesium carbonate, 0.22 g (~9.16e-4 mol) of palladium acetate, 0.34 g (6.87e-4 mol) of XPhos ("2-Dicyclohexylphosphino-2',4',6'-triisopropylbiphenyl"), and 0.14 g (~6.87e-4 mol) of t-Bu$_3$P in 2 mL dry toluene. Set variac/heating mantle to 40% output and turned on condenser water. Allowed to reflux overnight. TLC the next day confirmed reaction completion. Turned off heat and filtered reaction solution through celite/silica gel plug after cooling. Washed with ethyl acetate until all product was rinsed out of plug. Removed solvents via rotary evaporation and then washed almost dry solids in ice cold methanol for 1 hour. TLC of solids vs. filtrate showed many impurities dissolved in methanol. Dry product appears to be brownish crystalline solids and is a single spot on TLC. Amount: 3.79 g. NMR=good Amination

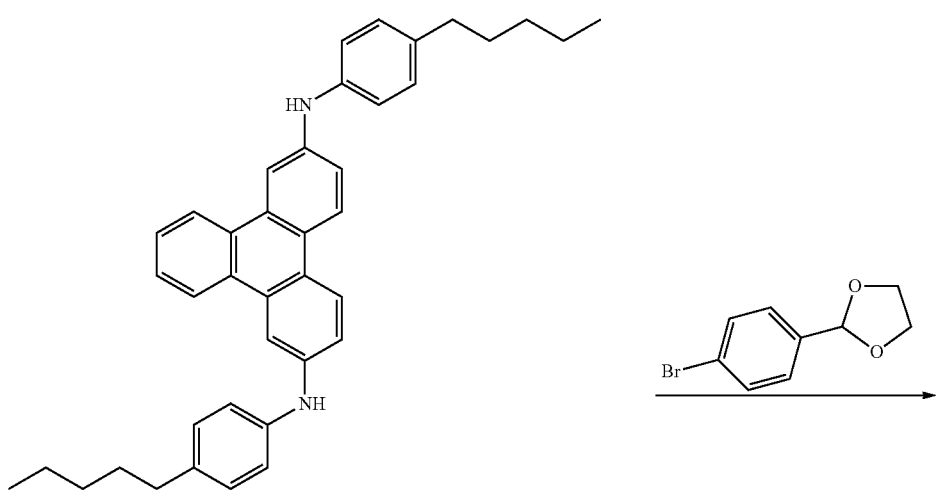

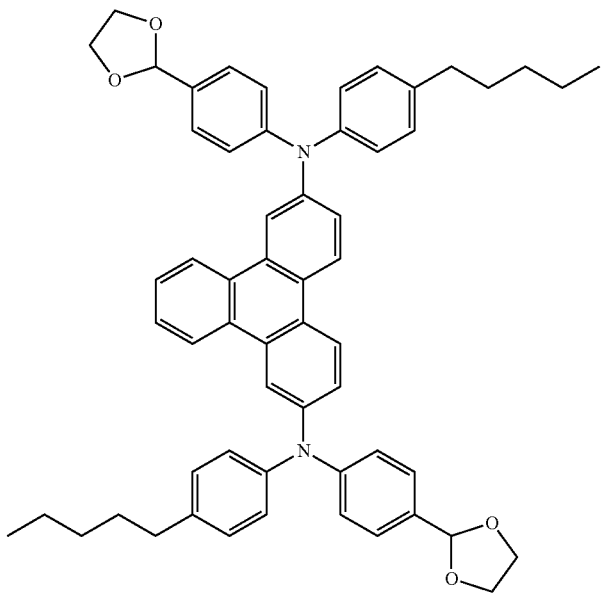

Prepped clean, oven and torch dried glassware: 1 L 3-neck round-bottom flask, stir bar, reflux condenser. Charged flask with 3.79 g (6.88e-3 mol) of $N^2,N^7$-bis(4-pentylphenyl)triphenylene-2,7-diamine and 3.78 g (1.65e-2 mol) of 2-(4-bromophenyl)-1,3-dioxolane. Transferred 400 mL anhydrous toluene via cannula to flask. Purged reaction solution with nitrogen for 60 minutes. After purging, charged flask with 1.98 g (~2.06e-2 mol) of tBuONa, 0.38 g (~4.13-4 mol) of $Pd_2(dba)_3$, and 0.25 g (~1.24e-3 mol) of t-$Bu_3P$ in 4 mL dry toluene. Set variac/heating mantle to 30% and turned on condenser water. Allowed to reflux for 3 hrs. TLC confirmed reaction completion. Filtered through celite/silica gel plug basified with 2% $Et_3N$/98% EtOAc. Washed with 2 L of basified EtOAc. Removed via rotary evaporation. Adsorbed crude to silica gel and chromatographed on a basified silica column. Solvent system was ethyl acetate/hexanes at an increasing gradient from 0%/100% to 15%/85%. Collected similar fractions and removed solvents. Redissolved in inhibitor free THF and precipitated in ice-cold methanol. Mass of solids after drying: 5.55 g. NMR=good

Dehalogenation 1&2

Prepared all clean, oven-dried glassware: 1 L three-neck round-bottom flask with a magnetic stir bar, reflux condenser. Purged reaction vessel with $N_2$. Dissolved 5.55 g (6.55e-3 mol) $N^2,N^7$-bis(4-(1,3-dioxolan-2-yl)phenyl)-$N^2,N^7$-bis(4-pentylphenyl)triphenylene-2,7-diamine in 400 mL dry THF. Transferred solution to reaction flask via cannula. Added 11 mL (~7.86e-2 mol) triethylamine via syringe. Added 2.5 mL (~6.55e-2 mol) formic acid via syringe. Fuming observed. Purged reactions olution with $N_2$ for 30 mins. Added 0.14 g (6.55e-4 mol) $Pd(OAc)_2$) via funnel. Added 0.20 g (~9.83e-4 mol) $tBu_3P$ dissolved in 4 mL toluene via syringe. Heated to reflux and allowed reaction to stir overnight. Solution turned black. Allowed to cool, then filtered through celite/silica gel plug. Pretreated silica with triethylamine in EtOAc, then washed with 2 L of EtOAc/1% triethylamine, until no spotting on TLC observed. Removed solvents via rotary evaporation and dried further under vacuum for ~2 hours.

Prepared all clean, oven-dried glassware: 1 L three-neck round-bottom flask with a magnetic stir bar, reflux condenser. Purged reaction vessel with $N_2$. Dissolved 5.55 g (6.55e-3 mol) $N^2,N^7$-bis(4-(1,3-dioxolan-2-yl)phenyl)-$N^2,N^7$-bis(4-pentylphenyl)triphenylene-2,7-diamine in 400 mL dry THF. Transferred solution to reaction flask via cannula. Added 11 mL (~7.86e-2 mol) triethylamine via syringe. Added 2.5 mL (~6.55e-2 mol) formic acid via syringe. Fuming observed. Purged reactions olution with $N_2$ for 30 mins. Added 0.14 g (6.55e-4 mol) $Pd(OAc)_2$) via funnel. Added 0.20 g (~9.83e-4 mol) $tBu_3P$ dissolved in 4 mL toluene via syringe. Heated to reflux and allowed reaction to stir for 2 hours. Solution turned black. Allowed to cool, then filtered through celite/silica gel plug. Pretreated silica with triethylamine in EtOAc, then washed with 2 L of EtOAc/1% triethylamine, until no spotting on TLC observed. Removed solvents via rotary evaporation and dried further under vacuum for ~2 hours. Redissolved in chloroform and precipitated into methanol. Mass of solids: 5.24 g. HPLC: 99.5%.

Deprotection

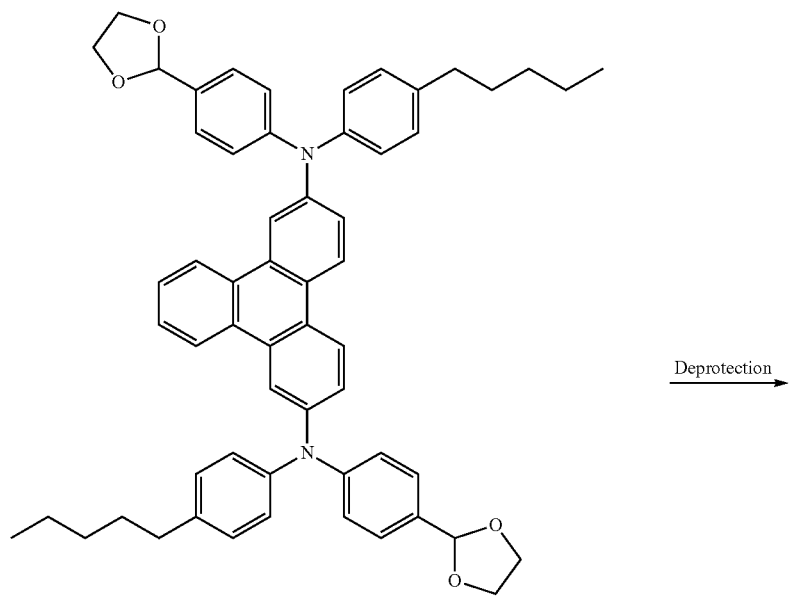

Deprotection →

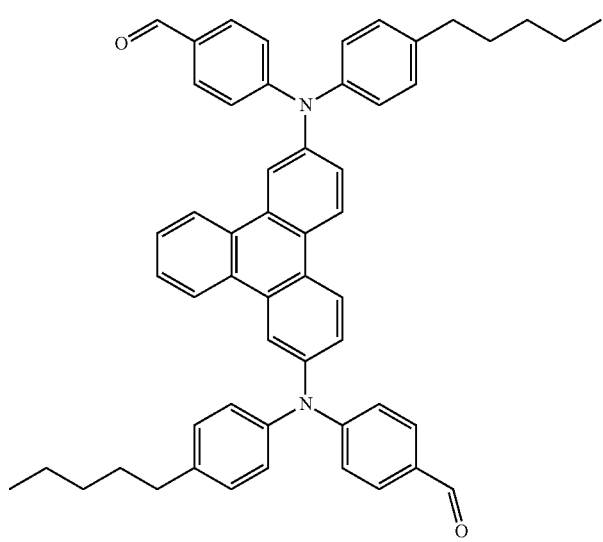

Prepared all clean, oven-dried glassware: 1000 mL three-neck round-bottom flask with a magnetic stir bar. Charged flask with 5.24 g (6.19e-3 mol) of $N^2,N^7$-bis(4-(1,3-dioxolan-2-yl)phenyl)-$N^2,N^7$-bis(4-pentylphenyl)triphenylene-2,7-diamine. Transferred 300 mL of dry THF to reaction flask via cannulae. Transferred 1.24 mL 1M HCl solution dropwise to flask via syringe. Added HCl dropwise at ~1 drop/sec. As acid hit reaction solution, some precipitate was observed to form, which quickly redissolved. After ~15 mins, addition of acid was complete. Let stir for 30 mins. TLC confirmed reaction completion. Poured reaction solution into a separatory funnel with 500 mL DI water. Extracted crude into 200 mL ethyl acetate. Washed 3×500 mL dionized water until pH was close to neutral. Collected organic layer and dried over magnesium sulfate, then filtered off hydrated salts. Removed solvent via rotary evaporation. Adsorbed crude to coarse silica gel and ran manual column chromatography using chloroform/hexanes. Collected TLC pure fractions. Mass of TLC pure: 4.39 g. NMR: Ok

Wittig

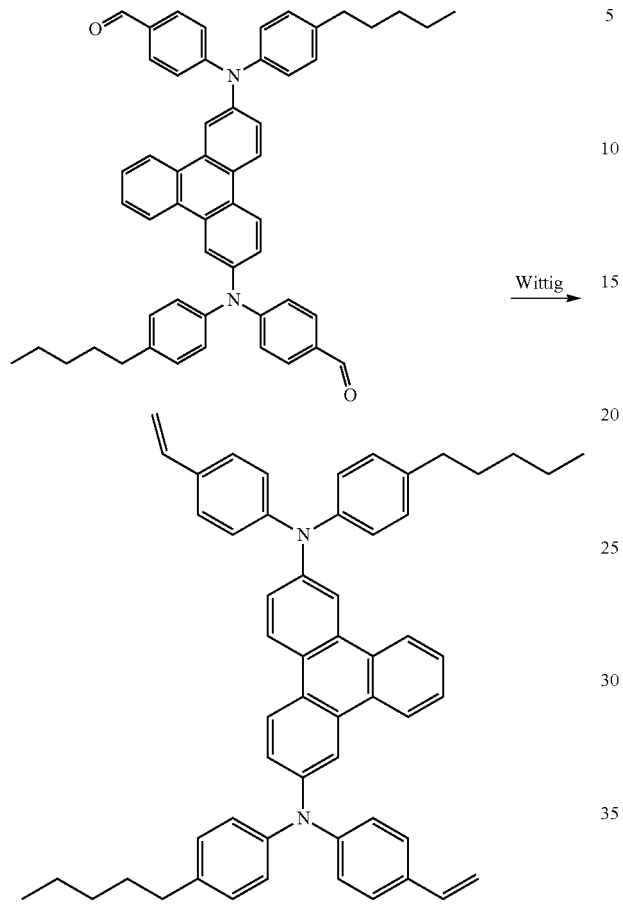

Prepared all clean, oven-dried glassware: 1 L three-neck round-bottom flask with a magnetic stir bar, 250 mL addition funnel. Charged reaction flask with 6.2 g (1.7e-2 mol) $CH_3PPh_3Br$ via funnel. Charged reaction flask with 2.01 (1.8e-2 mol) tBuOK via funnel. Added ~300 mL dry THF to reaction flask via cannula, to form a milky-yellow suspension. Let stir at 800 rpm for >15 mins and then covered reaction flask with foil. Dissolved 4.39 g (5.78e-3 mol) of 4,4'-(triphenylene-2,7-diylbis((4-pentylphenyl)azanediyl))dibenzaldehyde in dry THF and transferred via cannula to addition funnel. Began dropwise (3 Hz) addition of dialdehyde solution to reaction flask. After addition, solution appeared to be slightly reddened. Allowed solution to stir for 15 min. TLC confirmed reaction completion. Upon confirmation of reaction completion, the crude solution was filtered through celite/silica gel plug and washed with EtOAc until no spotting was observed on TLC. Removed solvents using a temperature no higher than 40° C. on the rotary evaporator. Dry loaded crude onto a silica gel column and eluted at 2% THF (inhibitor free)/98% Hexanes until product fully eluted. Collected similar fractions and removed the solvents via rotary evaporation. Redissolved TLC pure fractions in inhibitor free THF and precipitated into HPLC grade methanol. Filtered off solids and allowed to dry briefly through aspiration. After some time drying, transferred solids to tared amber vial. Dried solids under vacuum overnight. Mass of solids: 3.84 g. NMR solids confirm desired product: $N^2,N^7$-bis(4-pentylphenyl)-$N^2,N^7$-bis(4-vinylphenyl)triphenylene-2,7-diamine.

PLX-12-D

Synthesis of 2,9-dibromo-5,6-bis(2-ethylhexyl)naphtho[2,1-b:3,4-b']dithiophene

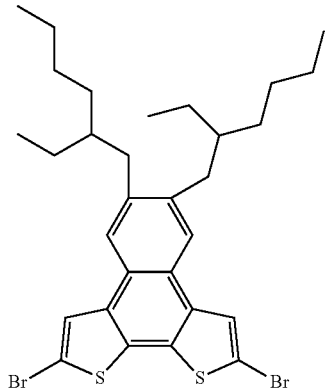 [SMILES: CCCCC(CC)Cc1cc2c(cc1CC(CC)CCCC)c1cc(Br)sc1c1sc(Br)cc21]

Procedures:

A round bottom flask was charged with 5,6-bis(2-ethylhexyl)naphtho[2,1-b:3,4-b']dithiophene (2.00 g, 0.0043 mol) and chloroform (125 mL). The reaction vessel was placed in an ice/water bath and cooled to a temperature of 0° C. N-bromosuccinimide (NBS, 1.69 g, 0.0095 mol) was added portion-wise and the reaction was allowed to stir for four hours. Reaction progress and completion was monitored via thin-layer chromatography. Once complete, the reaction solution was worked up with deionized water (4×200 mL). The organic fraction was dried over anhydrous magnesium sulfate. Solids were removed by vacuum filtration and solvent was removed from the filtrate by rotary evaporation. Further purification was carried out by chromatography on silica gel using hexane as an eluent. This provided $^1$H-NMR pure product. Product obtained: 2.33 g Synthesis of 5,6-bis(2-ethylhexyl)-N2,N9-diphenyl-N2,N9-di-m-tolylnaphtho[2,1-b:3,4-b']dithiophene-2,9-diamine

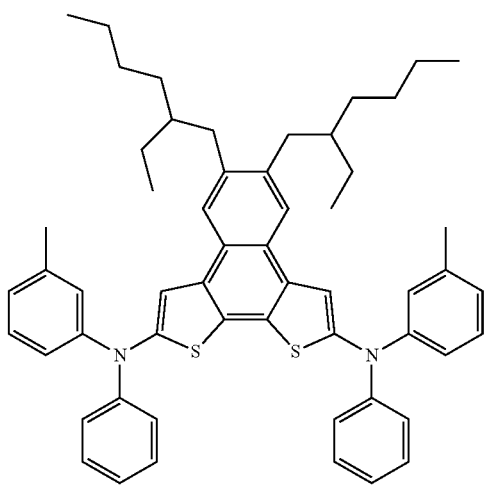 [SMILES: CCCCC(CC)Cc1cc2c(cc1CC(CC)CCCC)c1cc(N(c3ccccc3)c3cccc(C)c3)sc1c1sc(N(c3ccccc3)c3cccc(C)c3)cc21]

Procedures:

To an oven-dried three-neck round-bottom flask under nitrogen, were added anhydrous toluene (125 mL), 2,9-dibromo-5,6-bis(2-ethylhexyl)naphtho[2,1-b:3,4-b']dithiophene (1.00 g, 0.0016 mol), and 3-methyldiphenylamine (0.66 mL, 0.0039 mol). After the reaction mixture was degassed with strong nitrogen flow for thirty minutes, sodium tert-butoxide (0.46 g, 0.0048 mol), tris(dibenzylideneacetone)dipalladium(0) ($Pd_2dba_3$, 0.12 g, 0.00013 mol), and tri-tert-butyl phosphine (0.08 g, 0.00039 mol, in 5 mL toluene) were added. The reaction mixture was heated to reflux for three hours. Reaction completion confirmed by thin-layer chromatography, and upon completion, was cooled to room temperature. The reaction solution was filtered through a Celite/silica gel plug, washing thoroughly with acetone. Solvent was removed from the filtrate by rotary evaporation. Further purification was carried out by chromatography on silica gel using 1% ethyl acetate/99% hexane as an eluent. The product was precipitated from a minimum amount of acetone into methanol that had been chilled to a temperature of −30° C. which provided $^1$H-NMR pure material. Product obtained: 0.99 g

PLX-13-A

Suzuki Coupling

Prepared clean, dry 1 L three-neck round-bottom flask, magnetic stir bar, and reflux condenser. The flask was charged with 8 g (1.59e-2 mol) of 2,2'-(9,9-dihexyl-9H-fluorene-2,7-diyl)bis(1,3,2-dioxaborinane) and 15.5 (4.78e-2 mol) of 4-bromotriphenylamine. Using air-free techniques, 500 mL of dry toluene was transferred to the reaction flask to dissolve the starting materials. Reaction solution was bubbled with nitrogen for 20 minutes. Afterwards, the reaction flask was charged with 0.45 g (6.36e-4 mol) of bis(triphenylphosphino)palladium dichloride. Reaction solution was heated to reflux before the addition of 58.5 mL (7.95e-2 mol) of 20% w/w tetraethylammonium hydroxide (aq.) solution. Reaction solution was refluxed overnight and then allowed to cool.

Crude reaction solution was extracted into 600 mL of ethyl acetate and washed with deionized water until neutral. Organic fraction was dried over magnesium sulfate and then filtered. The crude mixture was adsorbed to silica and chromatographed in an ethyl acetate/hexanes gradient. Mass of TLC pure was 6.33 g. NMR corresponded to desired target: 4,4'-(9,9-dihexyl-9H-fluorene-2,7-diyl)bis(N,N-diphenylaniline).

PLX-13-B

Selective Amination

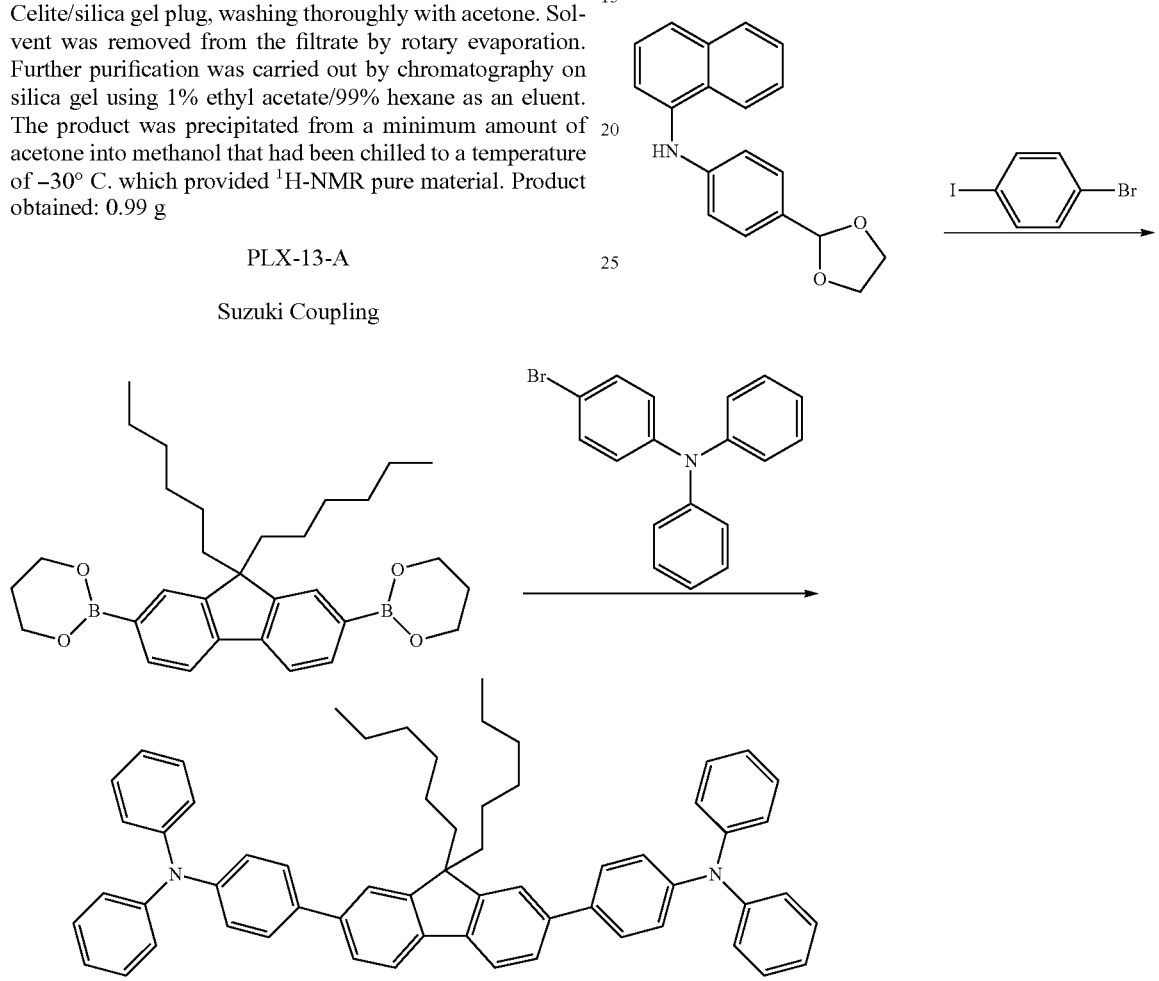

-continued

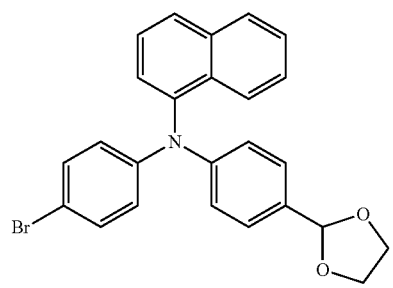

Prepared a clean, dry 2 L three-neck round bottom flask, magnetic stir bar, and reflux condenser. Under inert atmosphere, the flask was charged with 9.79 g (0.0336 mol) of N-(4-(1,3-dioxolan-2-yl)phenyl)naphthalen-1-amine and 28.52 g (0.101 mol) of 1-bromo-4-iodobenzene. Using air-free techniques, 600 mL of dry, inert toluene was transferred to the reaction flask. Nitrogen was then bubbled through the reaction solution for 20 minutes before the flask was charged with a dry mixture of 1.14 g (~2.01e-3 mol) of bis(diphenylphosphino)ferrocene and 0.77 g (8.4e-3 mol) of Pd$_2$(dba)$_3$. Solution was allowed to stir for ten minutes before addition of 4.84 g (0.0504 mol) sodium tert-butoxide. Solution was refluxed overnight. After reaction solution cooled down, it was filtered through a celite/silica gel plug and then adsorbed to silica gel for manual chromatography. The crude mixture was eluted at 10% ethyl acetate/90% hexanes. 12.3 g of TLC pure material isolated. NMR corresponded to desired target.

Suzuki Coupling increasing ethyl acetate/hexanes gradient. Collected similar fractions and removed solvents via rotary evaporation. Mass of product: 5.32 g. NMR: Good.

Dehalogenation 1&2

Prepared a clean, dry 1 L three-neck round bottom flask, magnetic stir bar, and reflux condenser. Under inert atmosphere, the flask was charged with 5.1 g (4.79e-3 mol) of N,N'-((9,9-dihexyl-9H-fluorene-2,7-diyl)bis(4,1-phenylene))bis(N-(4-(1,3-dioxolan-2-yl)phenyl)naphthalen-1-amine). Using air-free techniques, 400 mL of THF was transferred to the reaction flask to dissolve all of the starting material. 8 mL (5.75e-2 mol) of triethylamine was added to the flask via syringe. 1.81 mL (4.79e-2 mol) of formic acid was slowly added to the flask via syringe. Nitrogen was bubbled through the reaction solution for 30 minutes before the addition of 0.11 g (4.79e-3 mol) of palladium acetate. Transferred solution of 0.145 g (7.19e-4 mol) of tri-tert-butylphosphine in 5 mL of toluene to flask via inert syringe.

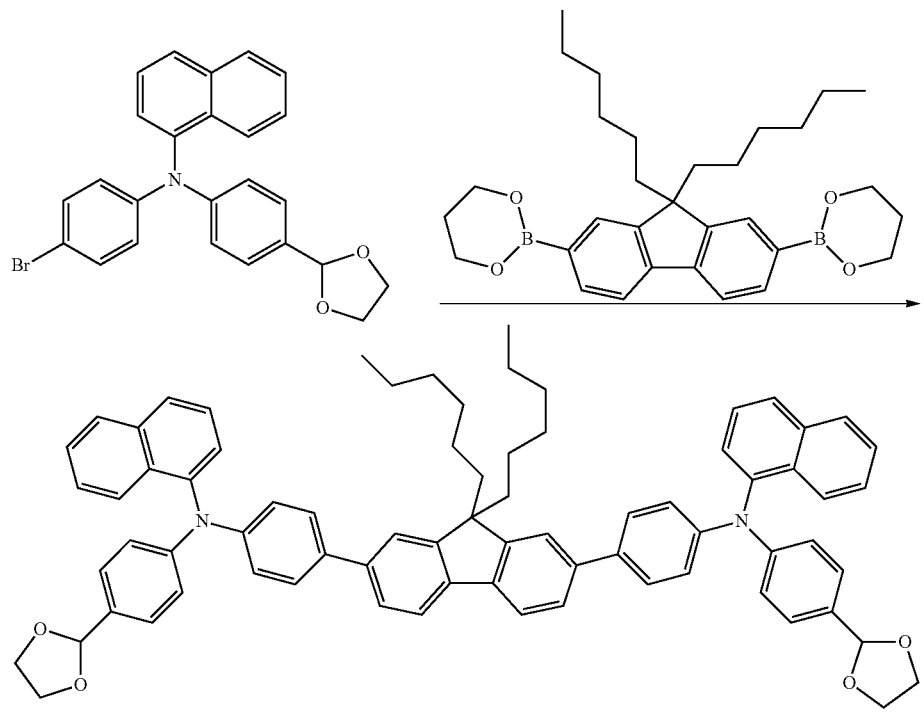

Prepared a clean, dry 1 L three-neck round bottom flask, magnetic stir bar, and reflux condenser. Under inert atmosphere, the flask was charged with 5 g (9.95e-3 mol) of 2,2'-(9,9-dihexyl-9H-fluorene-2,7-diyl)bis(1,3,2-dioxaborinane) and 10.66 g (2.39e-2 mol) of N-(4-(1,3-dioxolan-2-yl)phenyl)-N-(4-bromophenyl)naphthalen-1-amine. Using cannula transfer, dissolved both compounds in 500 mL of dry toluene. Nitrogen was bubbled through the solution for 20 minutes. The flask was then charged with 0.84 (1.19e-3 mol) of bis(triphenylphosphino)palladium dichloride. Via cannula, the flask was charged with 73.3 mL (9.95e-2 mol) of 20% w/w tetraethylammonium hydroxide (aq.) solution. Reaction solution was refluxed overnight. Extracted into ethyl acetate and washed with deionized water until neutral. Dried organic fraction over magnesium sulfate and filtered off salts. Adsorbed to coarse silica and chromatographed with Reaction solution was then refluxed for two hours. After reaction cooled, the crude mixture was filtered through a celite/silica gel plug and solvents were removed.

Prepared another clean, dry 1 L three-neck round bottom flask, magnetic stir bar, and reflux condenser. Under inert atmosphere, the flask was charged with a solution of ~5.1 g (4.79e-3 mol) of N,N'-((9,9-dihexyl-9H-fluorene-2,7-diyl)bis(4,1-phenylene))bis(N-(4-(1,3-dioxolan-2-yl)phenyl)naphthalen-1-amine) in ~400 mL of THF. 8 mL (5.75e-2 mol) of triethylamine was added to the flask via syringe. 1.81 mL (4.79e-2 mol) of formic acid was slowly added to the flask via syringe. Nitrogen was bubbled through the reaction solution for 30 minutes before the addition of 0.11 g (4.79e-3 mol) of palladium acetate. Transferred solution of 0.145 g (7.19e-4 mol) of tri-tert-butylphosphine in 5 mL of toluene to flask via inert syringe. Reaction solution was then refluxed overnight. After reaction cooled, the crude mixture was filtered through a celite/silica gel plug and solvents were removed. Redissolved solids in acetone and precipitated into ice-cold methanol. Filtered off solids and dried overnight. Mass of dry solids: 5.06 g Deprotection

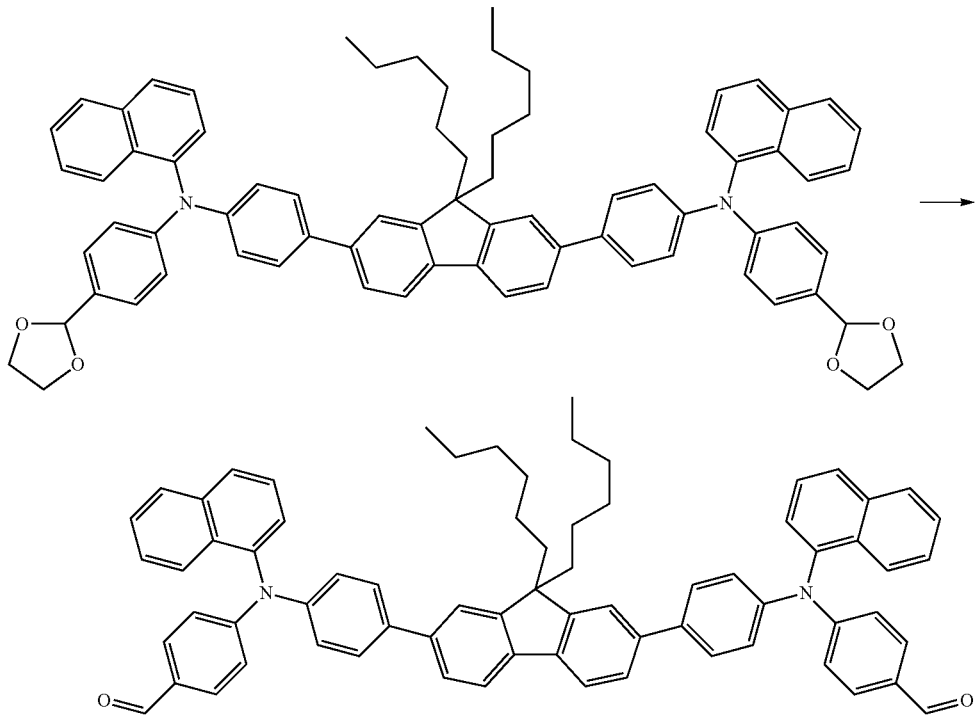

Prepared a clean, dry 500 mL round-bottom flask, and magnetic stir bar. Reaction flask was charged with 5.06 g (4.75e-3 mol) of N,N'-((9,9-dihexyl-9H-fluorene-2,7-diyl)bis(4,1-phenylene))bis(N-(4-(1,3-dioxolan-2-yl)phenyl)naphthalen-1-amine). The starting material was dissolved in 250 mL of acetone. 0.95 mL of 1M HCl solution was added slowly via syringe to flask. After addition was complete, solution was stirred for 15 minutes. TLC confirmed reaction completion. The crude mixture was extracted into 300 mL of ethyl acetate and washed with deionized water until neutral. Organic layer was dried over magnesium sulfate and then gravity filtered. Solvents were removed and the crude material was adsorbed to coarse silica and chromatographed. Similar fractions were collected and the solvents were removed via rotary evaporation. Mass of solids: 2.62 g NMR confirmed desired product.

Wittig

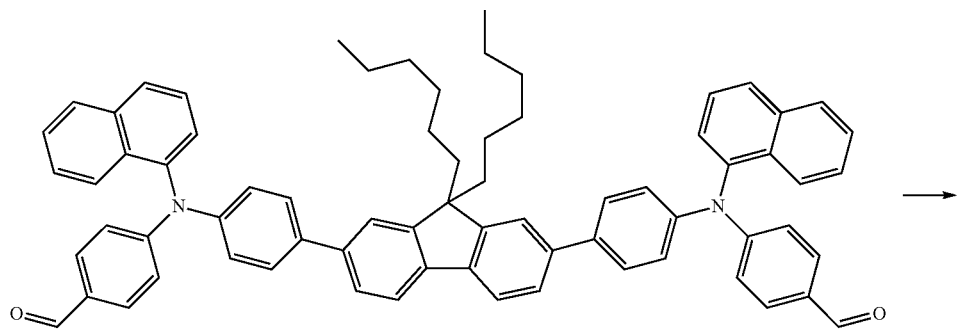

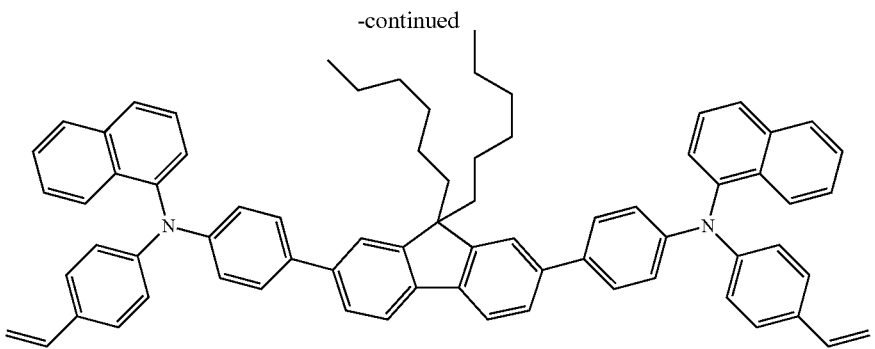

Prepared a clean, dry 1 L three-neck round-bottom flask, 150 mL addition funnel, and magnetic stir bar. The round-bottom flask was charged with 3.07 g (8.58e-3 mol) of methyltriphenylphosphonium bromide and 1 g (8.84e-3 mol) of potassium tert-butoxide. Via cannula, 300 mL of dry THF was added to the round-bottom flask to create a suspension of ylide. A 100 mL solution of 2.54 g (2.6e-3 mol) 4,4'-(((9,9-dihexyl-9H-fluorene-2,7-diyl)bis(4,1-phenylene))bis(naphthalen-1-ylazanediyl))dibenzaldehyde was transferred to the addition funnel via cannula. Reaction flask was covered in foil and addition was started. After addition was complete, reaction solution was allowed to stir for another 15 minutes. Crude reaction solution was filtered through a celite/silica gel plug and adsorbed to coarse silica. Crude mixture was chromatographed and similar fractions were collected. Solvents were removed via rotary evaporation. TLC pure material was redissolved in THF and precipitated into 80% methanol/20% hexanes. Solids were filtered off and dried under vacuum. Mass of solids: 1.44 g NMR indicated desired product: N,N'-((9,9-dihexyl-9H-fluorene-2,7-diyl)bis(4,1-phenylene))bis(N-(4-vinylphenyl)naphthalen-1-amine).

PLX-13-C

Dehalogenation of N-(3-(1,3-dioxolan-2-yl)phenyl)-N-(4-(1,3-dioxolan-2-yl)phenyl)-7-(4'-(naphthalen-1-yl(phenyl)amino)-[1,1'-biphenyl]-4-yl)-9,9-bis(3-phenylpropyl)-9H-fluoren-2-amine

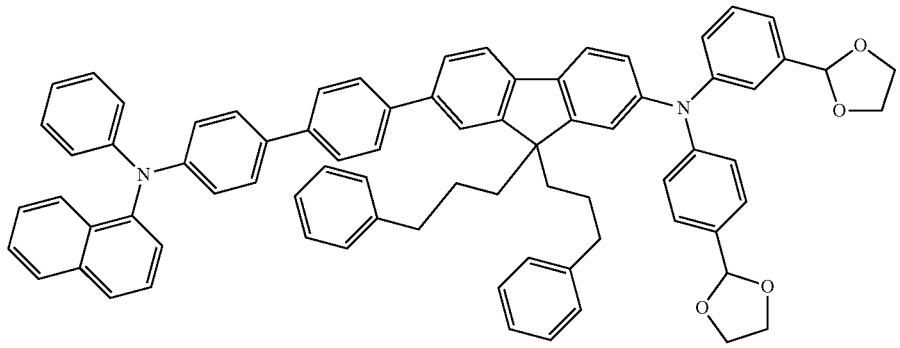

N-(3-(1,3-dioxolan-2-yl)phenyl)-N-(4-(1,3-dioxolan-2-yl)phenyl)-7-(4'-(naphthalen-1-yl(phenyl)amino)-
[1,1'-biphenyl]-4-yl)-9,9-bis(3-phenylpropyl)-9N-fluoren-2-amine Procedures:

A round bottom flask equipped with a reflux condenser was charged with N-(3-(1,3-dioxolan-2-yl)phenyl)-N-(4-(1,3-dioxolan-2-yl)phenyl)-7-(4'-(naphthalen-1-yl(phenyl)amino)-[1,1'-biphenyl]-4-yl)-9,9-bis(3-phenylpropyl)-9H-fluoren-2-amine (2.77 g, 0.0026 mol). Anhydrous THF (250 mL) was added to the flask via cannula. Triethylamine (3.6 mL, 0.0256 mol) was then added via syringe. Formic acid (0.9 mL, 0.0243 mol) was added slowly, drop-wise via syringe. The reaction solution and system was then purged with an inert gas flow for thirty minutes, after which Pd(OAc)$_2$ (0.12 g, 0.0003 mol) and tBu$_3$P (0.16 g in 5 mL anhydrous toluene) were added. The reaction was heated to reflux for approximately 2 hours and then cooled to room temperature. The solution was filtered through a Celite and triethylamine treated silica gel plug, washing with excess ethyl acetate. Solvent was then removed by rotary evaporation and the resulting solid material was placed under vacuum to be used in the second dehalogenation reaction.

Dehalogenation of N-(3-(1,3-dioxolan-2-yl)phenyl)-N-(4-(1,3-dioxolan-2-yl)phenyl)-7-(4'-(naphthalen-1-yl(phenyl)amino)-[1,1'-biphenyl]-4-yl)-9,9-bis(3-phenylpropyl)-9H-fluoren-2-amine

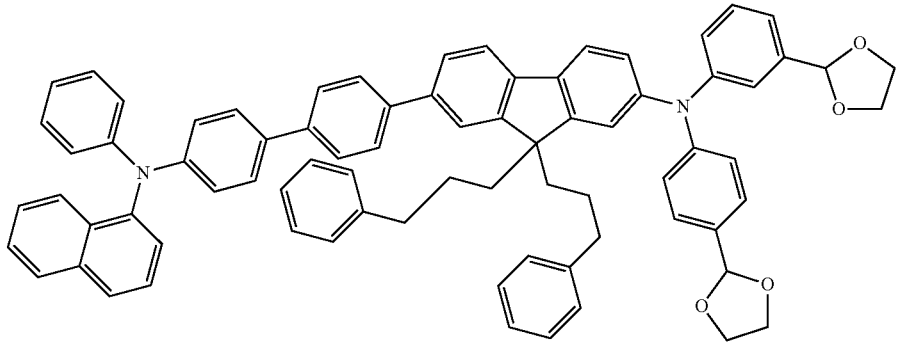

N-(3-(1,3-dioxolan-2-yl)phenyl)-N-(4-(1,3-dioxolan-2-yl)phenyl)-7-(4'-(naphthalen-1-yl(phenyl)amino)-[1,1'-biphenyl]-4-yl)-9,9-bis(3-phenylpropyl)-9H-fluoren-2-amine Procedures:

A solution of N-(3-(1,3-dioxolan-2-yl)phenyl)-N-(4-(1,3-dioxolan-2-yl)phenyl)-7-(4'-(naphthalen-1-yl(phenyl)amino)-[1,1'-biphenyl]-4-yl)-9,9-bis(3-phenylpropyl)-9H-fluoren-2-amine (2.77 g, 0.0026 mol from dehalogenation I) in anhydrous THF (250 mL) was prepared and transferred by cannula to a clean, dry round bottom flask equipped with a reflux condenser. Triethylamine (3.6 mL, 0.0256 mol) was then added via syringe. Formic acid (0.9 mL, 0.0243 mol) was added slowly, dropwise via syringe. The reaction solution and system was then purged with an inert gas flow for 30 minutes, after which Pd(OAc)$_2$ (0.12 g, 0.0003 mol) and tBu$_3$P (0.16 g in 5 mL anhydrous toluene) were added. The reaction was heated to reflux for approximately 2 hours and then cooled to room temperature. The solution was filtered through a Celite and triethylamine treated silica gel plug, washing with excess ethyl acetate. Solvent was then removed by rotary evaporation and the resulting solid material was placed under vacuum to be carried on to deprotection.

Synthesis of 3-((4-formylphenyl)(7-(4'-(naphthalen-1-yl(phenyl)amino)-[1,1'-biphenyl]-4-yl)-9,9-bis(3-phenylpropyl)-9H-fluoren-2-yl)amino)benzaldehyde Procedures:

A solution of N-(3-(1,3-dioxolan-2-yl)phenyl)-N-(4-(1,3-dioxolan-2-yl)phenyl)-7-(4'-(naphthalen-1-yl(phenyl)amino)-[1,1'-biphenyl]-4-yl)-9,9-bis(3-phenylpropyl)-9H-fluoren-2-amine (2.67 g, 0.0025 mol) was dissolved in acetone (500 mL) in a round bottom flask. Aqueous hydrochloric acid solution (39 mL, 10%) was added slowly dropwise by syringe. The reaction was allowed to stir for 1 hour and reaction completion was monitored via thin-layer chromatography. The reaction solution was worked up with ethyl acetate (400 mL) and deionized water (1×500 mL, 4×200 mL). The organic fraction was collected and dried over anhydrous magnesium sulfate. Solids were removed by vacuum filtration and solvent by rotary evaporation. The resulting solid crude product was placed under vacuum. Purification was carried out chromatography (EtOAc/Hexane gradient 0%-25%). TLC pure fractions were collected and solvent was removed by rotary evaporation. The resulting solids were taken up in a minimum amount of ethyl acetate and precipitated into methanol (250 mL). Product characterization was confirmed by $^1$H NMR.

Yield=1.88 g

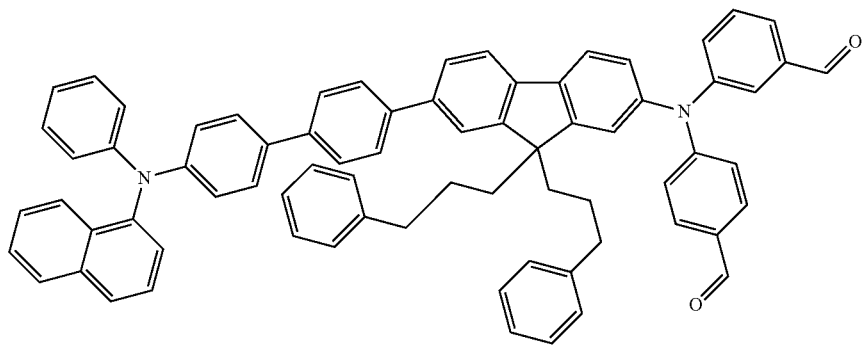

3-((4-formylphenyl)(7-(4'-(naphthalen-1-yl(phenyl)amino)-[1,1'-biphenyl]-4-yl)-9,9-bis(3-phenylpropyl)-9H-fluoren-2-yl)amino)benzaldehyde Synthesis of 7-(4'-(naphthalen-1-yl)phenyl)amino)-[1,1'-biphenyl]-4-yl)-9,9-bis(3-phenylpropyl)-N-(3-vinylphenyl)-N-(4-vinylphenyl)-9H-fluoren-2-amine

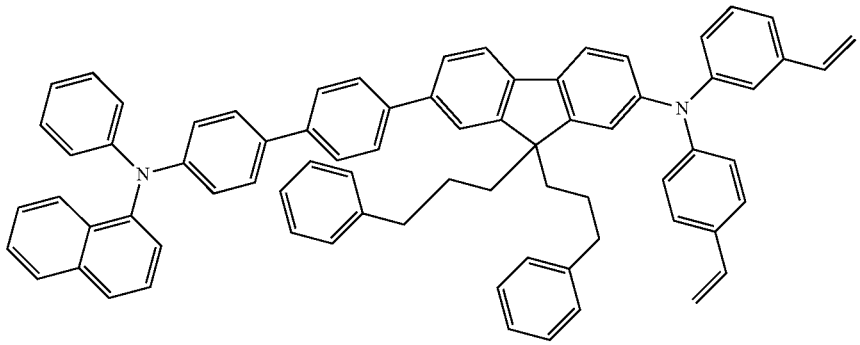

7-(4'-(naphthalen-1-yl(phenyl)amino)-[1,1'-biphenyl]-4-yl)-9,9-bis(3-phenylpropyl)-N-(3-vinylphenyl)-N-(4-vinylphenyl)-9H-fluoren-2-amine Procedures:

A solution of 3-((4-formylphenyl)(7-(4'-(naphthalen-1-yl(phenyl)amino)-[1,1'-biphenyl]-4-yl)-9,9-bis(3-phenylpropyl)-9H-fluoren-2-yl)amino)benzaldehyde (1.88 g, 0.0019 mol) was prepared in anhydrous THF (100 mL) in a clean, dry, and purged round bottom flask. To a dry round bottom flask equipped with an addition funnel methyltriphenylphosphonium bromide (2.02 g, 0.0057 mol) was added. Tetrahydrofuran (200 mL) was added to this reaction flask. Potassium tert-butoxide (0.66 g, 0.0059 mol) was then added to the reaction flask, and the flask was subsequently covered with aluminum foil. The solution of 3-((4-formylphenyl)(7-(4'-(naphthalen-1-yl(phenyl)amino)-[1,1'-biphenyl]-4-yl)-9,9-bis(3-phenylpropyl)-9H-fluoren-2-yl)amino)benzaldehyde/THF was then transferred to the addition funnel via cannula. This solution was then added to the reaction flask from the addition funnel dropwise over the course of twenty minutes. The reaction solution was allowed to stir for approximately one hour and completion was then monitored via thin-layer chromatography. Following confirmation of completion, the reaction solution was filtered through a celite/silica gel (treated with triethylamine) plug. Solvent was removed by rotary evaporation. The resulting solids were placed under vacuum. Crude mixture was purified by chromatography using ethyl acetate/hexanes as an eluent. Precipitation from a minimum amount of ethyl acetate into methanol yielded NMR pure product.

Yield=0.68 g

PLX-16-A

Amination

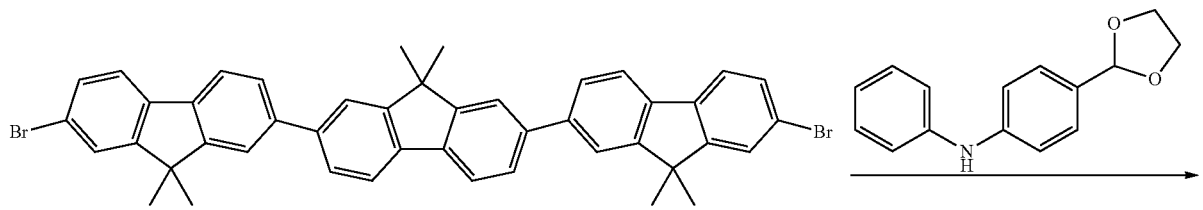

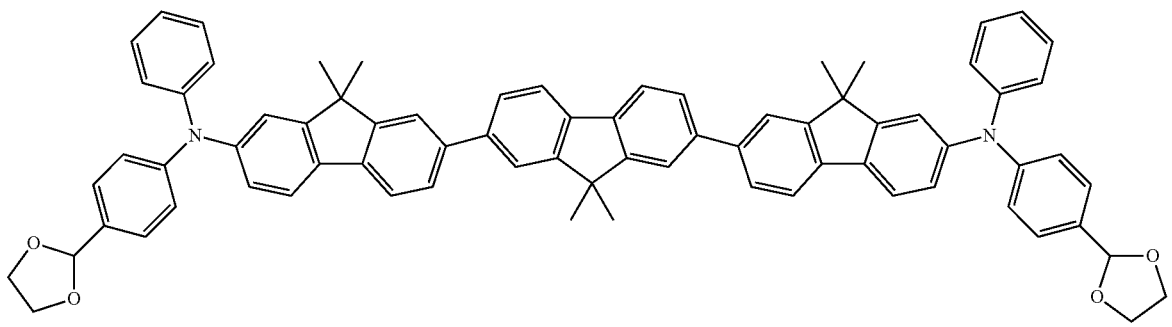

Prepared all clean, oven-dried glassware: 1 L three-neck round-bottom flask with a magnetic stir bar, and a reflux condenser. Charged flask with 2.5 g (3.40e-3 mol) of 2,7-dibromo-tris(9,9-dimethylfluorenylene). Charged flask with 2 g (~8.15e-3 mol) 4-(1,3-dioxolan-2-yl)-N-phenylaniline. Starting materials were dissolved with 500 mL of anhydrous, purged toluene transferred via cannula. Reaction solution was purged with strong nitrogen flow for about 30 minutes. A dry mixture of 1 g (~1.02e-2 mol) tBuONa and 0.13 g (~1.36e-4 mol) Pd2(dba)3 was added to the reaction flask. Via syringe, a solution of 2 mL toluene with 0.09 g (4.45e-4 mol) of tri-tert-butylphosphin was added to the flask. Reaction was brought to reflux for 2 hrs then monitored via thin-layer chromatography. TLC confirmed reaction completion. Reaction was removed from heat and allowed to cool to r.t. Crude reaction solution was filtered through a Celite/silica gel plug. Treated plug with chloroform/3% triethylamine solution. Washed plug with $CHCl_3$ basified with triethylamine (until the wash emerging from the funnel was clear). Removed most of solvent by rotary evaporation and adsorbed to silica. Chromatography was run initially using 100% hexane as an eluent, and then increasing to a 30% THF/70% Hexanes. A solubility problem was encountered that prolonged the column and hindered full separation. Collected similar fractions and removed solvents. 3.2 g of material isolated. NMR confirmed presence of desired product: $N^7,N^{7'''}$-bis(4-(1,3-dioxolan-2-yl)phenyl)-9,9,9',9',9'',9''-hexamethyl-$N^7,N^{7'''}$-diphenyl-9H,9'H,9''H-[2,2':7',2''-terfluorene]-7,7''-diamine. The 3.2 g of acetal was combined with 1.7 g from a previous reaction.

Dehalogenation 1&2

Prepared all clean, oven-dried glassware: 1000 mL three-neck round-bottom flask with a magnetic stir bar, and a reflux condenser. Dissolved 4.9 g (4.6e-3 mol) of $N^7,N^{7'''}$-bis(4-(1,3-dioxolan-2-yl)phenyl)-9,9,9',9',9'',9''-hexamethyl-$N^7,N^{7'''}$-diphenyl-9H,9'H,9''H-[2,2':7',2''-terfluorene]-7,7''-diamine in 400 mL dry THF. Transferred solution to reaction flask via cannulae. Added 7.76 mL triethylamine (5.6e-2 mol) via syringe. Added 1.75 mL formic acid (4.6e-2 mol) via syringe. Fuming observed. Reaction solution was purged with nitrogen for 30 mins. Added 0.12 g (~4.63e-4 mol) $Pd(OAc)_2$ via funnel. Added 0.141 g $tBu_3P$ (6.95e-4 mol) dissolved in 2 mL toluene via syringe. Reaction was refluxed for 2 hours. Solution turned black over time. Crude solution was filtered through celite/silica gel plug. The silica gel was pretreated with triethylamine in THF, then washed with 2 L of THF, until no spotting on TLC observed. Solvents were removed via rotary evaporation and carried to a second dehalogenation, which was carried out in an identical manner.

Deprotection

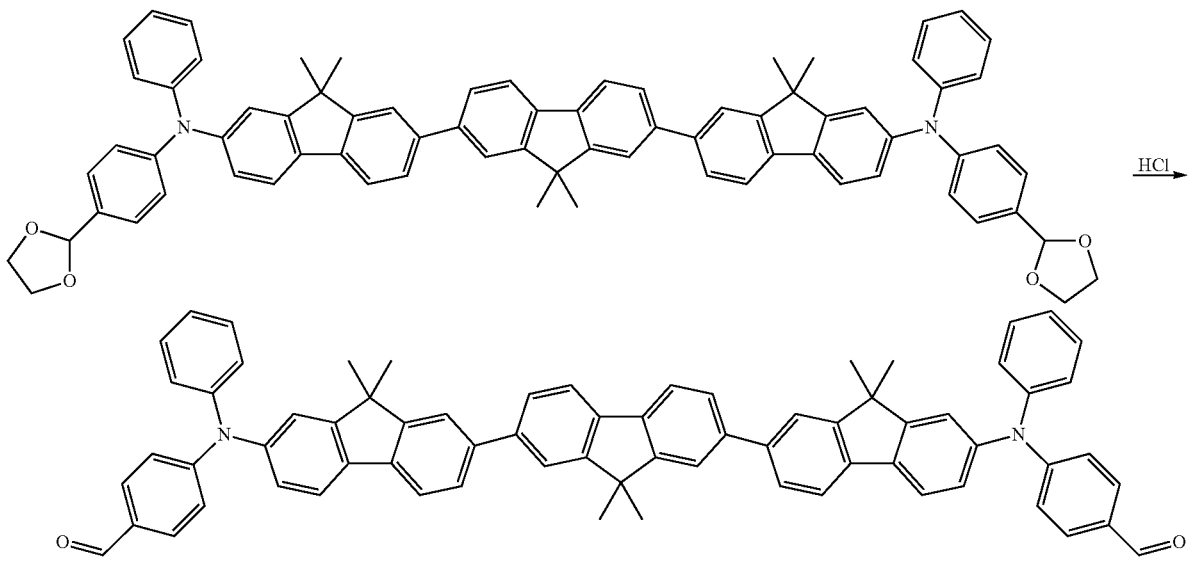

Prepared all clean, oven-dried glassware: 1000 mL three-neck round-bottom flask with a magnetic stir bar. Charged flask with 4.04 g (3.82e-3 mol) of $N^7,N^{7'''}$-bis(4-(1,3-dioxolan-2-yl)phenyl)-9,9,9',9',9'',9''-hexamethyl-$N^7,N^{7'''}$-diphenyl-9H,9'H,9''H-[2,2':7',2''-terfluorene]-7,7''-diamine. 500 mL of dry THF was transferred to the reaction flask via cannulae to dissolve all of the starting material. Transferred 7.64 mL 0.1M HCl solution dropwise to flask via syringe. As acid hit reaction solution, some precipitate was observed to form, which quickly redissolved. After ~15 mins, addition of acid was complete, and solution had yellowed slightly. Let stir for 30 mins. TLC confirmed reaction completion. Crude solution was extracted into 200 mL dichloromethane and washed with 3×500 mL of DI $H_2O$ until neutral. Dried organic layer over $MgSO_4$. Gravity filtered off salts. Removed solvents, store under vacuum. Column chromatography: Attempted chromatography in EtOAc/Hexane and Toluene/Hexane solvent systems, with solubility issues encountered in both. The mass of almost pure fractions was 2.8 g after drying. NMR confirmed the presence of desired product: 4,4'-((9,9,9',9',9'',9''-hexamethyl-9H,9'H,9''H-[2,2':7',2''-terfluorene]-7,7''-diyl)bis(phenylazanediyl))dibenzaldehyde.

Wittig

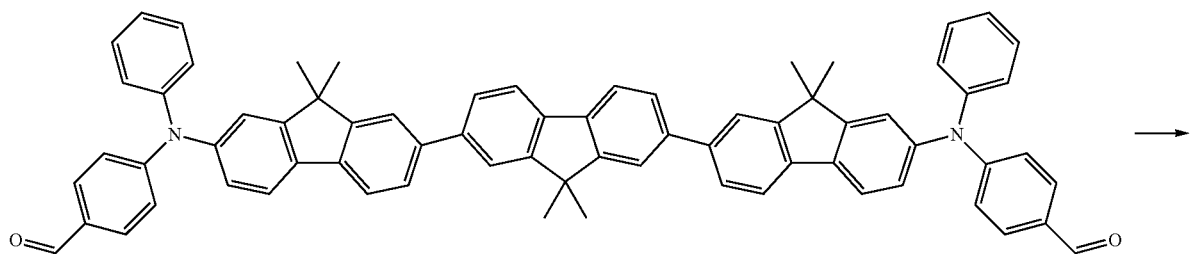

→

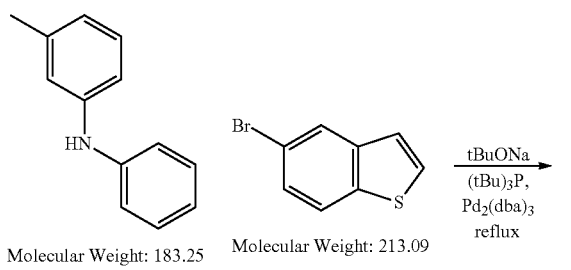

PLX-16-B

Prepared all clean, oven-dried glassware: 1000 mL three-neck round-bottom flask with a magnetic stir bar. Charged reaction flask with 3.1 g $CH_3PPh_3Br$ via funnel. Charged reaction flask with 1.01 tBuOK via funnel. Added ~400 mL dry THF to reaction flask via cannulae, attempting to dissolve $CH_3PPh_3Br$/tBuOK. Milky-yellow solution was formed, some larger solids observed. The suspension was allowed to stir at 800 rpm for >15 min before the reaction flask was covered in foil. The addition funnel was charged with 2.8 g of 4,4'-((9,9,9',9',9'',9''-hexamethyl-9H,9'H,9''H-[2,2':7',2''-terfluorene]-7,7''-diyl)bis(phenylazanediyl))dibenzaldehyde which was dissolved with ~40 mL dry THF transferred via syringe. The dialdehyde solution was added dropwise (2 Hz) to the reaction flask containing the ylide. After addition was complete, solution turned yellowish. TLC confirmed that reaction had completed. The crude reaction was filtered through celite/silica gel plug. The solvents were removed using a temperature no higher than 40° C. Crude mixture was dried under vacuum overnight and then redissolved in minimal chloroform. Wet loaded in 25% $CHCl_3$/75% hexanes onto a chromatography column at 15% $CHCl_3$/85% Hexanes and began elution. Collected similar fractions and removed solvents. Redissolved in $CH_2Cl_2$ and precipitated into room temperature HPLC grade MeOH. After some time drying, the solids were transferred to a tared vial. Mass of solids after drying was 1.65 g. NMR confirmed desired product: 9,9,9',9',9'',9''-hexamethyl-$N^7,N^{7'''}$-diphenyl-$N^7,N^{7'''}$-bis(4-vinylphenyl)-9H,9'H,9''H-[2,2':7',2''-terfluorene]-7,7''-diamine.

Synthesis of N-phenyl-N-(m-tolyl)benzo[b]thiophen-5-amine

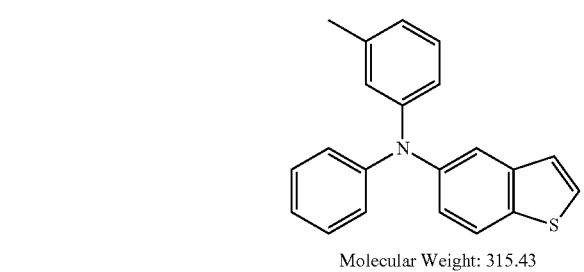

Procedure:

To a clean and dry 2 L three-neck round bottom flask was added 3-methyldiphenylamine (15.129 g, 0.083 mol) and 5-bromobenzo[b]thiophene (15.000 g, 0.070 mol). Anhydrous toluene (800 mL) was added via cannula. All starting materials dissolved. The solution was purged with strong nitrogen flow for 30 minutes. Following this, sodium tert-butoxide (10.151 g, 0.106 mol), Pd2(dba)3 (1.290 g, 0.0016 mol), and a solution of tri-tert-butylphosphine (0.92 g, 0.005 mol) in toluene (5 mL) were added to the reaction. Heat was applied to reflux, and the reaction was allowed to continue at this temperature overnight. Thin layer chromatography was able to determine reaction completion.

The reaction solution was filtered through a Celite/silica gel plug, washing thoroughly with ethyl acetate. The solution was nearly evaporated, at which point, acetone and silica gel were added to prepare a dry load mixture for column chromatography on silica gel. Column was run using a gradient eluent starting at 100% hexane and increasing in 2% increments of ethyl acetate until a final solution of 10% ethyl acetate/hexane was used. Solvent was then removed from product containing fractions by rotary evaporation. Resulting nearly-pure material was placed under vacuum to dry overnight. Product Obtained=20.5 g.

Synthesis of N-phenyl-N-(m-tolyl)-2-(trimethylstannyl)benzo[b]thiophen-5-amine

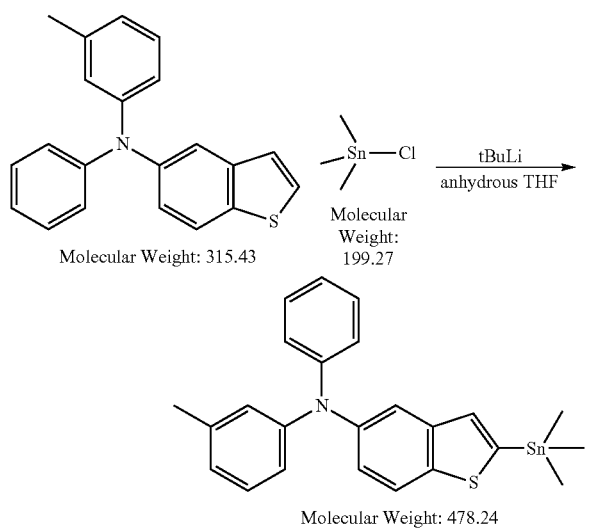

Procedure:

To a clean and dry 2 L three-neck round bottom flask equipped with magnetic stir bar, addition funnel, and low-temperature thermometer with adapter, N-phenyl-N-(m-tolyl)benzo[b]thiophen-5-amine (20.50 g, 0.0014 mL) was charged. Anhydrous tetrahydrofuran (THF) (700 mL) was then added via cannula. The reaction vessel was cooled to −78° C. in an acetone/liquid nitrogen bath. Upon reaching the desired temperature, t-butyllithium (1.7M, 76.5 mL) was transferred to the addition funnel via cannula and added to the reaction flask drop-wise. The reaction was allowed to stir for 30 minutes and was then warmed to a temperature of 0° C. Upon reaching this temperature, the reaction flask was again placed in the cooling bath until reaching −78° C. Trimethyltin chloride solution (1.0M, 136 mL) was added drop-wise via cannula. The reaction was allowed to stir at this temperature for 30 minutes before warming to ambient temperature.

The reaction solution was poured slowly into a 1 L RBF and placed on a rotary evaporator to reduce the volume to approximately 300 ml and then transferred into a 1 L separatory funnel. 200 ml of DI water and 200 ml of MTBE were added to the funnel. The organic layer was washed with DI H2O (3×200 mL) before being collected and solvent was removed by rotary evaporation at a temperature not to exceed 40° C. HPLC 76.91% Pure Crude Product: 22.76 g.

Synthesis of 2,2'-(((2,7-dibromo-9H-fluorene-9,9-diyl)bis(butane-4,1-diyl))bis(3,1-phenylene))bis(1,3-dioxolane)

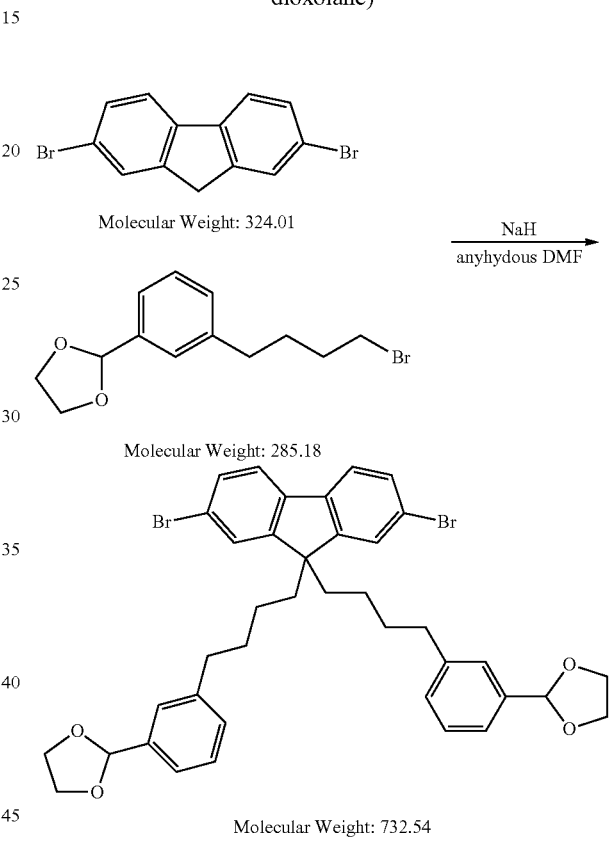

Procedure:

To a clean, dry 500 mL round bottom flask was added sodium hydride (0.825 g, 0.0344 mol). The reaction flask was equipped with a reflux condenser. A bubbler was added to one neck of the flask to allow any rapid gas formation to escape the system and was placed in an ice water bath. Anhydrous DMF (~250 mL) was added to the reaction flask via cannula and stirred vigorously. A solution of 2,7-dibromo-9H-fluorene (5.00 g, 0.0154 mol) in anhydrous DMF (~30 mL) was prepared and then added to the reaction flask slowly, drop-wise. Following the addition, the reaction was allowed to stir for an additional 30 minutes, after which the reaction was removed from the ice water bath and warmed to room temperature. At this point, a solution of 2-(3-(4-bromobutyl)phenyl)-1,3-dioxolane (5.265 g, 0.0185 mol) in anhydrous DMF (~30 mL) was added to the reaction flask slowly, drop-wise. Then reaction was then heated to 80° C. for one hour, and then monitored via TLC. Upon the confirmation of reaction completion, the reaction was cooled to room temperature.

The resulting solution was worked up with MTBE (300 mL) and DI H2O (5×200 mL). The organic fraction was collected and dried over anhydrous magnesium sulfate. Solids were removed by vacuum filtration and solvent by rotary evaporation. The resulting white solids were placed under vacuum overnight. The product was then prepped for a dry-load into a manual "wash" column with a gradient of 0%-20% ethyl acetate/hexane solutions in 5% increments. Product fractions were collected and solvents removed via rotary evaporation. Product Obtained: 6.370 g.

Synthesis of 2,2'-(9-(4-(3-(1,3-dioxolan-2-yl)phenyl) butyl)-9-(4-(4-(1,3-dioxolan-2-yl)phenyl)butyl)-9H-fluorene-2,7-diyl)bis(N-phenyl-N-(m-tolyl)benzo[b]thiophen-5-amine)

the mixture. The reaction was cooled to room temperature and filtered through a celite/silica gel plug. The filtrate was stripped of solvent by rotary evaporation. Following this the product was dissolved in a minimum amount of ethyl acetate and added slowly, drop-wise, into cold methanol. Solids were filtered through a Buchner funnel and washed thoroughly with methanol. Product Obtained: 10.1 g.

Dehalogenation of 2,2'-(9-(4-(3-(1,3-dioxolan-2-yl) phenyl)butyl)-9-(4-(4-(1,3-dioxolan-2-yl)phenyl) butyl)-9H-fluorene-2,7-diyl)bis(N-phenyl-N-(m-tolyl)benzo[b]thiophen-5-amine)

Procedure:
2,2'-(9-(4-(3-(1,3-dioxolan-2-yl)phenyl)butyl)-9-(4-(4-(1, 3-dioxolan-2-yl)phenyl)butyl)-9H-fluorene-2,7-diyl)bis(N-

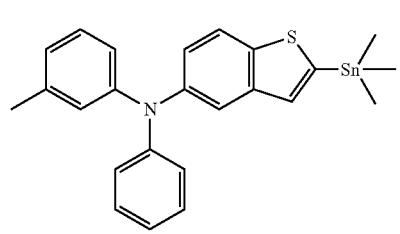

Molecular Weight: 478.24

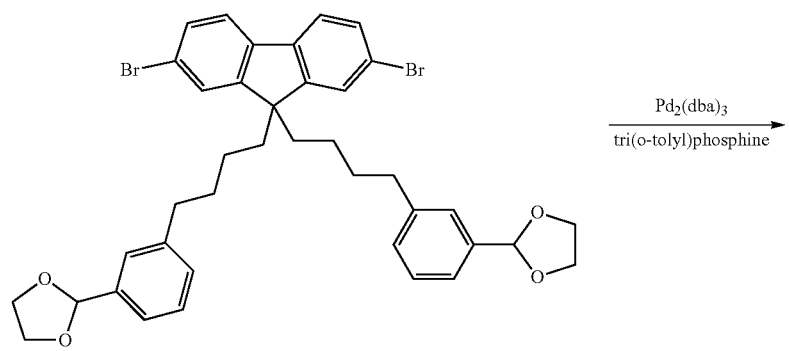

Molecular Weight: 732.54

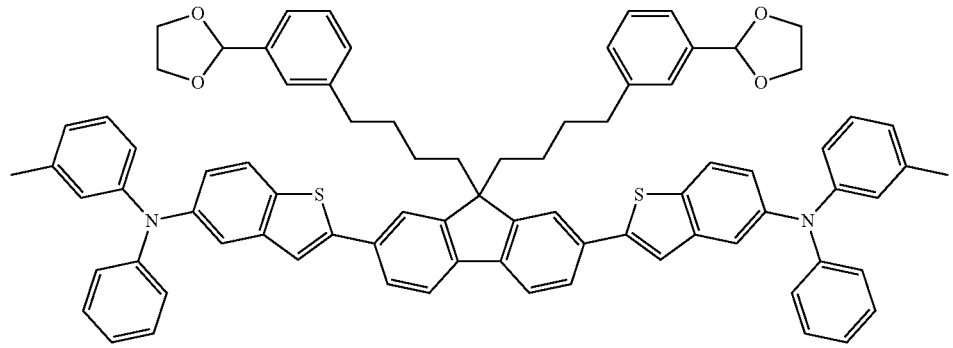

Molecular Weight: 1201.58

Procedure:
A clean and dry 1 L three-neck round bottom flask equipped with magnetic stir bar and reflux condenser was prepared and charged with 2,2'-(((2,7-dibromo-9H-fluorene-9,9-diyl)bis(butane-4,1-diyl))bis(3,1-phenylene))bis(1,3-dioxolane) (6.39 g, 0.0087 mol). All anhydrous toluene used in this reaction was purged with dry nitrogen flow over the weekend. A solution of N-phenyl-N-(m-tolyl)-2-(trimethylstannyl)benzo[b]thiophen-5-amine (76.91% purity, 29.6 g) in anhydrous toluene (400 mL) was prepared and transferred to the reaction flask via cannula. The reaction solution was purged with dry nitrogen flow for one hour. Pd2(dba)3 (0.796 g, 0.0009 mol) and tri(o-tolyl)phosphine (1.063 g, 0.003 mol) was added to the reaction flask manually. The reaction was heated to 110° C. for 24 hours, after which reaction completion was confirmed by TLC which indicated the disappearance of 2,2'-(((2,7-dibromo-9H-fluorene-9,9-diyl)bis(butane-4,1-diyl))bis(3,1-phenylene))bis(1,3-dioxolane) from phenyl-N-(m-tolyl)benzo[b]thiophen-5-amine) (10.1 g, 0.0084 mol) was dissolved in a 2 L 1N-RBF in anhydrous toluene (150 mL) via 50 mL syringe. All dissolved with stirring. Solution is golden in color. This 2,2'-(9-(4-(3-(1,3-dioxolan-2-yl)phenyl)butyl)-9-(4-(4-(1,3-dioxolan-2-yl) phenyl)butyl)-9H-fluorene-2,7-diyl)bis(N-phenyl-N-(m-tolyl)benzo[b]thiophen-5-amine) solution was transferred to a 500 mL 3N-RBF equipped with a reflux condenser via 50 mL syringe. Triethylamine (11 mL, 0.0841 mol) then formic acid (3 mL, 0.0799 mol) were added via 10 and 3 mL syringes, respectively. The solution was then purged with nitrogen for 1 hour. Then, Pd(OAc)2 (0.1797 g, 0.0008 mol) and tBu3P (0.2575 g, 0.0013 mol) in 5 mL anhydrous toluene were added. The reaction was heated to reflux at 110° C. via heating mantle and left to stir and heat at this temperature for 1 hour and 30 minutes. It was then cooled to room temperature. Filtered solution reaction through a celite/silica plug basified with triethylamine and washed with ethyl acetate. Product Obtained: 10.0 g.

Dehalogenation of 2,2'-(9-(4-(3-(1,3-dioxolan-2-yl) phenyl)butyl)-9-(4-(4-(1,3-dioxolan-2-yl)phenyl) butyl)-9H-fluorene-2,7-diyl)bis(N-phenyl-N-(m-tolyl)benzo[b]thiophen-5-amine)

Procedure:
2,2'-(9-(4-(3-(1,3-dioxolan-2-yl)phenyl)butyl)-9-(4-(4-(1,3-dioxolan-2-yl)phenyl)butyl)-9H-fluorene-2,7-diyl)bis(N-phenyl-N-(m-tolyl)benzo[b]thiophen-5-amine) (10.0 g, 0.0084 mol) was dissolved in a 1 L 1N-RBF in anhydrous toluene (150 mL) via 50 mL syringe. All dissolved with stirring. This 2,2'-(9-(4-(3-(1,3-dioxolan-2-yl)phenyl)butyl)-9-(4-(4-(1,3-dioxolan-2-yl)phenyl)butyl)-9H-fluorene-2,7-diyl)bis(N-phenyl-N-(m-tolyl)benzo[b]thiophen-5-amine) solution was transferred to a 500 mL 3N-RBF equipped with a reflux condenser via 50 mL syringe. Triethylamine (11 mL, 0.0841 mol) then formic acid (3 mL, 0.0799 mol) were added via 10 and 3 mL syringes, respectively. The solution was then purged with nitrogen for 1 hour. Then, Pd(OAc)2 (0.167 g, 0.0008 mol) and tBu3P (0.236 g, 0.0013 mol, in 5 mL anhydrous toluene were added. The reaction was heated to reflux at 110° C. via heating mantle and left to stir and heat at this temperature overnight. It was then cooled to room temperature. Filtered solution reaction through a celite/silica plug basified with triethylamine and washed with ethyl acetate. Following this, the solution was placed into a separatory funnel and washed with 5×200 mL and dried with magnesium sulfate. Solids were filtered off and the organic layer was placed on a rotary evaporator to remove excess solvents. Product Obtained: 8.6 g.

Synthesis of 3-(4-(9-(4-(4-formylphenyl)butyl)-2,7-bis(5-(phenyl(m-tolyl)amino)benzo[b]thiophen-2-yl)-9H-fluoren-9-yl)butyl)benzaldehyde

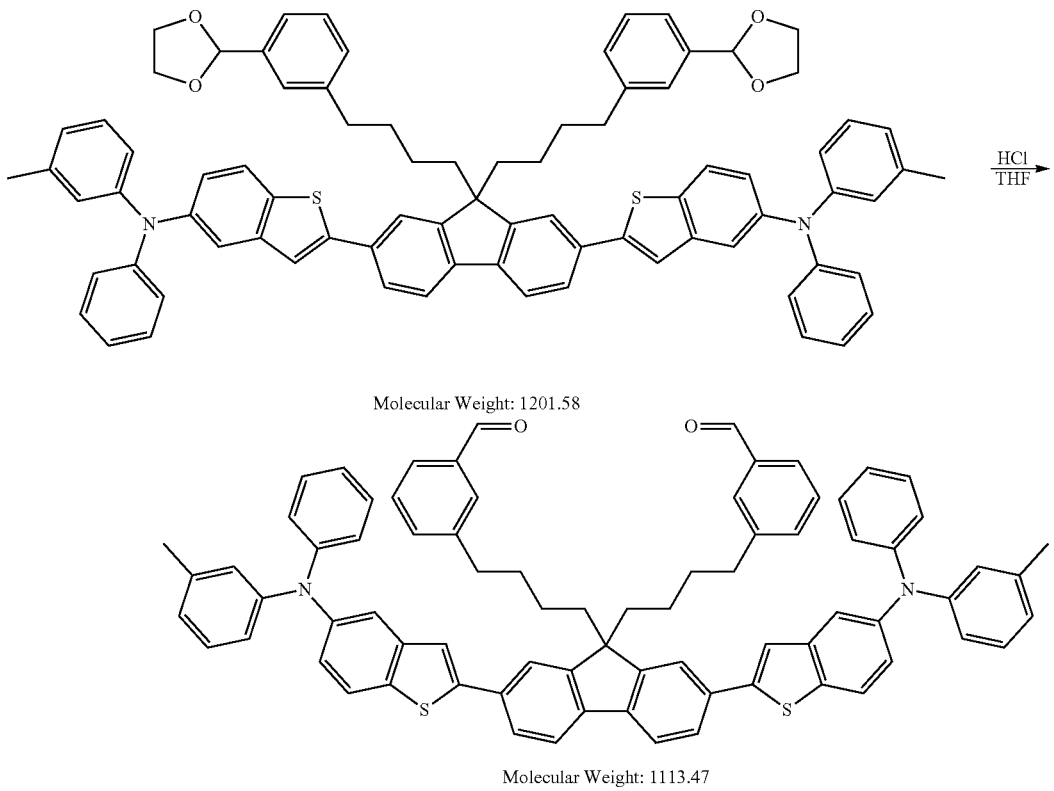

Procedure:
Chromasolv THF (150 mL) was added to a 250 mL single-neck round bottom flask that contained 2,2'-(9-(4-(3-(1,3-dioxolan-2-yl)phenyl)butyl)-9-(4-(4-(1,3-dioxolan-2-yl)phenyl)butyl)-9H-fluorene-2,7-diyl)bis(N-phenyl-N-(m-tolyl)benzo[b]thiophen-5-amine) (8.6 g, 0.0002 mol). All dissolved with stirring via stir plate. Solution was pale yellow in color. Aqueous hydrochloric acid solution (2.0 mL, 2.0 M) was then added drop-wise via 2 mL syringe. The reaction was permitted to stir for 15 minutes. Reaction completion was monitored via $^1$H NMR. It indicated that the reaction was complete. Triethylamine (2%) was added to the reaction flask to quench the reaction. Deionized water (150 mL) and MTBE (150 mL) were added to a 500 mL separatory funnel via glass funnel. The organic and aqueous layers were separated. The organic layer was washed 4×50 mL DI water. Solvents were removed from the organic layer via rotary evaporation. The product was then prepped for a dry-load into a manual column with a gradient of 0%-20% ethyl acetate/hexane solutions in 5% increments. Product fractions were collected and solvents removed via rotary evaporation. Product Obtained: 7.3 g.

Synthesis of 2,2'-(9,9-bis(4-(3-vinylphenyl)butyl)-9H-fluorene-2,7-diyl)bis(N-phenyl-N-(m-tolyl)benzo[b]thiophen-5-amine)

The solution was filtered through a celite/silica gel plug treated with 2% triethylamine/ethyl acetate solution (500 mL). It was washed with ethyl acetate (1 L). Solvents were removed via rotary evaporation. The product was adsorbed to silica gel as a dry load to a manual column. 3 L of 2% triethylamine/hexane, 1 L of 10% ethyl acetate/hexane/triethylamine, 1 L of 20% ethyl acetate/hexane/triethylamine, and 3 L of 30% ethyl acetate/hexane/triethylamine were placed through the column. Product fractions were collected and solvents evaporated off. The product left from the column was a liquid so it was precipitated into cold methanol and

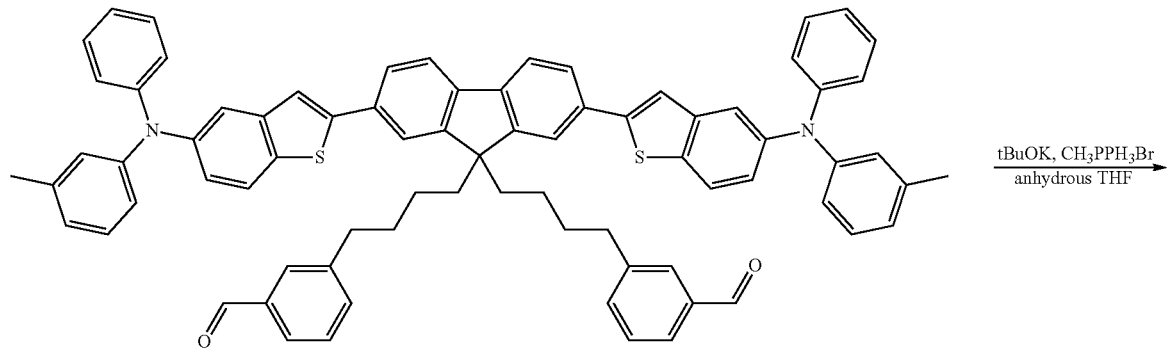

Molecular Weight: 1113.47

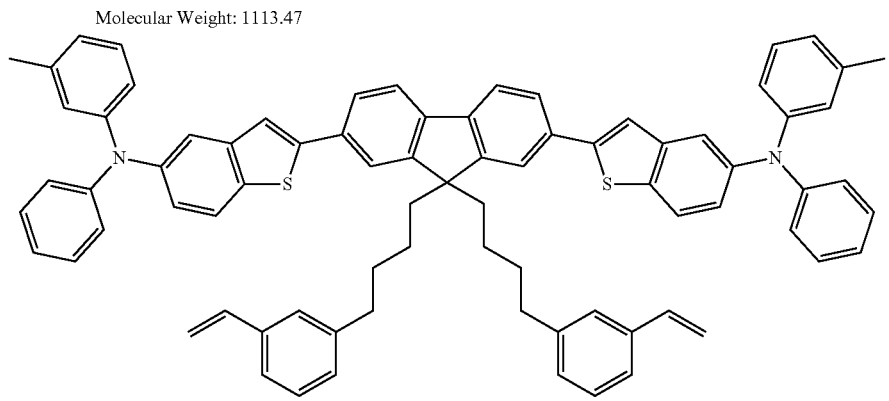

Molecular Weight: 1109.53

Procedure:

In a 500 mL single-neck round bottom flask, 3-(4-(9-(4-(4-formylphenyl)butyl)-2,7-bis(5-(phenyl(m-tolyl)amino)benzo[b]thiophen-2-yl)-9H-fluoren-9-yl)butyl)benzaldehyde (8.2 g, 0.0074 mol) was dissolved in anhydrous THF (200 mL) with swirling and vigorous stirring via stir plate. Methyltriphenylphosphonium bromide (7.9006 g, 0.0221 mol) was added to a 500 mL 3N-RBF equipped with an addition funnel. Anhydrous THF (50 mL) was added to the reaction flask via 50 mL syringe and permitted to stir. Potassium tert-butoxide (2.4880 g, 0.0221 mol) was then added to the reaction flask and the flask was subsequently covered with aluminum foil. The 3-(4-(9-(4-(4-formylphenyl)butyl)-2,7-bis(5-(phenyl(m-tolyl)amino)benzo[b]thiophen-2-yl)-9H-fluoren-9-yl)butyl)benzaldehyde solution was then transferred to the addition funnel via cannula. This solution was added drop-wise to the reaction flask from the addition funnel. The reaction was permitted to stir for 1 hour. Reaction completion was monitored via TLC and $^1$H NMR.

filtered through a Buchner funnel. Solid product was placed in the vacuum oven to dry over the weekend. Product Obtained: 5.96 g.

$^1$H NMR (CDCl3, 300 MHz) 0.75-0.9 (m, 4H), 1.30-1.45 (m, 4H), 2.05-2.15 (m, 4H), 2.3-2.4 (m, 4H), 5.12 (d, 2H), 5.62 (d 2H), 6.50-6.70 (m, 2H), 6.8-7.35 (m, 28H), 7.40-7.50 (m, 4H), 7.6-7.8 (m, 8H).

PLX-17-A 3,6-diphenylthieno[3,2-b]thiophene Synthesis

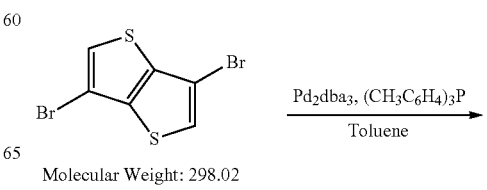

Molecular Weight: 298.02

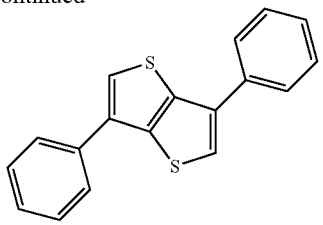

Molecular Weight: 292.42

Procedures:

In the glovebox, a 500 mL Schlenk flask was charged with 3,6-dibromothieno[3,2-b]thiophene (4.85 g, 0.0163 mol), Pd$_2$dba$_3$ (1.5 g, 0.0017 mol), and tri(o-tolyl)phosphine (2.0 g, 0.0066 mol). Outside the glovebox, added anhydrous toluene (163 mL) that was bubbled overnight via a strong nitrogen flow via syringe and trimethyl(phenyl)tin (15.7 g, 0.0653 mol) via syringe. The solution was degassed via five vacuum-nitrogen cycles. Solution was maroon in color. The solution was purged via a strong nitrogen flow for 30 minutes, and then placed in an oil bath pre-heated to 100° C. The solution became blacker in color. Additional Pd$_2$dba$_3$ (3.1 g, 0.0034 mol) and tri(o-tolyl)phosphine (3.99 g, 0.0131 mol) were added and the reaction was continued overnight. The next morning, the reaction was cooled to room temperature.

Ethyl acetate (150 mL) and aqueous hydrochloric acid solution (150 mL, 1.0M) were added to a 1 L separatory funnel via glass funnel, followed by the reaction solution. NaCl was added to break up the emulsion that formed, and then the organic and aqueous layers were separated. The organic layer was washed with aqueous hydrochloric acid solution (450 mL, 1.0M). NaCl was added to break up the emulsion that formed and the organic and aqueous layers were separated.

The organic layer was then filtered through a celite/silica gel plug, washing thoroughly with a 2% triethylamine/ethyl acetate solution (1.6 L), hexane (500 mL), and THF (375 mL). Solids precipitated from solution as solvents were removed via rotary evaporation. Dissolving the solids with chlorobenzene was not successful, even with heating via heat gun. Added methanol (400 mL) to the solution for a trituration in methanol and let this continue overnight at 65° C. The next morning, the solution was cooled to room temperature then placed in an ice-water bath in order to cool it to 0° C. and precipitate as much of the product as possible. The product was filtered through a Buchner funnel lined with filter paper, then dried under vacuum leading to 2.53 g product. Product purity was confirmed via HPLC. Product characterization was confirmed via $^1$H NMR.

In a 1 L single-neck round bottom flask, the product was dissolved in THF (10 mL) via syringe with stirring and extensive heating via heat gun. The solution was added dropwise via a glass pipette into methanol (50 mL, pre-chilled in an ice-water bath). After stirring at 0° C. the product was filtered through a Buchner funnel then dried under vacuum leading to 2.35 g of product.

2,5-dibromo-3,6-diphenylthieno[3,2-b]thiophene Synthesis

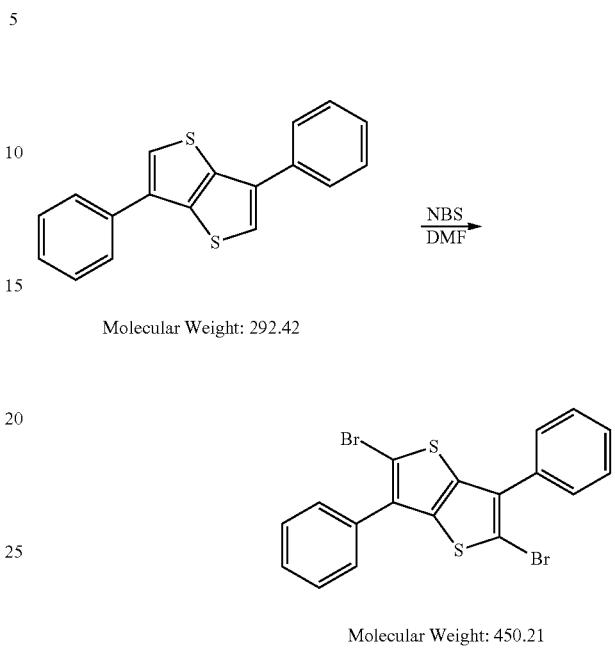

Procedures:

A 500 mL three-neck round bottom flask equipped with a thermometer was charged with 3,6-diphenylthieno[3,2-b]thiophene (2.9 g, 0.0099 mol). Anhydrous DMF (100 mL) was added via syringe. Solids all dissolved after additional anhydrous DMF (24 mL), stirring, and heating to 85° C. But, as this solution cooled back down to room temperature, the starting material precipitated. The solution was cooled to 0° C. via ice-water bath and stirred at 0° C. for 45 minutes. NBS (3.52 g, 0.0198 mol) was then added to the flask in one portion. Reaction completion was monitored via TLC and/or GC-MS. 1 hour and 30 minutes into the reaction, GC-MS indicated the presence of starting material and mono-brominated product (two spots on TLC). The ice-water bath was removed and the solution was allowed to warm up to room temperature. In an attempt to dissolve more starting material, chloroform (15-35 mL) was added via syringe in four portions over a 1 hour and 30 minute interval. After each chloroform addition, gentle heating was applied (warmed the solution up to 35° C.) via heat gun. GC-MS indicated the presence of mono- and di-brominated product. Acetic acid (5 mL) was added via syringe. GC-MS still indicated the presence of mono- and di-brominated product. In addition, still two spots on TLC. At this point, additional NBS (0.36 g, 0.0020 mol) was added and the reaction was stirred overnight at room temperature. The next morning, GC-MS indicated the presence of just the desired di-brominated product.

Deionized water (200 mL) was added and the solution was stirred for 30 minutes. Not all the product was in solution so the solution was first filtered through a Buchner funnel. The filtrate, as well as additional deionized water (200 mL), was added to a 1 L separatory funnel and the organic and aqueous layers were separated. The aqueous layer was back-extracted with chloroform (3×200 mL). The solids filtered previously in the Buchner funnel were dissolved with toluene (100 mL) and chloroform (800 mL) into a separate filter flask. The filtrate (500 mL) and deionized water (400 mL) were transferred to the 1 L separatory funnel via glass funnel. After separation, the aqueous layer was back-extracted with chloroform (2×200 mL).

The organic layer (1.5 L) was washed with deionized water (3×1.4 L). Solvents were removed from the organic layer via rotary evaporation, and then methanol (500 mL) was added. The solution was stirred at room temperature for 30 minutes, then placed in an ice-water bath and cooled to 0° C. The solution was filtered through a Buchner funnel. TLC indicated that the solids were the product. The product was further dried under vacuum. Product obtained: 3.05 g. Product purity was confirmed via HPLC.

4,4'-(3,6-diphenylthieno[3,2-b]thiophene-2,5-diyl)bis(N,N-diphenylaniline) Synthesis

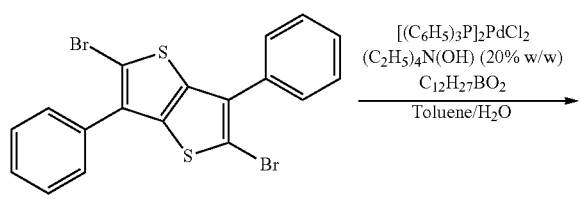

Molecular Weight: 450.21

Procedures:

A 500 mL Schlenk flask was charged with 2,5-dibromo-3,6-diphenylthieno[3,2-b]thiophene (2.3 g, 0.0052 mol) and 4-(diphenylamino)phenylboronic acid pinacol ester (4.74 g, 0.0128 mol). Anhydrous toluene (173 mL) that was purged overnight via a strong nitrogen flow was added via syringe. Solids did not all dissolve. Solution was light tan in color. Tetraethylammonium hydroxide (52 mL, 20% w/w) was added via syringe. The solution was purged via a strong nitrogen flow for 1 hour, and then degassed via five vacuum-nitrogen cycles. Dichloro-bis(triphenylphosphine)palladium (0.2 g, 0.0002 mol) was added. The reaction was heated to 100° C. Additional 4-(diphenylamino)phenylboronic acid pinacol ester (2.3 g, 0.0063 mol) and dichloro-bis(triphenylphosphine)palladium (0.1 g, 0.0002 mol) were added and the reaction was continued overnight. It was then cooled to room temperature.

The reaction solution was filtered through a celite/silica gel plug, washing thoroughly with dichloromethane (1 L) and a 2% triethylamine/chloroform solution (1 L). As solvents were removed via rotary evaporation, solids precipitated from the solution. Chloroform (40 mL) was added via syringe in an attempt to re-dissolve these solids without success. Acetone (200 mL) was then added and the solution was cooled to 0° C. The solids were filtered through a Buchner funnel lined with filter paper then further dried under vacuum. Product obtained: 2.1 g. Product purity was confirmed via HPLC.

Dehalogenation of 4,4'-(3,6-diphenylthieno[3,2-b]thiophene-2,5-diyl)bis(N,N-diphenylaniline) (Run Twice)

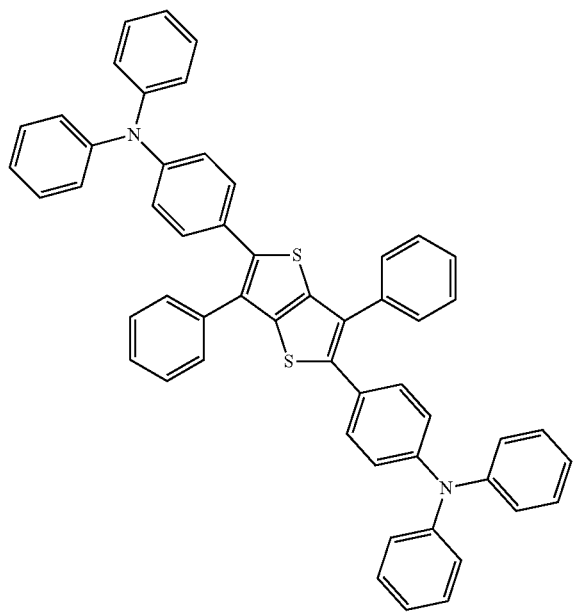

Molecular Weight: 779.02

Procedures:

A 250 mL three-neck round bottom flask equipped with a reflux condenser and thermometer was charged with 4,4'-(3,6-diphenylthieno[3,2-b]thiophene-2,5-diyl)bis(N,N-diphenylaniline) (2.1 g, 0.0027 mol). Anhydrous toluene (54 mL) was added via syringe. Solids did not all dissolve, even with stirring. Solution was brown in color. Next, triethylamine (3.80 mL, 0.0273 mol) was added via syringe. Then, formic acid (1.00 mL, 0.0265 mol) was added dropwise via syringe. The reaction solution was purged via a strong nitrogen flow for 1 hour, after which Pd(OAc)$_2$ (0.1 g, 0.0006 mol) and tBu$_3$P (0.1 g, 0.0006 mol, in 2 mL anhydrous toluene) were added. The reaction was heated to 100° C. and left to stir at this temperature for 2 hours, after which it was cooled to room temperature. It is important to note that this dehalogenation did not become black in color.

The reaction solution was filtered through a celite/silica gel plug, washing thoroughly with a 2% triethylamine/chloroform solution. As solvents were removed via rotary evaporation, the product precipitated from solution. In order to precipitate more of the product from solution, methanol (200 mL) was added. The solution was stirred at room temperature for 10 minutes, and then filtered through a Buchner funnel. It was then dried under vacuum. Product obtained: 2.0 g.

The dehalogenation procedure was repeated a second time to yield 1.91 g product. Purification on 0.957 g product was carried out via sublimation. Product obtained: 0.758 g. Product purity was confirmed via HPLC. Product characterization was confirmed via ¹H NMR. ¹H NMR (300 MHz, (CD$_3$)$_2$CO) 6.8-7.6 (m).

PLX-17-B 3,6-dibromothieno[3,2-b]thiophene Synthesis

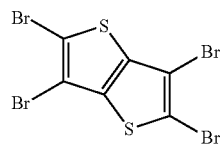

Molecular Weight: 455.81

HOAc, Zn, HCl/H$_2$O →

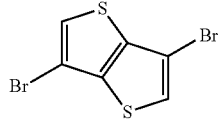

Molecular Weight: 298.02

Procedures:

A 1 L three-neck round bottom flask equipped with a reflux condenser was charged with perbromothieno[3,2-b]thiophene (30.0 g, 0.0658 mol) then glacial acetic acid (150 mL) via syringe. White solids remained undissolved in the clear solution. This solution was heated to 100° C. via oil bath and permitted to stir at this temperature for 30 minutes. Then, zinc dust (4.15 g, 0.0635 mol) was added. The reaction was permitted to stir at 100° C. for 1 hour, and then reaction completion was monitored via GC-MS. It indicated the presence of mono-, di-, tri-, and tetra-brominated product. More Zn dust (13.25 g, 0.2027 mol) was added in five portions over a 5 hour and 30 minute interval. It is also important to note that anhydrous toluene (100 mL) was added to the 500 mL three-neck round bottom flask after portion two of Zn dust was added. Even at the 5 hour and 30 minute point, GC-MS still indicated the presence of mono-, di-, tri-, and tetra-brominated product. Let the reaction cool to room temperature, then filtered it through a Buchner funnel. The solids were rinsed with toluene until no spotting observed on TLC.

The filtrate was transferred to a 2 L separatory funnel that contained deionized water (600 mL). NaCl was added along with additional chloroform (100 mL) to help break up the slight emulsion that formed. The organic layer/slight emulsion and aqueous layer were separated. The aqueous layer was back-extracted with chloroform (1×300 mL, 1×200 mL). The organic layer was washed with basic deionized water (4×700 mL) then deionized water (1×700 mL). The organic layer was filtered through a Buchner funnel to remove any residual salts and/or zinc, and then solvents were removed via rotary evaporation.

Methanol (100 mL) was added to the 1 L single-neck round bottom flask that contained the product and the solution was stirred and cooled to 0° C. via ice-water bath. The solution was stirred at 0° C. for 30 minutes, and then cooled to −35° C. to ensure maximum product precipitation. It was then filtered through a Buchner tunnel and the product was dried under vacuum. Product obtained: 16.62 g.

4,4'-(thieno[3,2-b]thiophene-3,6-diyl)bis(N,N-diphenylaniline) Synthesis

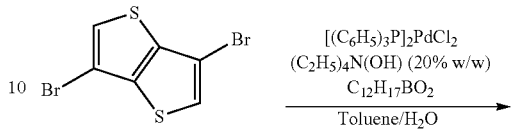

Molecular Weight: 298.02

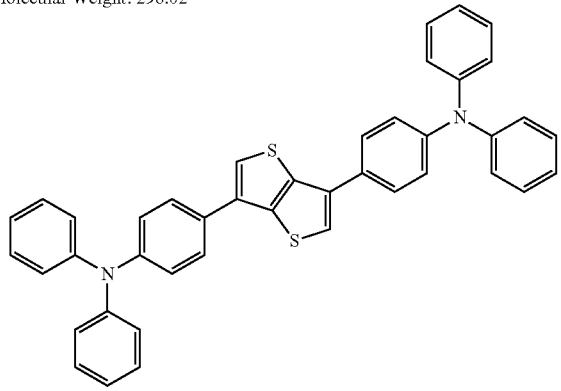

Molecular Weight: 626.83

Procedures:

A 2 L three-neck round bottom flask equipped with a reflux condenser and thermometer was charged with 3,6-dibromothieno[3,2-b]thiophene (5.02 g, 0.0168 mol) and 4-(diphenylamino)phenylboronic acid pinacol ester (15.0 g, 0.0403 mol). Anhydrous toluene (560 mL) that was purged overnight via a strong nitrogen flow was added via cannula. Solids all dissolved and the solution was peach in color. Tetraethylammonium hydroxide (168 mL, 20% w/w) was added via syringe. This solution was purged via a strong nitrogen flow for 1 hour and 30 minutes, then dichloro-bis(triphenylphosphine)palladium (0.08 g, 0.0001 mol) was added. The reaction was heated to 90° C. Additional dichloro-bis(triphenylphosphine)palladium (0.3 g, 0.0001 mol) and anhydrous toluene (18 mL) were added and the reaction was continued overnight. The next morning, TLC indicated that the reaction was complete. Let it cool to room temperature.

Deionized water (500 mL) and chloroform (500 mL) were added to a 2 L separatory funnel. The reaction solution was then transferred to the 2 L separatory funnel. NaCl was added to break up the slight emulsion that formed. The organic layer/slight emulsion and aqueous layer were separated. The aqueous layer was back extracted with chloroform (2×200 mL). The organic layer was washed with deionized water (3×1 L). The organic layer was then filtered through a celite/silica gel plug, washing thoroughly with ethyl acetate (1.5) and chloroform (1.5). Solvents were removed via rotary evaporation, and then the product was dried under vacuum. Product obtained 12.88 g.

The solids were purified by stirring at room temperature with acetone (300 mL), then filtration through a Buchner funnel. The product was then dried under vacuum. Product obtained 9.51 g. Product purity was confirmed via HPLC. Product characterization was confirmed via ¹H NMR.

4,4'-(2,5-dibromothieno[3,2-b]thiophene-3,6-diyl)bis(N,N-diphenylaniline) Synthesis

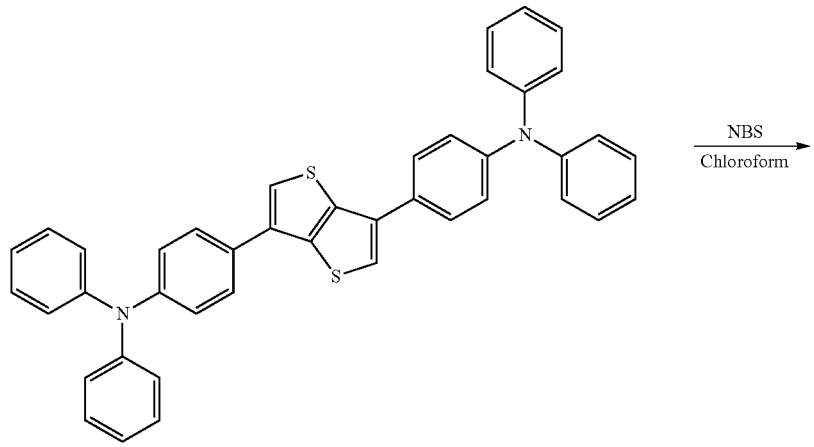

Molecular Weight: 626.83

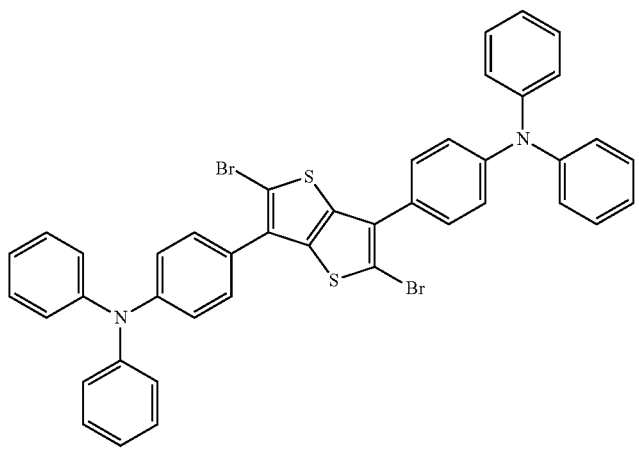

Molecular Weight: 784.62

Procedures:

A 500 mL three-neck round bottom flask equipped with a thermometer was charged with 4,4'-(thieno[3,2-b]thiophene-3,6-diyl)bis(N,N-diphenylaniline) (9.51 g, 0.0152 mol). Chloroform (152 mL) was added via syringe. Not all solids dissolved—even with stirring, extensive heating via heat gun, and additional chloroform (60 mL). Solution was tan in color. The solution was chilled to 0° C. via ice-water bath and permitted to stir at this temperature for 30 minutes. NBS (5.42 g, 0.0305 mol) was then added. 1-2 hours later, the reaction was stopped via the addition of methanol (250 mL), which precipitated the product. The solution was stirred at 0° C. for 30 minutes, and then filtered through a Buchner funnel. The product was then dried under vacuum. Product obtained: 11.74 g. Product purity was confirmed via HPLC.

(4-(1,3-dioxolan-2-yl)phenyl)trimethylstannane Synthesis

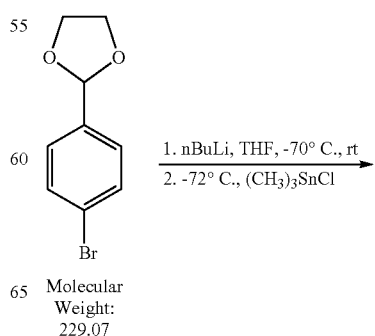

Molecular Weight: 229.07

-continued

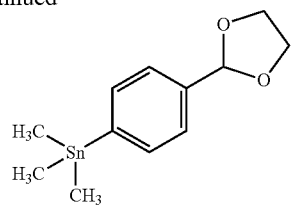

Molecular Weight: 312.98

Procedures:

A 3-L three-neck round bottom flask equipped with an addition funnel and a thermometer was charged with 2-(4-bromophenyl)-1,3-dioxolane (20.3 g, 0.0885 mol). Anhydrous THF (1.5 L) that was purged overnight via a strong nitrogen flow was added via cannula. Solids all dissolved with stirring. Solution was clear in color. The solution was cooled to −78° C. via dry ice-isopropanol bath, then tert-butyllithium solution (102 mL, 1.7M in pentane) was transferred to the addition funnel via cannula and added dropwise to the flask. The solution turned brown/grey then black/dark blue then dark blue/green. The solution was permitted to stir at −78° C. for 30 minutes, then the dry ice-isopropanol bath was removed and the solution was permitted to warm up to 0° C. The solution turned black. The solution was then placed back in the dry ice-isopropanol bath and cooled to −78° C. once again. Trimethyltin chloride (175 mL, 1.0 M in THF) was transferred to the addition funnel via syringe and added dropwise to the flask. The solution turned red/brown then peach. The solution was left in the dry ice-isopropanol bath for 30 minutes once all the trimethyl tin chloride was added. The dry ice-isopropanol bath was then removed and the solution was permitted to warm up to room temperature overnight. The next morning, the reaction solution was concentrated via rotary evaporation.

Deionized water (500 mL) and MTBE (500 mL) were added to a 2 L separatory funnel. The concentrated reaction solution was then transferred to the 2 L separatory funnel. The organic layer and aqueous layer were separated and the aqueous layer was back-extracted with MTBE (200 mL). The organic layer was washed with deionized water (3×800 mL). The organic layer was filtered through a Buchner funnel to remove solids that precipitated from it. Solvents were removed from the filtrate via rotary evaporation. The product was dried under vacuum. Product obtained: 19.85 g. Product purity was confirmed via HPLC. Product structure was confirmed via $^1$H NMR and GC-MS.

4,4'-(2,5-bis(4-(1,3-dioxolan-2-yl)phenyl)thieno[3,2-b]thiophene-3,6-diyl)bis(N,N-diphenylaniline) Synthesis

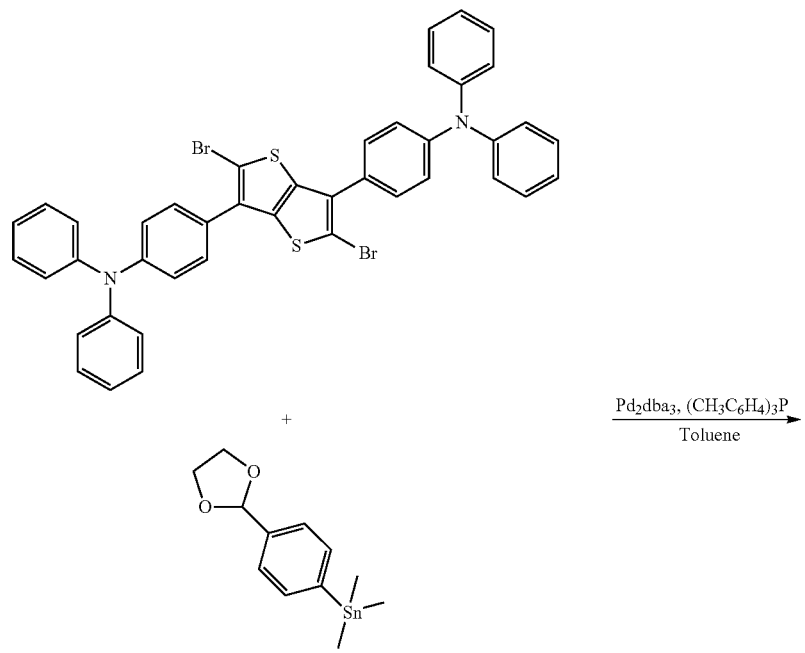

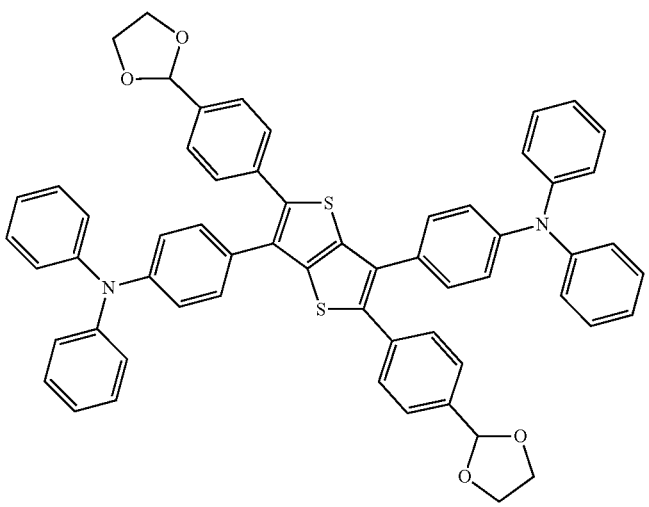

Molecular Weight: 923.15

Procedures:

In a 500 mL single-neck round bottom flask, (4-(1,3-dioxolan-2-yl)phenyl)trimethylstannane (12.0 g, 0.0384 mol) was dissolved in anhydrous toluene (50 mL) that was purged overnight via a strong nitrogen flow. Solids did not all dissolve—even with stirring. The solution was degassed via five vacuum-nitrogen cycles, and then transferred to a 500 mL Schlenk flask. 4,4'-(2,5-dibromothieno[3,2-b]thiophene-3,6-diyl)bis(N,N-diphenylaniline) (5.0 g, 0.0064 mol) was added to the 500 mL Schlenk flask. Solution was tan in color. The solution was degassed via three vacuum-nitrogen cycles, and then purged via a strong nitrogen flow for 30 minutes. Pd$_2$dba$_3$ (0.6 g, 0.0007 mol) was added. Solution turned red. The solution was degassed via another five vacuum-nitrogen cycles, and then placed in an oil-bath pre-heated to 95° C. After 1 hour, no color change was observed so additional Pd$_2$dba$_3$ (0.6 g, 0.0007 mol) was added followed by tri(o-tolyl)phosphine (0.79 g, 0.0026 mol). Solution turned black. 4 hours into the reaction, reaction completion was monitored via TLC. It indicated that the reaction was complete so the reaction was cooled to room temperature.

The reaction solution was filtered through a celite/silica gel plug, rinsing thoroughly with a 2% triethylamine/toluene solution (1.1 L) and a 2% triethylamine/chloroform solution (1 L). Solvents were removed via rotary evaporation, and then the product was dried under vacuum. Product obtained: 3.18 g. Product characterization was confirmed via $^1$H NMR.

Dehalogenation of 4,4'-(2,5-bis(4-(1,3-dioxolan-2-yl)phenyl)thieno[3,2-b]thiophene-3,6-diyl)bis(N,N-diphenylaniline) Synthesis (Run Twice)

Procedures:

A 250 mL three-neck round bottom flask equipped with a reflux condenser and thermometer was charged with 4,4'-(2,5-bis(4-(1,3-dioxolan-2-yl)phenyl)thieno[3,2-b]thiophene-3,6-diyl)bis(N,N-diphenylaniline) (3.18 g, 0.0034 mol). Anhydrous toluene (64 mL) was added via syringe. Solids did not all dissolve, even with stirring. Solution was yellow in color. Triethylamine (5.00 mL, 0.359 mol) was then added via syringe. Formic acid (1.20 mL, 0.0318 mol) was added dropwise via syringe. The solution was purged via a strong nitrogen flow for 30 minutes, after which Pd(OAc)$_2$ (0.1 g, 0.0006 mol) and tBu$_3$P (0.2 g, 0.0008 mol, in 3 mL anhydrous THF) were added. The reaction was heated to 100° C. and continued overnight. The next morning, it was cooled to room temperature.

The reaction solution was filtered through a celite/silica gel plug, rinsing thoroughly with a 2% triethylamine/dichloromethane solution (2 L). The filtered solution was transferred to a 4 L separatory funnel and washed with deionized water basified with triethylamine (3×1.4 L). Solvents were removed via rotary evaporation and resulting product was dried under vacuum. The product was purified by stirring with acetone (200 mL) at room temperature for 1 hour, then filtration through a Buchner funnel. Product obtained: 4.06 g. The dehalogenation procedure was repeated a second time to yield 4.02 g product.

4,4'-(3,6-bis(4-(diphenylamino)phenyl)thieno[3,2-b]thiophene-2,5-diyl)dibenzaldehyde Synthesis

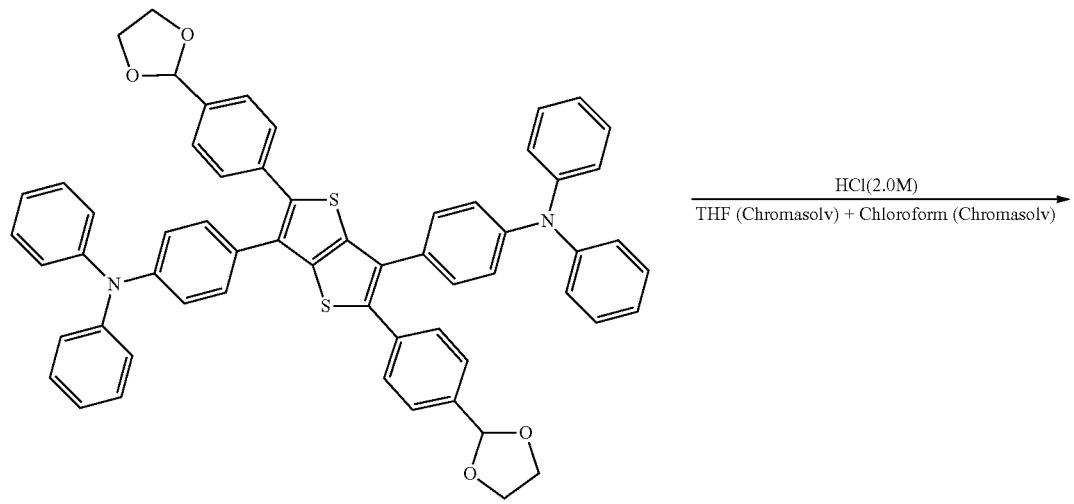

Molecular Weight: 923.15

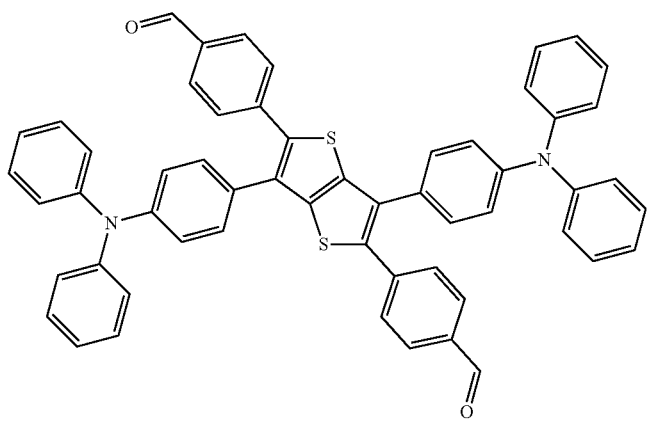

Molecular Weight: 835.04

Procedures:

In a 500 mL single-neck round bottom flask, 4,4'-(2,5-bis(4-(1,3-dioxolan-2-yl)phenyl)thieno[3,2-b]thiophene-3,6-diyl)bis(N,N-diphenylaniline) (4.0 g, 0.0044 mol) was dissolved in chloroform (20 mL). This solution was transferred to a 500 mL three-neck round bottom flask equipped with a reflux condenser, then THF was added via syringe. Solids precipitated from the solution. Solution was tan in color. Aqueous hydrochloric acid solution (1.65 mL, 2.0M) was then added dropwise via syringe. The reaction was heated to 60° C. and stirred at this temperature for 30 minutes. Reaction completion was then monitored via TLC and $^1$H NMR. Both indicated that the reaction was complete. Let it cool to room temperature. Deionized water basified with triethylamine (150 mL) and dichloromethane (150 mL) were added to a 1 L separatory funnel, followed by the reaction solution. After separation, the aqueous layer was back-extracted with dichloromethane (1×150 mL, 1×100 mL). The organic layer was washed with deionized water (600 mL). Dichloromethane (900 mL) was added to dissolve some solids and break up the emulsion that formed. The organic layer was then further washed with deionized water (2×600 mL). Solvents were removed via rotary evaporation, and then the resulting product was dried under vacuum.

The product was purified by trituration with methanol (150 mL) at room temperature for 1 hour, then filtration through a Buchner funnel. It was then dried under vacuum. Product obtained 3.25 g. Product purity was confirmed via HPLC. Product characterization was confirmed via $^1$H NMR.

4,4'-(2,5-bis(4-vinylphenyl)thieno[3,2-b]thiophene-3,6-diyl)bis(N,N-diphenylaniline) Synthesis

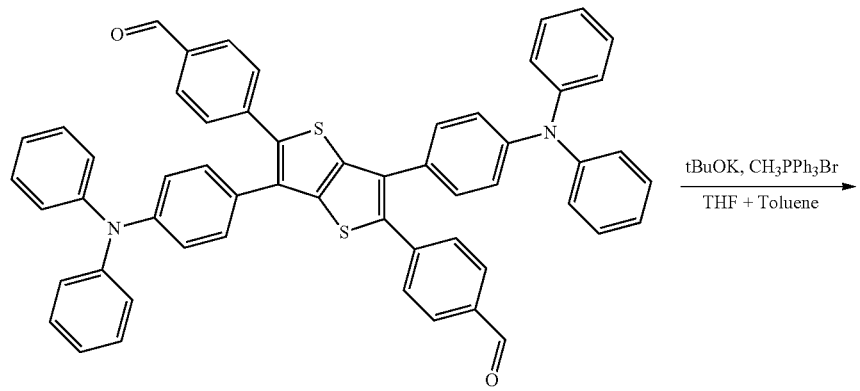

Molecular Weight: 835.04

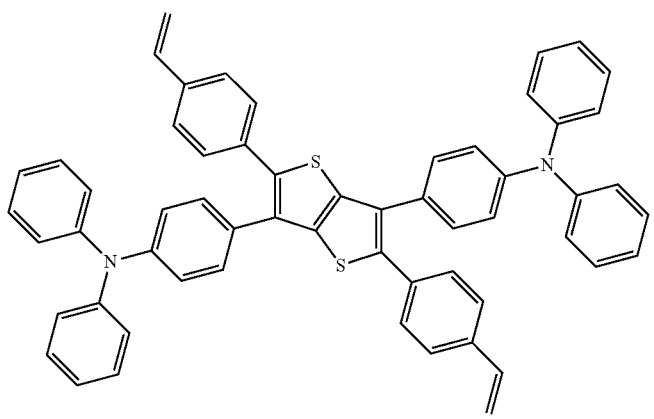

Molecular Weight: 831.10

Procedures:

In a 250 mL single-neck round bottom flask, 4,4'-(3,6-bis(4-(diphenylamino)phenyl)thieno[3,2-b]thiophene-2,5-diyl)dibenzaldehyde (3.02 g, 0.0361 mol) was dissolved in anhydrous THF (37 mL) and anhydrous toluene (37 mL) via syringe. Solids did not all dissolve. Solution was tan in color. The solution was degassed via five vacuum-nitrogen cycles. Methyltriphenylphosphonium bromide (3.93 g, 0.0110 mol) was added to a 500 mL three-neck round bottom flask along with anhydrous THF (37 mL) and anhydrous toluene (37 mL) via syringe. The solution was stirred at room temperature for 10 minutes, and then potassium tert-butoxide (1.34 g, 0.0119 mol) was added. Solution turned yellow. Aluminum foil was placed around the 500 mL three-neck round bottom flask, then the 4,4'-(3,6-bis(4-(diphenylamino)phenyl)thieno[3,2-b]thiophene-2,5-diyl)dibenzaldehyde solution was added to the flask dropwise via syringe. The solution was stirred at room temperature for 1 hour. Reaction completion was then monitored via TLC and $^1$H NMR. Both indicated that the reaction was complete.

The reaction solution was filtered through a celite/silica gel plug, washing thoroughly with a 2% triethylamine/dichloromethane solution (2 L). Solvents were removed via rotary evaporation, and then the product was dried under vacuum.

Purification was carried out via manual chromatography (dry load, silica gel). The manual column was run with a gradient from 2% chloroform/hexane (3 L) with triethylamine (20 mL) to 6% chloroform/hexane (1 L) with triethylamine (20 mL), followed by 100% chloroform (2 L) with triethylamine (20 mL) due to solubility issues. Solvents were removed via rotary evaporation, and then the product was dried under vacuum. Product obtained 1.90 g. Product purity was determined via HPLC and TLC, both of which indicated remaining impurities. The product was then purified by trituration in acetone (200 mL) in a 500 mL single-neck round bottom flask for 5 hours. The product was filtered through a Buchner funnel, and then further dried under vacuum. Product obtained 1.67 g. Product purity was confirmed via HPLC. Product characterization was confirmed via $^1$H NMR. $^1$H NMR (300 MHz, (CD$_3$)$_2$CO) 4.0-4.2 (m, 0.5H), 5.2-5.3 (d, 2H), 5.8 (d, 2H), 6-6.8 (q, 2H), 7.0-7.5 (m, 32H).

PLX-17-C 4,4'-(2,5-diphenylthieno[3,2-b]thiophene-3,6-diyl)bis(N,N-diphenylaniline) Synthesis

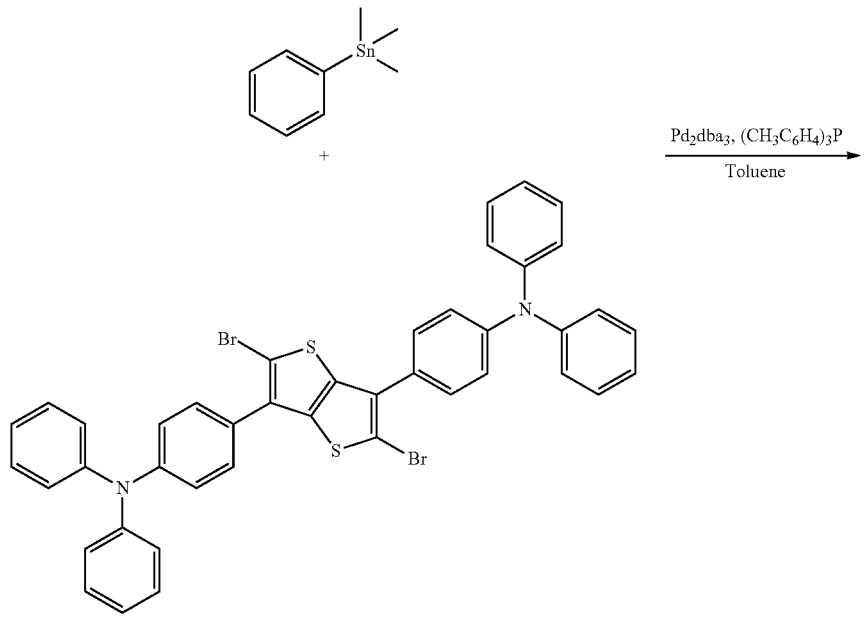

Molecular Weight: 784.62

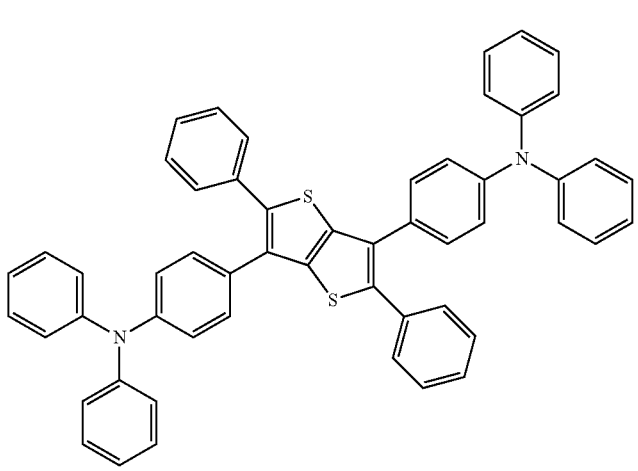

Molecular Weight: 779.02

Procedures:

A 200 mL Schlenk flask was charged with 4,4'-(2,5-dibromothieno[3,2-b]thiophene-3,6-diyl)bis(N,N-diphenylaniline) (3.0 g, 0.0038 mol) and anhydrous toluene (60 mL) that was bubbled overnight via a strong nitrogen flow. Solids did not all dissolve. Solution was tan in color. Next, trimethyl (phenyl)tin (5.55 g, 0.0230 mol) was added as well as tri(o-tolyl)phosphine (0.48 g, 0.0016 mol). The solution was degassed via five vacuum-nitrogen cycles then via a strong nitrogen flow for 45 minutes. $Pd_2dba_3$ (0.4 g, 0.0004 mol) was then added. The solution turned red. The reaction was placed in an oil bath pre-heated to 100° C. and continued overnight. The reaction was then cooled to room temperature.

The reaction solution was filtered through a celite/silica gel plug, washing thoroughly with a 2% triethylamine/chloroform solution (1.8 L). Solvents were removed via rotary evaporation, and then the product was dried under vacuum.

The product was purified by trituration in acetone (200 mL) for 1 hour at reflux, then filtration through a Buchner funnel. Product obtained: 2.18 g.

4,4'-(2,5-diphenylthieno[3,2-b]thiophene-3,6-diyl)bis(N,N-diphenylaniline) Synthesis (Run Twice)

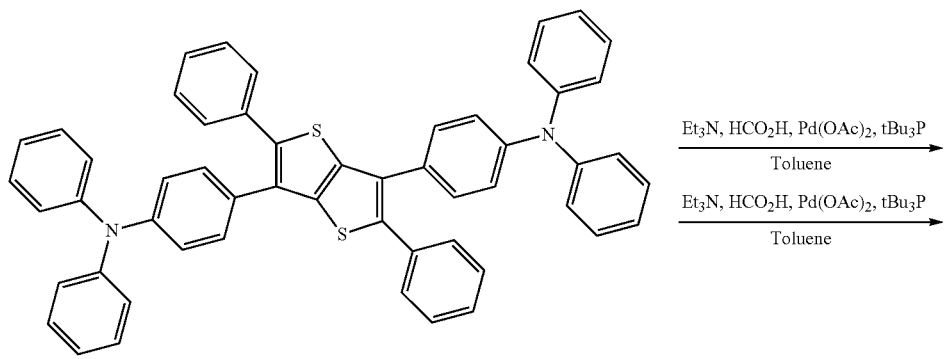

Molecular Weight: 784.62

Molecular Weight: 779.02

Procedures:

A 250 mL three-neck round bottom flask equipped with a reflux condenser and thermometer was charged with 4,4'-(2,5-diphenylthieno[3,2-b]thiophene-3,6-diyl)bis(N,N-diphenylaniline) (2.2 g, 0.0028 mol) and anhydrous toluene (54 mL). Solids did not all dissolve, even with stirring. Solution was light yellow/light orange in color. Triethylamine (4.00 mL, 0.0287 mol) was then added via syringe. Formic acid (1.00 mL, 0.0265 mol) was added dropwise syringe. The solution was purged via a strong nitrogen flow for 30 minutes, after which Pd(OAc)$_2$ (0.09 g, 0.0004 mol) and tBu$_3$P (0.1 g, 0.0006 mol, in 2 mL anhydrous toluene) were added. The reaction was heated to 100° C. and left to stir at this temperature for 2 hours after which it was cooled to room temperature.

The reaction solution was filtered through a celite/silica gel plug, washing thoroughly with a 2% triethylamine/chloroform solution (1.3 L). Solvents were removed via rotary evaporation, and then the product was dried under vacuum.

The product was purified by trituration in acetone (125 mL) at room temperature for 1 hour, then filtration through a Buchner funnel. Product obtained: 2.21 g.

The dehalogenation procedure was repeated a second time to yield 2.06 g product.

Purification on 1.09 g product was carried out via sublimation. Obtained 0.5960 g purified product. Product purity was confirmed via HPLC. Product characterization was confirmed via $^1$H NMR. $^1$H NMR (300 MHz, (CD$_3$)$_2$CO) 6.6-7.8 (m).

PLX-18-A

Synthesis of N3,N7-bis(4-(1,3-dioxolan-2-yl)phenyl)-5,5-dioctyl-N3,N7-di-m-tolyl-5H-dibenzo[b,d]silole-3,7-diamine

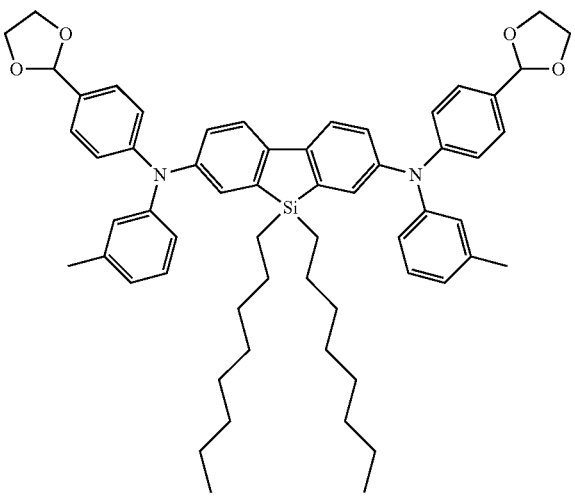 [SMILES: CCCCCCCC[Si]1(CCCCCCCC)c2cc(N(c3ccc(C4OCCO4)cc3)c3cccc(C)c3)ccc2-c2ccc(N(c3ccc(C4OCCO4)cc3)c3cccc(C)c3)cc21]

311

Procedures:

In a clean and dry three-neck flask equipped with magnetic stir bar and reflux condenser was added 3,7-dibromo-5,5-dioctyl-5H-dibenzo[b,d]silole (2.00 g, 0.0035 mol) and N-(4-(1,3-dioxolan-2-yl)phenyl)-3-methylaniline (2.17 g, 0.0085 mol). Anhydrous toluene (150 mL) was then added, and the reaction solution was purged with inert gas flow for thirty minutes. Sodium tert-butoxide (1.02 g, 0.0106 mol) and Pd$_2$dba$_3$ (0.26 g, 0.0003 mol) were then added, followed by the addition of tri-tert-butylphosphine (0.18 g, 0.0009 mol) in toluene solution (5 mL). The reaction was heated to reflux. When reaction completion was confirmed by thin-layer chromatography, the reaction was cooled to room temperature and filtered through a bed of celite and triethylamine treated silica gel, washing thoroughly with ethyl acetate. Solvent was removed from filtrate by rotary evaporation and the crude solids were dried under vacuum. Purification was carried out by chromatography on silica gel using ethyl acetate/hexane as an eluent. Product obtained: 2.79 g Dehalogenation of N3,N7-bis(4-(1,3-dioxolan-2-yl)phenyl)-5,5-dioctyl-N3,N7-di-m-tolyl-5H-dibenzo[b,d]silole-3,7-diamine

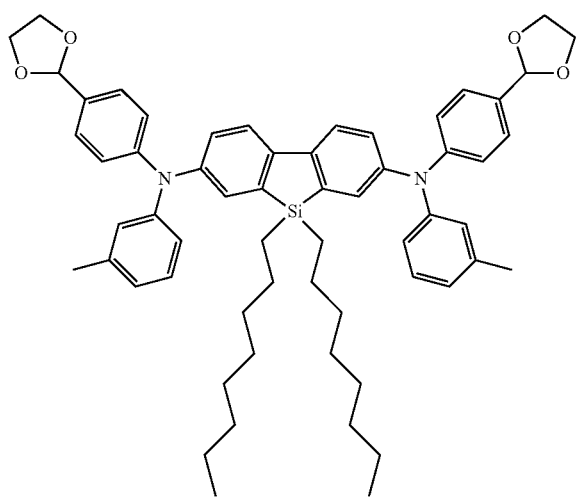 [SMILES: CCCCCCCC[Si]1(CCCCCCCC)c2cc(N(c3ccc(C4OCCO4)cc3)c3cccc(C)c3)ccc2-c2ccc(N(c3ccc(C4OCCO4)cc3)c3cccc(C)c3)cc21]

Procedures:

A solution of N3,N7-bis(4-(1,3-dioxolan-2-yl)phenyl)-5,5-dioctyl-N3,N7-di-m-tolyl-5H-dibenzo[b,d]silole-3,7-diamine (4.23 g, 0.0046 mol) in anhydrous THF (300 mL) was prepared and transferred by cannula to a clean, dry round bottom flask equipped with a reflux condenser. Triethylamine (6.5 mL, 0.0463 mol) was then added via syringe. Formic acid (1.7 mL, 0.0440 mol) was added slowly, dropwise via syringe. The reaction solution and system was then purged with an inert gas flow for thirty minutes, after which Pd(OAc)$_2$ (0.11 g, 0.0003 mol) and tBu$_3$P (0.14 g in 5 mL anhydrous toluene) were added. The reaction was heated to reflux for approximately 2 hours and then cooled to room temperature. The solution was filtered through a Celite and triethylamine treated silica gel plug, washing with excess ethyl acetate. Solvent was then removed by rotary evaporation and the resulting solid material was placed under vacuum to be carried on to the second dehalogenation reaction.

312

Dehalogenation of N3,N7-bis(4-(1,3-dioxolan-2-yl)phenyl)-5,5-dioctyl-N3,N7-di-m-tolyl-5H-dibenzo[b,d]silole-3,7-diamine

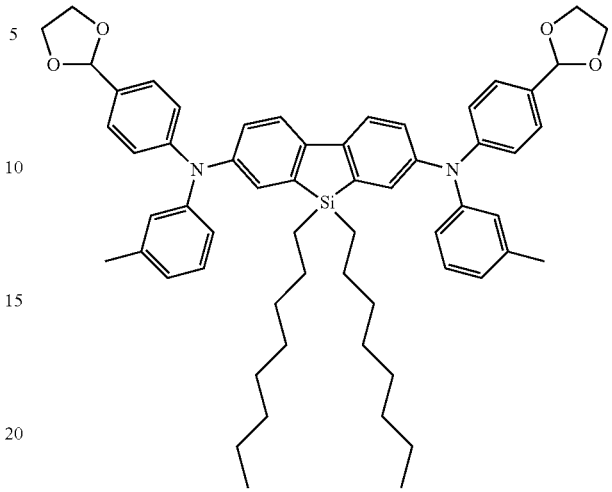

Procedures:

A solution of singly dehalogenated N3,N7-bis(4-(1,3-dioxolan-2-yl)phenyl)-5,5-dioctyl-N3,N7-di-m-tolyl-5H-dibenzo[b,d]silole-3,7-diamine (4.23 g, 0.0046 mol) in anhydrous THF (300 mL) was prepared and transferred by cannula to a clean, dry round bottom flask equipped with a reflux condenser. Triethylamine (6.5 mL, 0.0463 mol) was then added via syringe. Formic acid (1.7 mL, 0.0440 mol) was added slowly, dropwise via syringe. The reaction solution and system was then purged with an inert gas flow for thirty minutes, after which Pd(OAc)$_2$ (0.11 g, 0.0003 mol) and tBu$_3$P (0.14 g in 5 mL anhydrous toluene) were added. The reaction was heated to reflux for approximately 2 hours and then cooled to room temperature. The solution was filtered through a Celite and triethylamine treated silica gel plug, washing with excess ethyl acetate. Solvent was then removed by rotary evaporation and the resulting solid material was placed under vacuum to be carried on to the deprotection reaction. Product obtained: 1.88 g.

Synthesis of 4,4'-((5,5-dioctyl-5H-dibenzo[b,d]silole-3,7-diyl)bis(m-tolylazanediyl))dibenzaldehyde

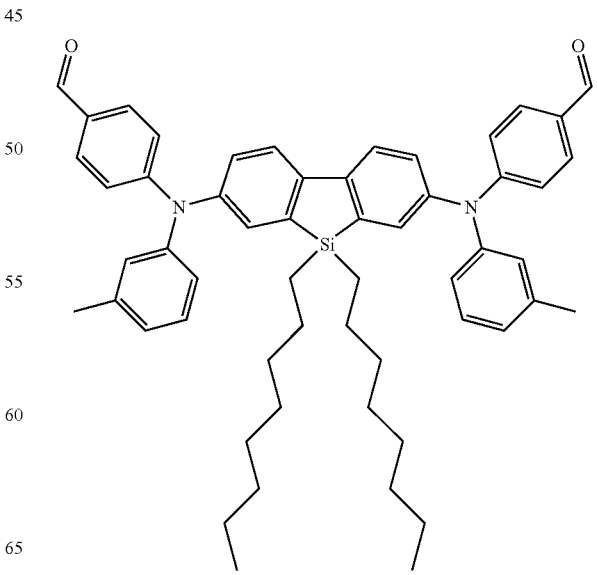

Procedures:

To a single neck round bottom flask containing doubly dehalogenated N3,N7-bis(4-(1,3-dioxolan-2-yl)phenyl)-5,5-dioctyl-N3,N7-di-m-tolyl-5H-dibenzo[b,d]silole-3,7-diamine (4.23 g, 0.0046 mol), acetone (400 mL) and a magnetic stir bar were added. Hydrochloric acid solution (0.3M, 3.1 mL) was added slowly dropwise. The reaction was allowed to stir for 30 minutes. A TLC plate was taken and showed that the reaction had finally completed. The solution was worked up with methyl tert-butyl ether (400 mL) and deionized water (3×300 mL) until neutral. The organic fraction was collected and dried over anhydrous sodium sulfate. The solids were separated by vacuum filtration, and the solvent was removed from the filtrate by rotary evaporation. Purification was carried out by chromatography on silica gel using a gradient of ethyl acetate/hexane as an eluent. This provided $^1$H-NMR pure product. Product obtained: 3.15 g Synthesis of 5,5-dioctyl-N3,N7-di-m-tolyl-N3,N7-bis(4-vinylphenyl)-5H-dibenzo[b,d]silole-3,7-diamine

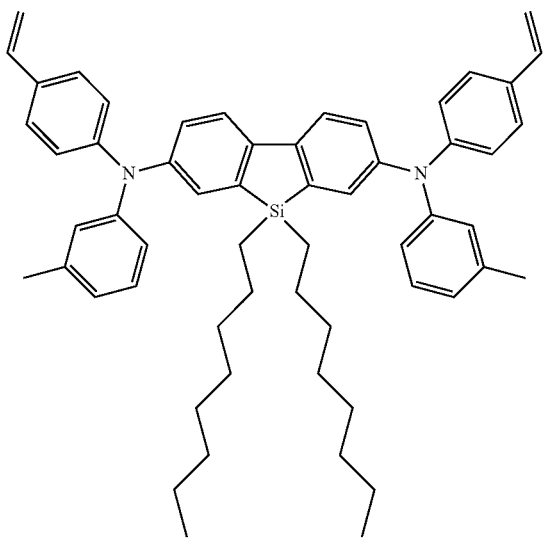 [SMILES: C=Cc1ccc(N(c2cccc(C)c2)c2ccc3c(c2)[Si](CCCCCCCC)(CCCCCCCC)c2cc(N(c4ccc(C=C)cc4)c4cccc(C)c4)ccc2-3)cc1]

Procedures:

A three-neck round bottom flask was charged with methyltriphenylphosphonium bromide (4.09 g, 0.0115 mol) and anhydrous tetrahydrofuran (250 mL) was added via cannula. Stirring was initiated, and potassium tert-butoxide (1.34 g, 0.0118 mol) was added manually. This solution was allowed to stir for ten minutes before an anhydrous solution of 4,4'-((5,5-dioctyl-5H-dibenzo[b,d]silole-3,7-diyl)bis(m-tolylazanediyl))dibenzaldehyde (3.15 g, 0.0038 mol) in tetrahydrofuran (100 mL) was added slowly, dropwise via syringe. The reaction was allowed to stir for thirty minutes before reaction completion was confirmed by thin-layer chromatography. The reaction solution was filtered through a bed of celite and silica gel (triethylamine treated), washing thoroughly with tetrahydrofuran. The filtrate was removed of solvent by rotary evaporation and the resulting crude material was placed under vacuum. The crude material was further purified by chromatography on silica gel using hexanes as an eluent. Precipitation from a minimum amount of ethyl acetate into methanol provided 1H-NMR pure product. Product obtained: 0.71 g.

PLX-18-B

Synthesis of N3,N7-bis(4-(1,3-dioxolan-2-yl)phenyl)-N3,N7-di([1,1'-biphenyl]-4-yl)-5,5-dioctyl-5H-dibenzo[b,d]silole-3,7-diamine

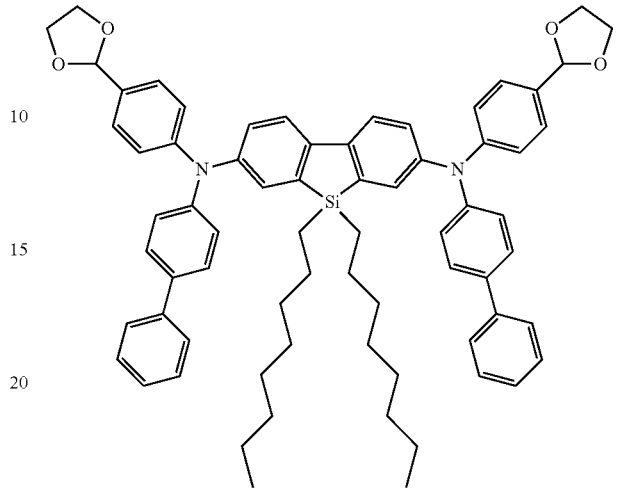

Procedures:

In a clean and dry three-neck flask equipped with magnetic stir bar and reflux condenser was added 3,7-dibromo-5,5-dioctyl-5H-dibenzo[b,d]silole (2.00 g, 0.0035 mol) and N-(4-(1,3-dioxolan-2-yl)phenyl)-[1,1'-biphenyl]-4-amine (2.70 g, 0.0085 mol). Anhydrous toluene (150 mL) was then added, and the reaction solution was purged with inert gas flow for thirty minutes. Sodium tert-butoxide (1.02 g, 0.0106 mol) and Pd$_2$dba$_3$ (0.26 g, 0.0003 mol) were then added, followed by the addition of tri-tert-butylphosphine (0.18 g, 0.0009 mol) in toluene solution (5 mL). The reaction was heated to reflux. When reaction completion was confirmed by thin-layer chromatography, the reaction was cooled to room temperature and filtered through a bed of celite and triethylamine treated silica gel, washing thoroughly with ethyl acetate. Solvent was removed from filtrate by rotary evaporation and the crude solids were dried under vacuum. Purification was carried out by chromatography on silica gel using ethyl acetate/hexanes as an eluent. Product obtained: 3.03 g Dehalogenation of N3,N7-bis(4-(1,3-dioxolan-2-yl)phenyl)-N3,N7-di([1,1'-biphenyl]-4-yl)-5,5-dioctyl-5H-dibenzo[b,d]silole-3,7-diamine

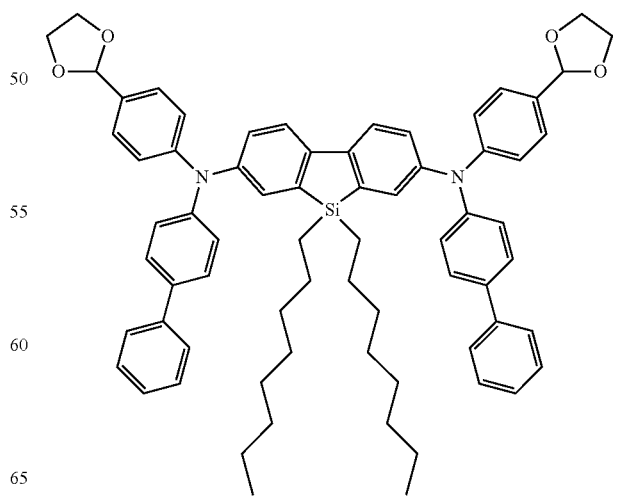

Procedures:

A solution of undehalogenated N3,N7-bis(4-(1,3-dioxolan-2-yl)phenyl)-N3,N7-di([1,1'-biphenyl]-4-yl)-5,5-dioctyl-5H-dibenzo[b,d]silole-3,7-diamine (3.03 g, 0.0029 mol) in anhydrous THF (225 mL) was prepared and transferred by cannula to a clean, dry round bottom flask equipped with a reflux condenser. Triethylamine (4.1 mL, 0.0292 mol) was then added via syringe. Formic acid (1.0 mL, 0.0277 mol) was added slowly, dropwise via syringe. The reaction solution and system was then purged with an inert gas flow for thirty minutes, after which Pd(OAc)$_2$ (0.07 g, 0.0003 mol) and tBu$_3$P (0.09 g in 5 mL anhydrous toluene) were added. The reaction was heated to reflux for approximately 2 hours and then cooled to room temperature. The solution was filtered through a Celite and triethylamine treated silica gel plug, washing with excess ethyl acetate. Solvent was then removed by rotary evaporation and the resulting solid material was placed under vacuum to be carried on to the second dehalogenation reaction.

Dehalogenation of N3,N7-bis(4-(1,3-dioxolan-2-yl)phenyl)-N3,N7-di([1,1'-biphenyl]-4-yl)-5,5-dioctyl-5H-dibenzo[b,d]silole-3,7-diamine

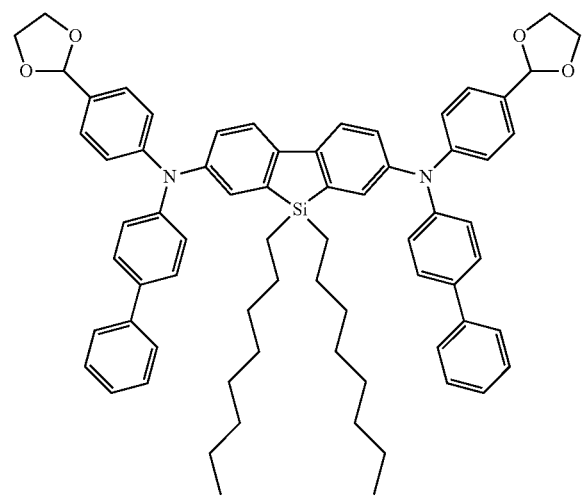 [SMILES: CCCCCCCC[Si]1(CCCCCCCC)c2cc(N(c3ccc(-c4ccccc4)cc3)c3ccc(C4OCCO4)cc3)ccc2-c2ccc(N(c3ccc(-c4ccccc4)cc3)c3ccc(C4OCCO4)cc3)cc21]

Procedures:

A solution of singly dehalogenated N3,N7-bis(4-(1,3-dioxolan-2-yl)phenyl)-N3,N7-di([1,1'-biphenyl]-4-yl)-5,5-dioctyl-5H-dibenzo[b,d]silole-3,7-diamine (3.03 g, 0.0029 mol) in anhydrous THF (225 mL) was prepared and transferred by cannula to a clean, dry round bottom flask equipped with a reflux condenser. Triethylamine (4.1 mL, 0.0292 mol) was then added via syringe. Formic acid (1.0 mL, 0.0277 mol) was added slowly, dropwise via syringe. The reaction solution and system was then purged with an inert gas flow for thirty minutes, after which Pd(OAc)$_2$ (0.07 g, 0.0003 mol) and tBu$_3$P (0.09 g in 5 mL anhydrous toluene) were added. The reaction was heated to reflux for approximately 2 hours and then cooled to room temperature. The solution was filtered through a Celite and triethylamine treated silica gel plug, washing with excess ethyl acetate. Solvent was then removed by rotary evaporation and the resulting solid material was placed under vacuum to be carried on to the deprotection reaction.

Synthesis of 4,4'-((5,5-dioctyl-5H-dibenzo[b,d]silole-3,7-diyl)bis([1,1'-biphenyl]-4-ylazanediyl))dibenzaldehyde

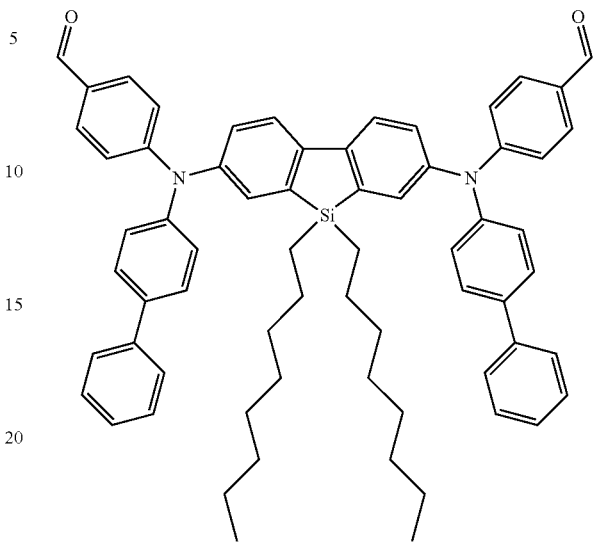

Procedures:

To a single-neck round bottom flask containing doubly dehalogenated N3,N7-bis(4-(1,3-dioxolan-2-yl)phenyl)-N3,N7-di([1,1'-biphenyl]-4-yl)-5,5-dioctyl-5H-dibenzo[b,d]silole-3,7-diamine (3.03 g, 0.0029 mol), acetone (400 mL) and a magnetic stir bar were added. Hydrochloric acid solution (0.3M, 3.1 mL) was added slowly dropwise. The reaction was allowed to stir for 30 minutes. A TLC plate was taken and showed that the reaction had finally completed. The solution was worked up with methyl tert-butyl ether (400 mL) and deionized water (3×300 mL) until neutral. The organic fraction was collected and dried over anhydrous sodium sulfate. The solids were separated by vacuum filtration, and the solvent was removed from the filtrate by rotary evaporation. Purification was carried out by chromatography on silica gel using a gradient of ethyl acetate/hexane as an eluent. This provided $^1$H-NMR pure product. Product obtained: 0.92 g Synthesis of N3,N7-di([1,1'-biphenyl]-4-yl)-5,5-dioctyl-N3,N7-bis(4-vinylphenyl)-5H-dibenzo[b,d]silole-3,7-diamine

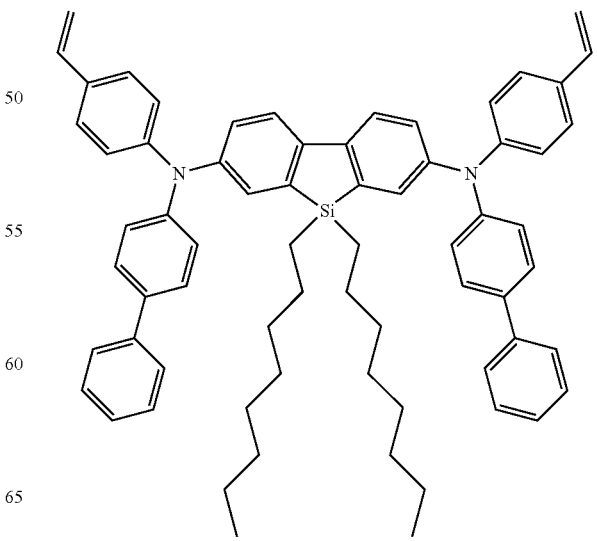

Procedures:

A three-neck round bottom flask was charged with methyltriphenylphosphonium bromide (1.06 g, 0.0030 mol) and anhydrous tetrahydrofuran (200 mL) was added via cannula. Stirring was initiated, and potassium tert-butoxide (0.35 g, 0.003 mol) was added manually. This solution was allowed to stir for ten minutes before an anhydrous solution of 4,4'4-(5,5-dioctyl-5H-dibenzo[b,d]silole-3,7-diyl)bis([1,1'-biphenyl]-4-ylazanediyl))dibenzaldehyde (0.92 g, 0.0010 mol) in tetrahydrofuran (50 mL) was added slowly, dropwise via syringe. The reaction was allowed to stir for thirty minutes before reaction completion was confirmed by thin-layer chromatography. The reaction solution was filtered through a bed of celite and silica gel (triethylamine treated), washing thoroughly with tetrahydrofuran. The filtrate was removed of solvent by rotary evaporation and the resulting crude material was placed under vacuum. The crude material was further purified by chromatography on silica gel using 1% ethyl acetate/2% triethylamine/97% hexane as an eluent. Precipitation from a minimum amount of ethyl acetate into methanol provided $^1$H-NMR pure product. Product obtained: 0.81 g

PLX-18-C

Synthesis of N-(4-(1,3-dioxolan-2-yl)phenyl)-3-methylaniline

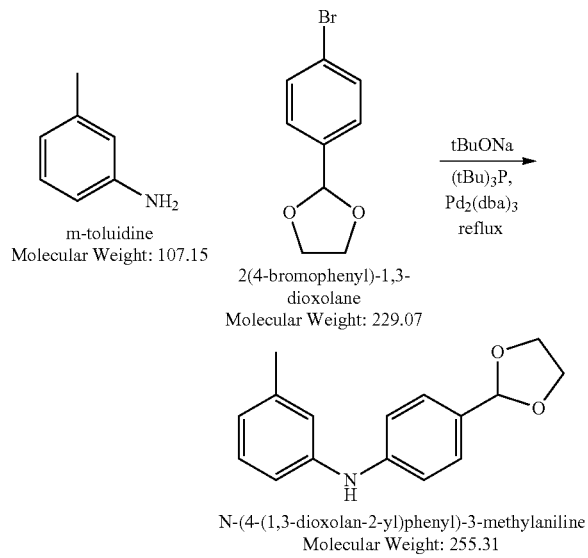

Procedures:

In a clean, dry 2 L 3-neck RBF equipped with a stir bar and reflux condenser, m-toluidine (10.000 g, 0.0933 mL) was dissolved in 1 L anhydrous toluene (bubbled for 1 hour) via cannulae. 2-(4-bromophenyl)-1,3-dioxolane (19.629 g, 0.0768 mol) was added to the flask and purged for 15 minutes. tBuONa (12.934 g, 0.135 mol) was quickly added vial funnel followed by a quick rinse with anhydrous toluene via 10 mL syringe. Reaction solution was allowed to stir until the color change completed (from pale yellow to green). Next, tBu$_3$P (0.7553 g, 0.0037 mol) and Pd$_2$(dba)$_3$ (1.069 g, 0.001 mol) were added all at once via funnel followed by a quick rinse with anhydrous toluene via 10 mL syringe. Reaction solution was then heated to reflux at 111° C. overnight. Reaction was confirmed complete via TLC and the reaction was quenched with 500 mL of DI water. Reaction solution was extracted in a 2 L separatory funnel with 500 mL of MTBE and 4×500 mL of DI water. Organic layer was collected and solvent was removed via rotary evaporation. Product was a large amount of liquid. Product was filtered through a celite (medium grain) and silica gel plug. Product was still impure so it was dry-loaded into a manual column. As the product became more and more pure it became harder and harder to remove from the column. Therefore, the column was flushed and the remaining product was recrystallized in ethyl acetate and hexane and filtered through a Buchner funnel. Product obtained: 10.335 g.

Synthesis of N3,N7-bis(4-(1,3-dioxolan-2-yl)phenyl)-5,5-diphenyl-N3,N7-di-m-tolyl-5H-dibenzo[b,d]silole-3,7-diamine

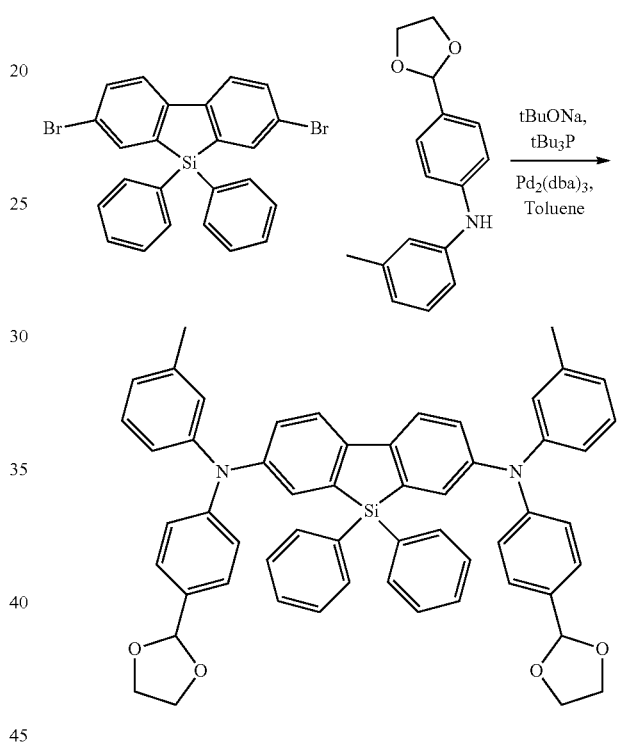

Procedures:

To a clean and dry 1 L three neck round bottom flask, equipped with a stir bar and reflux condenser, was added 3,7-dibromo-5,5-diphenyl-5H-dibenzo[b,d]silole (5.0 g, 0.0102 mol) and N-(4-(1,3-dioxolan-2-yl)phenyl)-3-methylaniline (5.705 g, 0.0223 mol). Anhydrous toluene (400 mL) was purged overnight and was added via cannulae. All starting materials dissolved. Following this, sodium tert-butoxide (2.44 g, 0.0254 mol), Pd$_2$(dba)$_3$ (0.1116 g, 0.1 mmol), and a solution of tri-tert-butylphosphine (0.0822 g, 0.4 mmol) in toluene (10 mL) were added to the reaction. Heat was applied to reflux, and the reaction was allowed to continue at this temperature overnight. Reaction completion was confirmed by thin-layer chromatography. $^1$H NMR show that the reaction did occur, however, it is still slightly impure.

Impure product was dry loaded onto a manual column increasing by 2% each liter until 20% ethyl acetate/hexane solution removed the final amount of more polar impurities. Then 2 L of 40% ethyl acetate/hexane solution was used to remove the pure product. Final product was a liquid so it was precipitated into cold methanol and placed in a drying oven for 1 hour. The product was TLC and NMR pure. Product obtained: 6.3 g.

Dehalogenation of N3,N7-bis(4-(1,3-dioxolan-2-yl)phenyl)-5,5-diphenyl-N3,N7-di-m-tolyl-5H-dibenzo[b,d]silole-3,7-diamine

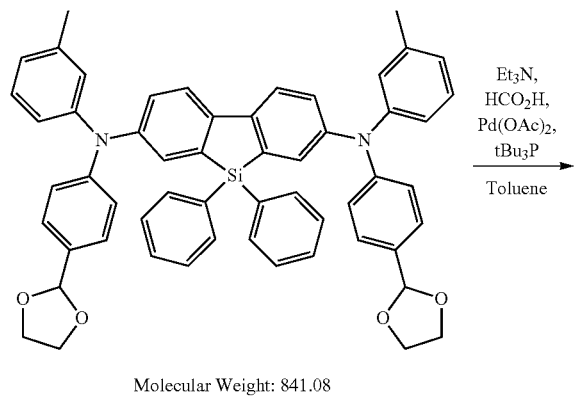

Molecular Weight: 841.08

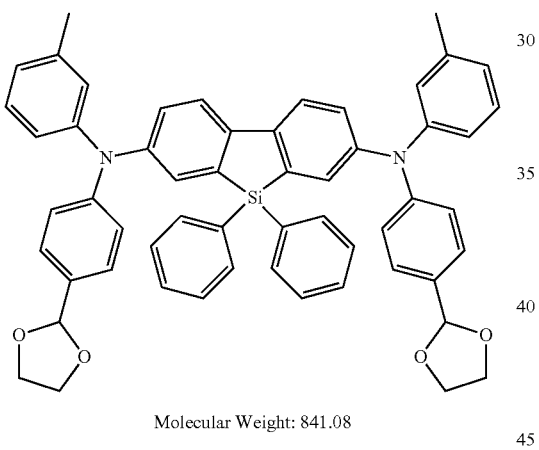

Molecular Weight: 841.08

Procedures:

N3,N7-bis(4-(1,3-dioxolan-2-yl)phenyl)-5,5-diphenyl-N3,N7-di-m-tolyl-5H-dibenzo[b,d]silole-3,7-diamine (6.3 g, 0.0075 mol) was dissolved in a 250 mL single-neck round bottom flask in anhydrous toluene (150 mL) via 50 mL syringe. All dissolved with heating via heat gun. Solution is golden in color. This N3,N7-bis(4-(1,3-dioxolan-2-yl)phenyl)-5,5-diphenyl-N3,N7-di-m-tolyl-5H-dibenzo[b,d]silole-3,7-diamine solution was transferred to a 1 L three-neck round bottom flask equipped with a reflux condenser via 50 mL syringe. Triethylamine (10.0 mL, 0.0749 mol) then formic acid (2.5 mL, 0.0712 mol) were added via 10 and 3 mL syringes, respectively. The solution was then purged with argon for 1 hour. Then, Pd(OAc)$_2$ (0.1694 g, 0.0007 mol) and tBu$_3$P (0.2474 g, 0.0012 mol, in 5 mL anhydrous toluene were added. The reaction was heated to reflux at 110° C. via heating mantle and left to stir and heat at this temperature for 1 hour and 30 minutes. It was then cooled to room temperature.

Filtered solution reaction through a celite/silica plug basified with triethylamine and washed with ethyl acetate. Following the filtration, filtrate was transferred to a separatory funnel and washed with DI water. Organic layer was placed on a rotary evaporator to remove solvent. Product from evaporation was a liquid. Therefore, it was dissolved in a minimum amount of ethyl acetate and precipitated into 150 mL of cold MeOH and filtered through a Buchner funnel. Product obtained: 4.440 g.

Synthesis of 4,4'-((5,5-diphenyl-5H-dibenzo[b,d]silole-3,7-diyl)bis(m-tolylazanediyl))dibenzaldehyde

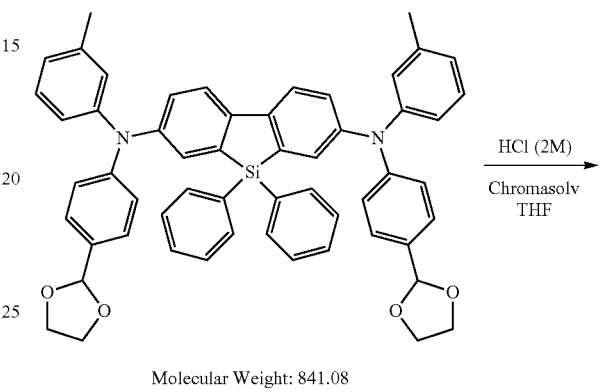

Molecular Weight: 841.08

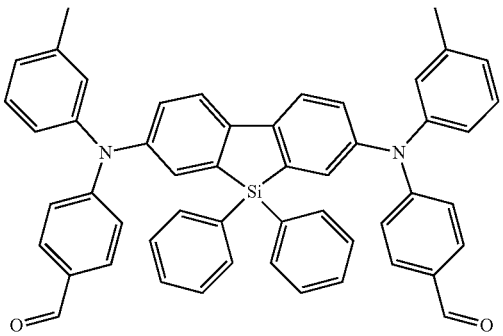

Molecular Weight: 752.97

Procedures:

Chromasolv THF (100 mL) was added to a 250 mL single-neck round bottom flask that contained N3,N7-bis(4-(1,3-dioxolan-2-yl)phenyl)-5,5-diphenyl-N3,N7-di-m-tolyl-5H-dibenzo[b,d]silole-3,7-diamine (4.00 g, 0.0048 mol) via 50 mL syringe. All dissolved with stirring via stir plate. Solution was pale yellow in color. Aqueous hydrochloric acid solution (2.0 mL, 2.0M), was then added dropwise via 3 mL syringe. The reaction was permitted to stir for 15 minutes. Reaction completion was monitored via $^1$H NMR. It indicated that the reaction was complete.

Triethylamine (2 mL or 2%) was added to the reaction flask to quench the reaction. Deionized water (150 mL) and MTBE (150 mL) were added to a 500 mL separatory funnel via glass funnel. The organic and aqueous layers were separated. The organic layer was washed 3×150 mL DI water. Solvents were removed from the organic layer via rotary evaporation. Product obtained 3.2 g.

Synthesis of 5,5-diphenyl-N3,N7-di-m-tolyl-N3,N7-bis(4-vinylphenyl)-5H-dibenzo[b,d]silole-3,7-diamine

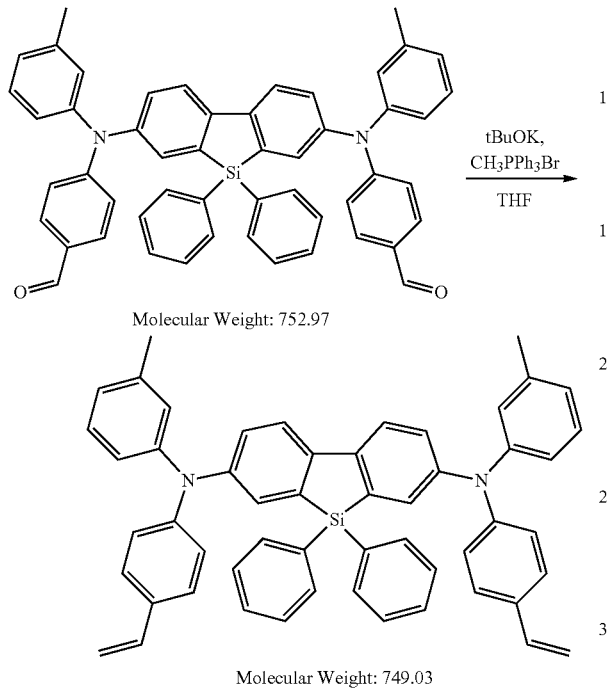

Procedures:

In a 50 mL single-neck round bottom flask, 4,4'-((5,5-diphenyl-5H-dibenzo[b,d]silole-3,7-diyl)bis(m-tolylazanediyl))dibenzaldehyde (3.2 g, 0.0042 mol) was dissolved in anhydrous THF (20 mL) with swirling and vigorous stirring via stir plate. Methyltriphenylphosphonium bromide (4.5607 g, 0.0127 mol) was added to a 250 mL three-neck round bottom flask equipped with an addition funnel. Anhydrous THF (80 mL) was added to the reaction flask via 50 mL syringe and permitted to stir. Potassium tert-butoxide (1.4391 g, 0.0127 mol) was then added to the reaction flask and the flask was subsequently covered with aluminum foil. The 4,4'-((5,5-diphenyl-5H-dibenzo[b,d]silole-3,7-diyl)bis(m-tolylazanediyl))dibenzaldehyde solution was then transferred to the addition funnel via 20 mL syringe. This solution was added drop-wise to the reaction flask from the addition funnel. The reaction was permitted to stir for 1 hour. Reaction completion was monitored via TLC and $^1$H NMR.

The solution was filtered through a celite/silica gel plug treated with 2% triethylamine/ethyl acetate solution (2 L). It was washed with ethyl acetate (1 L). Solvents were removed via rotary evaporation. The product was adsorbed to silica gel as a dry load to a manual column. 3 L of 2% triethylamine/hexane, 1 L of 10% ethyl acetate/hexane/triethylamine, 1 L of 20% ethyl acetate/hexane/triethylamine, and 3 L of 30% ethyl acetate/hexane/triethylamine were placed through the column. Product fractions were collected and solvents evaporated off. The product left from the column was a liquid so it was precipitated into cold methanol and filtered through a Buchner funnel. Solid product was placed in the vacuum oven to dry over the weekend. Product obtained: 1.802 g. $^1$H NMR (D-Acetone, 300 MHz) 0.9-1.0 (s, 1H) 2.0-2.1 (s, 3H) 2.2-2.3 (s, 6H) 2.8-2.9 (s, 2H) 5.1-5.2 (d, 2H) 5.6-5.8 (d, 2H) 6.6-6.8 (m, 2H) 6.8-7.2 (m, 13H) 7.3-7.5 (m, 9H) 7.5-7.7 (s, 6H) 7.8-7.9 (s, 2H)

PLX-19-A

Another embodiment can be represented by the following formula:

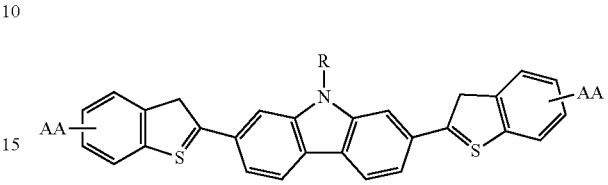

wherein AA can be the same or different aryl amine groups. Compounds of this formula can also be optionally substituted by intractability groups found anywhere on the molecule including the AA groups or the R group, for example. The R group can be, for example, an optionally substituted alkyl group, such as for example, a C1-C20 alkyl group, or a C1-C12 alkyl group. The R group can be straight or branched alkyl. A working example is provided below:

Synthesis of N-(4-(1,3-dioxolan-2-yl)phenyl)-3-methylaniline

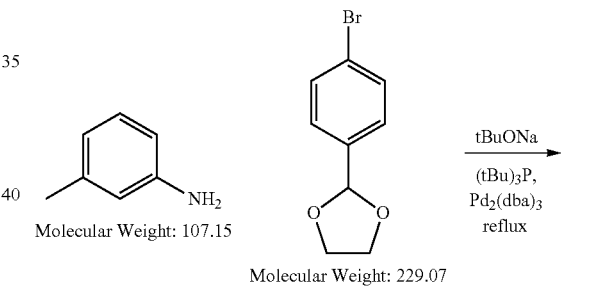

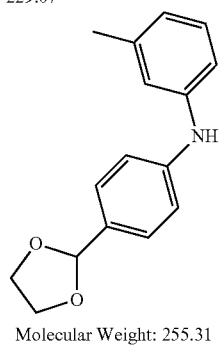

Procedure:

In a clean, dry 2 L 3-neck RBF equipped with a stir bar and reflux condensor, m-toluidine (10.000 g, 0.0933 mL) was dissolved in 1 L anhydrous toluene (bubbled for 1 hour) via cannulae. 2-(4-bromophenyl)-1,3-dioxolane (19.629 g, 0.0768 mol) was added to the flask and purged for 15 minutes. tBuONa (12.934 g, 0.135 mol) was quickly added vial funnel followed by a quick rinse with anhydrous toluene via 10 mL syringe. Reaction solution was allowed to stir until the color change completed (from pale yellow to green). Next, tBu₃P (0.7553 g, 0.0037 mol) and Pd₂(dba)₃ (1.069 g, 0.001 mol) were added all at once via funnel followed by a quick rinse with anhydrous toluene via 10 mL syringe. Reaction solution was then heated to reflux at 111° C. overnight. Reaction was confirmed complete via TLC and the reaction was quenched with 500 mL of DI water. Reaction solution was extracted in a 2 L separatory funnel with 500 mL of MTBE and 4×500 mL of DI water. Organic layer was collected and solvent was removed via rotary evaporation. Product was a large amount of liquid. Product was filtered through a celite (medium grain) and silica gel plug. Product was still impure so it was dry-loaded into auto-column. Product fractions were collected and solvents were removed via rotary evaporation. Product obtained: 8.3 g Synthesis of N-(4-(1,3-dioxolan-2-yl)phenyl)-N-(m-tolyl)benzo[b]thiophen-5-amine

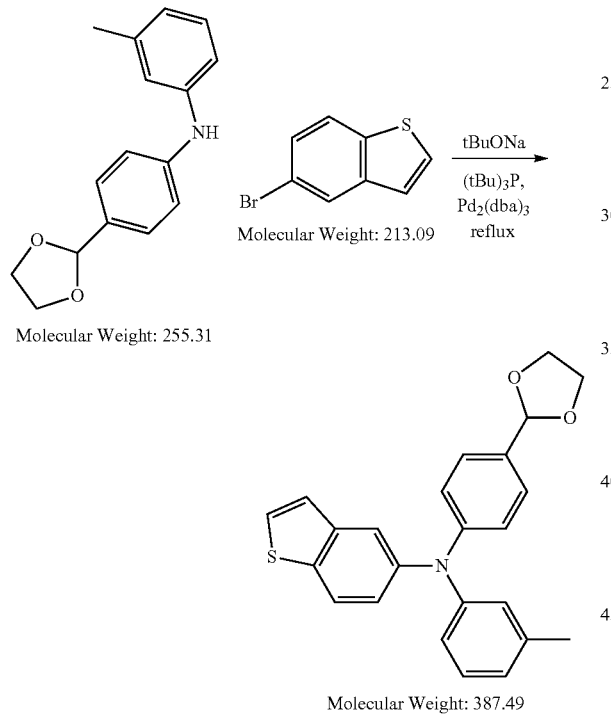

Procedure:

In a clean, dry 1 L 3-neck RBF equipped with a stir bar and reflux condenser, N-(4-(1,3-dioxolan-2-yl)phenyl)-3-methylaniline (4.900 g, 0.0192 mol) was dissolved in anhydrous toluene (500 mL) via cannulae. 5-bromobenzo[b]thiophene (4.908 g, 0.0230 mol) was added to the flask and purged for 15 minutes. tBuONa (2.582 g, 0.0269 mol) was quickly added vial funnel followed by a quick rinse with anhydrous toluene via 10 mL syringe. Reaction solution was allowed to stir until the color change completed (from pale yellow to green). Next, tBu₃P (0.1553 g, 0.0008 mol) and Pd₂(dba)₃ (0.2109 g, 0.0002 mol) were added all at once via funnel followed by a quick rinse with anhydrous toluene via 10 mL syringe. Reaction solution was then heated to reflux at 111° C. overnight. Reaction was confirmed complete via TLC and the reaction was quenched with 500 mL of DI water. Reaction solution was filtered through a celite (medium grain) and silica gel plug. Product was still impure so it was dry-loaded into an auto-column using 2× mass of celite to crude. Product obtained: 5.00 g.

Synthesis of N-(4-(1,3-dioxolan-2-yl)phenyl)-N-(m-tolyl)-2-(trimethylstannyl)benzo[b]thiophen-5-amine

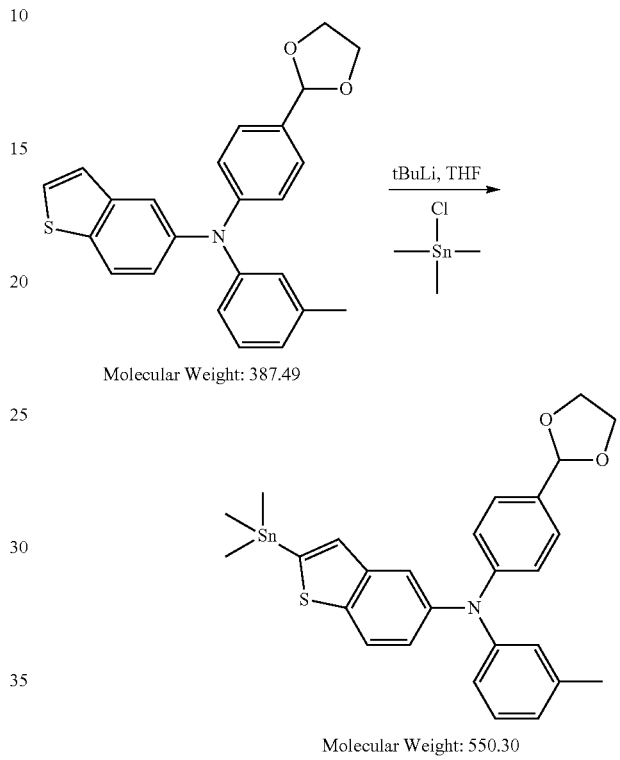

Procedure:

To a clean and dry 500 mL three-neck round bottom flask equipped with magnetic stir bar, addition funnel, and low-temperature thermometer with adapter, N-(4-(1,3-dioxolan-2-yl)phenyl)-N-(m-tolyl)benzo[b]thiophen-5-amine (5.00 g, 0.0129 mol) was charged. Anhydrous tetrahydrofuran (THF) (300 mL) was then added via cannula. The reaction vessel was cooled to −78° C. in an isopropyl alcohol/dry ice bath. Upon reaching the desired temperature, t-butyllithium (1.7M, 15.2 mL) was transferred to the addition funnel via 20 mL syringe and added to the reaction flask dropwise. The reaction was allowed to stir for 30 minutes and was then warmed to a temperature of 0° C. Upon reaching this temperature, the reaction flask was again placed in the cooling bath until reaching −78° C. Trimethyltin chloride solution (1.0M, 25.8 mL) was added to the addition funnel via 2×20 mL syringe. The reaction was allowed to stir at this temperature for 30 minutes before warming to ambient temperature. The reaction solution was poured slowly into a 1 L RBF and placed on a rotary evaporator to reduce the volume to approximately 300 ml and then transferred into a 1 L separatory funnel. 200 ml of DI water and 200 ml of MTBE were added to the funnel. The organic layer was washed with DI H₂O (3×200 mL) before being collected and solvent was removed by rotary evaporation at a temperature not to exceed 40° C. Crude product obtained: 6.95 g.

Synthesis of 2,2'-(9-dodecyl-9H-carbazole-2,7-diyl)
bis(N-(4-(1,3-dioxolan-2-yl)phenyl)-N-(m-tolyl)
benzo[b]thiophen-5-amine)

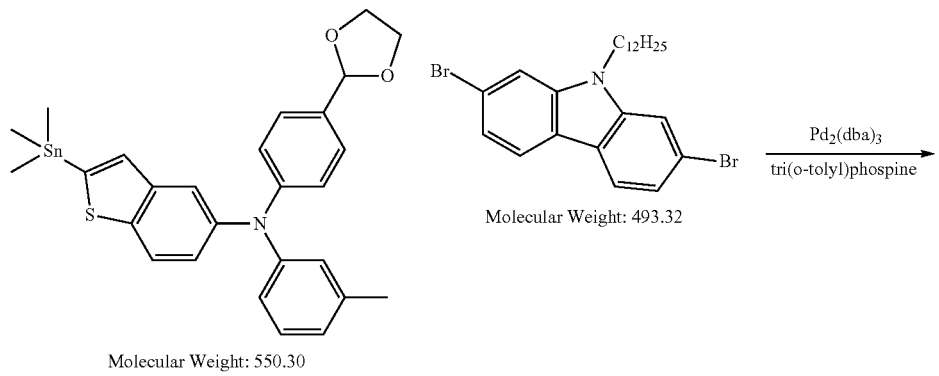

Molecular Weight: 550.30

Molecular Weight: 493.32

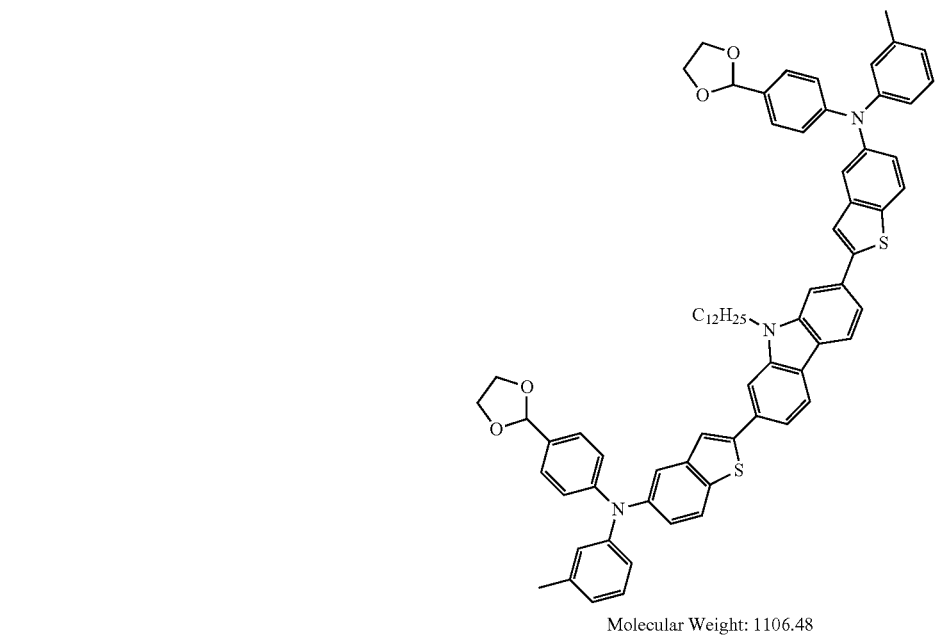

Molecular Weight: 1106.48

Procedure:

A clean and dry 1 L three neck round bottom flask equipped with magnetic stir bar and reflux condenser was prepared and charged with 2,7-dibromo-9-dodecyl-9H-carbazole (6.39 g, 0.0087 mol). All anhydrous toluene used in this reaction was purged with dry nitrogen flow over the weekend. A solution of N-(4-(1,3-dioxolan-2-yl)phenyl)-N-(m-tolyl)-2-(trimethylstannyl)benzo[b]thiophen-5-amine (76.91% purity, 29.6 g) in anhydrous toluene (150 mL) was prepared and transferred to the reaction flask via cannula. Anhydrous toluene (150 mL) was transferred to the reaction flask via cannula. The reaction solution was purged with dry nitrogen flow for one hour. $Pd_2(dba)_3$ (0.796 g, 0.0009 mol) and tri(o-tolyl)phosphine (1.063 g, 0.003 mol) was added to the reaction flask manually. The reaction was heated to 110° C. for 24 hours, after which reaction completion was confirmed by TLC which indicated the disappearance of 2,7-dibromo-9-dodecyl-9H-carbazole from the mixture. The reaction was cooled to room temperature and filtered through a celite/silica gel plug. The filtrate was stripped of solvent by rotary evaporation. Following this the product was dissolved in 15 mL of ethyl acetate and wet loaded onto an auto-column set at a gradient of 0-30% over 20 minutes with a 5 minute hexane/triethyl amine wash. Resulting six fractions were characterized via $^1H$ NMR and showed that the final three fractions contained product. Upon evaporation of solvent, the resulting solids were dissolved in ~20 mL of ethyl acetate and precipitated into room temperature methanol. Solids were filtered through a Buchner funnel and washed thoroughly with methanol and placed on a vacuum line for further drying. Further characterization shows final fraction to be product, $5^{th}$ fraction to be mono-substituted and starting material, and the $4^{th}$ fraction to be impurities. Product obtained: 2.330 g.

327

Dehalogenation of 2,2'-(9-dodecyl-9H-carbazole-2,7-diyl)bis(N-(4-(1,3-dioxolan-2-yl)phenyl)-N-(m-tolyl)benzo[b]thiophen-5-amine)

Procedure:

2,2'-(9-dodecyl-9H-carbazole-2,7-diyl)bis(N-(4-(1,3-dioxolan-2-yl)phenyl)-N-(m-tolyl)benzo[b]thiophen-5-amine) (2.33 g, 0.0021 mol) was dissolved in a 250 mL 3N-RBF equipped with a reflux condenser in anhydrous toluene (100 mL) via 50 mL syringe. All dissolved with stirring. Solution is golden in color. Triethylamine (2.9 mL, 0.021 mol) then formic acid (0.8 mL, 0.02 mol) were added via 3 and 1 mL syringes, respectively. The solution was then purged with nitrogen for 1 hour. Then, Pd(OAc)$_2$ (0.047, 0.0002 mol) and tBu$_3$P (0.068 g, 0.08 mol, in 5 mL anhydrous toluene were added. The reaction was heated to reflux at 110° C. via heating mantle and left to stir and heat at this temperature for 1 hour and 30 minutes. It was then cooled to room temperature and filtered the reaction solution through a celite/silica plug basified with triethylamine and washed with ethyl acetate. This procedure was then repeated. Product was dissolved in 15 mL of ethyl acetate and added slowly, drop-wise, into room temperature methanol. Solids were filtered through a Buchner funnel and placed on the vacuum line for further drying. Product was then dissolved in a minimum amount of ethyl acetate (5 mL) and wet loaded to flash chromatography with an initial wash with hexane/triethyl amine for 3 minutes and a subsequent gradient of 0-30% ethyl acetate/hexane over 20 minutes. Product obtained: 1.065 g.

Synthesis of 4,4'-((2,2'-(9-dodecyl-9H-carbazole-2,7-diyl)bis(benzo[b]thiophene-5,2-diyl))bis(m-tolylazanediyl))dibenzaldehyde

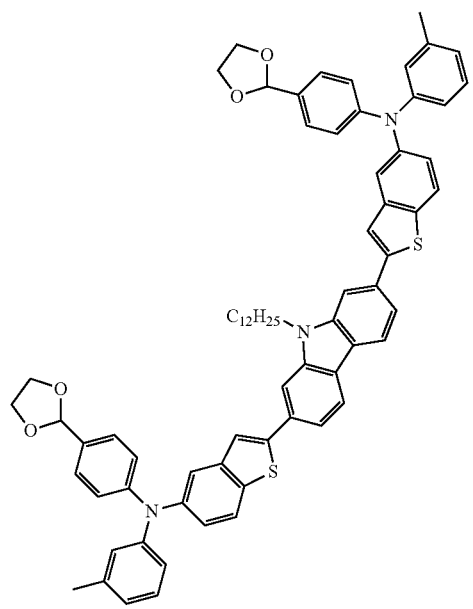

Molecular Weight: 1106.48

328

-continued

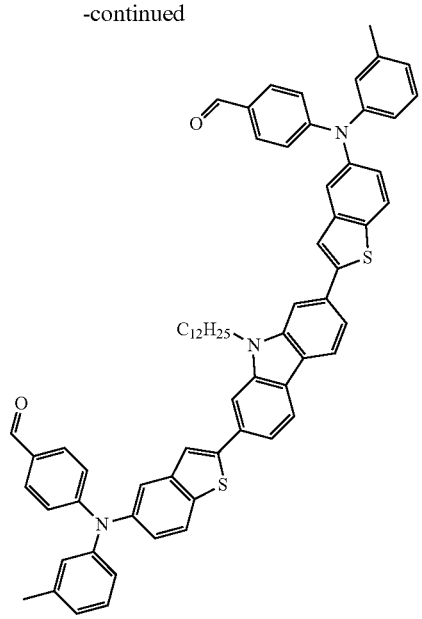

Molecular Weight: 1018.38

Procedure:

Chromasolv THF (100 mL) was added to a 50 mL single-neck round bottom flask that contained 2,2'-(9-dodecyl-9H-carbazole-2,7-diyl)bis(N-(4-(1,3-dioxolan-2-yl)phenyl)-N-(m-tolyl)benzo[b]thiophen-5-amine) (8.6 g, 0.0002 mol). All dissolved with stirring via stir plate. Solution was pale yellow in color. Aqueous hydrochloric acid solution (0.67 mL, 2.0 M), was then added dropwise via 1 mL syringe. The reaction was permitted to stir for 15 minutes. Reaction completion was monitored via $^1$H NMR. It indicated that the reaction was complete. Triethylamine (2 mL or 2%) was added to the reaction flask to quench the reaction. Deionized water (150 mL) and MTBE (150 mL) were added to a 500-mL separatory funnel via glass funnel. The organic and aqueous layers were separated. The organic layer was washed 4×50 mL DI water. Solvents were removed from the organic layer via rotary evaporation. Product obtained 0.94 g.

Synthesis of 2,2'-(9-tridecyl-9H-carbazole-2,7-diyl)bis(N-(m-tolyl)-N-(4-vinylphenyl)benzo[b]thiophen-5-amine)

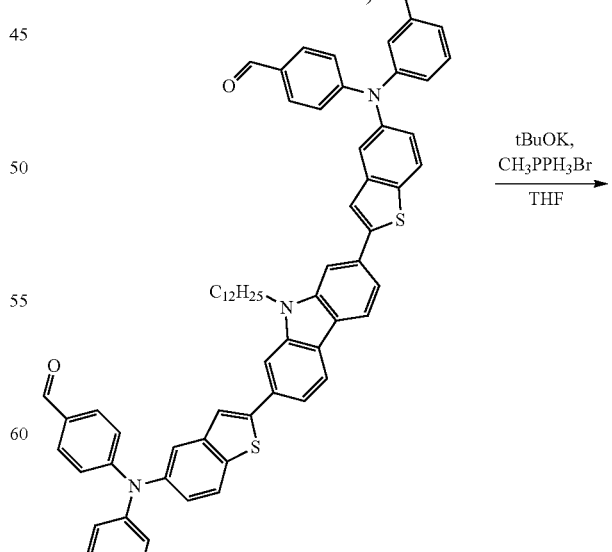

Molecular Weight: 1018.38

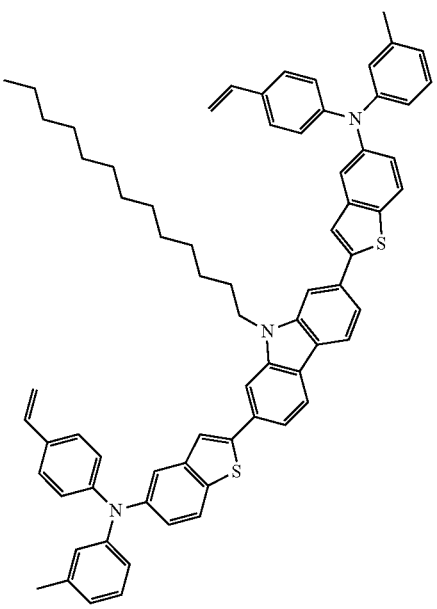

Molecular Weight: 1028.46

Procedure:

In a 50 mL 1N-RBF, 4,4'-((2,2'-(9-dodecyl-9H-carbazole-2,7-diyl)bis(benzo[b]thiophene-5,2-diyl))bis(m-tolylazanediyl))dibenzaldehyde (0.99 g, 0.001 mol) was dissolved in anhydrous THF (25 mL) with swirling and vigorous stirring via stir plate. Methyltriphenylphosphonium bromide (1.0418 g, 0.0029 mol) was added manually to a 250 mL 3N-RBF equipped with an addition funnel and stir bar. Anhydrous THF (25 mL) was added to the reaction flask via 50 mL syringe and permitted to stir. Potassium tert-butoxide (0.3272 g, 0.0029 mol) was then added to the reaction flask and the flask was subsequently covered with aluminum foil. The 4,4'-((2,2'-(9-dodecyl-9H-carbazole-2,7-diyl)bis(benzo[b]thiophene-5,2-diyl))bis(m-tolylazanediyl))dibenzaldehyde solution was then transferred to the addition funnel via 50 mL syringe. This solution was added drop-wise to the reaction flask from the addition funnel. The reaction was permitted to stir for 1 hour. Reaction completion was monitored via TLC and $^1$H NMR. After several attempts to purify this target including column chromatography, triturating, recrystallization, and precipitations, material purity was left as is. Product obtained: 0.222 g.

PLX-20-A

A need exists for improved synthetic methods for amination reactions to form aryl amine compounds. In above, the PLX-12-B embodiment was developed as one particular example where this need was found to exist. Buchwald-Hartwig aminations allow one to create a myriad of different materials, primarily through the palladium catalyzed C—N cross-coupling between aryl iodides or bromides and secondary or primary arylamines. For the aforementioned reagents, the Buchwald-Hartwig amination can be very reliable, and its use facilitates the synthesis of many new HTL's. In the cases where certain structures are unavailable as an aryl iodide/bromide or arylamine, other synthetic routes were developed. For example, work was carried out with the Pd catalyzed amination of compounds with a trifluoromethanesulfonate (triflate) substituent. This broadens one's scope of aminations to more readily available and often cheaper phenolic intermediates. A wide variety of phenols exist and make good options for new routes of syntheses; protected phenols can act as directing groups in certain reactions and can be easily converted to their corresponding triflates for subsequent aminations (Driver, et al. *J. Org. Chem.* 1997, 62, 1268-1273). Though existing literature points towards certain procedures for successful coupling with triflates (Driver, et al. *J. Org. Chem.* 1997, 62, 1268-1273; Wolfe et al., *J. Org. Chem.* 1997, 62, 1264-1267) unexpected results were needed to achieve the desired synthesis.

A new dual-ligand approach to triflate amination yielded good results.

Experimental Section:

All reactions were carried out under $N_2$ atmosphere in oven and flame dried glassware. 1-Naphthyl trifluoromethanesulfonate, diphenylamine, m-toluidine, and 4-pentylaniline, Sodium tert-butoxide, (+/−)BINAP, t-Bu$_3$P, anhydrous toluene, and anhydrous dioxane were all purchased from Sigma Aldrich and used without further purification. Palladium precatalysts were purchased from Frontier Scientific. Triphenylene-2,7-diyl bis(trifluoromethanesulfonate) was synthesized and purified in-house.

General Procedures for Catalytic Aminations of Aryl Triflates:

Methods A through D: A 3-neck round-bottom flask with condenser and stir bar was charged with an aryl triflate or ditriflate and primary or secondary arylamine. The listed solvent was added until all dissolved (or in the case of the triphenylene ditriflate, finely suspended). Solution underwent $N_2$ sparging for 30 minutes before addition of base, palladium precatalyst and ligand which were all weighed in inert, dry glovebox. Reaction solution was then refluxed for the listed time (until reaction completed or was observed to stall via TLC). Crude mixture was then cooled, filtered, and concentrated. All purifications were carried out with column chromatography and methanol washes. For Methods E and F, all steps were carried out exactly the same, with t-Bu$_3$P being charged via inert syringe in toluene solution.

TABLE 1

Catalytic Aminations of Aryl Triflates

| Entry | Triflate | Amine | Product |
|---|---|---|---|
| 1 | | | |
| 2 | | | |

TABLE 1-continued

Catalytic Aminations of Aryl Triflates

3. [m-toluidine structure with NH2] → [N-(1-naphthyl)-N-(m-tolyl)amine structure]

4. [2,7-bis(triflate)triphenylene: TfO—triphenylene—OTf] + [4-pentylaniline with NH2] → [2,7-bis((4-pentylphenyl)amino)triphenylene structure]

5.
6.
7.

| Entry | Conditions | Base | Ligand | Yield (%) |
|---|---|---|---|---|
| 1 | A | t-BuONa | DPPF | 0%* |
| 2 | B | K$_2$CO$_3$ | (+/−) BINAP | 0% no rxn |
| 3 | C | Cs$_2$CO$_3$ | (+/−) BINAP | >90% |
| 4 | C | Cs$_2$CO$_3$ | (+/−) BINAP | N/A isolated product is monosubstituted triflate |
| 5 | D | Cs$_2$CO$_3$ | Xphos | 0% no rxn† |
| 6 | E | Cs$_2$CO$_3$ | t-Bu$_3$P | 0% no rxn† |
| 7 | F (D + E) | Cs$_2$CO$_3$ | Xphos/t-Bu$_3$P | 90% isolated yield | a) Method A: 2.5 mol % Pd$_2$(dba)$_3$, DPPF/Pd$_2$(dba)$_3$ (2.4/1), B: t-BuONa, Dioxane;
b) Method B: 3 mol % Pd(OAc)$_2$, (+/−) BINAP/Pd(OAc)$_2$ (2/1), B: K$_2$CO$_3$, Toluene;
c) Method C: 3 mol % Pd(OAc)$_2$, (+/−) BINAP/Pd(OAc)$_2$ (1.5/1), B: Cs$_2$CO$_3$, Toluene;
d) Method D: 3 mol % Pd(OAc)$_2$, XPhos/Pd(OAc)$_2$ (1.5/1), B: Cs$_2$CO$_3$, Toluene;
e) Method E: 3 mol % Pd(OAc)$_2$, tBu$_3$P/Pd(OAc)$_2$ (1.5/1), B: Cs$_2$CO$_3$, Toluene;
f) Method F: 6 mol % Pd(OAc)$_2$, tBu$_3$P/XPhos/Pd(OAc)$_2$ (1.5/1.5/1), B: Cs$_2$CO$_3$, Toluene;
*all triflate cleaved to 1-naphthol
†reaction did not proceed until secondary ligand was added.

For Method A, all of the 1-naphthyl triflate was cleaved into 1-naphthol, evidenced by an m/z of 144 on GC/MS spectrum; presumably from a nucleophilic attack of tert-butoxide on the sulfur as was shown to occur in Buchwald and Åhman's work at MIT (Åhman, J.; Buchwald, S. L. *Tetrahedron Letters*. 1997, Vol. 38, No. 36, 6363-6366). According to TLC, formation of the 1-naphthol was quick and started within the first 30 minutes of heating, and appeared to be faster than any oxidative insertion, as no noticeable product was observed via TLC or GC/MS.

With this result, conditions in Method B were changed to employ a much weaker base, potassium carbonate. For this reaction, no product was formed, but the 1-naphthyl triflate was not cleaved, lending credence to the nucleophilicity of the butoxide in the previous conditions. The ligand was changed from DPPF to BINAP, as there was no clear accordance between Hartwig and Buchwald as to which bidentate ligand was superior (Driver, et al. *J. Org. Chem*. 1997, 62, 1268-1273; Wolfe et al., *J. Org. Chem*. 1997, 62, 1264-1267).

For Method C, the base was changed to cesium carbonate, which was touted as a more effective base in Buchwald and Åhman's paper (which also utilized BINAP as the ligand) (Åhman, J.; Buchwald, S. L. *Tetrahedron Letters*. 1997, Vol. 38, No. 36, 6363-6366). Diphenylamine was replaced with m-toluidine to facilitate NMR identification of any products. With these conditions, all starting triflate was consumed, and the desired product was formed and characterized via NMR. Method C appeared to be the appropriate conditions to attempt an amination with the triphenylene ditriflate. Initially, via TLC, the reaction looked like it had completed after 16 hours of reflux. All starting ditriflate was consumed and a bright fluorescent spot was the major product, which was assumed to be the diamine. However, after column chromatography, the isolated product was actually the monosubstituted 7-((4-pentylphenyl)amino)triphenylen-2-yl trifluoromethanesulfonate, as evidenced by NMR. The TLC of the crude was revisited, and a much smaller fluorescent spot of lower Rf was observed and raised suspicion. The impurities from the previous column were collected and ran through chromatography until the suspicious material was isolated. Though not present in any appreciable quantity, there was enough of this "side-product" present for NMR. NMR confirmed that the small amount of "side-product" was actually the desired diamine. Perhaps the reaction may have completed if refluxed for a longer time, but that was not optimal for an industry procedure. Using Surry and Buchwald's "Dialkylbiaryl phosphines in Pd-catalyzed amination: a user's guide", it was noted that XPhos was listed as an effective ligand for amination of aryl tosylates (Surry, D. S.; Buchwald, S. L. *Chem. Sci.*, 2011, 2, 27-50).

Method D switched out BINAP for XPhos to probe its efficacy with triflates. After refluxing overnight, TLC indicated a completely stalled reaction.

Given the high activity of t-$Bu_3P$ as a ligand for amination, Method E switched out XPhos for t-$Bu_3P$, but in lieu of setting up a completely different reaction, the tri-tert-butylphosphine was charged directly into the previous reaction solution containing XPhos. TLC after three hours showed formation of both monosubstituted and disubstituted triphenylene, and after refluxing overnight, the remaining monosubstituted triphenylene had been completely aminated. This was attributed to the tri-tert-butylphosphine, so a reaction using only t-$Bu_3P$ as the ligand was set up and refluxed overnight. TLC indicated another stalled reaction. XPhos and another round of palladium precatalyst were added to this reaction solution, and once again, the reaction began to proceed.

For method F, the reaction solution was charged with both XPhos and tri-tert-butylphosphine at the same time and refluxed. After 8 hrs, all starting material had been completely aminated. Product was precipitated in methanol to remove excess 4-pentylaniline and dried under vacuum. NMR confirmed the structure of the diamine at 90% yield. The shortened reaction time compared to the BINAP coupling could be attributed to a higher overall catalyst/ligand loading, or perhaps a change in the electron density or sterics of the monosubstituted triphenylene reduced BINAP's ability to couple to the remaining triflate.

In conclusion, an effective and relatively quick method for amination of triflates utilizing a combination of two different ligands as opposed to the commonly used bidentate ligands, DPPF and BINAP, was discovered. BINAP appears to function as a ligand for catalyzed amination of triflates, but at a much lower rate than the mixture of XPhos and t-$Bu_3P$. This dual-ligand system provided unexpectedly good results. See, for example, embodiment PLX-12-B above.

PLX-21-A

Mobility values were measured relative to a control as shown in below Table 2. The control composition and other compositions included use of compounds represented below as compound K and compound O.

The hole-only device comprises the following device stack: from the ITO surface, ca. 50 nm layer of hole-injection layer Plexcore OC polythiophene polymer was deposited by spin-casting, 150 nm of HTL layer (having composition shown in Table 2) deposited by spin-casting, a 5 nm layer of MoOx and a 100 nm layer of aluminum deposited by thermal evaporation as cathode.

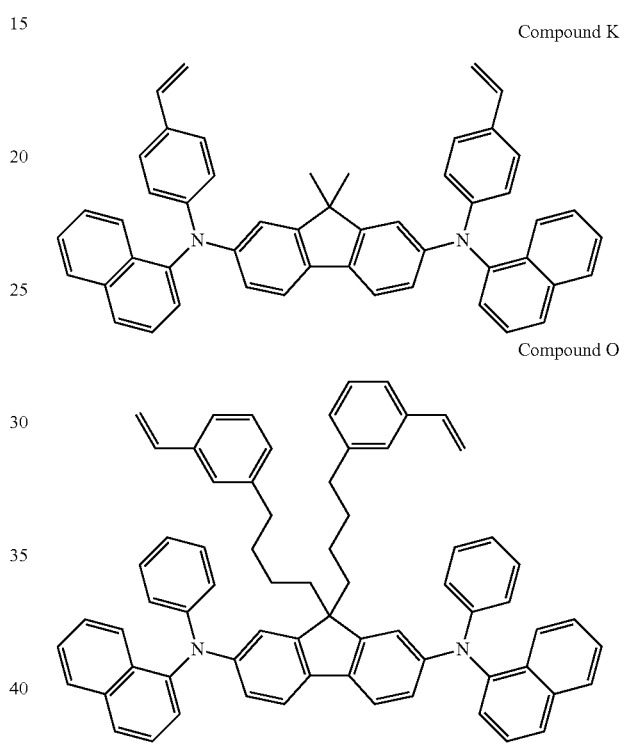

Compound K

Compound O

TABLE 2

Note that reverse bias measurement may provide a better indicator of mobility due to reduced injection barrier from the Mox side of the device compared to the HIL side of the device.

| Component 1 | 1 (wt. %) | Component 2 | 2 (wt. %) | Component 3 | Composition 3 | HOD reverse bias @ 3E7 V/m ratio of mobility versus control Ratio to Control | Forward bias voltage @ 10 mA/cm2 Ratio of mobility vs control Ratio to Control |
|---|---|---|---|---|---|---|---|
| (control)O | (control) 50 | (control) K | (control)50 | | | 1.00 | 1.00 |
| PLX-1-A | 100 | | | | | 1.73 | 1.07 |
| PLX-1-A | 50 | O | 50 | | | 1.99 | 0.83 |
| PLX-3-D | 50 | K | 50 | | | 0.69 | 1.09 |
| PLX-3-D | 100 | | | | | 12.38 | 0.37 |
| PLX-3-A | 50 | K | 50 | | | 15.45 | 0.72 |
| PLX-3-A | 100 | | | | | 21.01 | 0.50 |
| PLX-3-C-2 | 50 | K | 50 | | | 0.49 | 0.83 |
| PLX-3-C-2 | 100 | | | | | 6.97 | 0.42 |
| PLX-3-B | 50 | K | 50 | | | 0.25 | 1.53 |
| PLX-3-B | 100 | | | | | 2.24 | 0.51 |
| PLX-8-A | 100 | | | | | 46.26 | 0.30 |
| PLX-8-C | 50 | O | 50 | | | 5.52 | 1.23 |
| PLX-8-C | 100 | | | | | 0.86 | 1.11 |

TABLE 2-continued

Note that reverse bias measurement may provide a better indicator of mobility due to reduced injection barrier from the Mox side of the device compared to the HIL side of the device.

| Component 1 | 1 (wt. %) | Component 2 | 2 (wt. %) | Component 3 | Composition 3 | HOD reverse bias @ 3E7 V/m ratio of mobility versus control Ratio to Control | Forward bias voltage @ 10 mA/cm2 Ratio of mobility vs control Ratio to Control |
|---|---|---|---|---|---|---|---|
| PLX-8-B | 100 | | | | | 1.84 | 0.74 |
| PLX-8-B | 50 | Selkie | 50 | | | 0.25 | 2.33 |
| PLX-9-B | 100 | | | | | 0.07 | 1.20 |
| PLX-9-A | 100 | | | | | 0.57 | 1.02 |
| PLX-9-A | 50 | O | 50 | | | 2.09 | 0.72 |
| PLX-11-A | 100 | | | | | 10.92 | 0.72 |
| PLX-11-A | 50 | K | 50 | | | 6.76 | 0.74 |
| PLX-11-B | 100 | | | | | 33.87 | 0.30 |
| PLX-12-D | 100 | | | | | 394.60 | 0.13 |
| PLX-12-A | 100 | | | | | 54.68 | 0.16 |
| PLX-12-A | 50 | K | 50 | | | 25.21 | 1.30 |
| PLX-12-B | 100 | | | | | 0.31 | 1.41 |
| PLX-12-B | 50 | O | 50 | | | 0.35 | 1.13 |
| PLX-13-B | 100 | | | | | 0.17 | 2.35 |
| PLX-13-B | 50 | O | 50 | | | 0.71 | 1.47 |
| PLX-13-B | 30 | O | 70 | | | 0.31 | 1.58 |
| PLX-16-B | 100 | | | | | 12.18 | 0.33 |
| PLX-16-B | 50 | K | 50 | | | 2.67 | 1.04 |
| PLX-16-A | 100 | | | | | 0.36 | 1.56 |
| PLX-17-A | 100 | | | | | 4.17 | 0.17 |
| PLX-17-C | 100 | | | | | 10.67 | 0.70 |

What is claimed is:

1. A composition comprising at least one hole transporting compound, said hole transporting compound comprises a hole transporting core covalently bonded to one or more arylamine (AA) groups, each AA group is optionally substituted with one or more intractability groups, wherein the hole transporting compound is represented by:

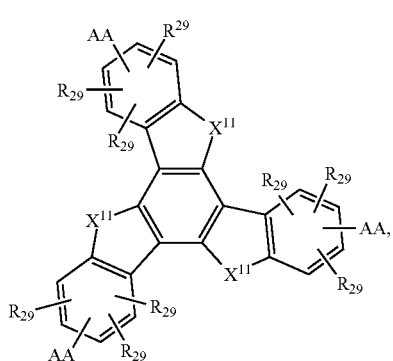

(viii-A)

wherein each of $X^{11}$ is S, O, NR, $CR_2$, $SiR_2$ or $GeR_2$, wherein each R is an optionally substituted alkyl, aryl, heteroalkyl, heteroaryl, or intractability group, and wherein each of $R^{29}$ is H, F, or an optionally substituted alkyl, aryl, heteroalkyl, heteroaryl, or intractability group, and wherein the arylamine group is a diarylamine or triarylamine group substituted with one or more vinyl groups.

2. The composition of claim 1, wherein the arylamine group is

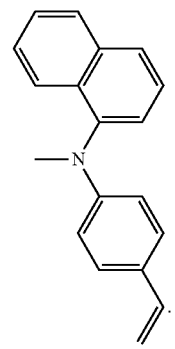 [SMILES: C=Cc1ccc(N(C)c2cccc3ccccc23)cc1]

3. A composition comprising at least one hole transporting compound, said hole transporting compound comprises a hole transporting core covalently bonded to one or more arylamine (AA) groups, each AA group is optionally substituted with one or more intractability groups, wherein the hole transporting compound is represented by:

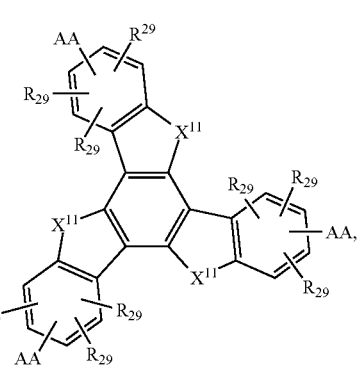

(viii-A)

wherein each of $X^{11}$ is S, O, NR, $CR_2$, $SiR_2$ or $GeR_2$, wherein each R is an optionally substituted alkyl, aryl, heteroalkyl, heteroaryl, or intractability group, and wherein each of $R^{29}$ is H, F, or an optionally substituted alkyl, aryl, heteroalkyl, heteroaryl, or intractability group, wherein the hole transporting compound comprises at least two intractability groups.

4. A composition comprising at least one hole transporting compound, said hole transporting compound comprises a hole transporting core covalently bonded to one or more arylamine (AA) groups, each AA group is optionally substituted with one or more intractability groups, wherein the hole transporting compound is represented by:

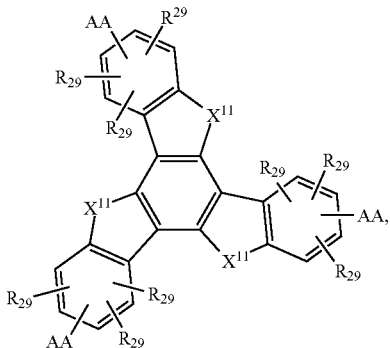

(viii-A)

wherein each of $X^{11}$ is S, O, NR, $CR_2$, $SiR_2$ or $GeR_2$, wherein each R is an optionally substituted alkyl, aryl, heteroalkyl, heteroaryl, or intractability group, and wherein each of $R^{29}$ is H, F, or an optionally substituted alkyl, aryl, heteroalkyl, heteroaryl, or intractability group, wherein the hole transporting compound comprises at least two intractability groups, wherein the intractability groups are crosslinking groups or polymerizable groups.

5. The composition of claim 3, wherein the hole transporting compound comprises at least two intractability groups, wherein the intractability groups are non-crosslinking groups.

6. The composition of claim 3, wherein the hole transporting compound comprises at least two intractability groups selected from the group consisting of

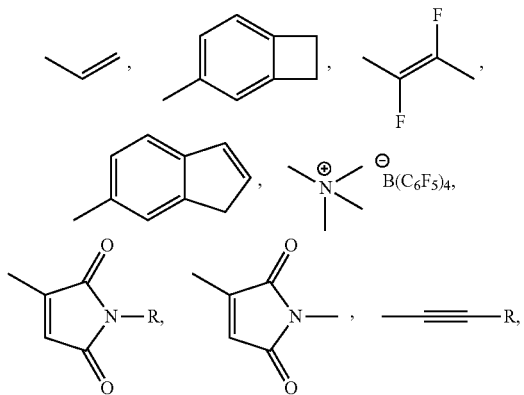

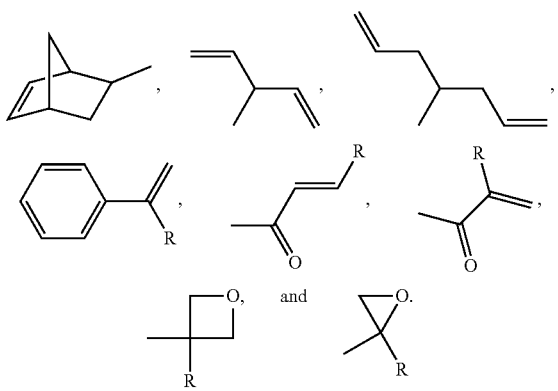

7. The composition of claim 3, further comprising at least one solvent.

8. The composition of claim 3, further comprising a second compound comprising one or more intractability groups.

9. A composition comprising a partially or fully reacted form of the composition of claim 3.

10. A device comprising a hole transport layer, wherein the hole transport layer comprises the composition of claim 9.

11. The device of claim 10, wherein the device is an OLED device.

12. The composition of claim 1, wherein the hole transporting compound is represented by

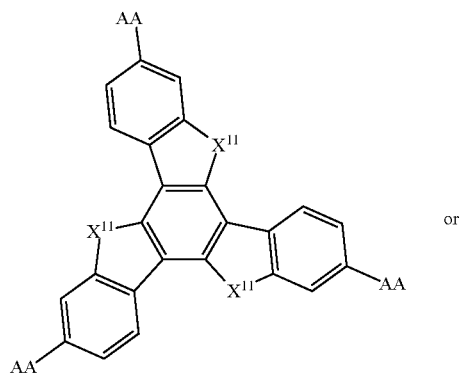

or

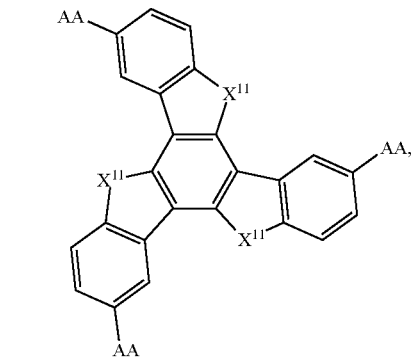

wherein each of $X^{11}$ is S, O, NR, $CR_2$, $SiR_2$ or $GeR_2$, and wherein each R is an optionally substituted alkyl, aryl, heteroalkyl, heteroaryl, or intractability group.

13. The composition of claim 1, wherein the hole transporting compound is represented by

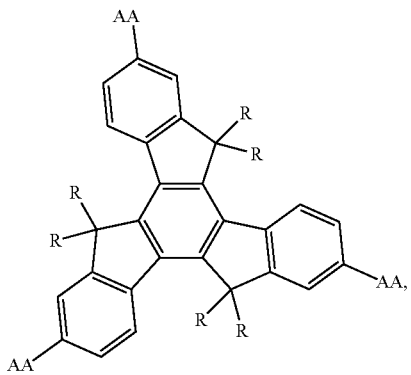

wherein each R is an optionally substituted alkyl, aryl, heteroalkyl, heteroaryl, or intractability group.

14. The composition of claim 3, wherein the arylamine (AA) group is a diarylamine or triarylamine group optionally substituted with one or more intractability groups.

15. A composition comprising a partially or fully reacted form of the composition of claim 1.

16. A composition comprising a partially or fully reacted form of the composition of claim 4.

17. A composition comprising a partially or fully reacted form of the composition of claim 5.

18. A composition according to claim 1, wherein the $X^{11}$ group is $CR_2$.

19. A composition according to claim 3, wherein the $X^{11}$ group is $CR_2$.

20. A composition according to claim 4, wherein the $X^{11}$ group is $CR_2$.

* * * * *